(12) United States Patent
Holm

(10) Patent No.: US 11,369,650 B2
(45) Date of Patent: Jun. 28, 2022

(54) METHODS FOR REVERSING MULTIPLE RESISTANCE IN ANIMAL CELLS

(71) Applicant: Per Sonne Holm, Furstenfeldbruck (DE)

(72) Inventor: Per Sonne Holm, Furstenfeldbruck (DE)

( * ) Notice: Subject to any disclaimer, the term of this patent is extended or adjusted under 35 U.S.C. 154(b) by 0 days.

(21) Appl. No.: 15/461,668

(22) Filed: Mar. 17, 2017

(65) Prior Publication Data

US 2017/0252443 A1    Sep. 7, 2017

Related U.S. Application Data

(63) Continuation of application No. 13/170,395, filed on Jun. 28, 2011, now abandoned, which is a continuation of application No. 12/556,560, filed on Sep. 9, 2009, now abandoned, which is a continuation of application No. 11/794,594, filed as application No. PCT/EP2006/000009 on Jan. 2, 2006, now abandoned.

(60) Provisional application No. 60/651,085, filed on Feb. 8, 2005.

(30) Foreign Application Priority Data

Dec. 31, 2004 (DE) .......................... 102004063639.7

(51) Int. Cl.
| | | |
|---|---|---|
| *C12N 15/861* | (2006.01) | |
| *C12N 15/63* | (2006.01) | |
| *A61K 35/761* | (2015.01) | |
| *A61K 48/00* | (2006.01) | |
| *A61P 35/00* | (2006.01) | |
| *C12N 7/00* | (2006.01) | |
| *A61K 45/06* | (2006.01) | |

(52) U.S. Cl.
CPC ............ *A61K 35/761* (2013.01); *A61K 45/06* (2013.01); *C12N 7/00* (2013.01); *C12N 15/861* (2013.01); *C12N 2710/10321* (2013.01); *C12N 2710/10332* (2013.01)

(58) Field of Classification Search
None
See application file for complete search history.

(56) References Cited

U.S. PATENT DOCUMENTS

| 6,228,646 B1 * | 5/2001 | Hardy ................. C12N 7/00 435/320.1 |
| 6,475,480 B1 * | 11/2002 | Mehtali ............... C07K 14/005 424/93.2 |
| 8,586,354 B2 * | 11/2013 | Holm .................. C12N 15/86 424/93.1 |
| 8,951,772 B2 * | 2/2015 | Holm .................. C07K 14/005 435/235.1 |
| 10,155,930 B2 * | 12/2018 | Holm .................. C07K 14/005 |
| 2002/0086411 A1 * | 7/2002 | Holm .................. A61K 38/1709 435/235.1 |
| 2003/0039633 A1 * | 2/2003 | Yu .................... A61K 38/162 424/93.2 |
| 2003/0095989 A1 * | 5/2003 | Irving ................. C07K 14/005 424/233.1 |
| 2004/0081637 A1 | 4/2004 | Curiel |
| 2005/0002965 A1 | 1/2005 | Yun et al. |
| 2006/0099178 A1 | 5/2006 | Holm et al. |
| 2006/0270016 A1 | 11/2006 | Holm et al. |
| 2007/0110719 A1 | 5/2007 | Holm et al. |
| 2007/0116670 A1 * | 5/2007 | Holm .................. A61K 48/00 424/93.2 |
| 2007/0202524 A1 * | 8/2007 | Murphy ................ A61K 31/70 435/6.1 |
| 2007/0292396 A1 * | 12/2007 | Fueyo ................. A61K 45/06 424/93.6 |
| 2010/0297731 A1 | 11/2010 | Holm et al. |
| 2010/0311145 A1 | 12/2010 | Holm et al. |

FOREIGN PATENT DOCUMENTS

| JP | 11-506311 | 6/1999 |
| JP | 2006/518589 | 8/2006 |
| JP | 2007/512211 | 5/2007 |
| JP | 2008/526189 | 7/2008 |
| WO | WO 0029573 | * 5/2000 |
| WO | WO 2001/02556 | 1/2001 |
| WO | WO 2003/099859 | 12/2003 |
| WO | WO 2004/001032 | 12/2003 |
| WO | WO 2004/035616 | 4/2004 |
| WO | WO 2004/083404 | 9/2004 |
| WO | WO 2005005679 | 1/2005 |
| WO | WO 2005051430 | 6/2005 |
| WO | WO 2005052143 | 6/2005 |
| WO | WO 2006/070024 | 7/2006 |

OTHER PUBLICATIONS

Russell et al, Oncolytic Virotherapy, Nat Biotechnol, 30(7), pp. 658-670, 2014.*
Yamamoto and CUriel, Current Issues and Future Directions of Oncolytic Adenoviruses, Molecular Therapy vol. 18 No. 2, 243-250 Feb. 2010.*
Freytag et al, Phase I Study of Replication-Competent Adenovirus-Mediated Double-Suicide Gene Therapy in Combination with Conventional-Dose Three-Dimensional Conformal Radiation Therapy for the Treatment of Newly Diagnosed, Intermediate-to High-Risk Prostate Cancer, Cancer Research 63, 7497-7506, Nov. 1, 200.*
Hill and Carlisle, Achieving systemic delivery of oncolytic viruses, Expert Opinion on Drug Delivery 2019, vol. 16, No. 6, 607-620.*
Liu et al, An E1B-19 kDa Gene Deletion Mutant Adenovirus Demonstrates Tumor Necrosis Factor-Enhanced Cancer Selectivity and Enhanced Oncolytic Potency, Molecular Therapy, 2004, pp. 786-803.*

(Continued)

*Primary Examiner* — Maria Marvich
(74) *Attorney, Agent, or Firm* — Casimir Jones, S.C.; Peter J. Schlueter

(57) ABSTRACT

The present invention is related to the use of a virus, preferably an adenovirus for reversing resistance in cells.

9 Claims, 51 Drawing Sheets

Specification includes a Sequence Listing.

(56) References Cited

OTHER PUBLICATIONS

Ahonen et al., Antitumor Activity and Bystander Effect of Adenovirally Delivered Tissue Inhibitor of Metalloproteinases, Mol Therapy, 5, 705-715, 2002.
Atadja et al., Selective growth inhibition of tumor cells by a novel histone deacetylase inhibitor, NVP-LAQ824, Cancer Res., 64, 689-695, 2004.
Avemann et al., Camptothecin, a Specific Inhibitor of Type 1 DNA Topoisomerase, Induces DNA Breakage at Replication Forks, Mol. Cell. Biol., 8, 3026-3034, 1988.
Bieler Alexa et al: "Novel three-pronged strategy to enhance cancer cell killing in glioblastoma cell lines: Histone deacetylase inhibitor, chemotherapy, and oncolytic adenovirus dl520" Human Gene Therapy, vol. 17, No. 1, Jan. 2006, pp. 55-70.
Binaschi, M. et al., Relationship between Lethal Effects and Topoisomerase If-Mediated Double Stranded DNA Breaks Produced by Anthracyclines with Different Sequence Specificity, Mol. Pharmacal., 1997, 51, 1053-1059.
Boulanger P. A. and Blair, G. E., Expression and interactions of human adenovirus oncoproteins, Biochem. J. 1991, 275, 281-299.
Brummelkamp et al., A system for stable expression of short interfering RNA's in Mammalian Cells, Science, 296, 550-553, 2002.
Camphausen K et al., Enhancement of Xenograft Tumor Radiosensitivity by the Histone Deacetylase Inhibitor MS-275 and Correlation with Histone Hyperacetylation, Clinical Canver Research 2004, 10, 6066-6071.
Descamps et al., Strategies for cancer gene therapy using adenoviral vectors, J. Mol. Med., 74, 183-189, 1996.
Dimitrev IF et al., Engineering of Adenovirus Vectors Containing Heterologous Peptide Sequences in the C Terminus of Capsid Proteing IX, Journal of Virology, 2002, 76, 6893-6899.
Dmitriev et al., J. Virol. 1998, pp. 9706-9713 , An Adenovirus Vector with Genetically Modified Fibers Demonstrates Expanded Tropism via Utilization of a Coxsackievirus and Adenovirus Receptor-Independent Cell Entry Mechanism.
Dobbelstein, M. et al., Nuclear export of the EIB 55-kDa and E4 34-kDA adenoviral oncoproteins mediated by a rev-like signal sequence, EMBO Journal, 16, 4276-4284, 1997.
Doronin et al., Tumor-specific, Replication-Competent Adenovirus Vectors Overexpressing the Adenovirus Death Protein, J. Virology, 74, 6147-6155, 2000.
Evdokimova V et al, Akt-Mediated YB-I Phosphorylation Activates Translation of Silent mRNA Species, Molecular and Cellular Biology, 26, 277-292, 2006.
Ferguson et al., "Systemic delivery on oncolytic viruses: hopes and hurdles," Advances in Virology (2012) 1-14.
Fribley A et al., Proteasome Inhibitor PS-341 Induces Apoptosis through induction of endoplasmic reticulum stress-reactive oxygen species in head and neck squamous cell carcinoma cells, Mol Cell Bioi Nov. 2004; 24(22): 9695-704.
Gilbert et al., Phase 1 clinical and pharmacokinetic study of Irinotecan in Adults with recurrent malignant glioma, Clinical Cancer Res., 9, 2940-2949, 2003.
Goldsmith, M., et al., "The Histone Deacetylase Inhibitor FK228 Preferentially Enhances Adenovirus Transgene Expression in Malignant Cells" Clin. Cancer Res., 9 [14] (Nov. 1, 2003) p. 5394-5401.
Helt and Galloway, Mechanisms by which DNA tumor virus oncoproteins target the Rb family of pocket proteins, Carcinogenesis, 24, 159-169, 2003.
Holm et al.: "Chapter 15: Inhibition of the Multidrug Resistance Phenotype by Different Delivery Systems of an Anti-MDR Ribozyme" 1998, R.G. Landes Company, Ed. Kevin Scanlon and M. Kashani-Sabet, p. 183-p. 194.
Holm Per S et al: "Multi drug-resistant cancer cells facilitate E1-independent adenoviral replication: Impact for cancer gene therapy" Cancer Research, vol. 64, No. 1, Jan. 1, 2004, pp. 322-328.

Holm, P. S. et al., YB-1 Relocates to the Nucleus in Adenovirus-infected cells and facilitates viral replication by inducing E2 Gene Expression through the E2 Late Promoter, JBC 277, 10427-10434, 2002.
Horwitz, M.S., Adenovirus Immunoregulatory Genes and Their Cellular Targets, Virology, 279, 1-8, 2001.
Hu Z, Jin S, Scotto KW., Transcriptional Activation of the MDR1 Gene by UV Irradiation, J Bioi. Chern. Jan. 28, 2000; 275(4):2979-85.
Jaboin et al., MS-27-275, an Inhibitor of Histon Deacetylase, Has Marked in vitro and in vivo Antitumor Activity against Pediatric Solid Tumors, Cancer Res., 62, 6108-6115, 2002.
Ji et al., Induction of Apoptosis and Inhibition of Tumorigenicity and Tumor growth by Adenovirus vector-mediated fragile histidine triad gene expression, Cancer Res., 59, 3333-3339, 1999.
Jurchott K et al., YB-I as a Cell Cycle-regulated Transcription Factor Facilitating Cylcin A and Cycllin B1 Gene Expression, JBC 2003, 278, 27988-27996.
Kitazono et al., Enhanced Adenovirus Transgene Expression in Malignant Cells Treated with the Histone Deacetylase Inhibitor FR901228, Cancer Res., 61, 6328-6330, 2001.
Koike K et al., Nuclear translocation of the Y-Box binding protein by ultraviolet irradiation, FEBS Letters, 417,390-394, 1997.
Koyama et al., Combined suicide gene therapy for human colon cancer cells using adenovirus-mediated transfer of *Escherichia coli* cytosine deaminase gene and *Escherichia coli* uracil phosphoribosyltransferase gene with 5-jlourocytosine, Cancer Gene Therapy, 7, 1015-1022, 2000.
Le QT et al., Phase 1 study of Tirapazamine plus cisplatin/etoposide and concurrent thoracic radiotherapy in limited-stage small cell lung cancer (s0004): A southwest Oncology Group Study, Clinical Cancer Res. 2004, 10, 5418-5424.
Lindemann RK. et al., Histone-Deacetylase Inhibitors for the Treatment of Cancer, Cell Cycle 2004, 3, 77-86.
Majumdar et al., Efficacy of herpes simplex virus thymidine kinase in combination with cytokine gene therapy in an experimental metastic breast cancer model, Cancer Gene Therapy, 7, 1086-1099,2000.
Mantwill, K. et al., "Inhibition of the multidrug-resistant phenotype by targeting YB-1 with a conditionally oncolytic adenovirus: implications for combinatorial treatment regimen with chemotherapeutic agents," Cancer Res. (2006) 66(14):7195-7202.
Nimmanapalli R et al., Histone Deacetylase Inhibitor LAQ824 Both Lowers Expression and Promotes Proteasonal Degradation of BCR-Ab1 and Induces Apoptosis of Imantinib Mesylate-sensitive or -refractor chronic myelogenous Leukemia-Blast crisis cells, Cancer Res. 2003, 63, 5126-5135.
Oda Y et al., Nuclear expression of YB-1 Protein Correlates with P-Glycoprotein Expression in Human Osteosarcoma, Clin. Cancer Res.,1998, 4, 2273-2277.
Ohga T, Dchiumi T, Makino Y, Koike K, Wada M, Kuwano M, Kohno K., Direct involvement of the Y-Box Binding Protein YB-1 in Genotoxic Stress-induced activation of the human multidrug resistance 1 gene, J Bioi Chern. 1998, 273(11):5997-6000.
Okamoto T et al., Direct Interaction of p53 with the Y-Box binding protein, YB-1: a mechanism for regulation of human gene expression, Oncogene, 19, 6194-6202, 2000.
Ornelles and Shenk, Localization of the Adenovirus Early Region IB 55-Kilodalton Protein during Lytic Infection: Association with Nuclear Viral Inclusions Requires the Early Region 4 34-Kilodalton Protein, J. Virology 65, 424-429, 1991.
Plumb et al., Pharmacodynamic Response and Inhibition of Growth of Human Tumor Xenografts by the Novel Histone Deacetylase Inhibitor PXD101, Mol. Cancer Ther., 8, 721-728, 2003.
Power et al., "Carrier cell-based delivery of an oncolytic virus circumvents antiviral immunity," Mol. Ther. (2007) 15(1):123-130.
Rajendra et al., Cancer Res., Differential Effects of the Breast Cancer Resistance Protein on the Cellular Accumulation and Cytotoxicity of 9-Aminocamptothecin and 9-Nitrocamptothecin, 63, 3228-3233, 2003.
Russell, S.J., "Replicating vectors for gene therapy of cancer: risks, limitations and prospects," Eur. J. Cancer (1994) 30A(8):1165-1171.

(56) References Cited

OTHER PUBLICATIONS

Russell, W. C., Update on adenovirus and its vectors, Journal of Virology, 81, 2573-2604, 2000.

Sandor, V., et al., "Phase I Trial of the Histone Deacetylase Inhibitor, Depsipeptide (FR901228, NSC 630176), in Patients with Refractory Neoplasms" Clin. Cancer Res., 8[3] (2002) p. 718-728.

Schneider et al., Expressions of LRP and MDRJ in Locally Advanced Breast Cancer predicts axillary node . . . ,Breast Cancer Res., 2001, 3, 183-191.

Shibao K et al., Enhanced Coexpression of YB-1 and DNA Topoisomerase II Alpha genes in human colorectal carcinomas, Int. Cancer, 83, 732-737, 1999.

Soff et al., Expression of Plasminogen Activator Inhibitor Type 1 by Human Prostate carcinoma cells inhibits primary tumor growth, tumor-associated angiogenesis, and metastasis to lung and liver in an athymic mouse model, J. Clin. Invest., 96, 2593-2600, 1995.

Steegenga, W. T. et al., The large EJB protein together with E4orf6 protein target p53 for active degradation in adenovirus infected cells, Oncogene 16, 349-357, 1998.

Stiewe et al., Inactivation of Retinoblastoma (RB) Tumor Suppressor by Oncogenic Isoforms of the p53 Family Member p73, J. Biol. Chern., 278, 14230-14236, 2003.

Su et al., Melanoma differentiation associated gene-7, mda711L-24, selectively induces growth suppression, apoptosis and radiosensitization in malignant gliomas in p53-independent manner, Oncogene, 22, 1164-1180, 2003.

Swaminathan and Thimmapaya, Transactivation of Adenovirus E2-early Promoter by EJA and E4 6/7 in the Context of Viral Chromosome, JBC 258, 736-746, 1996.

Thomas et al., "Progress and problems with the use of viral vectors for gene therapy," Nature (2003) 346(4):346-358.

Tollefson, J. Virology, The Adenovirus death protein is required at very late states of infection for efficient eel/lysis and release of adenovirus from infected cells, 70, 2296-2306, 1996.

Toth et al., Radiation increases the activity of oncolytic adenovirus cancer gene therapy vectors that overexpress the ADP protein, Cancer Gene Therapy, 10, 193-200, 2003.

Verma et al., "Gene therapy-promises, problems and prospects," Nature (1997) 389:239-242.

Vigushin et al., Trickostatin A is a Histone Deacetylase Inhibitor with Potent Antitumor Activity against Breast Cancer in Vivo, Clinical Cancer Research, 7, 971-976, 2001.

Wilhelm SM et al., BAY 43-9006 Exhibits Broad Spectrum Oral Antitumor Activity and Targets the RAF/MEKIERK Pathway and Receptor Tyrosine Kinases Involved in Tumor Progression and Angiogenesis, Cancer Res. 2004, 64, 7099-7109.

Wong und Ziff, Complementary Functions of E1a Conserved Region 1 Cooperate with Conserved Region 3 to Activate Adenovirus Serotypes 5 Early Promoters, J. Virol., 68, 4910-4920, 1994.

Wu, J. et al., "YB-1 is a transcription/translation factor that orchestrates the oncogenome by hardwiring signal transduction to gene expression," Translational Oncogenomics (2007) 2:49-65.

Wybranietz W. A. et al., Enhanced suicide gene effect by ademoviral transduction of a VP22-cytosine deaminase (DC) fusion gene, Gene Therapy, 8, 1654-1664, 2001.

Zhang and Degroot, Gene Therapy of Rat Follicular Thyroid Carcinoma Model with Adenoviral Vectors Transducing Murine Interleukin-12, Endocrinology, 144, 1393-1398, 2003.

Zhang et al., Identification of Human Uroplakin II Promoter and Its Use in the Construction of CG8840 . . . , Cancer Res., 62, 3743-3750, 2002.

Zhang H. et al., Therapeutic Monoclonal Antibodies for the ErbB Family of Receptor Tyrosine Kinases, Cancer Bioi. Ther. Jul.-Aug. 2003; 2 (4 suppl 1): S122-6.

Marie et al., "Multidrug Resistance (mdr1) Gene Expression in Adult Acute Leukemias: Correlations With Treatment Outcome and In Vitro Drug Sensitivity," Blood 78:3, 586-592 (1991).

Mickisch et al., "Pseudomonas Exotoxin Conjugated to Monoclonal Antibody mrk16 Specifically Kills Multidrug Resistant Cells in Cultured Renal Carcinomas and in MDR-Transgenic Mice," The Journal of Urology 149, 174-178 (1993).

\* cited by examiner

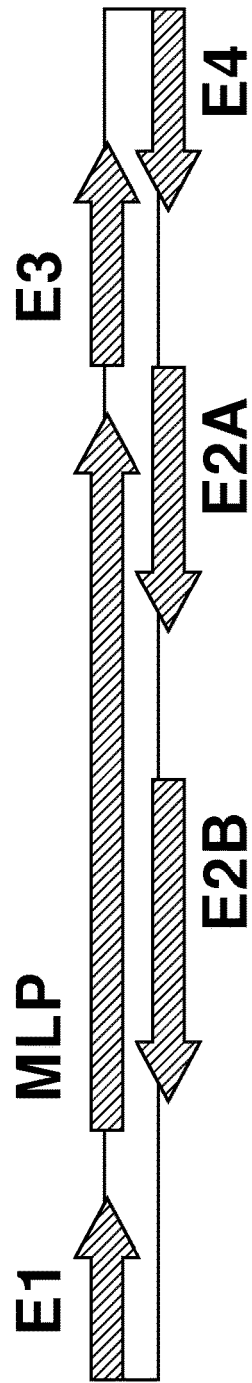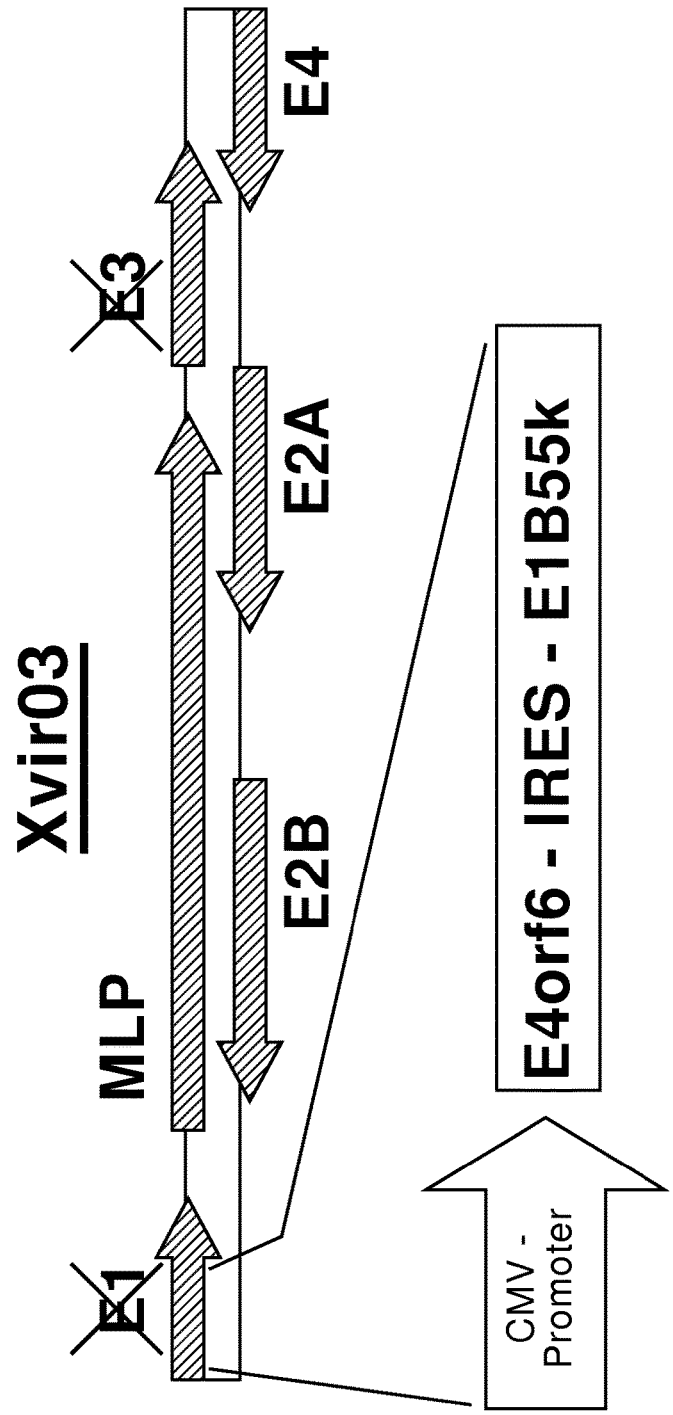
Fig. 16

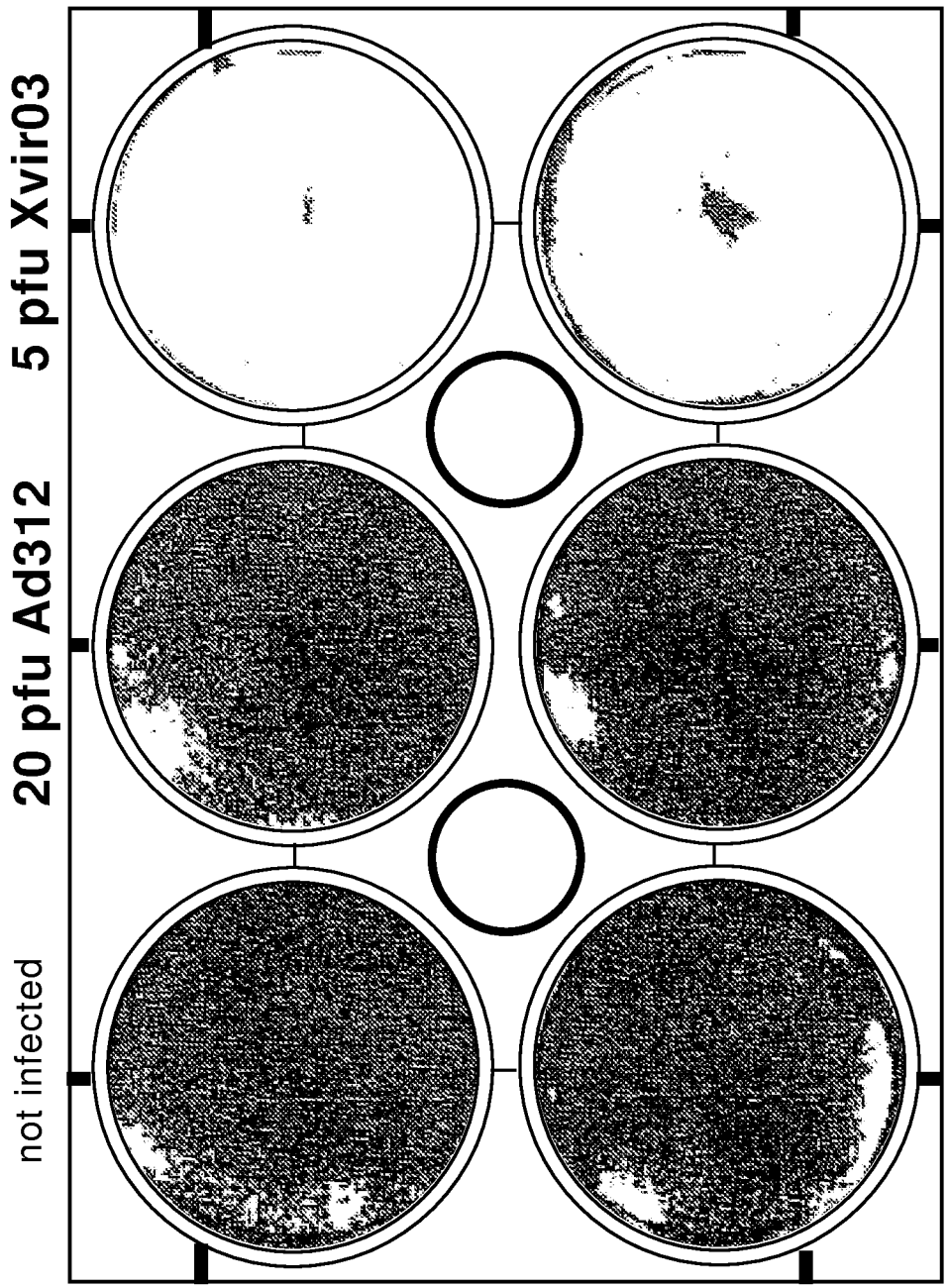

U373 cells infected with 10 pfu/cell dl520 after 24 h of incubation with 5μM Irinotecan Southern Blot Analysis U373 cells infected with 10 pfu/cell dl520 after 24 h of incubation with increasing concentration of Trichostatin Southern Blot Analysis FACS-Analysis: Car-Expression of U373 cells after 24 h of incubation with Trichostatin Oncolytic Effect of dl520 in U373 cells in combination with Irinotecan and Trichostatin E1B55k region:
ORF = 2019 - 3506 bp
BfrI cleavage site = 3534bp
3'UTR = 3506 - 4147bp

Fig. 24

The sequence of the E1B55k 3'UTR is shown from position 3507 to 4107 bp

5'tgaggtactgaaatgtgtgggcgtggcttaagggtgggaaagaatatataaggtggg
ggtcttatgtagttttgtatctgtttgcagcagccgccgccatgagcaccaactcgttt
gatggaagcattgtgagctcatatttgacaacgcgcatgccccatggccggggtgc
gtcagaatgtgatgggctccagcattgatggtcgcccgtcctgcccgcaaactctacta
ccttgacctacgagaccgtgtcggaacgcgttggagactgcagcctccgccgccgc
ttcagccgctgcagccaccgccgccgcttcatccgcccgttcagccgcctccgagcccgctt
gcaagcagtgcagctcccgttcatccgcccgatgacaagttgacggctctttggca
caattggattcttgacccgggaacttaatgtcgtttctcagcagctgttggatctgcgcca
gcaggtttctgccctgaaggcttcctccctccccaatgcggtttaaaacataaataaaaa
accagactctgtttggatttggatcaagcaagtgtcttgctctgtctttattlaggggtttgc Northern blot Analysis of the E2 gene expression in Ad312 infected cells Northern blot Analysis of the E2 gene expression in infected cells XvirPSJL1

Wildtype Adenovirus

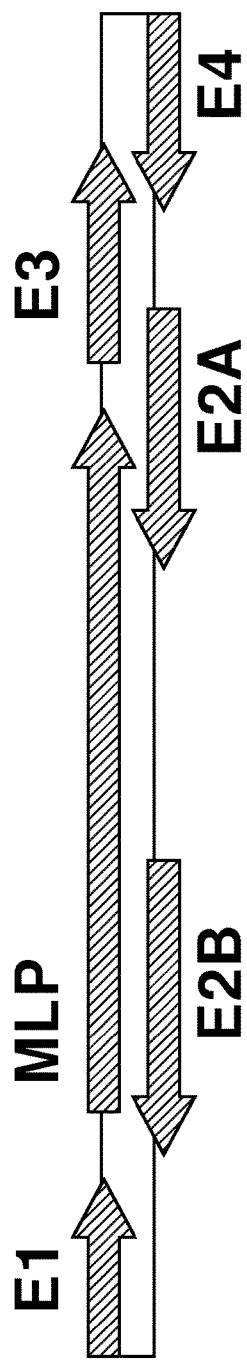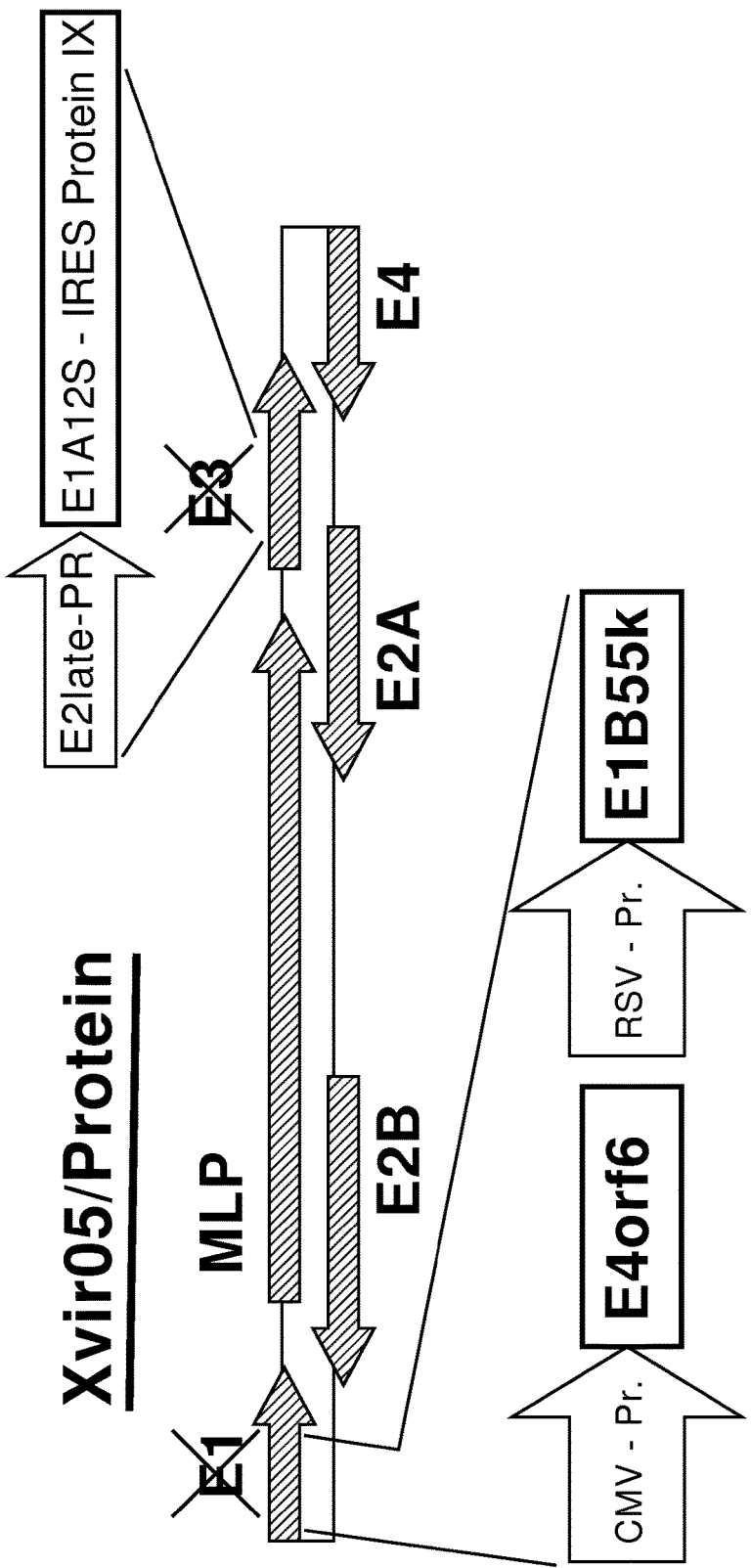
Fig. 39

METHODS FOR REVERSING MULTIPLE RESISTANCE IN ANIMAL CELLS

CROSS-REFERENCE TO RELATED APPLICATION(S)

This is a continuation of U.S. patent application Ser. No. 13/170,395, filed on Jun. 28, 2011, now abandoned, which is a continuation of U.S. patent application Ser. No. 12/556,560, filed on Sep. 9, 2009, now abandoned, which is a continuation of U.S. patent application Ser. No. 11/794,594, filed on Jun. 29, 2007, now abandoned, which is a U.S. national stage entry of International Patent Application No. PCT/EP2006/000009, filed on Jan. 2, 2006, which claims priority to U.S. Provisional Patent Application No. 60/651,085, filed on Feb. 8, 2005, and German Patent Application No. 102004063639.7, filed on Dec. 31, 2004, the entire contents of all of which are fully incorporated herein by reference.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Aug. 2, 2019, is named "36219-205_ST25.txt" and is 11,651 bytes in size.

The invention is related to means for reversing multiple drug resistance in animal cells.

Every year about 350,000 people develop a malignant tumour in the Federal Republic of Germany. Less than 50% of these patients can expect a definitive cure. Apart from surgical removal and radiation, chemotherapy using cytostatics is the most common form of treatment of cancer for the time being. The antineoplastically active substances used in connection therewith are, in principle, effective against all cells of the organism, however, tumour cells are more prone to chemosensitivity due to their increased proliferation rate. Good therapeutic results can be obtained for various tumour entities such as juvenile lymphatic leukaemia, some lymphoma and testicular carcinoma. However, these tumours represent only 10% of all malignant diseases. Most of the solid tumours do not respond or respond only weakly to a treatment using various cytostatics. This is particularly true for carcinoma derived from kidney, colon, pancreas and liver as well as melanoma and brain tumours. Additionally, e.g., mammary carcinoma, ovarian carcinoma and prostate carcinoma initially respond well to cytostatic treatment, however, get insensitive to the cytostatics used in the course of the therapeutical cycles. In accordance therewith, studies show that there is a high correlation between P-glycoprotein expression and occurrence of metastases. Although significant progress has been made in the previous years in the development of established therapeutic concepts such as chemotherapy and radiation therapy, all in all the treatment of solid tumours in particular is still not satisfactory.

Apart from the specific tumour entity, tumour cell heterogeneity and vascularization of the tumour, genetic and epigenetic changes of the tumour cells themselves are involved in the formation of resistance to cytostatics and radiation. These can be grouped into the following six major groups: 1. increased efflux activity; 2. modulation of the target protein; 3. increased repair; 4. modulation of apoptosis; 5. cell cycle; and 6. decreased influx.

During clinical treatment of malignant tumours it is frequently observed that the recurrent tumour is not only resistant to the initially used cytostatics, but also to other antineoplastics of different groups of compounds. This phenomenon is referred to as polydrug resistance or, in the style of the anglosaxon literature, as multidrug resistance (MDR). Apart from the atypical multidrug resistance the classical phenomenon of MDR is based on overexpression of the membrane-bound 170 kDa ATP dependent, transmembrane glycoprotein which predominantly exports lipophilic compounds from the cell. The MDR1 protein which is also referred to as Pgp and P-glycoprotein, respectively, is part of the group of ABC transporters to which, among others, also the MRP (multidrug related protein) and BCRP (breast cancer resistance protein) belong. The vesicular LRP protein (lung resistance-related protein) does not belong to the classical ABC transporter. However, it is also mentioned quite frequently in this connection, as it is also involved in transport processes related to the formation of resistance to cytostatics in tumour cells (Sugawara I et al., CANCER LETTERS 112, 23-31, 1997; Gottesman et al., Nat Rev Cancer. 2002, 2:48-58). It is known that the LRP promotor comprises an inverted CAAT-box (Y-box) (Scheider et al., Breast Cancer Res., 2001, 3, 183-191).

Thus, the problem underlying the present invention is to provide means for the treatment of such diseases, in particular for the treatment of the afore-described resistant diseases, i.e. tumors and tumor diseases the cells of which are resistant to cytostatics and/or radiation. Also, the problem underlying the present invention is to reverse or eliminate the afore-described and other resistances described herein. In a further aspect, the problem underlying the present invention is to provide means for restoring drug sensitivity, in particular drug sensitivity of cells forming or involved in tumour and tumour diseases, whereby such cells are not sensitive or no longer sensitive to cytostatics and/or radiation.

In accordance with the present invention these problems are solved by the use of viruses, in particular adenoviruses, which replicate in a YB-1 dependent manner. Also, these problems are solved in accordance with the present invention by the subject matter of the attached independent claims. Preferred embodiments result from the attached dependent claims.

The problem underlying the present invention is thus also solved in a first aspect by the use of a virus, preferably an adenovirus for reversing resistance in cells.

The problem underlying the present invention is thus also solved in a second aspect by the use of a virus, preferably an adenovirus for the manufacture of a medicament for reversing resistances in cells.

The problem underlying the present invention is thus also solved in a third aspect by the use of a virus, preferably an adenovirus for restoring drug sensitivity of cells.

The problem underlying the present invention is thus also solved in a fourth aspect by the use of a virus, preferably an adenovirus for the manufacture of a medicament for restoring drug sensitivity of cells.

In an embodiment according to the first to fourth aspect of the present invention cells are animal cells, preferably mammalian cells and more preferably human cells.

In a preferred embodiment the cells are tumor cells.

In a preferred embodiment the cells have a resistance to or are insensitive to one or several pharmaceutically active agents and/or radiation.

In a preferred embodiment the pharmaceutically active agent is a cytostatic.

The problem underlying the present invention is thus also solved in a fifth aspect by the use of a virus, preferably an adenovirus for inhibiting ABC transporters, in particular the expression of ABC transporters.

In an embodiment of the first, second, third and fourth aspect the resistance is mediated by an ABC transporter.

In an embodiment of the first, second, third, fourth and fifth aspect the resistance is a multiple resistance or polyresistance, particular a multiple or polyresistance against cytostatics and/or radiation.

The problem underlying the present invention is thus also solved in a sixth aspect by the use of a virus, preferably an adenovirus for the manufacture of a medicament for the treatment of diseases, in particular tumor diseases, whereby the cells involved in the disease or a part thereof, are resistant, in particular have an ABC transporter mediated resistance and/or a multiple resistance or polyresistance, preferably a multiple resistance or polyresistance against cytostatics and/or radiation.

In a alternative preferred embodiment of the sixth aspect the treatment comprises the administration of the adenovirus and a further pharmaceutically active agent, or the administration of an adenovirus and radiation of the cell or the organism to be treated, whereby the administration of the adenovirus causes or increases the efficacy of the further pharmaceutically active agent and/or of the radiation.

In a preferred embodiment of the sixth aspect the treatment comprises the administration of the adenovirus and a further pharmaceutically active agent or the administration of an adenovirus and radiation of the cell or the organism to be treated, whereby the administration of the further pharmaceutically active agent and/or the radiation causes or increases the efficacy of the adenovirus.

In an embodiment of the fifth and sixth aspect the ABC transporter is selected from the group comprising MRP and MDR, in particular MDR-1.

In an of the fifth and sixth aspect embodiment the adenovirus is administered at least at the beginning of the treatment prior to the administration of the further pharmaceutically active agent.

In an of the fifth and sixth aspect embodiment the adenovirus is administered at least prior to the radiation at the beginning of the treatment.

In an embodiment of the fifth and sixth aspect the adenovirus is administered about 1 to 3 days, preferably about 1 to 2 days prior to the administration of the further pharmaceutically active agent or prior to the radiation.

In an embodiment of the first, second, third, fourth, fifth and sixth aspect the resistance is a resistance against cytostatics and/or radiation.

In an embodiment of the sixth aspect the further pharmaceutically active agent is selected from the group comprising cytostatics.

In an embodiment of the sixth aspect the radiation is a radiation as used in the radiation of tumor diseases.

In an embodiment of the sixth aspect the radiation is performed at a dosage and using a radiation regimen and/or that the further pharmaceutically active agent is administered at a dosage or in accordance with a treatment regimen as with patients, whereby the patients are selected from the group comprising immune suppressed patients, patients having a bad or pathological blood picture and patients having bad or pathological kidney values.

In an embodiment of the sixth aspect in that the radiation is performed at the dosage or in accordance with a radiation regimen and/or the further pharmaceutically active agent is administered at a dosage or in accordance with a treatment regimen as in connection with patients suffering from a disease, whereby the cells involved in such disease or a part thereof are not resistant.

In an embodiment of the sixth aspect the administration of the adenovirus creates the prerequisite for the administration of the further pharmaceutically active agent or for the radiation.

In an embodiment of the first, second, third, fourth, fifth and sixth aspect the adenovirus is present as a virus, nucleic acid, vector, replication system, medicament or pharmaceutically composition.

In an embodiment of the first, second, third, fourth, fifth and sixth aspect the adenovirus is replicating in a YB-1 dependent manner.

In an embodiment of the first, second, third, fourth, fifth and sixth aspect the adenovirus is E1A minus.

In an embodiment of the first, second, third, fourth, fifth and sixth aspect the adenovirus is an oncolytic adenovirus.

In an embodiment of the first, second, third, fourth, fifth and sixth aspect the virus, preferably an adenovirus, is replication deficient in cells which lack YB-1 in the nucleus, and whereby the virus encodes an oncogene or oncogene product, in particular an oncogene protein, which transactivates at least one viral gene, preferably an adenoviral gene, whereby the gene is selected from the group comprising E1B55kDa, E4orf6, E4orf3 and E3ADP.

In a preferred embodiment of the first, second, third, fourth, fifth and sixth aspect the virus, in particular the adenovirus replicates in cells which have YB-1 in the nucleus.

In a more preferred embodiment of the first, second, third, fourth, fifth and sixth aspect the viral oncogene protein is E1A and/or the oncogene is the gene coding for E1A and/or the oncogene protein E1A.

In an embodiment of the first, second, third, fourth, fifth and sixth aspect the viral oncogene protein E1A is capable of binding a functional Rb tumor suppressor gene product.

In an embodiment of the first, second, third, fourth, fifth and sixth aspect the viral oncogene protein E1A is incapable of binding a functional Rb tumor suppressor gene product.

In an embodiment of the first, second, third, fourth, fifth and sixth aspect the viral oncoprotein E1A does not induce the localisation of YB-1 into the nucleus.

In an embodiment of the first, second, third, fourth, fifth and sixth aspect the medicament is for patients whose cells are Rb positive or Rb negative.

In an embodiment of the first, second, third, fourth, fifth and sixth aspect the cells are Rb negative and the cell nucleus is YB-1 positive, preferably YB-1 positive in the nucleus independent from the cell cycle.

In an embodiment of the first, second, third, fourth, fifth and sixth aspect the cells are p53 positive or p53 negative.

In an embodiment of the first, second, third, fourth, fifth and sixth aspect the oncogene protein exhibits one or several mutations or deletions compared to the wildtype oncogene protein E1A, whereby the deletion is preferably one selected from the group comprising deletions of the CR3 stretches and deletions of the N-terminus and deletions of the C-terminus.

In an embodiment of the first, second, third, fourth, fifth and sixth aspect the E1A oncogene protein is capable of binding to Rb.

In an embodiment of the first, second, third, fourth, fifth and sixth aspect the oncogene protein comprises one or several mutations or deletions compared to the wildtype oncogene protein, whereby the deletion is preferably a deletion in the CR1 region and/or CR2 region.

In a preferred embodiment of the first, second, third, fourth, fifth and sixth aspect the oncogene protein E1A is incapable of binding to Rb.

In an embodiment of the first, second, third, fourth, fifth and sixth aspect the viral oncogene protein, preferably E1A, is under the control of a tissue- and/or tumor-specific promoter.

In an embodiment of the first, second, third, fourth, fifth and sixth aspect the virus, particularly the adenovirus, codes for YB-1.

In an embodiment of the first, second, third, fourth, fifth and sixth aspect YB-1 is under the control of a tissue-specific and/or tumor-specific promoter.

In an embodiment of the first, second, third, fourth, fifth and sixth aspect the virus, preferably the adenovirus, codes for at least one protein, whereby the protein is selected from the group comprising E4orf6, E4orf3, E1B55k and adenoviral E3ADP protein.

In an embodiment of the first, second, third, fourth, fifth and sixth aspect the cells comprise YB-1 in the nucleus, preferably that the cells forming the tumor or part thereof have YB-1 in the nucleus.

In an embodiment of the first, second, third, fourth, fifth and sixth aspect the tumor comprises YB-1 in the nucleus after induction of the transport of YB-1 into the nucleus.

In a preferred embodiment of the first, second, third, fourth, fifth and sixth aspect the transport of YB-1 into the nucleus is triggered by at least one measure selected from the group comprising irradiation, administration of cytostatics and hyperthermia.

In a preferred embodiment of the first, second, third, fourth, fifth and sixth aspect the measure is applied to a cell, an organ or an organism, preferably an organism in need thereof, more preferably an organism suffering from said disease.

In an embodiment of the first, second, third, fourth, fifth and sixth aspect the virus, preferably the adenovirus, is selected from the group comprising AdΔ24, dl922-947, E1Ad/01/07, dl1119/1131, CB 016, dl520 and viruses lacking an expressed viral oncogene which is capable of binding a functional Rb tumor suppressor gene product.

In an embodiment of the first, second, third, fourth, fifth and sixth aspect the virus, preferably the adenovirus, is designed such that the replication is controlled by YB-1 through the activation of the E2-late promoter, preferably the activation is predominantly controlled through the activation of the E2-late promoter.

In an embodiment of the first, second, third, fourth, fifth and sixth aspect the virus comprises a nucleic acid coding for a transgene.

In an embodiment of the first, second, third, fourth, fifth and sixth aspect the virus comprises the translation and/or transcription product of a transgene.

In an embodiment of the first, second, third, fourth, fifth and sixth aspect the nucleic acid comprises a transgene or a nucleic acid coding for a transgene.

In an embodiment of the first, second, third, fourth, fifth and sixth aspect the transgene is selected from the group comprising prodrug genes, cytokines and genes for cytokines, apoptosis-inducing genes, tumor suppressor genes, genes for metalloproteinase inhibitors and genes for angiogenesis inhibitors.

In an embodiment of the first, second, third, fourth, fifth and sixth aspect the transgene is selected from the group comprising nucleic acids for siRNA, for aptamers, for antisense molecules and for ribozymes, whereby the siRNA, the aptamer, the antisense molecule and/or the ribozyme are targeting a target molecule.

In an embodiment of the first, second, third, fourth, fifth and sixth aspect the target molecule is selected from the group comprising resistance relevant factors, anti-apoptosis factors, oncogenes, angiogenesis factors, DNA synthesis enzymes, DNA repair enzymes, growth factors, receptors for growth factors, transcription factors, metalloproteinases, preferably matrix metalloproteinase kinases, and plasminogen activator of the urokinase type.

In an embodiment according to any of the first, second, third, fourth, fifth and sixth aspect the medicament further comprises at least one pharmaceutically active agent.

In an preferred embodiment of the first, second, third, fourth, fifth and sixth aspect the pharmaceutically active agent is selected from the group comprising cytokines, metalloproteinase inhibitors, angiogenesis inhibitors, cytostatics, cell cycle inhibitors, proteosome inhibitors, recombinant antibodies, inhibitors of the signal transduction pathway and inhibitors of protein kinases.

In an embodiment according to any of the first, second, third, fourth, fifth and sixth aspect the medicament comprises a combination of at least two agents, whereby each of said agents is individually and independently selected from the group comprising cytostatics.

In a preferred embodiment at least two of the agents are targeting different target molecules.

In a preferred embodiment at least two of the agents are active through different modes of action.

In an embodiment at least one agent increases the infectability of the cell in which the virus replicates.

In an embodiment at least one agent affects the availability of a component of the cell, preferably increases the availability of the component, whereby the component mediates the uptake of the virus.

In an embodiment at least one agent mediates the transport of YB-1 into the nucleus, preferably increases the same.

In an embodiment at least one agents is a histone deacetylase inhibitor.

In a preferred embodiment the histone deacetylase inhibitor is selected from the group comprising trichostatine A, FR901228, MS-27-275, NVP-LAQ824, PXD101, apicidine and striptaid.

In an embodiment the at least one agent is selected from the group comprising trichostatine A, FR901228, MS-27-275, NVP-LAQ824, PXD101, apicidine and striptaid.

In an embodiment at least one agent is a topoisomerase inhibitor.

In an preferred embodiment the topoisomerase inhibitor is selected from the group comprising Camptothecin, Irinotecan, Topotecan, DX-895If, SN-38, 9-aminocamptothecin, 9-nitrocamptothecin, Daunorubicn and Etoposid.

In an embodiment according to any of the first, second, third, fourth, fifth and sixth aspect the medicament comprises trichostatin A and irinotecan.

In an embodiment according to any of the first, second, third, fourth, fifth and sixth aspect the virus, in particular the virus as described in connection with any of the first, second, third, fourth, fifth and sixth aspect, is separated from the at least two agents in said medicament.

In an preferred embodiment at least one unit dosage of the virus is separated from at least one unit dose of one or the at least two agents.

In an embodiment according to any of the first, second, third, fourth, fifth and sixth aspect the virus, preferably the adenovirus expresses a first protein which is selected from the group comprising an E1B protein and an E4 protein, prior to a second protein which is selected from the group comprising an E1A-protein.

In a preferred embodiment the first protein is an E1B protein, preferably an E1B55kd protein.

In a more preferred embodiment the first protein is an E4 protein, preferably an E4orf6 protein.

In an embodiment the first protein is a combination of E1B protein and E4 protein, preferably a combination of E1B55kD protein and E4orf6 protein.

In an embodiment the E1A protein is an E1A12S protein.

In an embodiment according to any of the first, second, third, fourth, fifth and sixth aspect the virus comprises at least one nucleic acid coding for a protein which is selected from the group comprising E1B proteins, E4 proteins and E1A proteins, whereby the at least one protein is under the control of a promoter which is different from the promoter controlling the expression of the protein in a wildtype adenovirus.

In a preferred embodiment the at least one protein is an E1B protein, preferably an E1B55kD protein.

In a preferred embodiment the at least one protein is an E4 protein, preferably an E4orf6 protein.

In an embodiment at least one protein is an E1A protein, preferably an E1A12S protein.

In an embodiment the at least one protein is a combination of E1B protein and E4 protein, preferably a combination of E1B55kD protein and E4orf6 protein.

In an embodiment the at least one protein is a combination of E1B protein and E1A protein, preferably a combination of E1B55kD protein and E1A12S protein.

In an embodiment the at least one protein is a combination of E4 protein and E1A protein, preferably a combination of E4orf6 protein and E1A12S protein.

In an embodiment the at least one protein is a combination of E1B protein, E4 protein and E1A protein, preferably a combination of E1B55kD protein, E4orf6 protein and E1A12S protein.

In an embodiment the expression of the E1B protein is controlled by a promoter, whereby the promoter is selected from the group comprising tumor-specific promoters, organ-specific promoters, tissue-specific promoters, heterologous promoters and adenoviral promoters, whereby the adenoviral promoter is different from the E1B promoter.

In an embodiment the expression of the E4 protein is controlled by a promoter, whereby the promoter is selected from the group comprising tumor-specific promoters, organ-specific promoters, tissue-specific promoters, heterologous promoters and adenoviral promoters, whereby the adenoviral promoter is different from the E4 promoter.

In an embodiment the adenoviral promoter is the E1A promoter.

In an embodiment the expression of the E1A protein is controlled by a promoter, whereby the promoter is selected from the group comprising tumor-specific promoters, organ-specific promoters, tissue-specific promoters, heterologous promoters and adenoviral promoters, whereby the adenoviral promoter is different from the E1A promoter.

In an embodiment the expression of the E1A protein is YB-1 controlled or can be regulated by YB-1.

In an embodiment the promoter controlling the expression of the E1A protein is the adenoviral E2 late promoter.

In an embodiment the E4 protein, preferably the E4orf6 protein, and the E1B protein, preferably the E1B55kd protein, are under the control of the same or a common promoter.

In an embodiment according to any of the first, second, third, fourth, fifth and sixth aspect the virus provides YB-1 in the nucleus through at least one adenoviral protein or mediates the provision of YB-1 in the nucleus through at least one adenoviral protein, whereby preferably the adenoviral protein is different from E1A.

In an embodiment according to any of the first, second, third, fourth, fifth and sixth aspect the virus provides YB-1 for adenoviral replication through at least one adenoviral protein or mediates the provision of YB-1 for adenoviral replication through at least one adenoviral protein, whereby preferably the adenoviral protein is different from E1A.

In an embodiment the adenoviral protein is a complex of E4orf6 and E1B55kd.

In an embodiment according to any of the first, second, third, fourth, fifth and sixth aspect the nucleic acid of the adenovirus comprises at least one functionally inactive adenoviral region, whereby the region is selected from the group comprising the E1 region, the E3 region, the E4 region and combinations thereof.

In a preferred embodiment the region is the E1 region.

In an embodiment the region is the E3 region.

In an embodiment the region is the E4 region.

In an embodiment the region comprises the E1 region, the E3 region and the E4 region.

In an embodiment according to any of the first, second, third, fourth, fifth and sixth aspect the virus comprises at least one expression cassette, whereby the expression cassette comprises at least one promoter and a nucleic acid coding for an adenoviral protein, whereby the adenoviral protein is an E1B protein, preferably an E1B55kD protein.

In a preferred embodiment the promoter is different from the E1B promoter.

In a preferred embodiment the promoter is selected from the group comprising tumor-specific promoters, organ-specific promoters, tissue-specific promoters, heterologous promoters and adenoviral promoters, whereby the promoter is different from the E1B promoter.

In an embodiment according to any of the first, second, third, fourth, fifth and sixth aspect the virus comprises at least one expression cassette, whereby the expression cassette comprises at least one promoter and a nucleic acid coding for an adenoviral protein, whereby the adenoviral protein is an E4 protein, preferably an E4orf6 protein.

In a preferred embodiment the promoter is different from the E4 promoter.

In a preferred embodiment the promoter is selected from the group comprising tumor-specific promoters, organ-specific promoters, tissue-specific promoters, heterologous promoters and adenoviral promoters, whereby the adenoviral promoter is different from the E4 promoter.

In an embodiment the promoter is the E1A promoter.

In an embodiment according to any of the first, second, third, fourth, fifth and sixth aspect the virus comprises at least one expression cassette, whereby the expression cassette comprises at least one promoter and a nucleic acid coding for an adenoviral protein, whereby the adenoviral protein is an E1A protein, preferably an E1A12S protein.

In a preferred embodiment the promoter is different from the E1A promoter.

In a preferred embodiment the promoter is selected from the group comprising tumor-specific promoters, organ-specific promoters, tissue-specific promoters, heterologous promoters and adenoviral promoters.

In an embodiment the adenovirus comprises a nucleic acid, whereby the nucleic acid codes for YB-1.

In a preferred embodiment the nucleic acid coding for YB-1 is under the control of a promoter, whereby the promoter is preferably the E2 late promoter.

In an embodiment the nucleic acid coding for YB-1 is under the control of a promoter, whereby the promoter is YB-1 dependent and YB-1 controlled, respectively.

In an embodiment the nucleic acid coding for YB-1 is part of the expression cassette comprising a nucleic acid coding for an E1A protein, preferably a nucleic acid coding for an E1A12S protein.

In a preferred embodiment the nucleic acid coding for the E1A protein is separated from the nucleic acid coding for YB-1 through an IRES sequence.

In a embodiment the nucleic acid coding for the E4 protein, preferably the E4orf6 protein, and the nucleic acid coding for the E1B protein, preferably the E1B55kD protein, are contained in an expression cassette, whereby preferably the two coding sequences are separated through an IRES sequence.

In a preferred embodiment the promoter of the expression cassette is selected from the group comprising tumor-specific promoters, organ-specific promoters, tissue-specific promoters, heterologous promoters and adenoviral promoters, whereby the adenoviral promoter is different from the E4 promoter and different from the E1B promoter, preferably different from the wildtype E4 promoter and different from the wildtype E1B promoter.

In an embodiment the virus comprises an expression cassette comprising a promoter and a nucleic acid sequence, whereby the nucleic acid sequence is selected from the group comprising aptamers, ribozymes, aptazymes, antisense molecules and siRNA.

In an embodiment the virus comprises an expression cassette comprising a promoter and a nucleic acid sequence, whereby the nucleic acid sequence is a coding nucleic acid, whereby the nucleic acid codes for a molecule which is selected from the group comprising peptides, polypeptides, proteins, anticalines, antibodies and antibody fragments.

In an embodiment the virus comprises an expression cassette, whereby the expression cassette comprises a promoter and a nucleic acid sequence, whereby the nucleic acid sequence is selected from the group comprising apoptosis inducing genes, prodrug genes, protease inhibitors, tumor suppressor genes, cytokines and angiogenesis inhibitors.

In an embodiment the virus is a recombinant adenovirus.

In an embodiment the virus is an adenovirus mutant.

In an embodiment the virus is replication deficient.

In a preferred embodiment the virus is capable of replicating in cells comprising deregulated YB-1 or having YB-1 in the nucleus.

In a preferred embodiment the cells contain YB-1 in the nucleus independent of the cell cycle.

In an embodiment the medicament comprises at least one further pharmaceutically active agent.

In an embodiment the medicament is administered together with a further pharmaceutically active agent or is intended therefor.

In an embodiment the further pharmaceutically active agent is selected from the group comprising cytokines, metalloproteinase inhibitors, angiogenesis inhibitors, cytostatics, tyrosine kinase inhibitors, cell cycle inhibitors, proteosome inhibitors, inhibitors of the signal transduction cascade, inhibitors of protein kinase and recombinant antibodies.

In an embodiment the medicament comprises a combination of at least two agents, whereby each agent is individually and independently selected from the group comprising cytostatics.

In a preferred embodiment at least two of the agents are targeting different target molecules.

In a more preferred embodiment at least two of the agents are active through different modes of action.

In an embodiment at least one agent increases the infectability of a cell in which the virus replicates.

In an embodiment the agent affects the availability of a component of the cell, preferably increases the availability of the component, whereby the component mediates the uptake of the virus.

In an embodiment the agent mediates the transport of YB-1 into the nucleus, preferably increases the transport YB-1 into the nucleus.

In an embodiment the agent is a histone deacetylase inhibitor.

In a preferred embodiment the histone deacetylase inhibitor is selected from the group comprising trichostatine A, FR901228, MS-27-275, NVP-LAQ824, PXD101, apicidine and striptaid.

In an embodiment at least one agent is selected from the group comprising trichostatine A, FR901228, MS-27-275, NVP-LAQ824, PXD101, apicidine and striptaid.

In an embodiment at least one agent is a topoisomerase inhibitor.

In a preferred embodiment the topoisomerase inhibitor is selected from the group comprising Camptothecin, SN-38, Topotecan, DX-895If, Irinotecan, 9-aminocamptothecin, 9-nitrocamptothecin, Etoposid and Daunorubicin.

In an embodiment the agent comprises trichostatine A and irinotecan.

In an embodiment according to any of the first, second, third, fourth, fifth and sixth aspect the virus comprises:
  a lacking functional wildtype E1 region, and
  a transporter for the transport of YB-1 into the nucleus of a cell which is infected by the virus.

In an embodiment the virus expresses a nucleic acid coding for protein IX and expresses protein IX.

In an embodiment the lacking functional wildtype E1A region is E1A-minus.

In an embodiment the lacking functional wildtype E1 region is E1B-minus.

In a preferred embodiment the lacking wildtype E1 region is E1B55k-minus and/or E1B19k-minus and/or protein IX-minus.

In an embodiment the transporter is a transporter as provided by the virus preferably a heterologous transporter.

In a preferred embodiment the transporter is a viral transporter.

In an embodiment the transporter comprises the protein E4orf6.

In an embodiment the transporter comprises the protein E1B55k.

In an embodiment the transporter comprises a complex consisting of E4orf4 and E1B55k.

In an embodiment the transporter is encoded by a nucleic acid, whereby the nucleic acid is under the control of a promoter.

In a preferred embodiment the transporter is a complex consisting of at least two factors, whereby each factor is encoded by a nucleic acid, whereby both nucleic acids are controlled by a common promoter.

In a preferred embodiment the two coding nucleic acids are linked through an element regulating the expression level and whereby the element is preferably selected from the group comprising IRES.

In an embodiment the transporter is a complex consisting of at least two factors and each factor is encoded by a nucleic acid, whereby both nucleic acids are each controlled by an own promoter.

In an embodiment the promoter is different from the E4 promoter, in particular from the adenoviral E4 promoter, and is different from the E1B promoter, in particular from the adenoviral E1B promoter.

In an embodiment the promoter is selected from the group comprising tissue-specific promoters, tumor-specific tumors, viral promoters, CMV-promoters, in particular adenoviral promoters, under the proviso that they are different from the E4 promoter, the E1B promoter and preferably also different from the E2-late promoter.

In an embodiment the nucleic acid coding for the transporter comprises a 3'-UTR of the E1B55k at the 3' of the E1B55k.

In an embodiment if the lacking wildtype E1 region is E1B55k-positive, then the nucleic acid coding for the transporter does not comprise a nucleic acid coding for E1B55k.

In an embodiment the nucleic acid coding for the transporter codes for E1B55k and E1B19k.

In a preferred embodiment the nucleic acid coding for the transporter also codes for protein IX.

In an embodiment the nucleic acid coding for E1B55k and E1B19k is under the control of a promoter.

In an embodiment the nucleic acid coding for E1B55k and/or E1B19k and/or protein IX is under the control of a promoter, whereby the promoter is preferably different from an E1A-dependent promoter, whereby more preferably the nucleic acid codes for E1B55k, E1B19k and protein IX.

In an embodiment the lacking functional wildtype E1 region is E1A13S-minus and/or E1A12S-minus.

In an embodiment the lacking functional wildtype E1 region is E1A13S-minus.

In an embodiment preferably the lacking wildtype E1 region is E1A13S-minus and E1A12-minus, whereby the virus comprises a nucleic acid coding for the E1A12S protein, whereby the nucleic acid is preferably a heterologous nucleic acid.

In a preferred embodiment the nucleic acid coding for the E1A12S protein is under the control of a promoter, whereby the promoter is preferably a YB-1-dependent promoter and is more preferably selected from the group comprising the E2-late promoter, tumor-specific promoters and tissue-specific promoters.

In a preferred embodiment the nucleic acid(s) coding for the transporter codes/code for E4orf6 and E1B55k.

In an embodiment the nucleic acid coding for E1A12S and the nucleic acid coding for the protein IX are under the control of a common promoter, whereby preferably both coding nucleic acids are linked to each other through an element regulating the expression, whereby the element is more preferably selected from the group comprising IRES.

In an embodiment the nucleic acid coding for the E1A12S region and the nucleic acid coding for the protein IX are each under the control of a promoter, whereby the promoter preferably is the same promoter.

In an embodiment the promoter is a YB-1-dependent promoter, which is preferably selected from the group comprising the E2-late promoter, the MDR promoter and the DNA polymerase alpha promoter.

In an embodiment the virus comprises a nucleic acid coding for YB-1.

In a preferred embodiment the nucleic acid coding for the E1A12S protein and the nucleic acid coding for the YB-1 are under the control of a common promoter, whereby both coding nucleic acids are linked to each other by an expression-regulating element, whereby the element is preferably selected from the group comprising IRES.

In a more preferred embodiment the nucleic acid coding for YB-1 and the nucleic acid coding for the E1A12S protein are each under the control of a promoter, whereby the promoter is preferably the same promoter.

In an embodiment the promoter is a YB-1-dependent promoter which is preferably selected from the group comprising the E2-late promoter, the MDR promoter and the DNA polymerase alpha promoter.

In an embodiment the nucleic acid coding for the E1A12S is cloned into the E3 region or the E4 region.

In an embodiment the nucleic acid coding for the E1A12S and the nucleic acid coding for protein IX or the nucleic acid coding for YB-1 are cloned into the E3 region or the E4 region.

In an embodiment the expression of the nucleic acid coding for the protein IX is controlled by a promoter different from E1B, by E1B19k or by E1A12S.

In an embodiment the virus comprises at least a transgene which is preferably cloned into the E3 region.

In a preferred embodiment the virus comprises at least a transgene which is preferably cloned into the E4 region.

In a preferred embodiment according to any of the first, second, third, fourth, fifth and sixth aspect, where the virus comprises:
  a lacking functional wildtype E1 region, and
  a transporter for the transport of YB-1 into the nucleus of
    a cell which is infected by the virus,
the virus comprises a nucleic acid coding for the RGD motif.

In a preferred embodiment according to any of the first, second, third, fourth, fifth and sixth aspect, where the virus comprises:
  a lacking functional wildtype E1 region, and
  a transporter for the transport of YB-1 into the nucleus of
    a cell which is infected by the virus,
the virus comprises the MLP gene and/or the E2A gene and E1B gene and/or E3 gene and/or E4 gene.

In an embodiment the virus is replication deficient in cells which do not contain YB-1 in the nucleus.

In an embodiment the virus is capable of replicating in cells which have YB-1 in the nucleus, in particular have YB-1 in the nucleus independent of the cell cycle.

In an embodiment the virus is capable of replicating in cells in which YB-1 is present in a deregulated manner.

In an embodiment the medicament further comprises at least a pharmaceutically active agent.

In a preferred embodiment the pharmaceutically active agent is selected from the group comprising cytokines, metalloproteinases inhibitors, angiogenesis inhibitors, cytostatics, cell cycle inhibitors, proteosome inhibitors, recombinant antibodies, inhibitors to the signal transduction cascade and protein kinases.

In an embodiment the medicament comprises a combination of at least two agents, whereby each agent is individually and independently selected from the group comprising cytostatics.

In a preferred embodiment at least two of the agents are targeting different target molecules.

In a preferred embodiment at least two of the agents are active through a different mode of action.

In an embodiment at least one agent increases the infectability of a cell in which the virus replicates.

In an embodiment at least one agent affects the availability of a compound in the cell, preferably increases the availability of the compound, whereby the compound mediates the uptake of the virus.

In an embodiment the agent mediates the transport of YB-1 to the nucleus, preferably increases the transport of YB-1 into the nucleus.

In an embodiment at least one agent is a histone deacetylase inhibitor.

In an embodiment the histone deacetylase inhibitor is selected from the group comprising Trichostatin A, FR 901228, MS-27-275, NVP-LAQ824, PXD101 Apicidin and Scriptaid.

In an embodiment the agent is selected from the group comprising Trichostatin A, FR 901228, MS-27-275, NVP-LAQ824, PXD101 Apicidin and Scriptaid.

In an embodiment at least one agent is a topoisomerase inhibitor.

In a preferred embodiment the topoisomerase inhibitor is selected from the group comprising Camptothecin, Irinotecan, Topotecan, DX-895If, SN-38, 9-aminocamptothecin, 9-nitrocamptothecin, Daunorubicn and Etoposid.

In an embodiment the agent comprises trichostatine A and irinotecan.

In an embodiment the virus, in particular a virus according to any of the preceding claims, is separated from the at least two agents.

In an embodiment at least one unit dosage of the virus is separated from at least one unit dosage of one of or of the at least two agents.

In a seventh aspect the problem underlying the present invention is solved by a medicament as defined with the use of the viruses in connection with the present invention.

In an eighth aspect the problem underlying the present invention is solved by a method for the treatment of a patient in need thereof, whereby the medicament as defined and discloses, respectively, herein is administered to said patient.

The present inventor has surprisingly found that adenovirus which require YB-1 for replication, i.e. which are replicating in a YB-1 dependent manner, are suitable to eliminate and reverse, respectively, resistance of cells, in particular of animal cells. Without wishing to be bound thereto, it seems that, due to the use of YB-1 in the replication of the YB-1 dependent viruses, YB-1 is no longer available as an important factor for the formation of resistances. More particularly, YB-1, due to its involvement in the replication of this group of viruses and adenoviruses in particular, seems to be removed to such extent or no longer available to such extent that other YB-1 controlled processes, such as the YB-1 controlled transcription of resistance mediating genes, are no longer proceeding or, at least, are proceeding in a significantly reduced manner.

Therefore, it is within the present invention that in general any virus can be used in connection with the present invention and for the uses described herein, whereby such virus uses YB-1 for its replication, whereby preferably the replication results in the lyses of the infected cells (also referred to as CPE; cytopathic effect) and not only in transient replication.

The kind of resistance which is reduced or reversed, is basically only limited to those resistances, the transcription, translation and/or activity of which is controlled by YB-1, preferably activated by YB-1. In particular these are resistance mediating factors comprising an inverted CAAT-box (Y-box). Such resistances are in particular the following ones. Classical and atypic multidrug resistance (MDR), whereby apart from the atypical multidrug resistance the classical phenotype of MDR is based on the overexpression of a membrane-bound 170 kDa ATP-dependent, transmembrane glycoprotein which predominantly exports lipophilic compounds from the cell. The MDR1-protein or also Pgp and P-glycoprotein, respectively, are members of the group of ABC transporters to which, among others, also MRP (multidrug related protein) and BCRP (breast cancer resistance protein) belong. Accordingly, further resistances in the meaning of the present invention are resistances mediated by ABC transporters, MDR-1, Pgp, P-glycoprotein, MRP and/or BCRP. The vesicular LRP-protein does not form part of the classical ABC transporters (lung resistance-related protein). However, it is mentioned frequently in this connection as it is also involved in transport processes which are involved in the formation of resistance to cytostatics in tumour cells (Sugawara I et al., CANCER LETTERS 112, 23-31, 1997; Gottesman et al., Nat Rev Cancer. 2002, 2:48-58). It is known that the LRP promotor comprises an inverted CAAT-box (Y-box) (Scheider et al., Breast Cancer Res., 2001, 3, 183-191). Insofar also those resistances which are mediated by the vesicular LRP protein, are resistances in the meaning of the present invention. Further resistances are those which are described herein generally and more specifically in relation to the various tumours to be treated, including, but not limited to, MDR, MRP, topoisomerase, BCL2, glutathione-S-transferase (GST), and protein kinase C (PKC). As the effect of cytostatics is based, among others, on the induction of apoptosis, the expression of apoptosis-related genes plays an important role in the formation of resistance so that, therefore, also the following factors are relevant insofar, namely Fas, the BCL2-family, HSP 70 and EGFR [Kim et al., Cancer Chemther. Pharmacol. 2002, 50, 343-352] and thus define resistances in the meaning of the present invention.

The viruses used in accordance with the present invention, in particular adenoviruses, are viruses, which are YB-1 dependent, i. e. require YB-1 for replication. In connection therewith it is within the present invention that such viruses are already known in the prior art and can be used in accordance with the present invention accordingly, or that such virus can be designed based on the disclosure provided herein. It is to be noted that the term viruses or adenoviruses in accordance with the invention or viruses or adenoviruses used in accordance with the invention, is to be understood as synonymous for the purposes of the present invention insofar that the viruses described herein may be used in accordance with the present invention provided that they use YB-1 for replicating. The YB-1 used for replication can be YB-1 which is either deregulated or localized in the nucleus, in particular localized in the nucleus independent of the cell cycle, as will be outlined in the following in more detail.

Cells which contain YB-1 in the deregulated form, are those which comprise at least one of the following characteristics and/or those which contain YB-1, whereby the YB-1 exhibits at least one of the following characteristics: (1) YB-1 is overexpressed in the cells, preferably independent of the cell cycle, whereby, preferably, as a measure for expression the expression of YB-1 in normal cells is used, i. e. cells which are different from tumour cells or cells and cell lines, respectively, such as the followings: Hepatocytes as well as fibroblast cell lines WI38 and CCD32-Lu. Preferably, there is an overexpression when the expression is increased by a factor ranging from 2 to 10, preferably from 5 to 10. Methods for measuring the expression and in particular measuring the overexpression are known to the one skilled in the art and comprise, among others, measuring the protein concentration, in particular the protein concentration of YB-1, measuring RNA, in particular of YB-1, Western Blot analysis, Northern Blot analysis and RT-PCR, each preferably of or in relation to YB-1. Rather than YB-1, also surrogate markers can be used as described herein. Examples for cell lines which show an overexpression of YB-1, are the followings: colon carcinoma cell line 257RDB, pancreas carcinoma cell line 181RDB, mamma carcinoma cell line MCF-7Adr, prostate carcinoma cell line DU145, prostate carcinoma cell line PC3, glioma cell line U373, glioma cell line U87, lung carcinoma cell line A549, liver carcinoma cell lines Hep3B and HepG2. (2) The YB-1 present in the cell enables the replication of the viruses in accordance with the present invention. In connection with the present invention it is preferred, when the replication efficiency under such conditions is different from a replication which is significantly reduced.

In an embodiment a significantly reduced replication is in particular a replication which is, compared to wildtype, reduced by a factor of 2, preferably by a factor of 5, more preferably by a factor of 10 and most preferably by a factor of 100. In a preferred embodiment comparing the replication is done by using similar or identical cell lines, similar or identical virus titres for infection (multiplicity of infection, MOI or plaque forming unit, pfu) and/or identical or similar general experimental conditions. The term replication in particular refers to particle formation. In a further embodiment the extent of viral nucleic acid synthesis can be understood as measure for replication. Methods for determining the extent of viral nucleic acid synthesis are known to the one skilled in the art as well as methods for determining particle formation.

A further form of deregulated YB-1 as referred to herein is phosphorylated YB-1. The rational behind this is as follows. YB-1 is highly expressed in quite a number of tumours and barely detectable in normal cells. In addition it is established that YB-1 translocates into the nucleus by stress stimuli, such as UV irradiation and chemotherapeutic agents (Okamoto T et al., Oncogene, 19, 6194-6202, 2000: Koike K et al., FEBS Letters, 417, 390-394, 1997). Akt which is a serine/threonine kinase promotes tumor cell growth by phosphorylating transcription factors and cell cycle proteins (Nicholson K M and Anderson N G, Cell. Signal., 14, 381-395, 2002). In addition it was found that activated Akt (phosphorylated Akt) is positively correlated with the protein expression of YB-1 and that Akt binds to and phosphorylates the YB-1 cold shock domain at Ser102 (Sutherland B W et al., Oncogene, 24, 4282-4292, 2005). These data indicate that there are signal transduction pathways that alter the subcellular localization of YB-1 and as such direct its function. In addition, this phosphorylation increases the production of proteins such as MDR1 and MRP, which is involved in stress response, cell proliferation and oncogenic transformation (Evdokimova V et al., Molecular and Cellular Biology, 26, 277-292, 2006). However, phosphorylation of YB-1 by Akt weakens also its cap-binding capability, thereby facilitating translational activation of silenced mRNA species (Evdokimova V et al., Molecular and Cellular Biology, 26, 277-292, 2006). Since Akt is not active in normal cells YB-1 is not present in the phosphorylated form whereas in tumor cells YB-1 is present in "deregulated" form such as phosphorylated and/or overexpressed.

The various diseases and patients, respectively, to be treated using the viruses described herein and/or using the medicaments described herein, are those as described herein.

With regard to the timing between the administration of the viruses in accordance with the present invention and radiation or administration of the cytostatics it is to be noted that it is predominantly determined by the replication efficiency of the viruses and the kind and size of the tumour. It will be appreciated by the one skilled in the art that, upon administration of the viruses, it may last some time, typically about one to three days, until the replication and thus the complexing of YB-1 and, accordingly, its non-availability for the transcription of other factors and of respective resistance causing factors in particular, occurs. Insofar in particular at the beginning of the treatment of resistant diseases the administration of viruses prior to any further treatment, in particular administration of pharmaceutical active compounds such as pharmaceutically active agents and/or radiation, is advantageous.

The administration of a pharmaceutically active compound preferably comprises the administration of an antitumour or anti-cancer agent as disclosed herein by way of example. Further respective agents are known to the one skilled in the art. Particularly preferred are cytostatics. Exemplary cytostatics are those described herein in connection with the pharmaceutical compositions and the (pharmaceutical) agent which is administered together with the virus.

It is within the present invention that the dosages and treatments schemes as customary in the treatment of tumour diseases may also be applied in connection with the present invention, however, is not limited thereto. For example, the amount of the cytostatic to be administered is preferably calculated based on the body surface (as $m^2$); by means of example, the dosage of Doxorubicin is about 50 $mg/m^2$. The therapeutical schemes can be designed differently and comprise single day administration as well as administration of the cytostatic and radiation, respectively, for several days, weeks or even months. The administration and radiation may additionally occur in a cyclic manner. Radiation and/or administration of the cytostatic may in turn be a mono- or combination therapy which, in accordance with the present invention, is further complemented by the administration of the virus.

For a better understanding of the present invention the basics of viral replication shall be briefly outlined. The replication of adenoviruses is a very complex process and is usually based on the human transcription factor E2F. During viral infection at first the "early genes" E1, E2, E3 and E4 are expressed. The group of the "late genes" is responsible for the synthesis of the structural proteins of the virus. The E1 region consisting of two transcriptional units E1A and E1B which code for different E1A and E1B proteins, play a critical role for the activation of both the early and the late genes, as they induce the transcription of the E2, E3 and E4 genes (Nevins, J. R., Cell 26, 213-220, 1981). Additionally, the E1A proteins may initiate DNA synthesis in resting cells and thus trigger their entry into the S phase (c. f Boulanger and Blair, 1991). Additionally, they interact with the tumor suppressors of the Rb class (Whyte, P. et al., Nature 334, 124-127, 1988). In doing so, the cellular transcription factor E2F is released. The E2F factors may subsequently bind to corresponding promoter regions of both cellular and viral genes (in particular to the adenoviral E2 early promoter) and initiate transcription and thus replication (Nevins, J. R., Science 258, 424-429, 1992). The activity of pRb and E2F is regulated by phosphorylation. The hypophosphorylated form of pRb particularly exists in the G1 and M phase. In contrast thereto, the hyperphosphorylated form of pRb is present in the S and G2 phase. By phosphorylation of pRb E2F is released from the complex consisting of E2F and hypophosphorylated pRb. The release of E2F from the complex of E2F and hypophosphorylated pRb results in transcription of E2F dependent genes. The E1A protein binds only to the hypophosphorylated form of pRb, whereby the binding of E1A to pRb predominantly occurs through the CR2 region of the E1A protein. Additionally, it also binds to the CR1 region, however, with a lower affinity (Ben-Israel and Kleiberger, Frontiers in Bioscience, 7, 1369-1395, 2002; Helt and Galloway, Carcinogenesis, 24, 159-169, 2003).

The gene products of the E2 region are especially needed for the initiation and completion of the replication as they code for three essential proteins. The transcription of the E2 proteins is controlled by two promoters, the "E2 early E2F dependent" promoter, which is also referred to herein as E2-early promoter or early E2 promoter, and the "E2-late" promoter (Swaminathan and Thimmapaya, The Molecular Repertoire of Adenoviruses III: Current Topics in Microbiology and Immunology, vol 199, 177-194, Springer Verlag 1995). Additionally, the products of the E4 region together with the E1A and E1B-55kDa protein play a crucial role for the activity of E2F and the stability of p53. For example, the E2 promoter is even more transactivated by direct interaction of the E4orf6/7 protein encoded by the E4 region with the heterodimer consisting of E2F and DPI (Swaminathan and Thimmapaya, JBC 258, 736-746, 1996). Furthermore, the complex consisting of E1B-55kDa and E4orf6 is inactivated by p53 (Steegenga, W. T. et al., Oncogene 16, 349-357, 1998) in order to complete a successful lytic infectious cycle. Additionally, E1B-55kDa has a further important function insofar as it promotes, when interacting with E4orf6 protein, the export of viral RNA from the nucleus, whereas cellular RNAs are retained in the nucleus (Bridge and Ketner, Virology 174, 345-353, 1990). A further important observation is that the protein complex consisting of E1B-55kDa/E4orf6 is localised in the so-called "viral inclusion bodies". It is assumed that these structures are the sites of replication and transcription (Ornelles and Shenk, J. Virology 65, 424-429, 1991).

The E3 region is another important region for the replication and in particular for the release of adenoviruses. The E3 region more precisely contains the genetic information for a variety of comparatively small proteins which are not essential for the infectious cycle of adenovirus in vitro, i. e. in cell culture. However, they play a crucial role in the survival of the virus during an acute and/or latent infection in vivo as they have, among others, immune regulatory and apoptotic function(s) (Marshall S. Horwitz, Virologie, 279, 1-8, 2001; Russell, supra). It could be shown that a protein having a size of about 11.6 kDa induces cell death. This protein was, due to its function, named ADP—for the term adenovirus death protein—(Tollefson, J. Virology, 70, 2296-2306, 1996). The protein is predominantly formed in the late phase of the infectious cycle. Furthermore, the overexpression of the protein results in a better lysis of the infected cells (Doronin et al., J. Virology, 74, 6147-6155, 2000). In accordance therewith, the respective genes and proteins, respectively, are contained in the virus in accordance with the present invention.

In the following, some of the various adenoviruses are described which may be used as viruses in accordance with the present invention. In connection therewith, only for reasons of clarity they are categorized into groups and referred to as virus group § 1, virus group § 2 and virus group § 3. Such viruses are, for the reason of clarity and enablement disclosed in the following applications co-owned by the present applicant and incorporated by reference in their entirety. More specifically, virus group § 1 is described in international patent application PCT/EP/05583 published as WO 03/099859, filed on May 27, 2003 claiming the priorities of DE 102 23 534.1 of May 27, 2002, DE 102 25 400.1 of Jun. 7, 2002, DE 102 48 039.7 of Oct. 15, 2002 and DE 103 22 530.7 of May 19, 2003; virus group § 2 is described in international patent application PCT/EP03/11427 published as WO 2004/035616, filed on Oct. 15, 2003 and claiming the priorities of DE 102 48 039.7 of Oct. 15, 2002, DE 103 22 530.9 of May 19, 2003, DE 103 24 085.3 of May 27, 2003 and PCT/EP03/05583 of May 27, 2003; and virus group § 3 is described in international patent application entitled "E1-minus Adenovirusen and deren Verwendung", filed on Jan. 2, 2006 claiming the priority of DE 10 2004 063662.1 filed on Dec. 31, 2004.

It is within the present invention that the comments provided in relation to the individual groups are applicable to the other groups as well, provided that this is not explicitly excluded; this applies in particular to the definitions provided in the specific embodiments. Also it is within the present invention that any feature, embodiment, advantage or the like recited in connection with one aspect applies also the each and any other aspect of the invention as described herein. It is also within the present invention that any feature, embodiment, advantage or the like recited in connection with any virus or adenovirus in accordance with the present invention applies also to any use in accordance with a virus or adenovirus as described herein, and vice versa.

As used herein in an embodiment, the term functional wildtype E1 region refers in particular to an E1 region as contained in the adenovirus Ad5 of the wildtype. In an embodiment the term lacking functional wildtype E1 region refers to an E1 region which either does not comprise one or several functions or functionalities of the E1 region as present in wildtype adenoviruses or which does not completely comprise the same. The functionality or function, in the following generally referred to as function, is mediated by a nucleic acid or a protein, preferably is represented or mediated by a protein.

In connection with the present invention the lack of function can be caused by the function not being active at the level of translation, i. e. that the function mediating protein is not present although the nucleic acid coding therefore is still present in the viral genome. This can, for example, be caused by the regulatory elements controlling its translation being absent, such as, for example, the 3'UTR of the mRNA which, among others, provide for the stability of the mRNA. Preferably these regulatory elements are no longer present in the regulatory and controlling context as present in wildtype viruses for the respective function.

In connection with the present invention the lack of function can, alternatively or additionally, be caused by the function not being active at the level of transcription, i. e. that the protein mediating the function is not present and the nucleic acid coding therefore, is not contained in the viral genome or not completely contained in the viral genome. It is within this embodiment that the coding nucleic acid comprises one or several mutations which result in the loss of function. Such mutations are preferably point mutations and/or deletions comprising several bases and/or a complete deletion of the open reading frame or the nucleic acid coding for the protein.

A function is lacking in the sense of the above embodiments if the protein does not comprise all functions or activities as exhibited by the corresponding wildtype protein. In an embodiment, the extent of replication is used as a measure for activity which can be obtained under such conditions, whereby it is preferably significant different from a replication using the wildtype protein, genotype and/or phenotype.

In a preferred embodiment of the present invention there is a lack of function also when the function is, compared to the wildtype virus, contained in the virus in a different regulatory context. A different regulatory context is in a preferred embodiment a context in connection with which the function is, compared to other functions, expressed at a different point in time and/or is under the control of a different transcription and/or translation controlling or influencing element. Such an element is in a particular embodiment the promoter.

In an embodiment a strongly reduced replication herein in particular means a replication which is decreased compared to the wildtype by a factor of 2, preferably a factor of 5, more preferably a factor of 10 and most preferably a factor of 100. In a preferred embodiment the comparison of the replication is made using identical or similar cell lines, identical or similar virus titres for the infection (multiplicity of infection, MOI or plaque forming unit, pfu) and/or identical or similar general experimental conditions. Replication particularly means the formation of particles. In further embodiments the measure for replication may be the extent of viral nucleic acid synthesis. Methods for determining the extent of viral nucleic acid synthesis and methods for the determining particle formation are both known to the ones skilled in the art.

The lack of a function in the above sense is herein also indicated by the respective function being referred to as "minus". For example, the lack of E1A13S is indicated as E1A13S-minus.

Virus Group § 1

This group of viruses is based on the surprising finding that the DNA replication of E1A-modified adenoviruses in YB-1 nucleus positive tumour cells is based on the activation of the E2-late promoter. E1A-modified adenoviruses as used herein, are adenoviruses which (a) do not replicate in YB-1 nucleus-negative cells or show a reduced, preferably a strongly reduced replication in YB-1 nucleus-negative cells compared to the respective wildtype, (b) transactivate at least one viral gene, whereby the gene is in particular selected from the group comprising E1B-55kDa, E4orf6, E4orf3 and E3ADP, and/or (c) do not translocate cellular YB-1 through the adenovirus into the nucleus. Optionally the adenoviruses used in accordance with the present invention have the further characteristic that the binding of the adenoviral encoded E1A protein interferes with the binding of E2F to Rb and is able to dissolve the respective complex consisting of E2F and Rb, respectively. Adenoviruses which have at least one or several of the aforementioned features a) to c), preferably all of features a) to c), are replication deficient in cells which do not have YB-1 in the nucleus.

Without wishing to be bound by this in the following, the present inventor assumes that the E2-early promoter, i. e. the early E2 promoter which is controlled by the E2F transcription factor, is not of critical importance to the replication of the viruses used herein in accordance with the present invention. The switching on of the replication is independent of the Rb status of the cells, i. e. which means that the tumor cells which are infected using the viruses disclosed herein and which are preferably lysed subsequently thereafter, may comprise both functional as well as inactive Rb proteins. Additionally, adenoviral replication does neither need any functional p53 protein nor is it affected by its presence, when using the adenoviruses disclosed herein or under the conditions disclosed herein. Insofar, the technical teaching departs from the principle underlying the use of the oncolytic or tumorlytic adenoviruses of the AdΔ74, dl922-947, E1Ad/01/07, CB016 type or of those adenoviruses which are, for example, described in European patent EP 0 931 830, and into which one or several deletions have been introduced into the E1A protein under the assumption that intact functional Rb proteins are an obstacle to an efficient replication in vivo thus providing an adenoviral replication in vivo only in Rb-negative and Rb-mutated cells, respectively. These adenoviral systems according to the prior art are based on E1A in order to control in vivo replication of adenoviruses by means of the early E2 promoter (E2 early promoter) and "free E2F". Nevertheless, these viruses according to the prior art may be used in accordance with the present invention, i. e. for replication in cells which contain YB-1 in the nucleus independent from the cell cycle.

The viruses described in said European patent EP 0 931 830 and in particular adenoviruses may be used in accordance with the present invention. More particularly, the viruses described in said patent are replication deficient and lack an expressed viral oncoprotein which is capable of binding a functional Rb tumor suppressor gene product. The adenovirus can particularly be an adenovirus which is lacking expressed viral E1A oncoprotein which is capable of binding a functional tumor suppressor gene product, in particular Rb. The viral E1A oncoprotein can comprise an inactivating mutation, for example in the CR1 domain at amino acid positions 30 to 85 in Ad 5, nucleotide positions 697 to 790 and/or the CR2 domain at amino acid positions 120 to 139 in Ad 5, nucleotide positions 920 to 967 which are involved in the binding of p105 Rb protein, p130 and p107 protein. It can also be intended that the adenovirus is of type 2 dl 312 or the adenovirus is of type 5 NT dl 1010.

A further feature of the adenoviruses which are to be used in accordance with the present invention, is that they code for a viral oncoprotein which is also referred to herein as oncogene protein, whereby the oncogene protein is preferably E1A, whereby the oncogene protein is capable of activating at least one viral gene which can have an impact on the replication of the virus and/or cell lysis of the cells infected by the virus. It is preferred that the influence on replication is such that the virus replicates better in the presence of the oncogene protein compared to a situation where the oncogene protein of the respective virus is lacking. This process is referred to herein also as transactivating and in particular E1A transactivating, when the transactivation is mediated through E1A. The term "transactivate" or "transactivation" describes preferably the process that the respective viral oncoprotein has an impact on the expression and/or the transcription of one or several other genes different from the viral oncoprotein coding gene itself, i. e. is preferably controlling its expression and/or translation, and in particular activates this/these. Such viral genes are preferably E1B55kDa, E4orf6, E4orf3 and E3ADP as well as any combination of the aforementioned genes and gene products, respectively.

A further, although preferably optional, feature of the adenoviruses to be used in accordance with the invention, is the binding to and of tumor suppressor Rb. In principle it is within the present invention that the adenoviruses used in accordance with the present invention bind to Rb or do not bind to Rb. The use of both alternative embodiments of the adenoviruses is possible independently from the Rb status of the cell to be treated.

In order to confer the capability to not bind to Rb, the following deletions of the E1A oncoprotein are, for example, possible: Deletion in the CR1 region (amino acid positions 30-85 in Ad5) and deletion of the CR2 region (amino acid positions 120-139 in AD5). In doing so, the CR3 region is maintained and can have its transactivating function on the other early viral genes.

In contrast thereto, the following deletions to the E1A oncoprotein are in principle possible in order to impart E1A the capability to bind to Rb: deletion of the CR3 region (amino acid positions 140-185); deletion of the N-terminus (amino acid positions 1-29); deletion of amino acid positions 85-119; and deletion of the C-terminus (amino acid positions 186-289). The regions recited herein do not interfere with the binding of E2F to Rb. The transactivating function remains, however, is reduced compared to wildtype Ad5.

In connection with the present invention the modified E1A oncoprotein of the various adenoviruses which are to be used in accordance with the invention, is capable of transactivating the early viral genes such as, for example, E1B55K, E4orf3, E4orf6, E3ADP, in YB-1 nucleus-positive cells. In connection therewith, there are preferably otherwise no further changes to the viral genome and the respective adenovirus can otherwise correspond to an adenovirus of the wildtype or any derivative thereof.

The viruses disclosed herein which code for a transactivating oncogene protein in the sense of the present invention or which comprise such oncogene protein, comprise, for example, the adenoviruses AdΔ24, dl922-947, E1Ad/01/07, CB106 and/or the adenoviruses described in European patent EP 0 931 380, which are each capable of transactivating the early genes, such as E1B, E2, E3 and/or E4, and are comparable to adenoviruses of the wildtype, in particular wildtype Ad5. A particular region of the E1A protein is responsible for transactivation in these cases. Within various adenovirus serotypes there are three highly conserved regions in the E1A protein. The CR1 region from amino acid positions 41-80, the CR2 region from amino acid positions 120-139 and the CR3 region from of amino acid positions 140-188. The transactivating function is primarily based on the presence of the CR3 region in the E1A protein. The amino acid sequence of CR3 is unaltered in the aforementioned adenoviruses. This results in a transactivation of the early genes E1B, E2, E3 and E4 independent from the presence of YB-1 in the nucleus or in the cytoplasma.

In the recombinant adenovirus dl520, however, the CR3 region has been deleted. Thus dl520 expresses a so-called E1A12S protein which does not comprise the amino acid sequence of the CR3 region. As a consequence, dl520 can exert a very weak transactivating function only, in particular on the E2 region, and thus does not replicate in YB-1 nucleus-negative cells. In YB-1 nucleus-positive cells YB-1 is transactivating the E2 region and thus allows an efficient replication of dl520. This is the basis for the use of systems like dl520 and of systems on the basis of dl520 for the purposes disclosed herein, respectively. A further important difference between both the previously described groups of adenoviruses, i. e. delta 24 (herein also referred to as AdΔ74) and dl520 resides in the fact that with dl520 the early genes E1B, E3 and E4 are more strongly transactivated in YB-1 nucleus-positive cells compared to YB-1 nucleus-negative cells. In contrast, there are no or only minor differences with delta 24. The transactivation effect of dl520 and more particularly of the E1A12S protein, however, is significantly reduced compared to wildtype adenovirus. This transactivation is, however, sufficient in order to allow for an efficient replication in YB-1 nucleus-positive cells, as shown in example 10. The design of the E1A protein and of the nucleic acid coding therefor described herein and in particular in this context such that the E1A protein has one or several deletions and/or mutations compared to the wildtype oncogene protein E1A, whereby the deletion is preferably one selected from the group comprising deletions of the CR3 region and deletions of the N-terminus and deletions of the C-terminus, including and particularly preferred those embodiments of the E1A protein as described in connection with dl520 or AdΔ74, dl922-947, E1Ad/01/07, CB106 and/ or the adenoviruses described in European patent EP 0 931 830, are embodiments of viruses, in particular adenoviruses, the replication of which is controlled by YB-1 through the activation of the E2-late promoter, preferably predominantly through the activation of the E2-late promoter. Further embodiments of the E1A protein which allow this form of replication of adenoviruses, can be generated by the ones skilled in the art based on the disclosure provided herein.

In further adenoviruses which are to be newly constructed, which are also referred to herein as derivatives and which may be used in accordance with the present invention, typically have an E1 deletion, an E1/E3 deletion and/or an E4 deletion, i.e. the corresponding adenoviruses are not able to generate functionally active E1 and/or E3 and/or E4 expression products and respective products, respectively, or, in other words, these adenoviruses are only capable to generate functional inactive E1, E3 and/or E4 expression products, whereby a functionally inactive E1, E3 and/or E4 expression product as such which is either not present as an expression product at all, whether at the transcription level and/or the translation level, or it is present in a form in which it at least is lacking one of the functions it has in wildtype adenoviruses. The function(s) of the expression product of the wildtype adenovirus is/are known to the ones skilled in the art and, for example, described in Russell, W. C., Journal of Virology, 81, 2573-2604, 2000. Russell (supra) describes also principles for the construction of adenoviruses and adenoviral vectors which are incorporated herein by reference. It is also within the present invention that the modified E1A oncoprotein, E1B-55K, E4orf6 and/or E3ADP (adenoviral death protein (ADP)) (Tollefson, A. et al., J. Virology, 70, 2296-2306, 1996) is expressed in such a vector either individually or in any combination. In connection therewith, the individually named genes as well as the transgenes disclosed herein, can be cloned into the E1 and/or E3 and/or E4 region and be expressed independently by virtue of a suitable promoter or under the control of a suitable promoter. Basically, the regions E1, E3 and E4 are similarly suitable as cloning sites within the adenoviral nucleic acid, whereby the regions which are not used for the cloning may, either individually or all together, be present, partially deleted and/or completely deleted. In case these regions are present, in particular are completely present, it is within the present invention that they are either intact and preferably provide for a translation product and/or a transcription product, and/or are not intact and preferably do not provide for a translation product and/or a transcription product. Suitable promoters are, for example those, which are disclosed herein in connection with the control and expression, respectively, of E1A, in particular of modified E1A.

Finally, in one embodiment the adenoviruses which are to be used in accordance with the present invention, are deficient with regard to E1B, in particular with regard to E1B 19 kDa. As used herein, the term deficient generally means a condition in which E1B does not have all of the characteristics inherent to the wildtype but at least one of these characteristics is absent. The adenoviral BCL2 homologue E1B19k inhibits the E1A induced apoptosis by interacting with the pro-apoptotic proteins Bak and Bax. Because of this, a maximum replication and/or particle formation is possible in infected cells (Ramya Sundararajan and Eileen White, Journal of Virology 2001, 75, 7506-7516). The lack of E1B19k results in a better release of the viruses as it minimizes the function of the adenoviral death-protein, if present. The virus induced cytophatic effect is increased by such deletion (Ta-Chiang Liu et al., Molecular Therapy, 2004) and thus results in a stronger lysis of the infected tumour cells. Additionally, the lack of E1B19k results in TNF-alpha not having an impact on the replication of such recombinant adenovirus in tumour cells, whereas in normal cells the treatment results in a reduced replication and release of infectious viruses. Thus the selectivity and specificity is increased (Ta-Chiang Liu et al., Molecular Therapy 2004, 9, 786-803).

Some embodiments of the adenoviruses which are used in accordance with the invention disclosed herein, are, basically, known in the prior art.

The adenoviruses used in accordance with the present invention are preferably recombinant adenoviruses, particularly also when a change, compared to the wildtype, has been made in accordance with the technical teaching provided herein. It is within the skills of those of the art to delete or mutate those adenoviral nucleic acid sequences which are not essential for the present invention. Such deletions may, for example, be related to a part of the nucleic acid coding for E3 and E4 as also described herein. A deletion of E4 is particularly preferred if such deletion does not extend to the protein E4orf6, or, in other words, the adenovirus to be used in accordance with the present invention codes for E4orf6. In preferred embodiments these adenoviral nucleic acids may still be packed into the viral capsid and may thus form infectious particles. The same is true for the use of the nucleic acids in accordance with the present invention. It should be noted that in general the adenoviral systems may be deficient with regard to single or several expression products. In connection therewith it is to be taken into consideration that this may be either based on the fact that the nucleic acid coding for such expression product is completely mutated or deleted or mutated or deleted to the extent that essentially no expression product is produced anymore or based on the lack of promoters or transcription factors which control the expression, or which are active in a manner different from wildtype, either at the nucleic acid level (lack of a promoter; cis-acting element) or at the translation system and the transcription system, respectively (trans-acting elements). Particularly the latter aspect may be dependent on the cellular background.

Apart from using adenoviruses in accordance with the present invention, which are already known, also novel adenoviruses can be used to the same extent as has already been disclosed for the other adenoviruses described herein. The novel adenoviruses according to the invention result from the technical teaching provided herein. Particularly preferred representatives are, for example, the viruses Xvir03 and Xvir03/01 depicted in FIG. 16 and FIG. 17, the design principle of which is also further illustrated in examples 11 and 12.

In the case of vector Xvir03 a CMV promoter is cloned into the E1 region which codes the nucleic acids for E1B 55K and E4ORF6, which are separated by a IRES sequence. In connection therewith the E3 region can be partially or completely be deleted or can be present and intact.

Due to the introduction of these two genes and the gene products produced therefrom, respectively, a replication efficiency is created which nearly corresponds to the one of wildtype viruses, whereby the selectivity of the replication is maintained for cells, particularly tumor cells, insofar as a replication happens in particular in YB-1 nucleus-positive cells and more particularly in cells in which YB-1 is deregulated. Cells in which YB-1 is deregulated, are preferably those which show an increased expression of YB-1, preferably compartment-independent, compared to normal or non-tumor cells. The introduction of E1B55k and E4orf6 into the E4-region by cloning can also be performed, whereby the E3 region may be intact or/and partially or completely deleted.

A further development of virus Xvir03 is virus Xvir03/01 into which, in a preferred embodiment, therapeutic genes or transgenes are cloned under the control of a specific promoter, in particular a tumor-specific or tissue-specific promoter. It is also within the scope of such a virus that also the E4 region is functionally inactive, preferably is deleted. The transgenes described herein may also be cloned into the E4 region, whereby this may occur in addition or alternative to the cloning of a transgene into the E3 region, and the E3-region remains partially or completely intact. Transgenes, as used herein, may be therapeutic genes or viral genes, preferably adenoviral genes, which are preferably not present in the genome of the wildtype adenovirus or at the position in the genome, respectively, where they are present in the particular virus now.

In a preferred embodiment, with regard to the adenoviruses according to the present invention and the adenoviral replication system according to the present invention and the use of them according to the present invention, respectively, the adenoviral nucleic acid is deficient for the expression of the oncogene protein, particularly of the E1A protein, which means that it is either not coding for the 12S E1A protein or for the 13S E1A protein, or it is neither coding for the 12S E1A protein nor the 13S E1A protein, or is modified, as defined herein, and that the adenoviral replication system further comprises a nucleic acid of a helper virus, whereby the nucleic acid of the helper virus comprises a nucleic acid sequence which codes for the oncogene protein, in particular for the E1A protein, which has the following characteristics and imparts the following characteristics to the adenovirus, respectively, namely that it preferably is not replicating in YB-1 nucleus-negative cells but in cells which are independent from the cell cycle YB-1 nucleus-positive, transactivating at least one viral gene, in particular E1B55kDa, E4orf6, E4orf3 and/or E3ADP, in YB-1 nucleus-positive cells, and/or does not translocate cellular YB-1 into the nucleus. It is within the present invention that the transgenes described herein are coded individually or together by the helper virus and/or expressed therefrom.

Virus Group § 2

These viruses are categorized, again for reason of clarity, into group I and group II. The viruses first defined in the claims related to virus group § 2, are also referred to herein as adenovirus of group I, and the adenoviruses which comprise a transactivating oncogene protein such as E1A and/or those which are referred to herein and in particular above as to be used in accordance with the present invention, are also referred to herein as adenovirus of group II. Adenovirus of group I and group II are all together also referred to herein as adenoviruses or adenoviruses in accordance with the invention or viruses in accordance with the present invention. Again, it is within the present invention that, preferably, any feature, embodiment and/or use described herein in relation to group I is also applicable to group II and vice versa.

These viruses are based on the surprising finding that reversing the expression sequence of adenoviral genes results in an efficient replication and optionally in the lysis of the cell infected by the adenovirus. Preferably, such reversing is a chronological reversing of expression and/or availability of the genes and gene products, respectively, compared to the expression and/or availability order of the respective genes in wildtype virus, preferably wildtype adenovirus. With regard to the chronologically changed expression of the adenoviral genes particular emphasis is to be put on an E1B protein and an E4 protein which are also referred to herein, individually or collectively, as the first protein, which are expressed prior to a second protein. The second protein is selected from the group comprising E1A proteins. This expression sequence which is reversed compared to wildtype adenoviruses where first an E1A protein and only subsequently the E1B protein and an E4 protein are expressed, ensures that transcription factors are activated, for example transported, into the nucleus of the infected cell and influence the further replication activity or control the same there. The kinetics of the adenoviral transcripts in wildtype adenoviruses are, for example, described in Glenn G. M. and Ricciardi R. P. Virus Research 1988, 9, 73-91, who report that in the wildtype the E1A transcripts, i. e. the E1A12S transcript and the E1A13S transcript, are usually detectable prior to the transcripts and translation products, respectively, E4orf6 and E1B55k. In the present case the E1B protein is, and also herein in general if not indicated to the contrary, preferably the E1B-55 kD protein. In the present case, the E4 protein is, and also herein in general if not indicated to the contrary, preferably the E4orf6 protein. In the present case, the E1A protein is, and also herein in general if not indicated to the contrary, preferably an E1A12S protein or such an E1A protein as described herein in connection with the E1A-modified adenoviruses.

It is within these viruses that the E1A protein, in particular also the E1A12S protein may be substituted in principle. Such substituted E1A proteins and E1A12S proteins, respectively, are also referred to herein as E1A protein and E1A12S protein, respectively, or shall be deemed to be comprised by this term, if not indicated to the contrary. Instead of the E1A12S protein also an E1A protein may be used which has a tumor suppressor function, such as, for example, described by Dickopp A, Esche H, Swart G, Seeber S, Kirch H C, Opalka B. Cancer Gene Ther. 2000, July; 7(7):1043-50. Further derivatives of E1A proteins, in particular of the E1A12S protein, as used and/or as referred to as such herein, are generally also such proteins which are capable of releasing the factor E2F from the Rb/E2F complex. These are, among others, Simian virus 40 tumor antigen (SV40 large T antigen), papillomavirus E7 protein (HPV E7) as described by Chellappan S. et al., Proc. Natl. Acad. Sci. USA 1992, 89, 4549-4533.

It is also within these viruses that derivatives of E4orf6 and E1B55k may be used, whereby the term E4orf6 and E1B55k, as used herein, comprises such derivatives. The derivatives are, for example, described in Shen Y et al., J. of Virology 2001, 75, 4297-4307; Querido E. et al., J. of Virology 2001, 75, 699-709.

It is within these viruses that an E1B protein is expressed prior to the E1A protein, or that an E4 protein is expressed prior to an E1A protein, or that both an E1B protein and an E4 protein are expressed prior to the E1A protein, each as described above.

An adenovirus designed in such a way is capable of replicating at a particularly high level upon infection of a cell which expresses YB-1 in the nucleus, preferably expresses YB-1 in the nucleus independent from the cell cycle, or which comprises deregulated YB-1, preferably in the cytoplasm. Without wishing to be bound thereto in the following the present inventor assumes that a complex consisting of E1B protein and/or E4 protein and individual ones of these two proteins, respectively, is/are capable of transporting deregulated YB-1 into the cellular nucleus or is/are capable of initiating adenoviral replication there under the influence of the E1B protein and/or E4 protein being expressed prior to the E1A protein. Once in the cellular nucleus or being present there in activated form, YB-1 may, as described herein, in particular using the E2-late promoter, efficiently replicate. The chronologically early expression of an E1B protein and/or an E4 protein thus avoids the cascade as observed in wildtype going along with initial expression of E1A protein. In a preferred embodiment the E1A protein is an E1A protein which is in particular no longer transactivating or transactivating only to a very limited extent the E1B protein and/or the E4 protein. Preferably, this transactivation is neither sufficient to ensure an efficient replication, nor sufficient to ensure replication in cells which do not have YB-1 in the nucleus. It is preferred that the transactivation does not occur in cells which do not have YB-1 in the nucleus independent from the cell cycle or cells which do not have deregulated YB-1.

Furthermore, these viruses are based on the surprising finding that an adenovirus is capable of replicating in a particularly efficient manner if it comprises at least a nucleic acid which codes for a protein, whereby the protein is selected from the group comprising E1B proteins, E4 proteins and E1A proteins and that at least one protein thereof is under the control of a promoter which is different from the promoter which controls the expression of the respective protein in a wildtype adenovirus. Such replication is particularly efficient and usually results in tumor lysis in case the cells have YB-1 in the nucleus, in particular have YB-1 in the nucleus independent of the cell cycle, or in case the cells comprise deregulated YB-1, in particular comprise deregulated YB-1 in the cytoplasm. What has been said above about the E1B proteins, E4 proteins and E1A proteins applies also here. In wildtype adenoviruses the E1B protein is controlled by the E1B promoter, the E4 protein is controlled by the E4 promoter and the E1A protein is controlled by the E1A promoter. By selecting promoters which are different from those which control the expression of the aforementioned proteins in wildtype adenoviruses, the expression of the previously mentioned proteins and thus the regulatory interplay of the individual adenoviral nucleic acids and proteins is changed. By selecting the promoters a chronologically different expression pattern can be created which, without wishing to be bound thereto in the following, results in the observed replication in cells, whereby the mechanism may be the one as already previously described with regard to the chronologically different expression of the adenoviral proteins E1B, E4 and E1A. An example of a specific design for the control of said proteins through promoters different from those controlling the expression of the respective proteins in wildtype adenovirus, may be taken from the sub-claims and from the example part, whereby in particular the viruses referred to therein as XVirPSJL1 and XVirPSJL2 are representative thereof. Preferably, the E1B protein is the E1B55kD protein, the E4 protein is the E4orf6 protein and the E1A protein is the E1A12S protein.

The promoters which preferably control the E1B protein as well as the E4 protein, are selected from the group comprising tumor-specific promoters, organ-specific promoters, tissue-specific promoters, heterologous promoters and adenoviral promoters under the proviso that when adenoviral promoters are used, they are different from the E1B promoter in case of the expression control of the E1B protein, and are different from the E4 promoter in case of expression control of the E4 protein. The use of the E1A promoter for the expression control of the E1B protein and/or the E4 protein is particularly preferred. The E1A promoter is, for example, described by Boulanger P. A. and Blair, G. E. Biochem. J. 1991, 275, 281-299. Additionally, also the use of each and any other heterologous promoter is possible, i. e. a promoter which is different from the one which controls the expression of the respective protein in a wildtype adenovirus. A representative example is the CMV promoter, whereby other promoters will be obvious for the ones skilled in the art.

The promoter which is used for the control of the E1A protein, may also be selected from the group comprising tumor-specific promoters, organ-specific promoters, tissue-specific promoters, heterologous promoters and adenoviral promoters under the proviso that the adenoviral promoter is different from the E1A promoter. It is within the present invention that one or several of the aforementioned proteins, i. e. the E1B protein, the E4 protein or the E1A protein are under the control of the same promoter, whereby it is nevertheless preferred that particularly the E1B protein and the E4 protein are under the control of the same promoter. It is particularly preferred that the expression of the E1A protein is controlled by a YB-1-controlled promoter or a promoter which can be regulated by YB-1. Such promoters are disclosed herein in connection with other aspects of the present invention. The use of the adenoviral E2-late promoter is particularly preferred for the control of the expression of the E1A promoter as it can, first, be regulated by YB-1 and, second, shows only little transcription in the absence of YB-1 which can factually be neglected so that a very good expression control of the nucleic acid which is under the control of the E2-late promoter, is ensured. It is to be acknowledged that other YB-1 dependent or YB-1 controlled promoters can be used insofar which are either known to the ones skilled in the art or described herein. This considerably increases biological safety, particularly when applied in the field of medicine.

Furthermore, the present inventor has found that adenoviruses will replicate particularly well in cells which have YB-1 in the nucleus, particularly have YB-1 in the nucleus independent of the cell cycle, and/or which have deregulated YB-1, preferably have deregulated YB-1 in the cytoplasm, if YB-1 is provided for replication either directly or indirectly in particular in the cellular nucleus or if the provision of YB-1 is directly or indirectly mediated through an adenoviral protein, whereby such adenoviral protein is different from E1A. This aspect of the present invention is different from the aspect which is also disclosed herein, namely that the use of transactivating E1A-modified adenoviruses, preferably group II adenoviruses, allows for replication of these viruses in YB-1 nucleus-positive tumor cells, particularly YB-1 nucleus-positive cells which are YB-1 positive independent of the cell cycle, and those cells which have deregulated YB-1, particularly comprise YB-1 in the cytoplasm, insofar that the transactivating characteristics of the E1A protein, particularly the E1A13S protein are not used here, i. e. in connection with the group I adenoviruses, but rather in a preferred embodiment the E1A13S protein is functionally inactive and is thus no longer capable of transactivating also E4orf6 and E1B55k, which are involved in the transport and provision of YB-1, respectively, into the nucleus, either directly or indirectly. Consequently, an effective replication of the adenovirus is not possible in accordance with this aspect of the present invention. Insofar, the provision of YB-1 in the nucleus and the provision of YB-1 for adenoviral replication, respectively, is now no longer under the control of the direct or indirect involvement of the E1A protein but occurs through the expression of the E1B protein, particularly E1B55kD protein, and/or the E4 protein, particularly the E4orf6 protein, which is not controlled by E1A.

This embodiment of the adenovirus may also be provided by one of the above-described measures, for example by realizing, i.e. bringing forward, the earlier chronological expression of the E1B protein and/or the E4 protein compared to the expression of the E1A protein, or by putting one or several of the E1B proteins, E4 proteins and E1A proteins under the control of a promoter which is different from the promoter which controls the expression of the respective protein in wildtype adenovirus.

Finally, the present inventor starts from the surprising finding that an effective adenoviral replication may also occur, particularly in cells which have YB-1 in the nucleus, more particularly YB-1 in the nucleus independent of the cell cycle, or in cells which have deregulated YB-1, preferably in the cytoplasm, in case at least one of the E1B proteins, E4 proteins and E1A proteins, particularly the preferred forms thereof, are expressed in an expression cassette under the control of a promoter. In one embodiment of the present invention basically three expression cassettes each comprising a single one of said proteins are provided. In an alternative embodiment an expression cassette may also comprise two or more of the proteins E1B, E4 and E1A and their derivatives and possible substituents, respectively, particularly in case of E1A12S. What has previously been said in relation to the aspect that the adenoviruses comprise nucleic acids related to proteins E1B, E4 and E1A, is also applicable to the design of the various proteins and the respectively used promoters. When using such expression cassettes it is preferred that proteins and nucleic acids coding therefor in the genome of the wildtype adenovirus which correspond to the respective proteins of the expression cassettes, are either completely or partially deleted to ensure that the virus is stable and to avoid recombinations, at least to a bigger extent.

In principle, the expression cassettes can be cloned into each region and each site, respectively, of the adenovirus, whereby preferably one or several of the cassettes are inserted either individually or in combination with each other into the E1 region, the E3 region and/or the E4 region of the virus. It is possible that the nucleic acids of the E1, E3 and E4 region are completely deleted, partially deleted or not deleted at all, whereby it is preferred with regard to the adenoviruses according to the invention that the nucleic acid coding for the E1A13S gene is inactivated or deleted so as not to provide any transactivating E1A protein by the virus. The extent of such deletion in one or several of the regions E1, E3 and E4 is determined by the expression cassette used and, optionally, further introduced foreign genes or transgenes or the further expression cassettes comprising them, i. e. genes which are different from the adenoviral genes, at least different in the sense that they are not provided in the regulatory context of the adenoviral nucleic acid as prevailing in wildtype adenovirus or are not provided in the sequence of the adenoviral nucleic acids of wildtype adenoviruses at such site. It is within the present invention that the nucleic acids which are contained in one or several of the expression cassettes which code for an E1B protein, an E4 protein and/or an E1A protein, are partially or completely deleted in the adenoviral genome. In an embodiment, such as in the adenovirus according to the present invention XvirPSJL 1 or 2, the adenoviral nucleic acid coding for E4orf6 is partially or completely deleted, however, the complete nucleic acid coding therefor is contained in the expression cassette. Preferably, this will also be realised for the E1B55k (also referred to as E1 55Kd) protein and/or the E1A12S protein. The extent of the deletion is to be selected in preferred embodiments such that a maximum package size of about 103% of the maximum package size of the wildtype adenovirus is reached, although this limit is only a preferred limit. The possible deletions to be made in the adenoviral genome are only subject to limitations in preferred embodiments such as to make sure that still infectious and packed particles can be manufactured.

The precise extent of the deletions may be determined by the ones skilled in the art on the basis of the disclosure provided herein together with standard tests.

As a starting point for the construction of the adenoviruses described herein, any wildtype adenovirus may be used, but also other adenoviruses may be used provided that they are constructed in accordance with the technical teaching of the present invention. It is particularly preferred to have recourse to adenoviruses of subgroup C and within this group in turn to adenovirus 2 and adenovirus 5.

The terms E1B protein and E1B proteins, E4 protein and E4 proteins as well as E1A protein and E1A proteins are used herein in a synonymous manner, if not indicated to the contrary.

As used herein, the term "deregulated" YB-1 refers to a YB-1 molecule or YB-1 protein as described herein which is present in a form which is quantitatively and/or qualitatively different from YB-1 as normally present in cells, preferably in non-tumor cells. A deregulated YB-1 can be characterised and identified as such by particular viruses being able to replicate in the presence of deregulated YB-1 in a cellular background comprising such deregulated YB-1. The particular viruses in connection therewith are those the E1A protein of which is mutated and exhibits a transactivating function. Examples for these particular viruses are AD delta 24, dl 922-947, E1Ad/01/07 and CB 016 and/or those described by Howe, J. A et al., Molecular Therapy 2, 485-495, 2000; Fueyo J. et al., Oncogene 19, 2-12, 2000; Heise C. et al., Nature Medicine 6, 1134-1139, 2001; Balague, C et al., J. Virol. 75, 7602-7611, 2001; Bautista, D. S. et al., Virology 1991, 182, 578-596; Jelsma T. N. et al., Virology 1988, 163, 494-502; Wong, H. K. and Ziff E. B., J. of Virology 1994, 68, 4910-4920]. Such a cell and a cell, respectively, having such a background can be used for the replication of group I adenoviruses and/or group II adenoviruses. Additionally, tumors comprising such cells may be lysed by the adenoviruses according to the invention.

Furthermore, the present invention is based on the surprising finding that the DNA replication of E1A-modified adenoviruses in YB-1 nucleus-positive tumor cells is based on the activation of the E2-late promoter. E1A-modified adenoviruses are to be understood as those which (a) have, in YB-1 nucleus-negative cells, a reduced or no replication at all compared to wildtype, (b) have a transactivation activity on at least one viral gene, whereby the gene is particularly selected from the group comprising E1B-55kDa, E4orf6, E4orf3 and E3ADP, and/or (c) do not translocate cellular YB-1 into the nucleus by the adenovirus. Optionally, the adenoviruses used in accordance with the present invention have the further characteristic that the binding of the E1A protein encoded by the adenovirus is interfering with the binding of E2F to RB and is capable of dissolving the respective complex consisting of E2F and Rb. Adenoviruses which have one or several of the aforementioned features a) to c), preferably all of the features a) to c), are replication deficient in cells which do not have YB-1 in the nucleus.

Without wishing to be bound thereto, the present inventor assumes that the adenoviral E2 expression is not switched on to a sufficient manner by the E2-early promoter, i. e. the early E2 promoter, through the human cellular E2F transcription factor in connection with the replication of the viruses used in accordance with the present invention and in connection with the use in accordance with the present invention of the adenoviruses disclosed hererin. Under such circumstances the start of the replication is independent of the Rb status of the cells, i. e. the tumor cells which are infected by using the viruses disclosed herein and which are preferably lysed subsequently, may contain either functional as well as inactive Rb proteins. In addition, adenoviral replication using the adenoviruses disclosed herein or using the conditions disclosed herein, does not require any functional p53 protein, however is neither negatively affected by its presence. Insofar the technical teaching turns away from the principle underlying the use of oncolytic or tumorlytic adenoviruses of the type of AdΔ24, dl922-947, E1Ad/01/07, CB016 or those adenoviruses described, for example, in European patent EP 0 931 830, which had been made subject to one and/or several deletion(s) in the E1A protein under the assumption that intact functional Rb proteins would hinder an efficient in vivo replication and thus provide for adenoviral replication in vivo only in Rb-negative and Rb-mutated cells. These adenoviral systems of the prior art are based on E1A in order to control in vivo replication of adenoviruses by means of the early E2 promoter (E2-early promoter) and "free E2F". Nevertheless, these known viruses of the prior art may be used in accordance with the present invention for the replication in cells which contain YB-1 in the nucleus independent of the cell cycle, or in cells which comprise deregulated YB-1.

The viruses in particular adenoviruses described in said European patent EP 0 931 830 may be used in accordance with the present invention. More specifically, the viruses described in said patent are viruses which are replication deficient and which lack an expressed viral oncoprotein which is capable of binding a functional Rb tumor suppressor gene product. The adenovirus can particularly be any adenovirus which lacks expressed viral E1A oncoprotein which is capable of binding a functional tumor suppressor gene product, more particularly Rb. The viral E1A oncoprotein can exhibit an inactivating mutation, for example in the CR1 domain at the amino acid positions 30 to 85 in adenovirus Ad5, which is also referred to herein as Ad5, Ad 5, the nucleotide positions 697-790 and/or the CR2 domain at amino acid positions 120 to 130 in Ad 5, the nucleotide position 920 to 967 which are involved in the binding of p105 Rb protein, p130 and p107 protein. However, it is within the present invention that the adenovirus is of type 2 dl 312 or type 5 NT dl 1010.

A further feature of a part of the adenoviruses to be used in accordance with the present invention which are different from other adenoviruses of the present invention, is that they code for a viral oncogene which is also referred to herein as oncogene protein, whereby the oncogene protein is preferably E1A and whereby the oncogene protein is capable of activating at least one viral gene which has an impact on the replication of the virus and/or cell lysis of the cell infected by said virus. Preferably, the impact on the replication is such that the virus replicates better in the presence of the oncogene protein compared to the scenario where the oncogene protein of the respective virus is absent. This process is also referred to herein as transactivating and particularly as E1A transactivating in case the transactivation is mediated by E1A. The term "transactivate" or "transactivation" preferably describes the process that the respective viral oncoprotein has an impact on the expression and/or on the transcription of one or several other genes which are different from the gene coding for the viral oncogene protein itself, i. e. controls its/their expression and/or translation and particularly activates it/them. Such viral genes are preferably E1B55kDa, E4orf6, E4orf3 and E3ADP as well as any combination of the aforementioned genes and gene products, respectively.

A further, although only optional feature of the adenoviruses to be used in accordance with the present invention as well as of the adenoviruses of the present invention is their binding characteristics and the binding characteristics of particular ones of the proteins coded by them, respectively, to tumor suppressor Rb. Basically, it is within the present invention that the adenoviruses used in accordance with the present invention may or may not bind to Rb. The use of any of the two alternative embodiments of the adenoviruses is independent of the Rb status of the cells treated or the cells to be treated.

In order to confer to E1A the ability not to bind to Rb, the following deletions can be made to the E1A oncoprotein: deletion in the CR1 region (amino acid positions 30-85 in Ad5) and deletion of the CR2 region (amino acid positions 120-139 in Ad5). In doing so, the CR3 region is preserved and can exercise its transactivating function on the other early viral genes.

In order to confer to E1A the ability to bind to Rb, the following deletions to E1A oncoprotein, however, are basically possible: deletion of the CR3 region (amino acid positions 140-185); deletion of the N-terminus (amino acid positions 1-29); deletion of the amino acid positions 85-119; and deletion of the C-terminus (amino acid positions 186-289). The regions listed above do not interfere with the binding of E2F to Rb. The transactivating function remains intact, however, is reduced compared to wildtype Ad5.

It is also within the present invention, particularly with regard to the adenoviruses of the present invention, that the E1A protein, particularly the E1A12S protein is designed such that, in an embodiment, it is capable of binding to Rb and, in a different embodiment, is not capable of binding to Rb, whereby such E1A12S protein is an E1A protein and particularly an E1A12S protein in the meaning of the present invention which is nevertheless referred to in the prior art sometimes as modified E1A12S. The respective design of the E1A12S protein is within the skills of those of the art, particularly with regard to the aforementioned deletions of the E1A protein which is also referred to herein simply as E1A.

Such adenoviruses which are basically already known in the prior art and which do not show any transactivation, are generally regarded as replication deficient. However, it is the merit of the present inventor that he has recognised that such viruses are nevertheless capable of replicating in a suitable background, in particular a suitable cellular background. Such suitable cellular background is caused or provided by the presence of YB-1 in the nucleus, preferably a cell cycle independent presence of YB-1 in the nucleus, or by deregulated YB-1. The term cells or cellular systems as used herein in connection with each and any other aspect of the present invention, comprises fragments or fractions of cell extracts as well as cells which are present in vitro, in vivo or in situ. Insofar, the term cellular systems or cells also comprises cells which are present in cell culture, tissue culture, organ culture or in any tissue or organ in vivo and in situ, respectively, isolated, in groups or as part of tissues, organs or organisms, but which may also be present as such in a preferably living organism. The organism is preferably any vertebrate organism and more preferably a mammal. More preferably the organism is a human organism. Other preferred organisms are those disclosed in connection with the various aspects of the present invention.

In connection with the present invention the modified E1A oncoprotein of the various adenoviruses to be used in accordance with the present invention is capable of transactivating the early viral genes such as E1B55K, E4orf3, E4orf6, E3ADP in YB-1 nucleus-positive cells or cells which comprise deregulated YB-1. There are preferably no other changes made to the viral genome and the respective adenovirus may insofar correspond otherwise to a wildtype adenovirus or a derivative thereof.

The viruses disclosed herein which code or comprise a transactivating oncogene protein in the meaning of the present invention, comprise, for example, the adenoviruses AdΔ24, dl922-947, E1Ad/01/07, CB106 and/or the adenoviruses described in European patent EP 0 931 830 which are each capable of transactivating the early genes such as E1B, E2, E3 and/or E4 and which are comparable to the adenoviruses of wildtype, particularly wildtype Ad5. In these cases, a distinct region of the E1A protein is responsible for the transactivation. Within the various adenoviral serotypes there are three highly conserved regions within the E1A protein. The region CR1 from amino acid positions 41-80, CR2 from amino acid positions 120-139 and CR3 from amino acid positions 140-188. The transactivating function is mainly based on the presence of the CR3 region within the E1A protein. The amino acid sequence of CR3 is present in an unchanged manner in the above mentioned adenoviruses. This results in a transactivation of the early genes E1B, E2, E3 and E4 independent of whether YB-1 is present in the nucleus or in the cytoplasm.

In contrast thereto, the CR3 region has been deleted in the recombinant adenovirus dl520. Thus, dl520 expresses a so-called E1A12S protein which does not comprise the amino acid sequence of the CR3 region. Consequently, dl520 may exercise only a very weak transactivating function, particularly on the E2 region, and thus does not replicate in YB-1 nucleus-negative cells. In YB-1 nucleus-positive cells YB-1 is responsible for the transactivation of the E2 region and thus allows for an efficient replication of dl520. The use of systems like dl520 or systems originating therefrom for the purposes disclosed herein, is based thereon. A further important difference between the two previously described groups of adenoviruses such as, for example, delta 24 (also referred to herein as AdΔ24) and, for example, dl520, resides in the fact that the early genes E1B, E3 and E4 are more comprehensively transactivated in cells being YB-1 nucleus-positive cells independent of the cell cycle or in cells containing deregulated YB-1, compared to YB-1 nucleus-negative cells or cells which do not comprise deregulated YB-1. In contrast thereto, there are no or only minor differences in delta 24. The transactivation of dl520, more specifically of the E1A12S protein is, however, significantly reduced compared to wildtype adenovirus. This transactivation, however, is sufficient so as to provide for an efficient replication in YB-1 nucleus-positive cells as also shown in example 10. The design of the E1A protein as described herein and in particular as described in this connection, and of the nucleic acid coding therefor, such that the E1A protein has, compared to the wildtype oncogene protein E1A, one or several deletions and/or mutations, including and particularly preferably those designs of the E1A protein as described in connection with dl520 or AdΔ24, dl922 to 947, E1Ad/01/07, CB106 and/or the adenoviruses described in European patent EP 0 931 830, are embodiments of viruses, in particular of adenoviruses, the replication of which is controlled, preferably predominantly controlled by the activation of the E2-late promoter. Preferably, the deletion is such that it is selected from the group comprising deletions of the CR3 region and deletions of the N-terminus and deletions of the C-terminus. Further embodiments of the E1A protein which allow this kind of replication of adenoviruses, can be generated by the ones skilled in the art based on the disclosure provided herein. The embodiment of the E1A protein as described previously is an embodiment which may also be used in connection with the adenoviruses of the present invention which are also referred to herein as adenoviruses of the present invention or group I adenoviruses.

The adenoviruses of the present invention, particularly the group I adenoviruses, which are also referred to herein as derivatives and which may be used in accordance with the present invention, typically comprise an E1 deletion, an E1/E3 deletion and/or an E4 deletion, i. e. the corresponding adenoviruses are not capable of generating functionally active E1 and/or E3 and/or E4 expression products and corresponding products, respectively. Or in other words these adenoviruses are only capable of generating functionally inactive E1, E3 and/or E4 expression products, whereby a functionally inactive E1, E3 and/or E4 expression product is an expression product which is either not present as an expression product at all, either at the transcription level and/or at the translation level, or is present in a form which at least does not have one of the functions attributed to it in a wildtype adenovirus. This/these function(s) inherent to the expression product in wildtype adenovirus is/are known to the ones skilled in the art and, for example, described in Russell, W. C., Journal of Virology, 81, 2573-2604, 2000. Russell (supra) also describes design principles of adenoviruses and adenoviral vectors which are incorporated herein by reference. It is also within the present invention that the modified E1A oncoprotein, i. e. the no longer transactivating E1A protein and other proteins such as E1A12S, E1B-55K, E4orf6 and/or E3ADP (adenoviral death protein (ADP)) (Tollefson, A. et al., J. Virology, 70, 2296-2306, 1996) are expressed in such vector either alone or in any combination. The individual mentioned genes as well as the transgenes disclosed herein, may be, independently from each other, cloned into the E1 and/or E3 and/or E4 region and expressed using a suitable promoter or under the control of a suitable promoter. Basically, each of the E1, E3 and E4 region is suitable as cloning site within the adenoviral nucleic acid, whereby the region which is not used for the cloning can either be present, or partially and/or completely deleted. In case these regions are present, in particular are completely present, it is within the present invention that these are either intact and preferably provide a translation product and/or a transcription product, and/or are not intact and preferably do not provide a translation product and/or transcription product. In embodiments suitable promoters are those as disclosed herein in connection with the controlling and expression, respectively, of E1A, in particularly of the modified E1A.

Finally, in an embodiment, the group II adenoviruses used in accordance with the present invention are E1B deficient, particularly E1B 19 kDa deficient. The term deficient as generally used herein refers to a condition, wherein the E1B does not exhibit all of the characteristics of the wildtype E1B and lacks at least one of these characteristics.

The adenovirus BCL2-homologue E1B19k avoids the E1A induced apoptosis by interaction with the pro-apoptotic proteins Bak and Bax. Because of this a maximum replication and/or particle formation is possible in infected cells (Ramya Sundararajan and Eileen White, Journal of Virology 2001, 75, 7506-7516). The absence of E1B 19k results in a better release of virus as, if present, it assumingly minimizes the function of the adenoviral death protein. The virus induced cytopathic effect is increased by such deletion (Ta-Chiang Liu et al., Molecular Therapy, 2004) and thus results in a more pronounced lysis of infected tumour cells. Additionally, the absence of E1B19k causes that TNF-alpha does not have any effect on the replication of such adenoviruses in tumour cells whereas in normal cells the treatment results in a less pronounced replication and release of infectious virus. Insofar both selectivity and specificity are increased (Ta-Chiang Liu et al., Molecular Therapy, 2004, 9, 786-803).

At least some embodiments of the group II adenoviruses as used in accordance with the invention disclosed herein, are as such known in the art. The adenoviruses used in accordance with the invention are preferably recombinant adenoviruses, particularly also if, compared to the wildtype, a change has been made in the sense of the technical teaching provided herein. It is within the skills of those of the art to delete and mutate, respectively, the adenoviral nucleic acid sequences which are irrelevant for the invention. Such deletions may be related to, e. g. a part of the E3 and E4 coding nucleic acids as also described herein. A deletion of E4 is particularly preferred provided that such deletion does not extend to the protein E4orf6, in other words the adenovirus to be used in accordance with the invention codes for E4orf6. In preferred embodiments, these adenoviral nucleic acids may still be packed into viral capsids and thus form infectious particles. This is also true for the use of the nucleic acids in accordance with the invention. Generally it is also to be acknowledged that the adenoviral systems may be deficient with regard to single or several expression products. In connection therewith it is to be taken into consideration that this, in connection with both the group I adenoviruses and the group II adenoviruses, may be caused by the mutation or deletion of the nucleic acid coding the expression product, whereby such mutation and deletion, respectively, is either a complete one or performed to the extent that no expression product is formed anymore or by the regulatory elements and elements controlling the expression such as promoters and transcription factors being missing or being active in a way different from wildtype, either at the level of the nucleic acid (lack of a promoter; cis acting elements) or at the level of the translation and transcription system (transacting elements), respectively. Particularly the latter aspect may depend on the respective cellular background.

Apart from using adenoviruses which are as such already known, in accordance with the present invention also novel adenoviruses such as group II adenoviruses may be used for the purposes already disclosed for the other adenoviruses described herein. The new adenoviruses of the invention result from the technical teaching provided herein. Particularly preferred representatives are, for example, the viruses Xvir03 and Xvir03/01 which are depicted in FIGS. 16 and 17, the design principle of which is further illustrated in examples 11 and 12.

In case of vector Xvir03 a CMV promoter was cloned into the E1 region which controls the nucleic acids for E1B 55k and E4orf6 which are separated by an IRES sequence. In connection therewith, the E3 region and the E4 region can be deleted and/or be present and intact. Due to the cloning of these two genes into the virus and due to the gene products generated therefrom, respectively, a high replication efficiency results which factually corresponds to the one of wildtype viruses, whereby the selective replication in cells, preferably tumor cells, is maintained insofar as a replication occurs particularly in YB-1 nucleus-positive cells and more particularly in those cells which comprise deregulated YB-1 in the sense of the present disclosure. Cells in which deregulated YB-1 is present are, in an embodiment, cells which show an increased expression of YB-1, preferably compartment independent expression of YB-1, compared to normal or non-tumour cells. However, the introduction of E1B 55k and E4orf6 by cloning can also be made into the E4 region, whereby the E3 region can be either intact or can be deleted.

A further development of virus Xvir03 is virus Xvir03/01 into which in a preferred embodiment therapeutic genes or transgenes have been cloned under the control of a specific promoter, in particular a tumor-specific or tissue-specific promoter. In connection therewith the E3 and E4 region can be deleted and/or be resent and intact. In connection with such virus also the E4 region is functionally inactive, is preferably deleted. The transgenes described herein may also be cloned into the E4 region, whereby this can be done either alternatively or in addition to the cloning of the transgenes into the E3 region.

The transgenes described herein and particularly described in the following, may also be expressed in connection with or by the adenoviruses of the present invention, i. e. group I adenoviruses and their nucleic acids, respectively, or the replication systems of the invention and are thus comprised in connection with an expression cassette comprising a promoter and a nucleic acid sequence, whereby such nucleic acid sequence codes for one or several of said transgenes. The E1, E3 and/or E4 regions are particularly suitable cloning sites in the adenoviral genome, however, the cloning sites are not limited thereto. Transgenes, as used herein, may be therapeutic genes or viral genes, preferably adenoviral genes, which, preferably, are not contained in the genome of wildtype adenovirus or are not present at the site in the genome where they are present now in the particular virus.

The nucleic acid coding for YB-1 which may be part of the adenoviruses in an embodiment of the adenoviruses to be used in accordance with the invention, particularly group II adenoviruses, but also of the adenoviruses according to the invention, i. e. group I adenoviruses, may comprise a nucleic acid sequence which mediates the transport of YB-1 into the nucleus. The nucleic acids, adenoviruses and adenoviral systems according to the invention as well as the adenoviruses known in the prior art such as, for example, Onyx-15, AdΔ24, dl922-947, E1Ad/01/07, CB016, dl 520 and the adenoviruses described in patent EP 0 931 830 may be used, as adenoviruses and adenoviral systems, respectively, and the corresponding nucleic acids, in combination with these nucleic acids in accordance with the invention. Suitable nucleic acid sequences mediating nuclear transport are known to the ones skilled in the art and, for example, described in Whittaker, G. R. et al., Virology, 246, 1-23, 1998; Friedberg, E. C., TIBS 17, 347, 1992; Jans, D. A. et al., Bioassays 2000 Jim; 22(6): 532-44; Yoneda, Y., J. Biochem. (Tokyo) 1997 May; 121(5): 811-7; Boulikas, T., Crit. Rev. Eukaryot. Gene Expr. 1993; 3(3): 193-227; Lyons R H, Mol. Cell Biol., 7 2451-2456, 1987). The nucleic acid sequences mediating nuclear transport may realise different principles. One such principle is that YB-1 forms a fusion protein with a signal peptide or is provided with such signal peptide and is transferred into the cellular nucleus because of the signal peptide, whereupon the replication of the adenoviruses in accordance with the invention occurs.

A further principle which may be used in the design of the adenoviruses to be used in accordance with the invention, particularly group II adenoviruses, but also with the adenoviruses in accordance with the present invention, i. e. the group I adenoviruses, is providing YB-1 with a transport sequence which results in the transfer or translocation of YB-1 into the cellular nucleus, preferably starting from a synthesis in the cytoplasm, and prompts viral replication there. An example for a particularly effective nucleic acid sequence mediating transport into the nucleus, is the TAT sequence of HIV which is, for example, described together with other suitable nucleic acid sequences of that kind in Efthymiadis, A., Briggs, L J, Jans, D A., JBC 273, 1623-1628, 1998. It is within the present invention that the adenoviruses to be used in accordance with the invention, particularly group II adenoviruses, but also the adenoviruses according to the present invention, i. e. group I adenoviruses, comprise the nucleic acid sequences which code for the peptides which mediate nuclear transport.

It is within the present invention that YB-1 is present in its full length, particularly in a form which corresponds to wildtype YB-1. Furthermore, it is within the invention that YB-1 is used or present as a derivative, for example in a shortened or truncated form. A YB-1 derivative as may be used or may be present in connection with the present invention, is a YB-1 which is preferably capable of binding to the E2 late promoter and thus activates gene expression of the adenoviral E2 region. Such derivatives particularly comprise the YB-1 derivatives disclosed herein. Further derivatives can be generated by deletion of single or several amino acids at the N-terminus, the C-terminus or within the amino acid sequence. It is within the present invention that also YB-1 fragments are used as YB-1 proteins in the sense of the present invention. In the paper of Jürchott K et al. [JBC 2003, 278, 27988-27996] various YB-1 fragments are disclosed which are characterised by deletions at the C- and the N-terminus. The distribution of the various YB-1 fragments has shown that both the cold shock domain (CSD) as well as the C-terminus is relevant for the cell cycle regulated transport of YB-1 into the cellular nucleus. It is thus within the present invention that a shortened YB-1 (herein also referred to as YB-1 protein) in connection with the inventive expression of E1B55k and E4orf6 migrates better into the nucleus and thus induces a stronger CPE without necessarily binding better to the E2-late promoter compared to native YB-1, whereby it cannot be excluded that also a shortened YB-1 migrates better into the nucleus and is causing both effects, i. e. induces CPE and binds to the E2-late promoter. Finally, such shortened YB-1 fragments may also migrate better into the nucleus and bind more efficiently to the E2-late promoter without inducing a better CPE. It is also within the present invention that shortened YB-1 proteins and fragments, respectively, comprise further sequences as disclosed herein in connection with the full length YB-1, in particular cell localisation signal sequences (NLS) and the like.

In connection with the present invention it is possible that the adenoviruses used in accordance with the invention, particularly group II adenoviruses, but also group I adenoviruses and the nucleic acids coding therefor, is any respective adenoviral nucleic acid which as such or in combination with further nucleic acid sequences results in a replication event. It is possible, as explained herein, that the sequences and/or gene products necessary for replication are provided by helper viruses. To the extent it is referred to coding nucleic acid sequences and said nucleic sequences are nucleic sequences which are known, it is within the present invention that not only the identical sequence is used but also sequences derived therefrom. Herein, derived sequences shall mean in particular any sequences which still result in a gene product, either a nucleic acid or a polypeptide which has a function which corresponds to a or the function of the non-derived sequence. This can be tested by routine tests known to the one skilled in the art. An example for such derived nucleic acid sequences are those nucleic acid sequences which code for the same gene product, in particular for the same amino acid sequence, which, however, have a different base sequence due to the degeneracy of the genetic code.

With regard to the adenoviruses according to the invention of group II and/or the corresponding adenoviral replication system according to the invention and their use in accordance with the invention, respectively, in an embodiment the adenoviral nucleic acid is deficient for the expression of the oncogene protein, in particular is E1A protein deficient, i. e. does either not code for the 12S E1A protein (herein also referred to as E1A12S protein) or for the 13S E1A protein (herein also referred to as E1A13S protein) or does not code for both the 12S E1A protein and the 13S E1A protein, or is modified, as defined herein, if not indicated to the contrary, and that the adenoviral replication system further comprises a nucleic acid of a helper virus, whereby the nucleic acid of the helper virus comprises a nucleic acid sequence which codes for the oncogene protein, particularly the E1A protein, which has the following characteristics and confers the following characteristics to the adenovirus, respectively: It is preferably non-replicating in YB-1 nucleus-negative cells but is replicating in cells which are independent of the cell cycle in YB-1 nucleus-positive or in cells exhibiting deregulated YB-1, is transactivating at least one viral gene, in particular E1B55kDa, E4orf6, E4orf3 and/or E3ADP, in YB-1 nucleus-positive cells, and/or does not transfer cellular YB-1 into the nucleus. It is within the present invention that the transgenes described herein are either individually or collectively coded and/or expressed by the helper virus. This applies to helper viruses for both group I adenoviruses and group II adenoviruses.

Group I adenoviruses and/or group II adenoviruses, but also virus group § 1 and § 3, are characterised by the various nucleic acids and gene products, respectively, disclosed herein and may otherwise comprise all those elements known to the ones skilled in the art and which are inherent to the wildtype adenoviruses (Shenk, T.: Adenoviridae: The virus and their replication. Fields Virology, vol. 3, editors Fields, B. N., Knipe, D. M., Howley, P. M. et al., Lippincott-Raven Publishers, Philadelphia, 1996, chapter 67).

As already mentioned, group I and/or group II adenoviruses are capable of replicating in such cells and cellular systems, which have YB-1 in the nucleus. For the question whether also these adenoviruses used in accordance with the invention are capable of replicating and are thus capable of tumor lysis, the status of the cells with regard to the presence or absence of Rb, i. e. the retinoblastome tumor suppressor product, is irrelevant. Furthermore, for the use of said adenoviruses in accordance with the present invention, it is not necessary to take into account the p53 status of the infected cells, of the cells to be infected or of the cells to be treated as, when using the adenoviral systems disclosed herein in connection with YB-1 nucleus-positive cells, i. e. cells having YB-1 in the nucleus independent of the cell status, the p53 status as well as the Rb status does not have any impact on the replication of the adenovirus for the practising the technical teaching disclosed herein.

The transactivating oncogene and oncogene protein, respectively, in particular E1A, preferably of the group II adenoviruses, can be either under the control of the proprietary natural adenoviral promoters and/or be controlled through a tumor-specific or tissue-specific promoter. Suitable non-adenoviral promoters can be selected from the group comprising cytomegalovirus promoter, RSV (rous sarcoma virus) promoter, adenovirus-based promoter Va I and the non-viral YB-1 promoter (Makino Y. et al., Nucleic Acids Res. 1996, 15, 1873-1878). Further promoters which may be used in connection with any aspect of the invention disclosed herein, are the telomerase promoter, the alpha-fetoprotein (AFP) promoter, the caecinoembryonic antigen promoter (CEA) (Cao, G., Kuriyama, S., Gao, J., Mitoro, A., Cui, L., Nakatani, T., Zhang, X., Kikukawa, M., Pan, X., Fukui, H., Qi, Z. Int. J. Cancer, 78, 242-247, 1998), the L-plastin promoter (Chung, I., Schwartz, P E., Crystal, R C., Pizzorno, G, Leavitt, J., Deisseroth, A B. Cancer Gene Therapy, 6, 99-106, 1999), argenine vasopressin promoter (Coulson, J M, Staley, J., Woll, P J. British J. Cancer, 80, 1935-1944, 1999), E2f promoter (Tsukada et al., Cancer Res., 62, 3428-3477, 2002), uroplakin II promoter (Zhang et al., Cancer Res., 62, 3743-3750, 2002) and the PSA promoter (Hallenbeck P L, Chang, Y N, Hay, C, Golightly, D., Stewart, D., Lin, J., Phipps, S., Chiang, Y L. Human Gene Therapy, 10, 1721-1733, 1999), tyrosinase promoter (Nettelbeck, D M. Anti-Cancer Drugs, 14, 577-584, 2003), cyclooxygenase 2 promoter (Nettelbeck, D M., Rivera, A A, Davydova, J., Dieckmann, D., Yamamoto, M., Curiel, D T. Melanoma Res., 13, 287-292, 2003) and inducing systems such as tetracycline (Xu, X L., Mizuguchi, H., Mayumi, T., Hayakawa, T. Gene, 309, 145-151, 2003). Furthermore, the YB-1 dependent E2 late promoter of adenoviruses as described in German patent application DE 101 50 984.7 is a promoter which may be used in connection with the present invention.

It is within the present invention that the various promoters described above are also used in connection with the various embodiments of the adenoviruses in accordance with the invention, preferably the group I adenoviruses but also in connection with virus group § 1 and virus group § 2, particularly in case a promoter is to be used which is different from the one which controls the expression of the respective protein or expression product in wildtype adenoviruses. The aforementioned promoters are thus suitable heterologous promoters in the meaning of the present invention. In preferred embodiments of the adenoviruses in accordance with the invention, particularly the group I adenoviruses, it is contemplated that when applying, directly or indirectly, the adenoviruses in connection with or to cells having either YB-1 in the nucleus in a cell cycle independent manner or not having YB-1 in the nucleus un a cell cycle independent manner but comprising deregulated YB-1 as defined herein, this occurs such that the expression of the E1B protein and/or the E4 protein starts from such heterologous promoters, whereby preferably, but not exclusively, the expression of the E1A protein is controlled by YB-1. The expression of the E1A protein is in this and other embodiments under the control of a YB-1 controllable promoter such as for example the adenoviral E2-late promoter. This is also true in that case where the E1B protein and/or the E4 protein is/are expressed in an expression cassette.

In preferred embodiments of the adenoviruses in accordance with the invention, particularly the group I adenoviruses, it is contemplated that when applying the adenoviruses in connection with cells which do not contain YB-1 in the nucleus, particularly not in a cell-independent manner, and which do not contain any deregulated YB-1, the promoter is each and independently a tumor-specific, organ-specific or tissue-specific promoter. In connection therewith it is sufficient when at least one of the promoters which control the expression of the E1B protein, the E4 protein and/or the E1A protein, is such a specific promoter. By this tumor, organ and tissue specificity, it is ensured that replication of the adenoviruses in accordance with the invention happens only in cells of the respective tumor, organ or tissue and that, apart from that, no further tissue is damaged by the replication of the adenoviruses such as, for example, is lysed. Preferably, still a second and more preferably all three proteins are controlled by such tumor-specific, organ-specific or tissue-specific promoters. Using such adenoviruses it is possible to lyse also those cells which do not form a tumor or which cannot develop into such tumor, but which are for other reasons such as medicinal reasons to be destroyed or to be removed from the organism, preferably a mammalian and more preferably an human organism, for example because they produce an undesired factor or produce such factor at a too high level.

Virus Group § 3

This group of viruses is based on the surprising finding that the viruses according to the invention, i. e. viruses which lack a functional E1-region as present in wildtype adenoviruses, and which at the same time comprise a transporter and in particular code for such transporter which may transport or translocate YB-1 into the nucleus, are capable of replicating in cells which either contain YB-1 in the nucleus in a cell cycle independent manner, or in cells which have or comprise deregulated YB-1.

Furthermore, the present inventor has found that the viruses according to the present invention may also replicate independently of E1A13S, in particularly if the replication is mediated through YB-1. The replication occurs under such conditions in particular in the afore-described cells. As used herein, cell which contain YB-1 in the nucleus, preferably contain YB-1 in the nucleus independent of the cell cycle, are also those cells which contain YB-1 in the nucleus due to the use of the viruses in accordance with the present invention and in particular due to the infection of the cells with them.

Finally, the present inventor has also recognized that protein IX is an important factor in particular for the efficacy of the viruses in accordance with the present invention, particularly when used as oncolytic viruses, and that the constructs disclosed herein provide for an expression of this factor which results in a high-level particle formation also in YB-1-mediated E1A13S-independent viral replication. In so far this group of viruses also comprises a virus replicating in a YB-1 dependent manner, whereby the virus comprises or encodes for protein IX.

The viruses in accordance with the present invention comprise a transporter for the transport of YB-1 to the cell nucleus. In a preferred embodiment the transporter is a protein, preferably a viral protein. The YB-1 which is transported into the nucleus of a cell by the transporter, is preferably a deregulated YB-1, in particular as defined herein. However, it is also within the present invention that YB-1 is one that is encoded, alternatively or additionally, to the deregulated YB-1 by the virus in accordance with the present invention and is expressed in the cell which is infected by the virus. Insofar the respective features as outlined in connection with the virus group § 2 herein, are also applicable to virus group § 3.

The cells, in which the transporter of the viruses in accordance with the present invention transports YB-1 into the nucleus, are preferably those which contain regulated YB-1.

It is within the skills of those of the art to assess whether and if so a virus comprises such a transporter or codes therefor. In connection therewith, in one embodiment, a cell which comprises YB-1 in the nucleus in a cell cycle independent manner, such as for example the cervix carcinoma cell line HeLa or the osteosarcoma cell line U2OS can be used and subsequently be determined, whether due to the infection and the subsequent replication of the virus the corresponding infected cell contains YB-1 in the nucleus. In an alternative embodiment a cell is used as a cell in connection therewith which contains deregulated YB-1. YB-1 can be detected under such experimental conditions in the nucleus using the means described herein, in particular an antibody directed against YB-1, as can be made by the one skilled in the art. If, under the influence of the virus, YB-1 is detected in the cell nucleus, the tested virus comprises the transporter.

It is within the present invention that the E1A-region is "minus" with regard to one or both protein groups coded by the E1-region in the meaning of the afore-mentioned embodiments. Said two protein groups are the group of E1A proteins, in particular the E1A13S protein, also referred to herein as E1A13S, and the E1A12S protein, also referred to herein as E1A12S, and the group of E1B proteins, in particular the E1B55k protein, also referred to herein as E1B55k, the E1B19k protein, also referred to herein as E1B19k, and the protein IX.

It is within an embodiment of the present invention that the virus is E1A13S-minus if E1A13S is under the control of a promoter which is different from the E1A promoter, preferably the adenoviral E1A-promoter and more preferably the adenoviral E1A-promoter of the wildtype; the virus is E1A12S-minus if E1A12S is under the control of a promoter which is different from the E1A promoter, preferably the adenoviral E1A-promoter and more preferably the adenoviral E1A promoter of the wildtype. The virus is E1B55k-minus if E1B55k is under the control of a promoter which is different from the E1B promoter, preferably the adenoviral E1A promoter and more preferably the adenoviral E1B promoter of the wildtype; the virus is E1B19k-minus if E1B19k is under the control of a promoter which is different from the E1B promoter, preferably the adenoviral E1B promoter and more preferably the adenoviral E1B promoter of the wildtype; and it is protein IX-minus if protein IX is under the control of a promoter which is different from the E1B IX-promoter, preferably the adenoviral E1B IX-promoter and more preferably the adenoviral E1B IX-promoter of the wildtype or if it is under the control of the E1B IX-promoter, however said promoter is inactive due to the lack of in particular viral factors which direct the activity of the E1B IX-promoter; the latter is thus an example that the regulatory context is changed, more specifically that the regulatory context is indirectly changed or changed at a higher integration or regulatory level. In general, the term changed regulatory context thus comprises also changes which are either indirectly or at a higher integration or regulatory level active, however, in any case are different from the particularities of the wildtype, in particular the wildtype adenovirus. In connection with a protein or protein function and the respective nucleic acid(s)

coding therefore being "minus", it is to be acknowledged that such protein, protein function and nucleic acid(s) coding therefore may nevertheless be contained in preferred embodiments of the viruses, but in a context which is different from the respective context in the wildtype virus. Such protein, protein function and respective nucleic acid(s) is under such conditions also referred to herein as heterologous.

In an embodiment of the present invention the virus is E1A13S-minus. In a further embodiment the virus is also E1A12-minus. In connection therewith it is particularly preferred when the viral E1A12S is under the control of a promoter the activity of which is controlled by YB-1, in particularly is activated by YB-1. These promoters are referred to herein as YB-1-dependent promoters. A particularly preferred YB-1-dependent promoter is the adenoviral E2-late promoter. By this construction it is ensured that E1A12S is activated in the course of viral replication only when YB-1 is present in the nucleus. This is achieved in case of cells with deregulated YB-1 through the transporter of the viruses in accordance with the present invention, which translocates the deregulated YB-1 into the nucleus of the infected cell. Due to the chronologically reversed expression of the viral transporter and of E1A12S compared to the expression in wildtype, E1A12S is specifically only expressed in such cells which contain YB-1 in a deregulated form and thus limit replication of the virus to these cells and, consequently, limit the lysis to particularly these cells which represents a significant advantage of this viral design in terms of safety.

Under these circumstances the particle number in connection with YB-1-dependent replication was to be increased. The present inventor has recognized that protein IX also plays an important role in YB-1 dependent replication and that its expression is not effected by the aforedescribed chronological change in the expression of the transporter, which is preferably provided by the proteins of the E1B region, and of E1A12S when realizing the designs disclosed herein. The adenoviral designs described in the prior art for YB-1-dependent replication exhibited despite outstanding oncolytic activities a particle formation which was low for some applications which, for example, required a further application of the oncolytic virus. Such further application of viruses is in principle possible, however is not desired in the majority of cases. Particle formation could significantly be improved by the constructs described herein, in particular with the constructs described herein in connection with virus group § 3.

The adenoviral protein IX cements the capsid structure and is important for the packaging of viral DNA into virions (Boulanger et al., Journal of Virology, 44, 783-800, 1979; Jones und Shenk, Cell, 17, 683-689, 1979). The gene is located in the viral genome between positions 3581 and 4071 (Colby und Shenk T, Journal of Virology, 1981, 39, 977-980), whereby the gene for protein IX is expressed only from replicating DNA-molecules (Matsui T et al., Molecular and Cellular Biology, 1986, 6, 4149-4154).

Virus Xvir03-3'UTR which is described in the prior art and which performs a YB-1-dependent replication, comprises both the promoter as well as the sequence for protein IX as has been shown in analysis performed in the meantime in connection with the present invention, as the 3'UTR sequence contains the same. However, the protein is only weakly expressed in tumour cells and results in a comparatively low particle formation compared to wildtype virus. The virus Xvir03-3'UTR expresses the viral proteins E1B55k and E4orf6 as mediated by the heterologous CMV promoter (company Clonetech: Plasmid pShuttle) introduced into Xvir03-3'UTR. Rather than the CMV promoter, also all those promoters described herein as disclosed in connection with the expression of E1A may be used. The open reading frames of both genes are linked to each other by means of a so-called IRES sequence (engl. internal ribosomal entry site) (Pelletier, J. and Sonenberg, N. Nature, 1988, 334, 320-325). This element (company Novagen: pCITE) allows the expression of two proteins from one mRNA. A further option for the expression of two proteins from one RNA is the use of short peptides (2A), which are derived from foot and mouth disease virus (Pablo de Felipe, Genetic Vaccines and Therapy, 2004, 2, 13). This element can in principle be used as an alternative to the regulatory IRES sequence in the various embodiments described herein.

From the regulatory background of the expression of protein IX in YB-1-dependently replicating viruses and in particular adenoviruses, which has been unknown prior to the present application, the present inventor recognized that the expression of protein IX in connection with YB-1-dependent replication and in case of viruses which replicate in a YB-1-dependent manner, can basically be provided by the following different strategies:

1. By means of an independent promoter which preferably controls the expression of protein E1A12S and protein E1B19k, respectively.

The independent promoter is preferably a promoter which is different from the E1B IX promoter. Preferably the independent promoter is selected from the group comprising tissue-specific, tumour-specific, YB-1-dependent and viral promoters.

2. Controlling the expression of protein IX by E1A12S. The induction of the S phase in an infected cell occurs by the expression of the E1A12S protein which results in protein IX being activated by its natural promoter.

It is within the present invention that in principle such promoters are used for the expression of the transporter which are different from the promoter which controls the expression of the transporter in the wildtype virus. In preferred embodiment this means that E1B55k is controlled by a promoter different from E1B, and E4orf6 by a promoter different from the E4 promoter. In a further embodiment the promoter is a promoter which is E1A independent, i. e. its activity is not influenced by E1A. Preferred promoters are thus preferably tissue-specific promoters, tumour-specific promoters and viral promoters, in particular those described herein.

YB-1 dependent promoters which can be used within the present invention, in particular in connection with any aspect thereof, comprise, but are not limited to, the adenoviral E2-late promoter, the MDR-promoter [Stein et al, J. Biol. Chem, 2001, 276, 28562-28569;] as well as the DNA polymerase alpha-promoter [En-Nia et al, J. Biol. Chem., 2004, Epub ahead of print].

Suitable non-adenoviral promoters which are useful within the present invention, can be selected from the group comprising cytomegalovirus promoter, RSV-(Rous sarcoma Virus)-Promotor, adenovirus-based promoter Va I and the non-viral YB-1-promoter (Makino Y. et al., Nucleic Acids Res. 1996, 15, 1873-1878). Further promoters which may be used in connection with any aspect of the invention disclosed herein, are the telomerase promoter, the alpha-fetoprotein (AFP)-promoter, the caecinoembryonic antigen promoter (CEA) (Cao, G., Kuriyama, S., Gao, J., Mitoro, A., Cui, L., Nakatani, T., Zhang, X., Kikukawa, M., Pan, X., Fukui, H., Qi, Z. Int. J. Cancer, 78, 242-247, 1998), the L-plastin-promoter (Chung, I., Schwartz, P E., Crystal, R C., Pizzorno, G, Leavitt, J., Deisseroth, A B. Cancer Gene Therapy, 6, 99-106, 1999), argenine-vasopressin-promoter (Coulson, J M, Staley, J., Woll, P J. British J. Cancer, 80, 1935-1944, 1999), E2f-promoter (Tsukada et al. Cancer Res., 62, 3428-3477), uroplakin II promoter (Zhang et al., Cancer Res., 62, 3743-3750, 2002) and the PSA promoter (Hallenbeck P L, Chang, Y N, Hay, C, Golightly, D., Stewart, D., Lin, J., Phipps, S., Chiang, Y L. Human Gene Therapy, 10, 1721-1733, 1999). Furthermore the YB-1 dependent E2-late promoter of adenoviruses as disclosed in German patent application DE 101 50 984.7 is a promoter which may be used within the present invention.

The viruses in accordance with the present invention allow for a significantly increased particle formation compared to YB-1 dependent viruses of the prior art. Preferably, the particle formation is increased by a factor of 2 to 50, more preferably by a factor of 10 to 50.

Finally, in a preferred embodiment, the adenovirus used in accordance with the invention is deficient with regard to E1B, in particular E1B19k deficient. As generally used herein, the term deficient refers to a condition in which E1B does not exhibit the entirety of characteristics inherent to the wildtype and at least one of these characteristics is lacking. The adenovirus BCL2-homologue E1B19k prevents the E1A induced apoptosis by interaction with the pro-apoptotic proteins Bak and Bax. Thus the maximum replication and/or particle formation is possible in infected cells (Ramya Sundararajan and Eileen White, Journal of Virology 2001, 75, 7506-7516). The absence of E1B19k results in a better release of the viruses as, if present, minimizes the function of the adenoviral death protein. The virus induced cytopathic effect is increased by such deletion (Ta-Chiang Liu et al., Molecular Therapy, 2004) and results in a stronger lysis of the infected tumour cells. Additionally, the absence of E1B19k results in TNF-alpha not having any effect on the replication of such recombinant adenoviruses in tumour cells, whereas the treatment results in a reduced replication and release of infectious viruses in normal cells. Thus the selectivity and specificity are increased (Ta-Chiang Liu et al., Molecular Therapy 2004, 9, 786-803).

The following aspects, features and embodiments are applicable to all of the viruses used in accordance with the present invention and to be used in accordance with the present invention, in particular adenoviruses.

As used herein, the term transgene comprises in an embodiment all those genes which are either not contained in the virus, in particular the adenovirus of wildtype and more preferably adenovirus Ad5 wildtype, or contained in a different regulatory context, as defined herein. It is within an embodiment of the present invention that one or several of the transgenes as described herein are coded and/or expressed by one or several helper viruses.

The findings described herein and the methods, uses or nucleic acids, proteins, replication systems and the like, respectively, are not necessarily limited to adenoviruses. In principle such systems also exist in other viruses which are herewith also encompassed and disclosed.

When using the viruses in accordance with the present invention or when using in accordance with the present invention the viruses described replicate to an extent comparable to the one of wildtype viruses, preferably wildtype adenovirus, whereby such extent can already be realized with an infection number of 1 to 10 pfu/cell compared to 10 to 100 pfu/cell according to the prior art.

The viruses in accordance with the present invention provide for a significantly increased particle formation compared to the YB-1-dependent viruses of the prior art. Preferably, the particle formation is increased by a factor of 2 to 50, more preferably by a factor of 10 to 50.

It is within the skills of those of the art to delete and mutate, respectively, the adenoviral nucleic acid sequences which are irrelevant for the invention. Such deletions can, for example, be related to a part of the E3 and E4 coding nucleic acid as also described herein. In case of a deletion of E4 it is particularly preferred if it does not extent to the protein E4orf6, which means that the adenovirus to be used in accordance with the present invention codes for E4orf6. In preferred embodiments these adenoviral nucleic acids may still be packed into the viral capsid and thus form infectious particles. This is also true for the use of the nucleic acids in accordance with the present invention. In general it is to be noted that the adenoviral systems may be deficient with regard to single or several expression products. In connection therewith it is to be taken into consideration that this may, on the one hand, be based on the fact that the nucleic acid coding the expression product is completely mutated or deleted or to the extent mutated or deleted that essentially no expression product is formed any more or that the regulatory and the expression controlling elements such as promoters or transcription factors are lacking or are active in a manner different from wildtype, either at the level of the nucleic acid (lack of promoter; cis-acting elements) or at the level of the translation or transcription system (trans-acting elements). In particular the last aspect may depend on the respective cellular background.

In a further aspect of the present invention the viruses, viral systems, the replication systems coding or comprising the same, the nucleic acid(s) coding therefore, the vectors comprising the same are used for the manufacture of a medicament. Preferable the medicament is for the treatment of the diseases described herein, in particular described in connection with the use in accordance with the present invention of the various viruses described herein.

The use of the adenoviruses in accordance with the present invention as medicaments and in particular in connection with systemic administration can be improved by a suitable targeting of the adenoviruses. The infection of tumor cells by adenovirus depends to a certain extent, among others, on the presence of the coxsackievirus-adenovirus receptor CAR and particular integrins. If these are strongly expressed in cells, in particular tumor cells, an infection is already possible at very low titers (pfu/cell). Different strategies have so far been followed in order to achieve a so called re-targeting of the recombinant adenovirus by, for example, insertion of heterologous sequences in the fiber knob region and the C-terminus of protein IX, use of bi-specific antibodies, coating of the adenoviruses with polymers, introduction of ligands in the Ad-fibre, substitution of the serotype 5 knop and serotype 5 fiber shaft, respectively, and knop by the serotype 3 knop and Ad35 fiber shaft and knop and modification of the penton base (Nicklin S. A. et al., Molecular Therapy 2001, 4, 534-542; Magnusson, M. K. et. al., J. of Virology 2001, 75, 7280-7289; Barnett B. G. et al., Biochimica et Biophysica Acta 2002, 1575, 1-14; Dimitrev I P et al., Journal of Virology, 2002, 76, 6893-6899; Mizuguchi and Hayakawa, Human Gene Therapy, 2004, 15, 1034-1044). Realizing such further designs and characteristics in connection with the adenoviruses in accordance with the present invention and the adenoviruses used in accordance with the present invention, in their various embodiments of the present invention, is within the present invention.

It will be acknowledged that some of the viruses described herein comprise one or several transgenes as described herein. Such transgenes are either important or helpful with regard to the mode of action, more precisely mode of replication of the viruses, or with regard to their use as medicaments in which case the transgenes are, in some embodiments, therapeutic genes.

The various transgenes, including E1B55kD, E4orf6, ADP and the like, in particular if they are viral genes, may in principle be cloned from any respective virus, preferably adenovirus and more preferably adenovirus Ad5. A variety of plasmids are additionally described in the prior art which contain the respective genes and from which these may accordingly be taken and introduced into both the adenoviruses in accordance with the present invention as well as the viruses to be used in accordance with the present invention. An example for a plasmid expressing E1B55kD is, for example, described by Dobbelstein, M. et al., EMBO Journal, 16, 4276-4284, 1997. The coding region of the E1B55K gene can, for example, can be excised together with the 3' non-coding region (the 3'UTR region lies preferably at about base position 3507-4107 of the adenovirus wildtype genome) of this gene by means of Bam HI from the plasmid pDCRE1B. The respective fragment comprising the E1B55kD gene as well as the 3' non-coding region corresponds to nucleotides 2019 to 4107 of the adenovirus type 5. It is, however, also within the present invention that the E1B55kD gene is excised from the plasmid by means of the restriction enzymes Bam HI and BfrI and XbaI, respectively, and subsequently cloned into the adenovirus. It is also within the present invention that also analogues thereof and in particular analogues of the 3' UTR region may be used within the present invention. An analogue of the 3' UTR region is any sequence which has the same effect as the 3' UTR region, particularly the same effect with regard to the expression of a gene, preferably the E1B55kD gene. Such analogues can be determined by routine experiments performed by the ones skilled in the art, e. g. by extending or shortening the 3' UTR region by one or several nucleotides and subsequently testing whether the thus obtained analogue still has the same effect as the 3' UTR region as described previously. In an embodiment the term 3' UTR region thus comprises also each and any analogue thereof.

Those viruses where therapeutic genes or transgenes are cloned in a preferred embodiment preferably under the control of a specific promoter, in particular a tumor-specific or tissue-specific promoter, are further developments of the viruses in accordance with the present invention. It is also within such viruses that also the E4 region is functionally inactive and is preferably deleted. The transgenes described herein can also be cloned into the E4 region, whereby this may be performed alternatively or additionally to the cloning of the transgenes into the E3 region and the E3 region may remain partially or completely intact, respectively. Transgenes as used herein may be therapeutic genes or viral genes, preferably adenoviral genes, which preferably are not present in the genome of wildtype adenoviruses and which are not present, respectively, at a site of the genome at which they are located in the particular virus now.

Therapeutic genes can be prodrug genes, genes for cytokines, apoptosis inducing genes, tumor suppressor genes, genes for metalloproteinase inhibitors and/or angiogenesis inhibitors, and tyrosine kinase inhibitors. Additionally, siRNA, aptamers, antisense molecules and ribozymes may be expressed which are preferably directed against cancer-relevant target molecules. Preferably the individual or the several target molecules are selected from the group comprising the resistance-relevant factors, anti-apoptosis factors, oncogenes, angiogenesis factors, DNA synthesis enzymes, DNA repair enzymes, growth factors and their receptors, transcription factors, metalloproteinases, particularly matrix metalloproteinases, and plasminogen activator of the urokinase type. Preferred embodiments thereof are already disclosed herein.

In an embodiment the resistance-relevant factors are preferably selected from the group comprising P-glycoprotein, MRP and GST and also comprise the nucleic acids coding therefor.

Possible prodrug genes as may be used in preferred embodiments, are, for example, cytosine deaminase, thymidine kinase, carboxypeptidase, uracil phosphoribosyl transferase; or purine nucleoside phosphorylase (PNP); Kin) et al, Trends in Molecular Medicine, volume 8, no. 4 (suppl), 2002; Wybranietz W. A. et al., Gene Therapy, 8, 1654-1664, 2001; Niculescu-Duvaz et al., Curr. Opin. Mol. Therapy, 1, 480.486, 1999; Koyama et al., Cancer Gene Therapy, 7, 1015-1022, 2000; Rogers et al., Human Gene Therapy, 7, 2235-2245, 1996; Lockett et al., Clinical Cancer Res., 3, 2075-2080, 1997; Vijayakrishna et al., J. Pharmacol. And Exp. Therapeutics, 304, 1280-1284, 2003.

Possible cytokines as may be used in preferred embodiments, are, for example, GM-CSF, TNF-alpha, Il-12, Il-2, Il-6, CSF or interferon-gamma; Gene Therapy, Advances in Pharmacology, volume 40, editor: J. Thomas August, Academic Press; Zhang and Degroot, Endocrinology, 144, 1393-1398, 2003; Descamps et al., J. Mol. Med., 74, 183-189, 1996; Majumdar et al., Cancer Gene Therapy, 7, 1086-1099, 2000.

In an embodiment the anti-apoptosis factors are selected from the group comprising BCL2 and comprise also the nucleic acids coding therefor. In an embodiment the oncogenes are selected from the group comprising Ras, particularly mutated Ras, Rb and Myc, and comprises also the nucleic acids coding therefor. In an embodiment the angiogenesis factors are selected from the group comprising VEGF and HMG proteins, and also comprise the nucleic acids coding therefor. In an embodiment the DNA synthesis enzymes are selected from the group comprising telomerase, and also comprise the nucleic acids coding therefor. In an embodiment the DNA repair enzymes are selected from the group comprising Ku-80, and also comprise the nucleic acids coding therefor. In an embodiment the growth factors are selected from the group comprising PDGF, EGF and M-CSF, and also comprise the nucleic acids coding therefor. In a further embodiment the receptors are in particular those of growth factors, whereby preferably the growth factors are selected from the group comprising PDGF, EGF and M-CSF, and also comprise the nucleic acids coding therefor. In an embodiment the transcription factor is selected from the group comprising YB-1, and also comprises the nucleic acid coding therefor. In an embodiment the metalloproteinases are in particular matrix metalloproteinases. In a preferred embodiment the matrix metalloproteinases are selected from the group comprising MMP-1 and MMP-2, and also comprise the nucleic acids coding therefor. In an embodiment the plasminogen activators of the urokinase type are selected from the group comprising uPa-R, and also comprise the nucleic acids coding therefor.

Possible apoptosis-inducing genes as may be used in preferred embodiments, are, for example, Decorin: Tralhao et al., FASEB J, 17, 464-466, 2003; retinoblastoma 94: Zhang et al., Cancer Res., 63, 760-765, 2003; Bax and Bad: Zhang et al., Hum. Gene Ther., 20, 2051-2064, 2002; apoptin: Noteborn and Pietersen, Adv. Exp. Med. Biol., 465, 153-161, 2000; ADP: Toth et al., Cancer Gene Therapy, 10, 193-200, 2003; bcl-xs: Sumantran et al., Cancer Res, 55, 2507-2512, 1995; E4orf4: Braithwaite and Russell, Apoptosis, 6, 359-370, 2001; FasL, Apo-1 and Trail: Boehringer Manheim, Guide to Apoptotic Pathways, Arai et al., PNAC, 94, 13862-13867, 1997; Bims: Yamaguchi et al., Gene Therapy, 10, 375-385, 2003; GNR163: Oncology News, 17 Jun. 2000.

Possible tumor suppressor genes as may be used in preferred embodiments, are, for example, E1A, p53, p16, p21, p27 or MDA-7: Opalka et al., Cell Tissues Organs, 172, 126-132, 2002, Ji et al., Cancer Res., 59, 3333-3339, 1999, Su et al., Oncogene, 22, 1164-1180, 2003.

Possible angiogenesis inhibitors as may be used in preferred embodiments, are, for example, endostatin or angiostatin: Hajitou et al., FASEB J., 16, 1802-1804, 2002, and antibodies against VEGF: Ferrara, N., Semin Oncol 2002 December; 29 (6 suppl 16): 10-4.

Possible metalloproteinase inhibitors as may be used in preferred embodiments, are, for example, Timp-3 [Ahonen et al., Mol Therapy, 5, 705-715, 2002]; PAI-1 [Soff et al., J. Clin. Invest., 96, 2593-2600, 1995]; Timp-1 [Brandt K. Curr. Gene Therapy, 2, 255-271, 2002].

Further transgenes in the sense of the present invention which may be expressed by both group I adenoviruses and group II adenoviruses in accordance with the present invention are also tyrosine kinase inhibitors. Exemplary tyrosine kinases are EGFR (epidermal growth factor receptor) [Onkologie, Entstehung and Progression maligner Tumoren; author: Christoph Wagner, Georg Thieme Verlag, Stuttgart, 1999]. A preferred tyrosine kinase inhibitor is herceptin [Zhang H et al., Cancer Biol Ther. 2003, July-August; 2 (4 suppl 1): S122-6].

SiRNA (short interfering RNA), as may be used within the present invention, consists of two, preferably separate RNA strands which hybridise to each other due to base complementarity which means that they are present essentially base paired and preferably have a length of up to 50 nucleotides, preferably between 18 and 30 nucleotides, more preferably less than 25 nucleotides and most preferably 21, 22 or 23 nucleotides, whereby these figures refer to the single strand of the siRNA, particularly to the length of the stretch of the single strand which hybridises to or is base paired with a, more precisely the second single strand. siRNA specifically induces or mediates the degradation of mRNA. The specificity required theretofore is mediated by the sequence of the siRNA and thus its binding site. The target sequence to be degraded is essentially complementary to the first or to the second of the siRNA forming strands. Although the precise mode of action is not yet clear, it is assumed that siRNA is a biological strategy for cells in order to inhibit distinct alleles during development and to protect themselves against viruses. siRNA mediated RNA interference is used as a method for the specific suppression or complete elimination of the expression of a protein by introducing a gene specific double-stranded RNA. For higher organisms a siRNA comprising 19 to 23 nucleotides is insofar particularly suitable as it does not result in the activation of a non-specific defense reaction such as an interleukin response. The direct transfection of double-stranded RNA of 21 nucleotides having symmetrical 2-nt 3' overhangs was suitable to mediate RNA interference in mammalian cells and is highly efficient compared to other technologies such as ribozymes and antisense molecules (Elbashir, S. Harborth J. Lendeckel W. Yalvcin, A. Weber K, Tuschl T: Duplexes of 21-nucleotide RNAs mediate RNA interference in cultured mammalian cells. Nature 2001, 411: 494-498). As little as a few siRNA molecules are sufficient so as to suppress expression of the target gene. In order to avoid the limitations of exogenously added siRNA which particularly reside in the transient nature of the interference phenomenon and specific delivery (delivery) of the siRNA molecules, vectors are used in the prior art which allow for an endogenous siRNA expression. For such purpose, for example, oligonucleotides having a length of 64 nucleotides are introduced into the vector which comprise the 19 nucleotide long target sequence both in the sense and in the antisense orientation, separated by, for example, a 9 nucleotide spacer sequence. The resulting transcript folds into a hairpin structure with a stem structure (stem) of, for example, 19 base pairs. The loop is rapidly degraded in the cell so that a functional siRNA molecule is generated (Brummelkamp et al., Science, 296, 550-553, 2002).

In a still further embodiment the medicament further comprises at least one pharmaceutically active compound or pharmaceutically active agent, whereby the terms compound and agent are used in an interchangeable manner if not explicitly indicated to the contrary.

In a preferred embodiment the pharmaceutically active compound is selected from the group comprising cytokines, metalloproteinase inhibitors, angiogenesis inhibitors, cytostatics such as Irinotecan and CPT-11 against colorectal carcinoma and Daunorubicin against leukemia, cell cycle inhibitors such as CYC202 which inhibits CDK2/CyclinE kinase activity and can be used against colorectal tumors (McClue S J, Int. J. Cancer 2002, 102, 463-468) and BAY 43-9006 which inhibits Raf-1 and is, for example, effective against mamma carcinoma (Wilhelm S M et al., Cancer Res. 2004, 64, 7099-7109), proteosome inhibitors such as PS-341 which inhibits the 26S proteasome activity and is used against squamous-cell carcinoma (Fribley A et al., Mol Cell Biol 2004 November; 24(22): 9695-704), recombinant antibodies such as against the EGF receptor (Herceptin for breast carcinoma and prostate tumor; H. G. van der Poel, European Urology 2004, 1-17; Erbitux against head and neck tumors; Bauman M et al., Radiother. Oncol., 2004, 72, 257-266), and inhibitors of the signal transduction cascade such as STI 571 which represses, among others, c-kit and can be used against gastrointestinal tumors (H. G. van der Poel, European Urology 2004, 45, 1-17), ABT-627 an endothelin inhibitor which may be used, among others, against prostate tumors (H. G. van der Poel, European Urology 2004, 45, 1-17), SU5416 which inhibits phosphorylation of the VEGF tyrosine kinase receptor and which may be used against glioblastoma and prostate cancer (Bischof M et al Int. J. Radiat. Oncol. Biol. Phys. 2004; 60 (4): 1220-32), ZD1839 which inhibits EGFR tyrosine activity and may be used, among others, against prostate tumors (H. G. van der Poel, European Urology 2004, 45, 1-17); rapamycin derivatives such as CCI-779 and RAD001 which inhibit mTOR and can be used against prostate tumors. It is within the present invention that the various adenoviruses described herein and the adenoviruses to be used in accordance with the present invention, respectively, can, in principle, be used with each and any of the aforementioned compounds for each and any of the indication described in connection therewith. In a particularly preferred embodiment the indication is the one which is described for any of the previously mentioned pharmaceutically active compounds or agents.

The present inventor has furthermore surprisingly found that the efficacy of the viruses described herein and in particular the viruses used in accordance with the present invention can be increased by using in combination at least two compound whereby each of the at least two compounds is individually and independently selected from the group comprising cytostatics.

As used herein in a preferred embodiment, cytostatics are in particular chemical or biological compounds which, during or after the administration to a cell or an organism containing a or such cell, result in the cell no longer growing and/or no longer dividing or slowing down cell division and/or cell growth. Cytostatics also comprise compounds or agents which turn into a cytostatic in the aforedescribed sense only in the cell or in an organism containing such cell. Insofar, the term cytostatics also comprises pre-cytostatics.

Cytostatics are grouped according to their mode of action. The following groups are distinguished which, in principle, can all be used within the present invention:

Alkylating agents, i. e. chemical compounds which cause their cytotoxic effect by alkylating phosphate, amino, sulphydryl, carboxy and hydroxy groups of the nucleic acid as well as proteins. Such compounds are often cancerogenic themselves. Typical examples of this group of cytostatics are cis-platin and platin derivatives, cyclophosphamide, dacarbazine, mitomycin, procarbazine.

Antimetabolites, i. e. compounds which, due to their structural similarity or ability for binding block a metabolic process or affect the same. Within the group of antimetabolites it is distinguished between structurally similar antimetabolites, structure changing antimetabolites and the indirectly acting antimetabolites. The structurally similar antimetabolites compete due to chemical similarity with the metabolite without exerting the function thereof. Structure changing antimetabolites bind to the metabolites which impedes its function or resorption or chemically modifies the metabolite. Indirectly acting antimetabolites interfere with the function of the metabolite, for example by the binding of ions. Typical examples of this group are folic acid antagonists such as methotrexate, pyrimidine analogues such as fluorouracil, purine analogues such as azathioprine and mercaptopurine.

Mitosis inhibitors, i. e. compounds which inhibit cell division. Within the group of mitosis inhibitors it is distinguished between cell division toxins, spindle toxins and chromosome toxins. Typical examples of this group are taxanes and vinca alkaloids. The taxanes in turn can be divided into the two major groups of taxoles and taxoters, whereby a particularly preferred taxole is paclitaxel, and a particularly preferred taxoter is docetaxel.

Antibiotics having an inhibitory effect on the DNA-dependent RNA polymerase. Typical examples are the anthracyclines, such as, e. g., bleomycin, daunorubicin, doxorubicin and mitomycin.

Topoisomerase inhibitors, in particular topoisomerase I inhibitors. Topoisomerase inhibitors are chemical compounds which determine the tertiary structure of the DNA by catalysing the change of the DNA twist number in a three stage process. Essentially, two forms of topoisomerases are distinguished. Topoisomerases of type I cleave only a DNA strand and are ATP-independent, whereas topoisomerase of type II cleave both strands of a DNA, whereby they are ATP-dependent. Typical examples for topoisomerase I inhibitors are irinotecan and topotecan, and for topoisomerase II inhibitors etoposide and daunorubicin.

Within the present invention at least one and preferably two agents are selected from the aforementioned group. It is, however, also within the invention that in particular also three, four or five different agents are selected. The following comments are made for the embodiment of the present invention where only one and preferably two agents are used together with the virus. These considerations are basically also applicable to the embodiments where more than two agents are used.

Preferably the agents differ from each other such that they address different target molecules or are described in literature as targeting different molecules. It is within the present invention that the agent also comprises two or more different agents which bind to the same target molecule. It is also within the present invention that one such agent binds to a first site of the target molecule, whereas the second such agent binds to a second site of the target molecule.

It is also within the present invention that at least two of the agents are active using different modes of action. Active means in a preferred embodiment that the cell growth and/or cell division inhibiting or retarding effect of the chemical compound is mediated through a different mode of action. In a particularly preferred embodiment the term active means that the replication efficiency of a virus, in particular the virus in accordance with the present invention, of the viruses described herein and of the viruses to be used in accordance with the present invention, is increased compared to a scenario where one and/or both of the agents are not used. As a measure for the efficiency of viral replication preferably the number of viruses required for cell lysis is used, preferably expressed as pfu/cell.

In a particularly preferred embodiment at least one of the at least two agents is one which increases the infectability of the cell in which the replication of the virus is to occur, preferably is to occur in a selective manner, preferably with the virus described herein and/or the virus to be used in accordance with the present invention. This can, e. g., be performed by increasing the uptake of the virus by the cell. The uptake of the virus, in particular of adenovirus, is, for example, mediated by the coxsackievirus-adenovirus receptor (CAR) (Mizuguchi and Hayakawa, GENE 285, 69-77, 2002). An increased expression of CAR is, for example, caused by trichostatin A (Vigushin et al., Clinical Cancer Research, 7, 971-976, 2001).

In a further embodiment one of the at least two agents is one which increases the availability of a component within the cell, whereby the component is one which increases the replication of the virus, preferably the virus described herein and/or the virus to be used in accordance with the present invention.

In a further embodiment one of the at least two agents is one which mediates the transport of YB-1 into the nucleus. Such an agent can be selected from the group comprising topoisomerase inhibitors, alkylating agents, antimetabolites and mitosis inhibitors. Preferred topoisomerase inhibitors are camptothecin, irinotecan, etoposide and their respective analogues. Preferred mitosis inhibitors are daunorubicin, doxorubicin, paclitaxel and docetaxel. Preferred alkylating agents are cis-platin and their analogues. Preferred antimetabolites are fluorouracil and methotrexate.

In a particularly preferred embodiment one of the at least two agents is one which increases the infectability of the cell, in particular the expression of CAR, and the second of the at least agents is one which increases the transport of YB-1 into the nucleus, whereby preferably as chemical compound a compound is used which exhibits the respective required characteristic as preferably described above.

In a further embodiment the one of the at least two agents is a histone deacylase inhibitor. A preferred histone deacylase inhibitor is one which is selected from the group comprising trichostatin A, FR901228, MS-27-275, NVP-LAQ824 and PXD101. Trichostatin A is, for example, described in Vigushin et al., Clinical Cancer Research, 7, 971-976, 2001; FR901228 is, for example, described in Kitazono et al., Cancer Res., 61, 6328-6330, 2001; MS-27-275 is described in Jaboin et al., Cancer Res., 62, 6108-6115, 2002; PXD101 is described in Plumb et al., Mol. Cancer Ther., 8, 721-728, 2003; NVP-LAQ824 is described in Atadja et al., Cancer Res., 64, 689-695, 2004.

In an embodiment at least one agent is selected from the group comprising trichostatin A (against glioblastoma, Kim J H et al., Int. J. Radiation Oncology Biol. Phys. 2004, 59, 1174-1180), FR 901228 (against pancreas tumors, Sato N et al., Int. J. Oncol. 2004, 24, 679-685; MS-27-275 (against prostate tumors; Camphausen K et al., Clinical Canver Research 2004, 10, 6066-6071), NVP-LAQ824 (against leukemiae; Nimmanapalli R et al., Cancer Res. 2003, 63, 5126-5135; PXD101 (against ovary tumors, Plumb J A et al, Mol. Cancer Ther. 2003, 2, 721-728), scriptaid (against breast carcinoma, Keen J C et al., Breast Cancer Res. Treat. 2003, 81, 177-186), apicidin (against melanoma, Kim S H et al., Biochem. Biophys. Res. Commun. 2004, 315, 964-970) and CI-994 (against various tumors, Nemunaitis J J et al., Cancer J. 2003, 9, 58-66). The mode of action of histone deacetylase inhibitors is, among others, described in Lindemann R K et al., Cell Cycle 2004, 3, 77-86. It is within the present invention that the various adenoviruses described herein and the adenoviruses to be used in accordance with the present invention, may be used with the aforementioned compounds, in principle, for each and any of the indications described herein in connection therewith. In a particularly preferred embodiment the indication is one as has been described for each and any of the aforementioned pharmaceutically active compounds.

In a still further embodiment the one of the at least two agents is a topoisomerase inhibitor, preferably a topoisomerase I inhibitor. A preferred topoisomerase inhibitor is one which is selected from the group comprising camptothecin, irinotecan, topotecan, SN-38, 9-aminocamptothecin, 9-nitrocamptothecin, DX-895If and daunorubicin. Irinotecan and SN-38 are, for example, described in Gilbert et al., Clinical Cancer Res., 9, 2940-2949, 2003; DX-8951F is described in van Hattum et al., British Journal of Cancer, 87, 665-672, 2002; camptothecin is described in Avemann et al., Mol. Cell. Biol., 8, 3026-3034, 1988; 9-aminocamptothecin, 9-nitrocamptothecin are described in Rajendra et al., Cancer Res., 63, 3228-3233, 2003; daunorubicin is described in M. Binaschi et al., Mol. Pharmacol., 51, 1053-1059.

In a preferred embodiment the topoisomerase inhibitor is selected from the group comprising camptothecin, irinotecan, topotecan, DX-895If, SN-38, 9-aminocamptothecin, 9-nitrocamptothecin, etoposide and daunorubicin. These may be used against various tumors, for example, colorectal tumors, pancreas tumors, ovary carcinomas and prostate carcinomas. The fields of application are, among others, described by Recchia F et al., British J. Cancer 2004, 91, 1442-1446; Cantore M et al., Oncology 2004, 67, 93-97; Maurel J. et al., Gynecol. Oncol 2004, 95, 114-119; Amin A. et al., Urol. Oncol. 2004, 22, 398-403; Kindler H L et al., Invest. New Drugs 2004, 22, 323-327, Ahmad T. et al., Expert Opin. Pharmacother. 2004, 5, 2333-2340; Azzariti A. et al., Biochem Pharmacol. 2004, 68, 135-144; Le Q T et al., Clinical Cancer Res. 2004, 10, 5418-5424. It is within the present invention that the various adenoviruses described herein and the adenoviruses to be used in accordance with the present invention, respectively, may in principle be used with the aforementioned compounds for each and any of the indications described herein in connection therewith. In a particularly preferred embodiment the indication is such as described for each of the aforementioned pharmaceutically active compounds.

In an embodiment at least one agent is selected from the group comprising trichostatin A, FR 901228 (against pancreas tumors, Sato N et al., Int. J. Oncol. 2004, 24, 679-685; MS-27-275 (against prostate tumors; Camphausen K et al., Clinical Canver Research 2004, 10, 6066-6071), NVP-LAQ824 (against leukemiae; Nimmanapalli R et al., Cancer Res. 2003, 63, 5126-5135; PXD101 (against ovary tumors, Plumb J A et al, Mol. Cancer Ther. 2003, 2, 721-728) scriptaid (against breast carcinoma, Keen J C et al., Breast Cancer Res. Treat. 2003, 81, 177-186), apicidin (against melanoma, Kim S H et al., Biochem. Biophys. Res. Commun. 2004, 315, 964-970) and CI-994 (against various tumors, Nemunaitis J J et al., Cancer J. 2003, 9, 58-66). The mode of action of histone deacetylase inhibitors is, among others, described in Lindemann R K et al., Cell Cycle 2004, 3, 77-86. It is within the present invention that the various adenoviruses described herein and the adenoviruses to be used in accordance with the present invention, may be used with the aforementioned compounds, in principle, for each and any of the indications described herein in connection therewith. In a particularly preferred embodiment the indication is one as has been described for each and any of the aforementioned pharmaceutically active compounds.

In a preferred embodiment the topoisomerase inhibitor is selected from the group comprising camptothecin, irinotecan, topotecan, DX-895If, SN-38, 9-aminocamptothecin, 9-nitrocamptothecin, daunorubicin and etoposide. These may be used against various tumors, for example, colorectal tumors, pancreas tumors, ovary carcinomas, lung tumors and prostate carcinomas. The fields of application are, among others, described by Recchia F et al., British J. Cancer 2004, 91, 1442-1446; Cantore M et al., Oncology 2004, 67, 93-97; Maurel J. et al., Gynecol. Oncol 2004, 95, 114-119; Amin A. et al., Urol. Oncol. 2004, 22, 398-403; Kindler H L et al., Invest. New Drugs 2004, 22, 323-327, Ahmad T. et al., Expert Opin. Pharmacother. 2004, 5, 2333-2340; Azzariti A. et al., Biochem Pharmacol. 2004, 68, 135-144; Le Q T et al., Clinical Cancer Res. 2004, 10, 5418-5424. It is within the present invention that the various adenoviruses described herein and the adenoviruses to be used in accordance with the present invention, respectively, may in principle be used with the aforementioned compounds for each and any of the indications described herein in connection therewith. In a particularly preferred embodiment the indication is such as described for each of the aforementioned pharmaceutically active compounds.

In a particularly preferred embodiment the one of the at least two agents is a histone deacylase inhibitor and the other one of the at least two agents is a topoisomerase inhibitor.

In a preferred embodiment of each and any aspect of the present invention the further pharmaceutically active compound is selected from the group comprising cytokines, metalloproteinase inhibitors, angiogenesis inhibitors, cytostatics such as irinotecan and CPT-11 against colorectal carcinoma and daunorubicin against leukemia, cell cycle inhibitors such as CYC202 which inhibits CDK2/CyclinE kinase activity and can be used against colorectal tumors (McClue S J, Int. J. Cancer 2002, 102, 463-468) and BAY 43-9006 which inhibits Raf-1 and is effective against mamma carcinoma (Wilhelm S M et al., Cancer Res. 2004, 64, 7099-7109), proteosome inhibitors such as PS-341 which inhibits the 26S proteasome activity and is used against brain tumors (Yin D. et al., Oncogene 2004), recombinant antibodies such as against the EGF receptor (Herceptin for breast carcinoma and prostate tumor; H. G. van der Poel, European Urology 2004, 1-17; Erbitux against head and neck tumors; Bauman M et al., Radiother. Oncol., 2004, 72, 257-266), and inhibitors of the signal transduction cascade such as STI 571 which represses, among others, c-kit and can be used against gastrointestinal tumors (H. G. van der Poel, European Urology 2004, 45, 1-17), ABT-627 an endothelin inhibitor which may be used, among others, against prostate tumors (H. G. van der Poel, European Urology 2004, 45, 1-17), SU5416 which inhibits phosphorylation of the VEGF tyrosine kinase receptor and which may be used against head/neck tumors (Cooney et al., Cancer Chemother. Pharmacol 2004), ZD1839 which inhibits EGFR tyrosine activity and may be used, among others, against prostate tumors (H. G. van der Poel, European Urology 2004, 45, 1-17); rapamycin derivatives such as CCI-779 and RAD001 which inhibit mTOR and can be used against prostate tumors (H. G. van der Poel, European Urology 2004, 45, 1-17). It is within the present invention that the various adenoviruses described herein and the adenoviruses to be used in accordance with the present invention, respectively, can, in principle, be used with each and any of the aforementioned compounds for each and any of the indications described in connection therewith. In a particularly preferred embodiment the indication is the one which is described for any of the previously mentioned pharmaceutically active compounds.

In an embodiment the means according to the present invention and/or the means prepared in accordance with the present invention contains the virus separate from one or several of the at least one and preferably at least two agents which are combined or administered together with the virus in accordance with the present invention. It is preferred that the virus is separate from any agent which is combined with the virus. Preferably the separation is a spatial separation. The spatial separation can be such that the virus is present in a different package than the agent. Preferably the package is a single dose unit, i. e. the virus and the agent(s) are packed as single dosages. The single dose units may in turn be combined to form a package. However, it is also within the present invention that the single dosages of the virus are combined with one or several single dosages of one or several of the agents or packed therewith.

The kind of package depends on the way of administration as known to the one skilled in the art. Preferably the virus will be present in a lyophilized form or in a suitable liquid phase. Preferably, the agents will be present in solid form, e. g. as tablets or capsules, however, are not limited thereto. Alternatively, also the agents can be present in liquid form.

It is within the present invention that the virus is systemically or locally administered. It is also within the present invention that the agents combined with the virus are systemically or locally administered individually and independently from each other or together. Other modes of administration are known to the ones skilled in the art.

It is within the present invention that the virus and the agents combined with it, are administered in a chronologically separate manner or at the same time. In connection with a chronologically separate manner it is preferred that the agent is administered prior to the administration of the virus. How long the agent is administered prior to the virus depends on the kind of the agent used and is obvious for the one skilled in the art from the mode of action of the agent used. Also the administration of the at least two agents can occur at the same or at different points in time. In connection with a chronologically different administration the points of time again result from the modes of action underlying the agents and can, based thereon, be determined by the ones skilled in the art.

The above considerations, given in connection with the medicaments according to the present invention which are also referred to herein as pharmaceutical compositions, are roughly also applicable to any composition, including compositions as used for the replication of viruses, preferably for the in vitro replication of viruses in accordance with the present invention. The above considerations are also applicable to the kit in accordance with the present invention and the kit to be used in accordance with the present invention, respectively, which may apart from the viruses described herein and the viruses to be used in accordance with the invention, also comprise an agent or a combination of agents as described herein. Such kits comprise the virus and/or the one or the several agents in a form ready for use and preferably instructions for use. Furthermore, the above considerations apply also to the nucleic acids as disclosed herein, and the nucleic acids used in accordance with the present invention, and the replication systems in accordance with the present invention and the nucleic acids coding therefor, and the replication systems used in accordance with the present invention and the nucleic acids coding therefor used in accordance with the present invention.

The medicament in connection with which or for the manufacture of which the adenoviruses disclosed herein are used in accordance with the present invention, is intended to be applied, usually, in a systemic manner, although it is also within the present invention to apply or deliver it locally. The application is intended to infect particularly those cells with adenoviruses and it is intended that adenoviral replication particularly occurs therein, which are involved, preferably in a causal manner, in the formation of a condition, typically a disease, for the diagnosis and/or prevention and/or treatment of which the inventive medicament is used.

Such a medicament is preferably for the treatment of tumor diseases. Those tumor diseases are particularly preferred where YB-1 is, due to the mechanism underlying the tumor disease, in particular due to the underlying pathological mechanism, already located in the nucleus, or where the presence of YB-1 in the cellular nucleus is caused by exogenous measures whereby such exogenous measures are suitable to transfer YB-1 into the cellular nucleus or to induce or to express it there. The term tumor or tumor disease shall comprise herein both malignant as well as benign tumors, and respective diseases. In an embodiment the medicament comprises at least one further pharmaceutically active compound. The nature and the amount of such further pharmaceutically active compound or agent will depend on the kind of indication for which the medicament is used. In case the medicament is used for the treatment and/or prevention of tumor diseases, typically cytostatics such as cis-platin and taxole, daunoblastina, daunorubicin, adriamycin and/or mitoxantrone or others of the cytostatics or groups of cytostatics described herein, are used.

The medicament in accordance with the invention can be present in various formulations, preferably in a liquid form. Furthermore, the medicament will contain adjuvants such as stabilisers, buffers, preservatives and the like which are known to the one skilled in the art of formulations.

The medicament in connection with which or in connection with the manufacture of which the adenoviruses described herein are used in accordance with the present invention is envisaged to be typically administered in a systemic manner, although it is also within the present invention that it is applied locally or delivered locally. The application intends to infect those cells with the adenovirus and to cause adenoviral replication therein, which are involved, preferably in a causal manner, in the formation of a condition, typically a disease for the diagnosis and/or prevention and/or treatment of which the medicament according to the present invention is used.

Such a medicament is preferably for the treatment of tumor diseases. Those tumor diseases are particularly preferred where YB-1 is, due to the mechanism underlying the tumor disease, in particular due to the underlying pathological mechanism, already located in the nucleus, or where the presence of YB-1 in the cellular nucleus is caused by exogenous measures whereby such exogenous measures are suitable to transfer YB-1 into the cellular nucleus or to induce or to express it there. The term tumor or tumor disease shall comprise herein both malignant as well as benign tumors, and respective diseases. In an embodiment the medicament comprises at least one further pharmaceutically active compound. The nature and the amount of such further pharmaceutically active compound will depend on the kind of indication for which the medicament is used. In case the medicament is used for the treatment and/or prevention of tumor diseases, typically cytostatics such as cis-platin and taxole, daunoblastina, daunorubicin, adriamycin and/or mitoxantrone or others of the cytostatics or groups of cytostatics described herein.

The medicament in accordance with the invention can be present in various formulations, preferably in a liquid form. Furthermore, the medicament will contain adjuvants such as stabilisers, buffers, preservatives and the like which are known to the one skilled in the art of formulations.

The present inventor has surprisingly found that the viruses in accordance with the present invention can be used with a very high rate of success with those tumors where YB-1 is contained in the nucleus independent of the cell cycle and such tumors which contain deregulated YB-1. Normally, YB-1 is present in the cytoplasma and in particular also in the perinuclear plasma. YB-1 is present in the nucleus of both normal as well as tumor cells during the S-phase of the cell cycle. This, however, is not sufficient so as to provide for a viral oncolysis when using such modified adenoviruses. The comparatively low efficiency of such attenuated adenoviruses as reported in the prior art, is ultimately based on the wrong application thereof. In other words, such adenovirus systems could be used, in particular also with an increased efficacy under conditions where the molecular biological prerequisites for viral oncolysis using the attenuated or modified adenoviruses as described herein, are met. Such prerequisites are given in tumor diseases the cells of which have YB-1 in the nucleus independent of the cell cycle or contain deregulated YB-1. This form of nuclear localisation may be caused by the nature of the tumor itself, or be caused by the agents in accordance with the present invention as described herein or by applying the measures described herein. The present invention thus defines a new group of tumours and tumour diseases, respectively and thus also of patients which may be treated using the virus in accordance with the present invention and in particular also with the attenuated or modified adenoviruses already described in the prior art.

A further group of patients which may be treated using the viruses in accordance with the present invention, are those patients where it is ensured that YB-1 migrate into the nucleus or is induced there or is transported there upon applying or realizing certain conditions, including the use of the viruses in accordance with the present invention. The use of the adenoviruses in accordance with the present invention in connection with this group of patients is insofar based on the finding that the induction of viral application is based on the nuclear localisation of YB-1 with subsequent binding of YB-1 to the E2-late-promoter. This applies also to those cells which are YB-1 nucleus-positive and/or cells where YB-1 is present in a deregulated manner in the meaning of the present application. Insofar the adenoviruses in accordance with the present invention can be used in accordance with the present invention for the treatment of diseases and groups of patients, which comprise cells having these characteristics, particularly if these cells are involved in the forming of the respective disease to be treated. A further group of patients which can be treated by using the viruses in accordance with the present invention, in particular adenoviruses, are those which are YB-1 nucleus-positive as a result of the subsequently described treatments and/or patients which have undergone one of the measures described herein, preferably in the sense of a treatment, or have experienced the administration of the viruses in accordance with the present invention or experience them together with the administration of the virus in accordance with the present invention. It is within the present invention that YB-1 nucleus-positive patients are patients which have YB-1 in the nucleus independent of the cell cycle and in particular in a number of tumour forming cells. These measures comprise the administration of such cytostatics as they are generally described herein and/or as they are used in connection with a tumour therapy. Furthermore this group of measures comprises radiation, in particular radiation as used in connection with a tumour therapy. Radiation means in particular the radiation with energy-rich radiation, preferably radioactive radiation, preferably as used in connection with tumour therapy. A further measure is hyperthermia and the application of hyperthermia, preferably hyperthermia as used in connection with tumour therapy. In a particularly preferred embodiment hyperthermia is applied locally. Finally, a further measure is hormone treatment, in particular hormone treatment as used in connection with tumour treatment. In connection with such hormone treatment anti-estrogens and/or anti-androgens are used. In connection therewith, anti-estrogens such as Tamoxifen, are particularly used in the therapy of breast cancer, and anti-androgens as, for example, Flutamide and Cyproteronacetate, are used in the therapy of prostate cancer.

It is within the present invention that some of the tumor forming cells which either inherently contain YB-1 in the nucleus or do so or after induction and active introduction into the nucleus or which comprise deregulated YB-1 in the meaning of the present disclosure. Preferably about 5% or any percentage higher than that, i. e. 6%, 7%, 8% etc., of the tumor forming cells are such YB-1 nucleus-positive cells or cells in which deregulated YB-1 is present. For other tumors such as breast tumor, osteosarcoma, ovarian carcinoma, synovial carcinoma or lung carcinoma the percentage of tumor cells which comprise deregulated YB-1 or which show nuclear localisation of YB-1 independent of the cell cycle, may be about 30 to 50% [Kohno K. et al., BioEssays 2003, 25, 691-698]. Such tumors may preferably be treated using the adenoviruses in accordance with the present invention. Nuclear localisation of YB-1 may be induced by outside stress and locally applied stress, respectively. This induction may occur through irradiation, particularly UV-irradiation, application of cytostatics as, among others, also disclosed herein, and hyperthermia. In connection with hyperthermia it is important that it may be realized in a very specific manner, particularly a local manner, and that thus also a specific nuclear transport of YB-1 into the nucleus may be caused and, because of this, the prerequisites for replication of the adenovirus and thus of cell and tumor lysis are given, which preferably is locally limited (Stein U, Jurchott K, Walther W, Bergmann, S, Schlag P M, Royer H D. J Biol Chem. 2001, 276(30):28562-9; Hu Z, Jin S, Scotto K W. J Biol Chem. 2000 Jan. 28; 275(4):2979-85; Ohga T, Uchiumi T, Makino Y, Koike K, Wada M, Kuwano M, Kohno K. J Biol Chem. 1998, 273(11):5997-6000).

The medicament of the invention would thus also be administered to patients and groups of patients or would be designed for them, where by appropriate pre-treatment or concomitant treatment a transport of YB-1, particularly in the respective tumor cells, is caused and deregulated YB-1 is generated in the cell, respectively.

With regard to the characteristics of the cells for the lysis of which the adenoviruses described herein are used in accordance with the present invention, it is in envisaged that these have, in an embodiment, a resistance, preferably a multiple resistance or poly-resistance. Resistance as used herein preferably refers to a resistance to the cytostatics described herein and/or radiation. This multiple resistance preferably goes along with the expression, preferably an overexpression of the membrane-bound transport protein P-glycoprotein which is a marker for the determination of respective cells and thus also of tumors exhibiting the same and the corresponding patient groups. The term resistance as used herein comprises both the resistance which is also referred to as classical resistance and is mediated by the P-glycoprotein, as well as the resistance which is also referred to as atypical resistance and which is mediated by MRP or other, non-P-glycoprotein mediated resistances. Further resistances as referred to herein and which are characteristic for the tumors and patients, respectively, to be treated, are those which hare mediated by the following genes, however, are not limited thereto: MDR, MRP, topoisomerase, BCL2, glutathione-S-transferase (GST), protein kinase C (PKC). As the effect of cytostatics is, among others, based on the induction of apoptosis, the expression of apoptosis relevant genes plays an important role in the formation of resistance so that also the following factors are relevant insofar, namely Fas, the BCL2-family, HSP70 and EGFR [Kim et al., Cancer Chemther. Pharmacol. 2002, 50, 343-352]. A further marker which correlates with the expression of YB-1 is Topoisomerase II a. Insofar, rather than or in addition to determining YB-1 in the nucleus the expression of Topoisomerase II or any of the other markers described herein, can be used in a screening method to determine whether a patient may be treated with the adenoviruses in accordance with the present invention with an expectation of success. A marker which can in principle be used similarly to the P-glycoprotein, is MRP. A further marker at least to the extent that the colorectal carcinoma cells or patients having a colorectal carcinoma are afflicted, is PCN (proliferating cell nuclear antigen) (Hasan S. et al., Nature, 15, 387-391, 2001) as, for example, described in Shibao (Shibao K et al., Int. Cancer, 83, 732-737, 1999). Finally, at least for breast cancer and osteosarcoma cells the expression of MDR (English: multiple drug resistance) is a marker in the afore-described sense (Oda Y et al., Clin. Cancer Res., 4, 2273-2277). A further possible marker which can be used in accordance with the present invention, is p73 (Kamiya, M., Nakazatp, Y., J Neurooncology 59, 143-149 (2002); Stiewe et al., J. Biol. Chem., 278, 14230-14236, 2003).

It is a particular advantage of the present invention that also those patients may be subject to treatment using in accordance with the invention the adenoviruses described herein, which otherwise cannot be treated anymore in the medicinal-clinical sense and where thus a further treatment of the tumor diseases using the methods of the prior art is no longer possible with an expectation of success, in particular where the use of cytostatics and irradiation is no longer reasonably possible and cannot be successfully carried out any longer in the sense of influencing or reducing the tumor. Herein the term tumor refers in general also to any tumor or cancer disease which either inherently contains YB-1 in the cellular nucleus, preferably independent of the cell cycle, or does so by applying exogenous measures, as disclosed herein, and/or which contains deregulated YB-1.

Furthermore, the viruses described herein can be used, in principle, for the treatment of tumours.

The tumours which can in particular be treated by the viruses described herein are preferably those tumours which are selected from the group comprising tumours of the nervous system, ocular tumours, tumours of the skin, tumours of the soft tissue, gastrointestinal tumours, tumours of the respiratory system, tumour of the skeleton, tumours of the endocrine system, tumours of the female genital system, tumours of a mammary gland, tumours of the male genital system, tumours of the urinary outflow system, tumours of the haematopoietic system including mixed and embryonic tumours. It is within the present invention that these tumours are in particular resistant tumours as in particular defined herein.

The group of tumors of the nervous system preferably comprises:
1. Tumors of the skull as well as of the brain (intracranial), preferably astrocytoma, oligodendroglioma, meningioma, neuroblastoma, ganglioneuroma, ependymoma, schwannoglioma, neurofibroma, haemangioblastoma, lipoma, craniopharyngioma, teratoma and chondroma;
2. Tumors of the spinal cord and of the vertebral canal, preferably glioblastoma, meningioma, neuroblastoma, neurofibroma, osteosarcoma, chondrosarcoma, haemangiosarcoma, fibrosarcoma and multiple myeloma; and
3. Tumors of the peripheral nerves, preferably schwannoglioma, neurofibroma, neurofibrosarcoma and perineural fibroblastoma.

The group of the ocular tumors preferably comprises:
1. Tumors of the eyelids and of the lid glands, preferably adenoma, adenocarcinoma, papilloma, histiocytoma, mast cell tumor, basal-cell tumor, melanoma, squamous-cell carcinoma, fibroma and fibrosarcoma;
2. Tumors of the conjunctiva and of the nictitating membrane, preferably squamous-cell carcinoma, haemangioma, haemangiosarcoma, adenoma, adenocarcinoma, fibrosarcoma, melanoma and papilloma; and
3. Tumors of the orbita, the optic nerve and of the eyeball, preferably retinoblastoma, osteosarcoma, mast cell tumor, meningioma, reticular cell tumor, glioma, schwannoglioma, chondroma, adenocarcinoma, squamous-cell carcinoma, plasma cell tumor, lymphoma, rhabdomyosarcoma and melanoma.

The group of skin tumors preferably comprises:
Tumors of the histiocytoma, lipoma, fibrosarcoma, fibroma, mast cell tumor, malignant melanoma, papilloma, basal-cell tumor, keratoacanthoma, haemangiopericytoma, tumors of the hair follicles, tumors of the sweat glands, tumors of the sebaceous glands, haemangioma, haemangiosarcoma, lipoma, liposarcoma, malignant fibrous histiocytoma, plasmacytoma and lymphangioma.

The group of tumors of the soft-tissues preferably comprises:

Tumors of the alveolar soft-tissue sarcoma, epithelioid cell sarcoma, chondrosarcoma of the soft-tissue, osteosarcoma of the soft-tissues, Ewing's sarcoma of the soft-tissues, primitive neuroectodermal tumors (PNET), fibrosarcoma, fibroma, leiomyosarcoma, leiomyoma, liposarcoma, malignant fibrous histiocytoma, malignant haemangiopericytoma, haemangioma, haemangiosarcoma, malignant mesenchymoma, malignant peripheral nerve sheath tumor (MPNST, malignant schwannoglioma, malignant melanocytic schwannoglioma, rhabdomyosarcoma, synovial sarcoma, lymphangioma and lymphangiosarcoma.

The group of gastrointestinal tumors preferably comprises:
1. Tumors of the oral cavity and of the tongue, preferably squamous-cell carcinoma, fibrosarcoma, Merkel cell tumor, inductive fibroameloblastoma, fibroma, fibrosarcoma, viral papillomatosis, idiopathic papillomatosis, nasopharyngeal polyps, leiomyosarcoma, myoblastoma and mast cell tumor;
2. Tumors of the salivary glands, preferably adenocarcinoma;
3. Tumors of the oesophagus, preferably squamous-cell carcinoma, leiomyosarcoma, fibrosarcoma, osteosarcoma, Barrett carcinoma and paraoesophageal tumors;
4. Tumors of the exocrine pancreas, preferably adenocarcinoma; and
5. Tumors of the stomach, preferably adenocarcinoma, leiomyoma, leiomyosarcoma and fibrosarcoma.

The group of the tumors of the respiratory system preferably comprises:
1. Tumors of the nose and nasal cavity, of the larynx and of the trachea, preferably squamous-cell carcinoma, fibrosarcoma, fibroma, lymphosarcoma, lymphoma, haemangioma, haemangiosarcoma, melanoma, mast cell tumor, osteosarcoma, chondrosarcoma, oncocytoma (rhabdomyoma), adenocarcinoma and myoblastoma; and
2. Tumors of the lung, preferably squamous-cell carcinoma, fibrosarcoma, fibroma, lymphosarcoma, lymphoma, haemangioma, haemangiosarcoma, melanoma, mast cell tumor, osteosarcoma, chondrosarcoma, oncocytoma (rhabdomyoma), adenocarcinoma, myoblastoma, small-cell carcinoma, non-small cell carcinoma, bronchial adenocarcinoma, bronchoalveolar adenocarcinoma and alveolar adenocarcinoma.

The group of the skeleton tumors preferably comprises: osteosarcoma, chondrosarcoma, parosteal osteosarcoma, haemangiosarcoma, synovial cell sarcoma, haemangiosarcoma, fibrosarcoma, malignant mesenchymoma, giant-cell tumor, osteoma and multilobular osteoma.

The group of the tumors of the endocrine system preferably comprises:
1. Tumors of the thyroid gland/parathyroid, preferably adenoma and adenocarcinoma;
2. Tumors of the suprarenal gland, preferably adenoma, adenocarcinoma and pheochromocytoma (medullosuprarenoma);
3. Tumors of the hypothalamus/hypophysis, preferably adenoma and adenocarcinoma;
4. Tumors of the endocrine pancreas, preferably insulinoma (beta cell tumor, APUDom) and Zollinger-Ellison syndrome (gastrin secernent tumor of the delta cells of the pancreas); and
5. as well as multiple endocrine neoplasias (MEN) and chemodectoma.

The group of the tumors of the female sexual system tumors preferably comprises:
1. Tumors of the ovaries, preferably adenoma, adenocarcinoma, cystadenoma, and undifferentiated carcinoma;
2. Tumors of the uterine, preferably leiomyoma, leiomyosarcoma, adenoma, adenocarcinoma, fibroma, fibrosarcoma and lipoma;
3. Tumors of the cervix, preferably adenocarcinoma, adenoma, leiomyosarcoma and leiomyoma;
4. Tumors of the vagina and vulva, preferably leiomyoma, leiomyosarcoma, fibroleiomyoma, fibroma, fibrosarcoma, polyps and squamous-cell carcinoma.

The group of tumors of the mammary glands preferably comprises:
fibroadenoma, adenoma, adenocarcinoma, mesenchymal tumora, carcinoma, carcinosarcoma.

The group of the tumors of the male sexual system preferably comprises:
1. Tumors of the testicles, preferably seminoma, interstitial-cell tumor and Sertoli cell tumor;
2. Tumors of the prostate, preferably adenocarcinoma, undifferentiated carcinoma, squamous-cell carcinoma, leiomyosarcoma and transitional cell carcinoma; and
3. Tumors of the penis and the external genitals, preferably mast cell tumor and squamous-cell carcinoma.

The group of tumors of the urinary outflow system preferably comprises:
1. Tumors of the kidney, preferably adenocarcinoma, transitional cell carcinoma (epithelial tumors), fibrosarcoma, chondrosarcoma (mesenchymal tumors), Wilm's tumor, nephroblastoma and embryonal nephroma (embryonal pluripotent blastoma);
2. Tumors of the ureter, preferably leiomyoma, leiomyosarcoma, fibropapilloma, transitional cell carcinoma;
3. Tumors of the urinary bladder, preferably transitional cell carcinoma, squamous-cell carcinoma, adenocarcinoma, botryoid (embryonal rhabdomyosarcoma), fibroma, fibrosarcoma, leiomyoma, leiomyosarcoma, papilloma and haemangiosarcoma; and
4. Tumors of the urethra, preferably transitional cell carcinoma, squamous-cell carcinoma and leiomyosarcoma.

The group of tumors of the haematopoietic system preferably comprises:
1. Lymphoma, lymphatic leukemia, non-lymphatic leukemia, myeloproliferative leukemia, Hodgkin's lymphoma, Non-Hodgkin's lymphoma.

The group of the mixed and embryonal tumors preferably comprises:
Haemangiosarcoma, thymoma and mesothelioma.

In a particularly preferred embodiment these tumors are selected from the group comprising breast cancer, ovary carcinoma, prostate carcinoma, osteosarcoma, glioblastoma, melanoma, small-cell lung carcinoma and colorectal carcinoma. Further tumors are those which are resistant as described herein, preferably those which are multiple resistant, particularly also those tumors of the group described above. Especially preferred tumors are also those selected from the group comprising breast tumors, bone tumors, stomach tumors, intestinal tumors, gallbladder tumors, pancreatic tumors, liver tumors, kidney tumors, brain tumors, ovary tumors, tumors of the skin and of cutaneous appendages, head/neck tumors, uterus tumors, synovial tumors, larynx tumors, oesophageal tumors, tongue tumors and prostate tumors. It is preferred that the tumors are those which are disclosed herein regarding their manifestations.

Further tumours which can be treated using the viruses in accordance with the present invention are leukaemia and metastatizing tumours, in particular metastatizing tumours of the afore-mentioned tumours. Further tumours which may be treated in accordance with the present invention, are selected from the group comprising primary tumours, secondary tumours, tertiary tumours and metastatizing tumours. It is preferred if the tumours comprise at least one of the following features, namely that they have YB-1 in the nucleus independent of the cell cycle, regardless what the reason therefore is, and/or that they comprise deregulated YB-1. A further group of tumours which may be treated using the viruses in accordance with the present invention, are all of the afore-mentioned tumours and tumours, respectively, which are described as being treatable using the viruses according to the present invention, provided that they have one or several of the resistances disclosed herein.

It is further within the present invention that also such tumours can be treated using the viruses in accordance with the present invention, which do neither contain YB-1 in the nucleus, preferably independent of the cell cycle, nor deregulated YB-1. This is realized in particular if the viruses themselves code for YB-1. For reasons of specific expression of YB-1 and thus of specific replication of the viruses, the expression of the viruses is put under the control of a preferably highly regulated promoter in a preferred embodiment. Such a promoter could be any of promoters which can be activated in a specific manner so that the viruses can only replicate in the intended cells. Particularly preferred promoters are in particular tumour-specific promoters and tissue-specific promoters which are known to the ones skilled in the art.

YB-1 belongs to the group of highly conserved factors which bind to an inverted CAAT sequence, the so-called Y-box. They may be active in a regulatory manner both at the level of transcription as well as translation (Wolffe, A. P. *Trends in* Cell Biology 8, 318-323, 1998).

The nucleic acid coding for YB-1 which, in an embodiment of the viruses to be used in accordance with the present invention, is part of the viruses, may also comprise a nucleic acid sequence mediating the transport of YB-1 into the nucleus. The nucleic acids, viruses and viral systems in accordance with the invention as well as the adenoviruses known in the prior art such as, for example, Onyx-015, AdΔ24, dl922-947, E1Ad/01/07, CB016, dl 520 and the adenoviruses described in patent EP 0 931 830, can be used as such or in combination with these nucleic acids in accordance with the invention in connection therewith as adenoviruses and adenoviral systems and thus as the corresponding nucleic acids. Suitable nucleic acid sequences which mediate nucleus transport, are known to the ones skilled in the art and, for example, described in (Whittaker, G. R. et al., Virology, 246, 1-23, 1998; Friedberg, E. C., TIBS 17, 347, 1992; Jans, D. A. et al., Bioessays 2000 June; 22(6): 532-44; Yoneda, Y., J. Biochem. (Tokyo) 1997 May; 121(5): 811-7; Boulikas, T., Crit. Rev. Eukaryot. Gene Expr. 1993; 3(3): 193-227; Lyons R H, Mol. Cell Biol., 7, 2451-2456, 1987). In connection with the nucleus transport mediating nucleic acid sequences, different principles can be used. One such principle may, for example, be that YB-1 is formed as a fusion protein together with a signal peptide and is introduced into the nucleus and that the replication of the adenoviruses according to the present invention thus occurs.

A further principle which may be realised in the design of the adenoviruses used in accordance with the invention, is that YB-1 can be provided with a transporter sequence which, preferably starting from synthesis in the cytoplasma, introduces YB-1 into the cell nucleus or which translocates YB-1 into the cell nucleus, and promotes viral replication there. An example for a particularly effective nucleic acid sequence mediating nucleus transport is the TAT sequence of HIV which is, among other suitable nucleic acid sequences of that type described in Efthymiadis, A., Briggs, L J, Jans, D A., JBC 273, 1623-1628, 1998. It is within the present invention that the adenoviruses which are used in accordance with the present invention, comprise nucleic acid sequences which code for peptides coding for nuclear transportation.

It is within the present invention that YB-1 is present in its full length, particularly in a form which corresponds to the wildtype of YB-1. It is within the present invention that YB-1 is used or present as a derivative, such as, e. g. in shortened or truncated form. A YB-1 derivative as used or present within the present invention, is a YB-1 which is capable of binding to the E2-late promoter and thus activates gene expression of the adenoviral E2 region. Such derivatives particularly comprise the YB-1 derivatives disclosed herein. Further derivatives may be generated by deletion of single or several amino acids at the N-terminus, at the C-terminus or within the amino acid sequence. It is within the present invention that YB-1 fragments are also used and referred to as YB-1 proteins in the meaning of the present invention. Various YB-1 fragments are disclosed in the paper of Jürchott K et al. [JBC 2003, 278, 27988-27996] which are characterized by deletions in the C-terminus and the N terminus. The distribution of the various YB-1 fragments indicated that both the cold-shock domain (CSD) as well as the C-terminus are important for the cell cycle-regulated transport of YB-1 into the nucleus. It is thus within the present invention that a truncated YB-1 (which is also referred to herein as YB-1 protein) is migrating in a better way into the nucleus in combination with the expression of E1B55k and E4orf6 in accordance with the present invention and thus induces a stronger CPE without necessarily binding better to the E2-late promoter compared to native YB-1, whereby it cannot be excluded that also a truncated YB-1 is migrating better into the nucleus and exhibits both activities, i.e. induces CPE and binds to the E2-late promoter. Finally, such truncated YB-1 fragments can also migrate into the nucleus better and bind to the E2-late promoter better without inducing a better CPE. It is also within the present invention that truncated YB-1 proteins or fragments comprise further sequences such as described herein in connection with the full length YB-1, in particular cellular localization signal sequences (NLS) and the like.

It is within the present invention that the medicament for the manufacture of which the viruses are used in accordance with the present invention represents in its various embodiments a further aspect of the present invention in itself.

The invention is related in a further aspect to a method for the screening of patients which, preferably suffer or are suspect to suffer from a tumour or tumour disease and which may be treated using the viruses in accordance with the present invention, whereby the method comprises the following steps:
  Analysing a sample of the patient, preferably a sample of the tumor tissue and
  Determining whether YB-1 is localised in the nucleus independent of the cell cycle, or whether the cell contain deregulated/overexpressed YB-1 in one or several of the cells of the sample.

Instead of or in addition to YB-1 also the presence of the afore-described markers which, preferably, act or are known to act as surrogate markers, can be assessed.

Alternatively, the sample can be tested whether the cells contained therein are resistant in the meaning of the present invention.

In case that the tumor tissue or a part thereof comprises YB-1 in the nucleus, preferably independent of the cell cycle, or comprises deregulated YB-1, or the cells are resistant in the meaning of the present invention, the viruses as disclosed herein, may be used in accordance with the present invention.

In an embodiment of the method according to the invention it is contemplated that the analysis of the tumor tissue occurs by means of an agent which is selected from the group comprising antibodies against YB-1, YB-1 specifically binding peptides, aptamers against YB-1, spiegelmers against YB-1 as well as anticalines against YB-1. In principle, the same kind of agents can also be made and used, respectively, for the respective markers. The manufacture of antibodies, in particular monoclonal antibodies, is known to the ones skilled in the art. A further agent for specific detection of YB-1 or the markers are peptides which bind with a high affinity to their target structures, in the present case YB-1 or said markers. In the prior art methods are known such as, for example, phage-display, in order to generate such peptides. For such purpose, it is started from a peptide library whereby the individual peptides have a length of about 8 to 20 amino acids and the size of the library is about $10^2$ to $10^{18}$, preferably $10^8$ to $10^{15}$ different peptides. A particular form of target molecule binding polypeptides are the so-called anticalines which are, for example, described in German patent application DE 197 42 706.

A further agent for specifically binding to YB-1 or to the corresponding alternative markers disclosed herein and thus for the detection of a cell cycle independent localisation of YB-1 in the nucleus, are the so-called aptamers, i. e. D-nucleic acids, which, based on RNA or DNA, are present as either a single strand or a double strand and specifically bind to a target molecule. The generation of aptamers is, for example, described in European patent EP 0 533 838. A special embodiment of aptamers are the so-called aptazymes which, for example, are described by Piganeau, N. et al. (2000), Angew. Chem. Int. Ed., 39, no. 29, pages 4369-4373. They are a particular embodiment of aptamers insofar as they comprise apart from the aptamer moiety a ribozyme moiety and, upon binding or release of the target molecule binding to the aptamer moiety, the ribozyme moiety becomes catalytically active and cleaves a nucleic acid substrate which goes along with generation of a signal.

A further form of the aptamers are the so-called spiegelmers, i. e. target molecule binding nucleic acids which consist of L-nucleic acids. The method for the generation of such spiegelmers is, for example, described in WO 98/08856.

The sample of the tumor tissue can be obtained by punctuation or surgery. The assessment whether YB-1 is located in the nucleus independent of the cell cycle is frequently done by the use of microscopic techniques and/or immunohistoanalysis, typically using the antibody or any of the further agents described above. Further methods for the detection of YB-1 in the nucleus and that its localisation there is independent of the cell cycle, are known to the one skilled in the art. For example, localisation of YB-1 can easily be detected when scanning tissue slices stained against YB-1. The frequency of YB-1 being in the nucleus is already an indication that the localisation in the nucleus is independent of the cell cycle. A further possibility for cell cycle independent detection of YB-1 in the nucleus is the staining against YB-1 and assessment whether YB-1 is localised in the nucleus and determining the phase of the cells. This and the detection of YB-1, respectively, however, can also be performed using the afore-mentioned agents directed against YB-1. The detection of the agents is done by procedures known to the one skilled in the art. Because said agents are specifically directed against YB-1 and insofar do not bind to other structures within the sample to be analysed, particularly other structures of the cells, both the localisation of said agents by means of a suitable labelling of the agents and due to their specific binding to YB-1, also the localisation of YB-1 can be detected and assessed accordingly. Methods for the labelling of the agents are known to the ones skilled in the art.

It is within the present invention that the viruses described herein, whether they are the viruses in accordance with the present invention, or whether they are the viruses to be used in accordance with the present invention, may also be used in connection with diseases, in particular tumor diseases and more preferably tumor diseases where at least part of the tumor cells exhibit a multiple resistance, in particular a multidrug resistance, whereby YB-1 is present in a deregulated form. This applies also to each and any of the other aspects as described herein in connection with cells and tumors, provided that they refer to the cells and diseases where YB-1 is present in the nucleus, preferably independent of the cell cycle.

Although the viruses in accordance with the present invention and as disclosed herein, are preferably adenoviruses the insights, methods and uses, nucleic acids, proteins, replication systems and the like are not limited to adenoviruses but apply to other viruses and viral systems.

The aforementioned considerations, including any use as well as the generation of the adenoviruses and adenoviral systems, apply equally to the nucleic acids coding therefore and vice versa.

In connection with the present invention it is possible that the adenoviruses which are used in accordance with the present invention and the nucleic acids coding therefore, respectively, is any corresponding adenoviral nucleic acid which result in a replication event per se or in combination with further nucleic acid sequences. It is possible, as explained herein, that by means of helper viruses the sequences and/or gene products are provided which are necessary for replication. To the extant it is referred to coding nucleic acid sequences and to the extent they are nucleic acid sequences which are known, it is within the present invention that not only the identical sequence, but also sequences derived therefrom, are used. Derived sequences are in particularly those sequences which still result in a gene product, either nucleic acid or a polypeptide having a function which corresponds to one or the function of the non-derived sequence. This can be determined by simple routine tests known to the one skilled in the art. An example for such derived nucleic acid sequences are nucleic acid sequences which code for the same gene product, in particularly the same amino acid sequence, however, due to the degeneracy of the genetic code, exhibit a different base sequence.

It is within the present invention that the viruses in accordance with the present invention are present as replication systems with or without helper viruses.

It is further within the present invention that in case of such adenoviral replication system in accordance with the present invention that the adenoviral nucleic acids and/or the nucleic acid is present as a replicable vector.

It is further within the present invention that the nucleic acid(s) coding for the adenoviruses which are used in accordance with the present invention, are present in an expression vector and that this expression vector is used in accordance with the present invention.

In a further aspect the present invention is related also to a vector group comprising at least two vectors, whereby the vector group in its entirety comprises an adenoviral replication system as described herein, and the vector group is used in accordance with the present invention. It is within the invention that each of the components of the adenoviral replication system is present on a separate vector, preferably an expression vector.

Finally, the present invention is related in a further aspect to the use of a cell which contains one or several of the nucleic acids which code for the viruses which are used in accordance with the present invention, and which are to be used in accordance with the invention of and/or a corresponding viral replication system and/or a corresponding vector and/or a vector group according to the invention, for the very same purpose as described herein for the various adenoviruses.

The above described constructs of viruses and in particular their nucleic acids and the nucleic acids coding therefor, may also be introduced in a multipartite form into a cell, preferably a tumour cell, whereby due to the presence of the various individual components they act together as if the individual components were derived from a single nucleic acid and a single or several viruses, respectively.

The nucleic acids which are used in accordance with the invention and which code for viruses, viral systems or parts thereof, may also be present as vectors. Preferably these vectors are viral vectors. In case the nucleic acids comprise viral nucleic acids, preferably the virus particle is the vector. It is, however, also within the present invention that said nucleic acids are present in a plasmid vector. In each case the vector comprises elements which allow for and control the propagation of inserted nucleic acid, i. e. replication and the optional expression of the inserted nucleic acid. Suitable vectors, preferably expression vectors, and respective elements are known to the ones skilled in the art and, for example, described in Grunhaus, A., Horwitz, M. S., 1994, Adenoviruses as cloning vectors. In Rice, C., editor, Seminars in Virology, London: Saunders Scientific Publications.

The aspect related to the vector groups takes into account the afore-described embodiment that the various elements of said nucleic acid are not necessarily contained in a single vector only. Accordingly, a vector group consists of at least two vectors. Apart from that, any statements made in relation to the vectors is also applicable to the vectors and the vector group, respectively.

The viruses and in particular adenoviruses, used in accordance with the present invention are characterised by the various nucleic acids and gene products, respectively, disclosed herein and may otherwise preferably comprise all those elements known to the ones skilled in the art and which are inherent to the wildtype adenoviruses (Shenk, T.: Adenoviridae: The virus and their replication. Fields Virology, vol. 3, editors Fields, B. N., Knipe, D. M., Howley, P. M. et al., Lippincott-Raven Publishers, Philadelphia, 1996, chapter 67).

In a further aspect the present invention is related to a method for the treatment of tumor diseases comprising the administration of a virus in accordance with the present invention, such nucleic acid, vectors, replication systems, medicaments or pharmaceutical compositions. The tumor disease is one as disclosed herein. The patient is in need of such treatment and is preferably a patient selected from the groups of patients disclosed herein.

It is within the present invention that, if not indicated to the contrary, the features and embodiments disclosed for the respective viruses, nucleic acid, vectors, replication systems, medicaments and pharmaceutical compositions, each in accordance with the present invention, are also applicable to each and any of the other aspects of the present invention. It is within the present invention that the various transgenes can be cloned into appropriate sites within the viral genome. Particularly preferred are the E1-, E2A-, E2B-, E3- and E4-region. The cloning of the transporter into the E1 region is particularly preferred. It will be acknowledged by the one skilled in the art that the cloning of the transgenes into the respective sites of the viral genome will partially or completely inactivate or delete the genes encoded by these sites. However, it is within the present invention that the genes encoded by the particular site can remain partially or completely active.

The viruses in accordance with the present invention are preferably adenoviruses.

The term treatment of a disease or disorder comprises in a preferred embodiment also the prevention of this disease or disorder.

In the following the present invention shall be further illustrated by reference to the figures and examples from which new features, embodiments and advantages may be taken.

Figure 12:
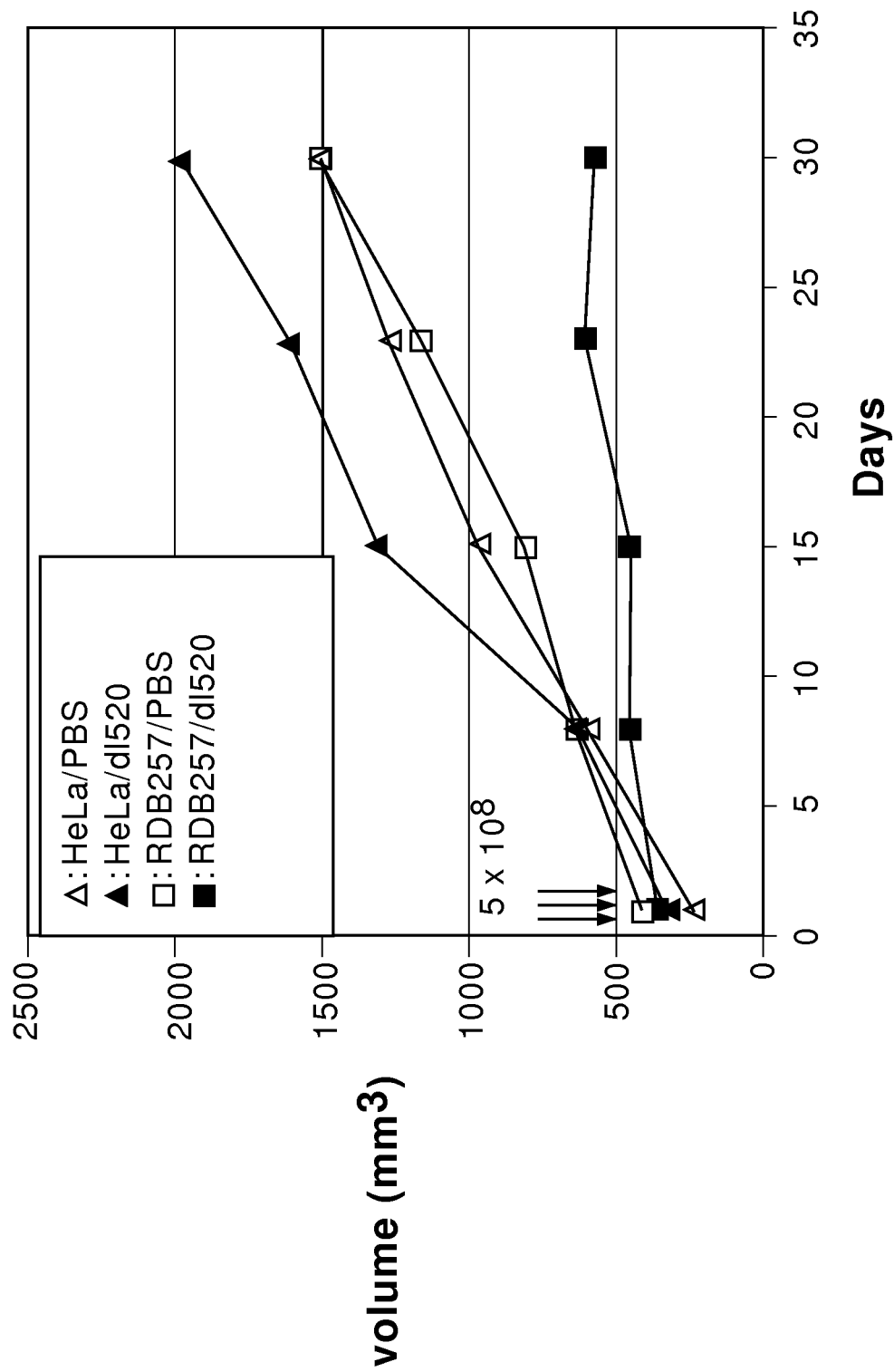

FIG. 12 is a diagram of the tumor volume of tumors having different origins (RDB257 and HeLa) as a function of time after treatment with PBS and dl520, respectively.

Figure 13:
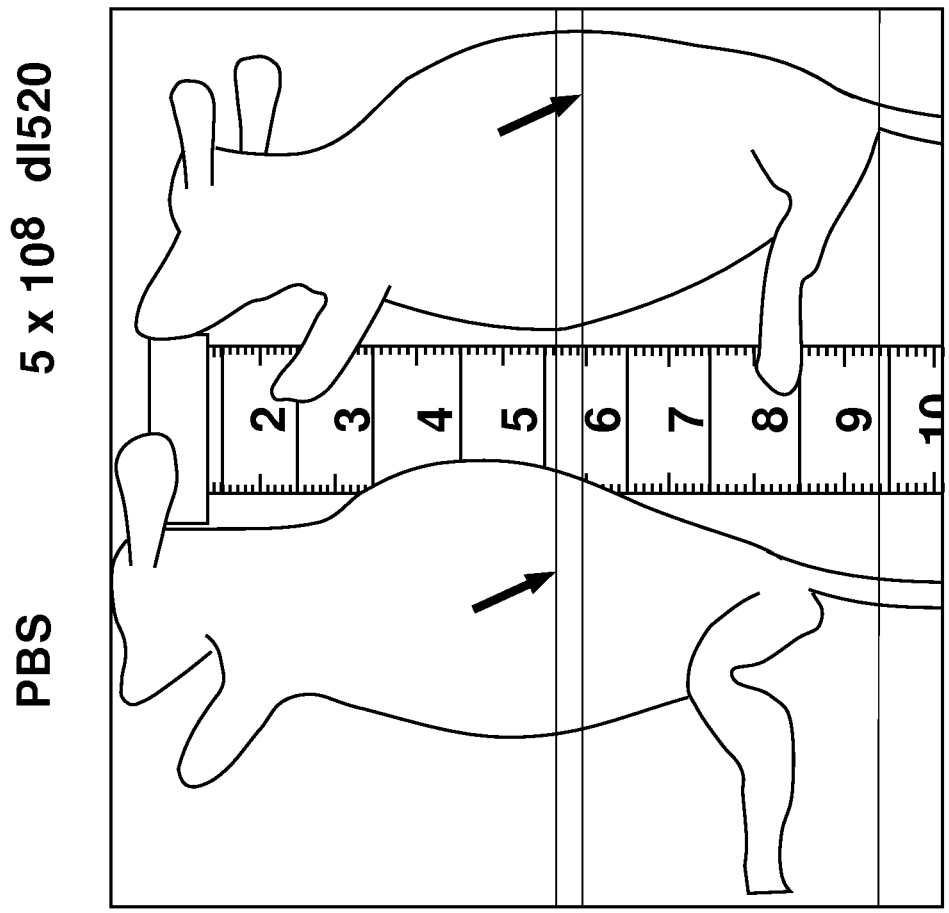

FIG. 13 shows pictures of sacrificed mice which developed a tumor based on RDB257 cells after treatment with PBS and $5 \times 10^8$ pfu dl520, respectively.

Figure 14:
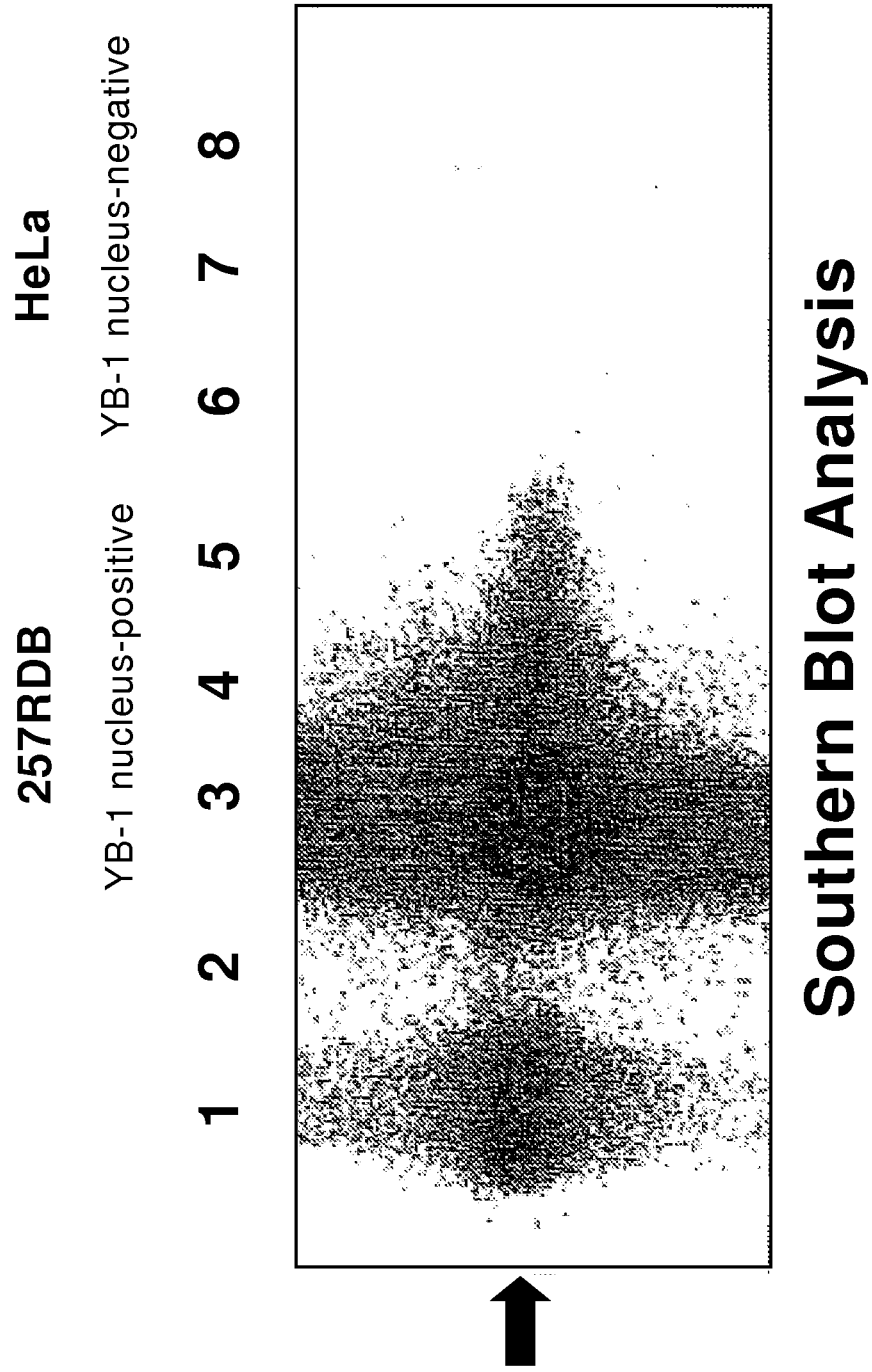

FIG. 14 is the result of a Southern Blot analysis of a cell extract (of the tumors grown subcutaneously) of RDB257 cells and HeLa cells after infection with dl520.

Figure 15:
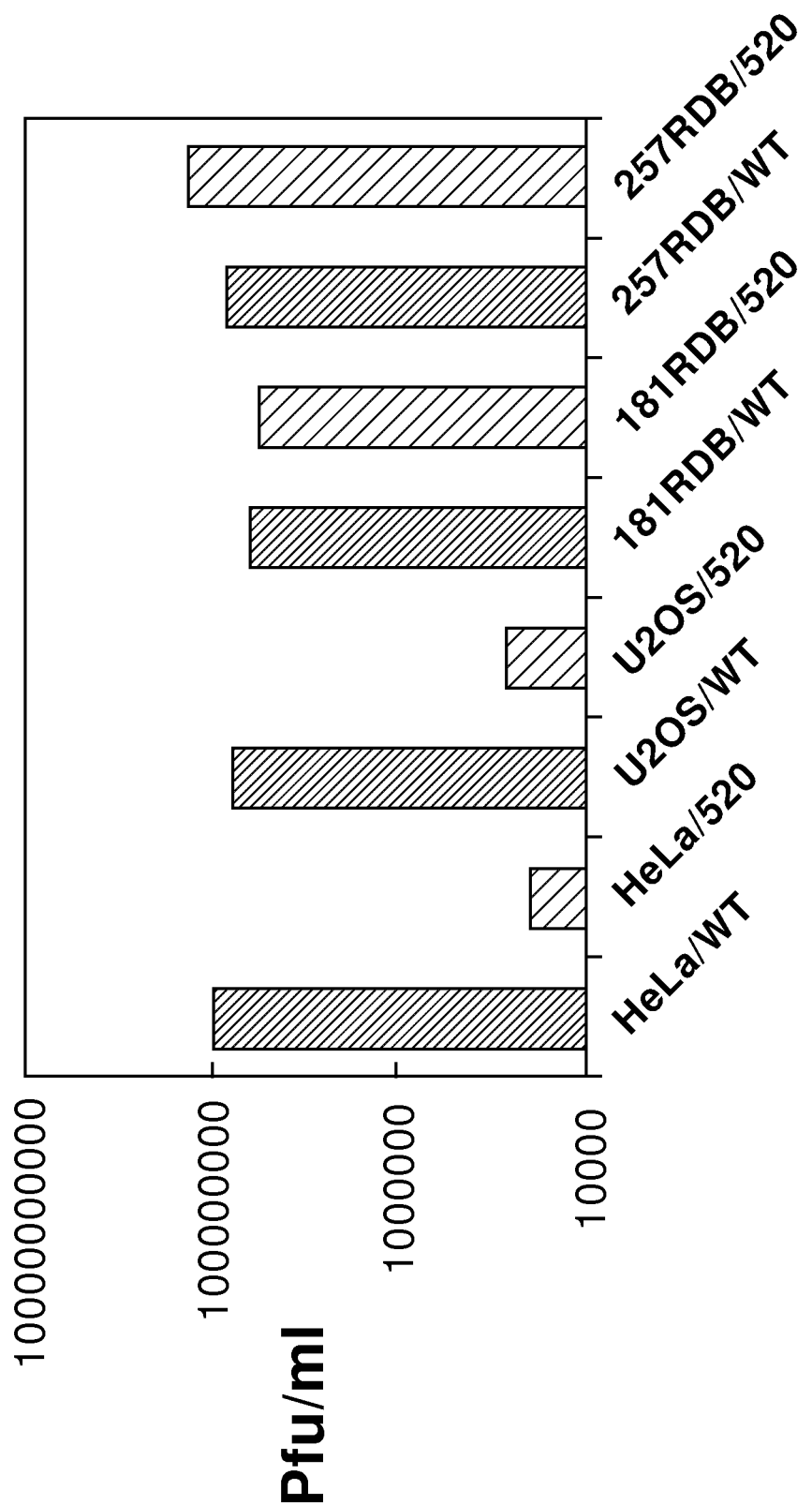

FIG. 15 is a column diagram showing the replication efficiency and particle formation, respectively, of dl520 and wildtype adenoviruses in YB-1 nucleus-positive tumor cells (257RDB and 181RDB) and YB-1 nucleus-negative tumor cells (HeLa, U2OS).

FIG. 16 shows the structural design of wildtype adenovirus and adenoviral vector AdXvir03.

Figure 17:
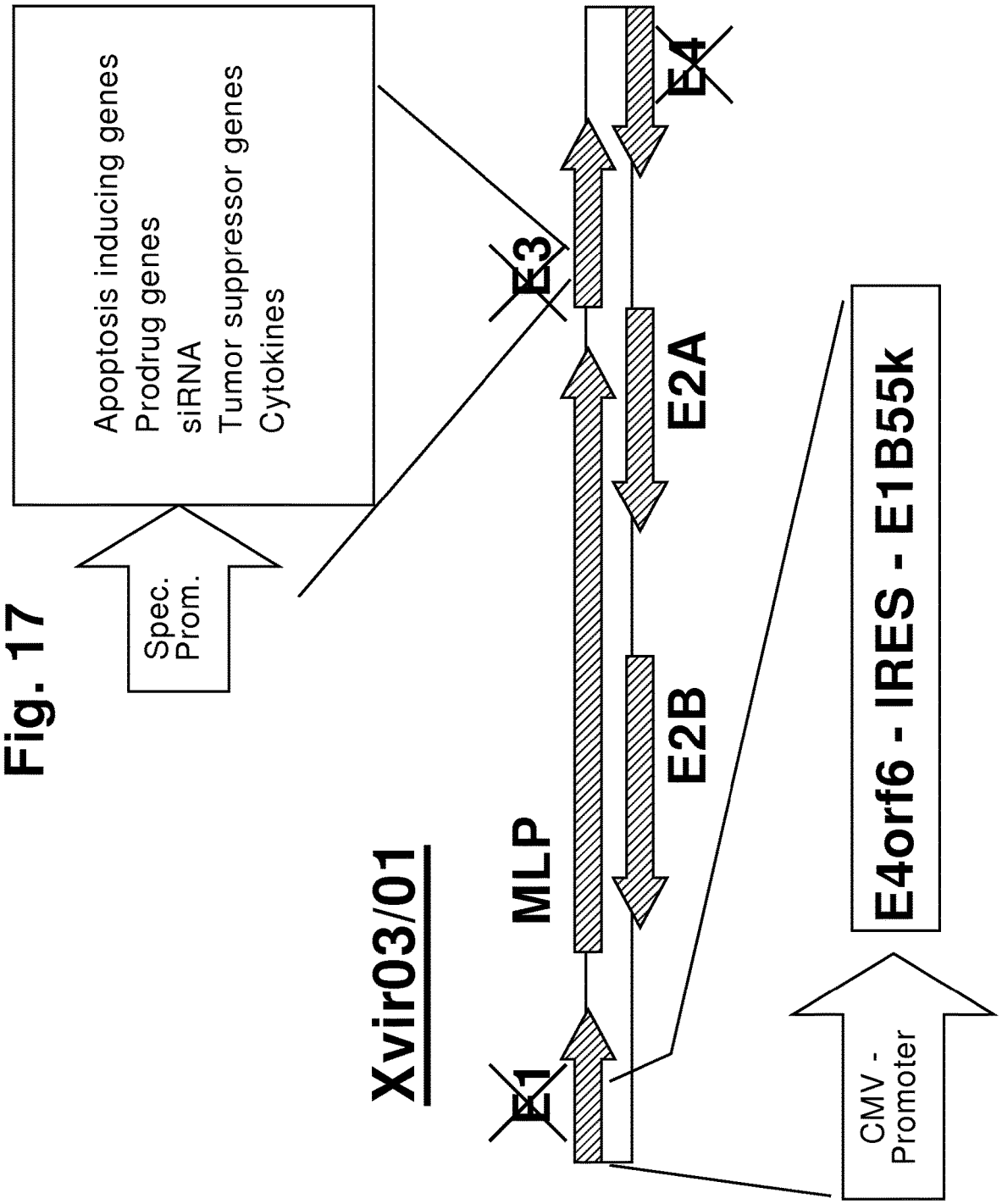

FIG. 17 shows the structural design of adenoviral vector AdXvir03/01.

Figure 18B:
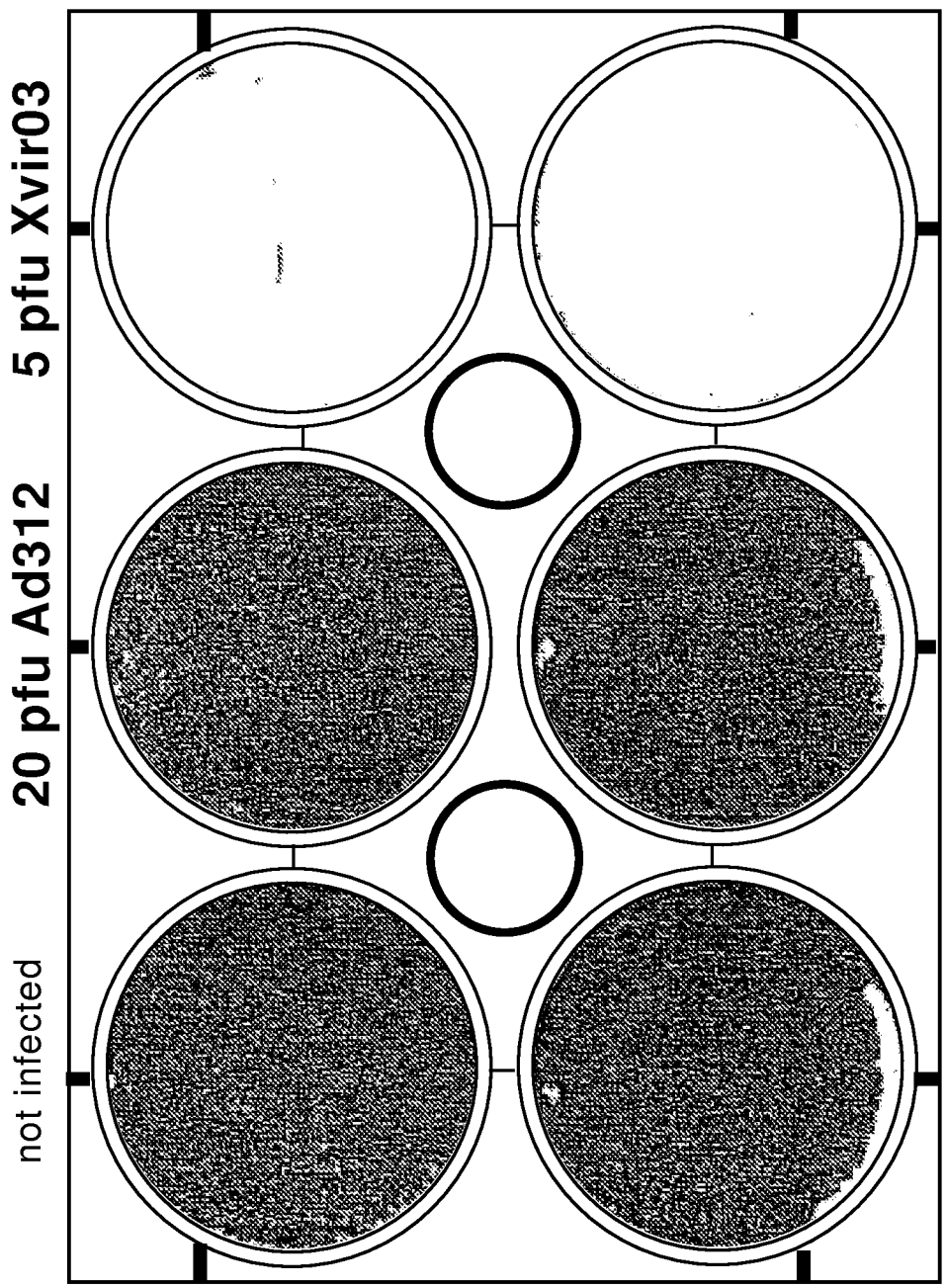
Figure 19:
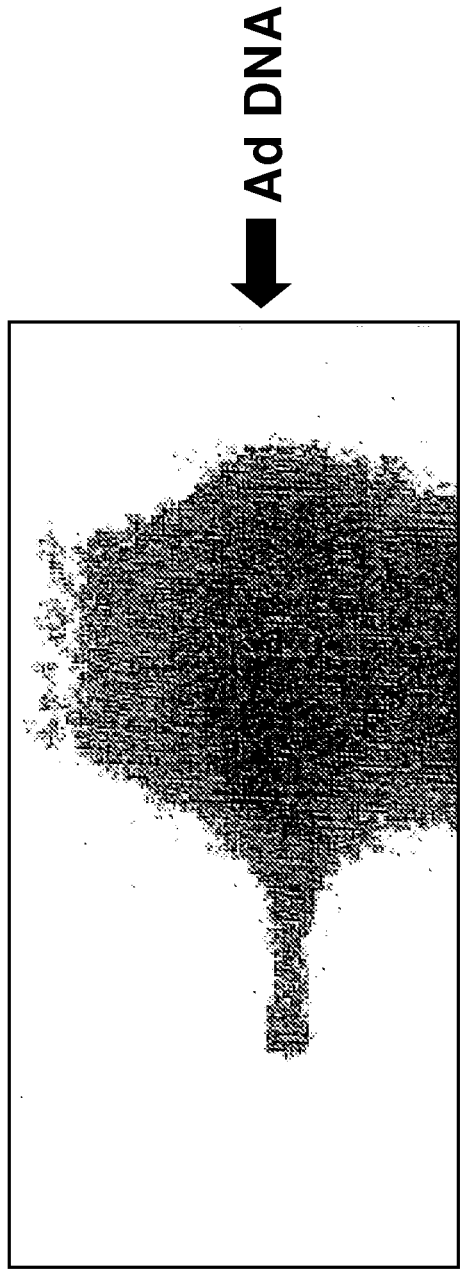
Figure 20:
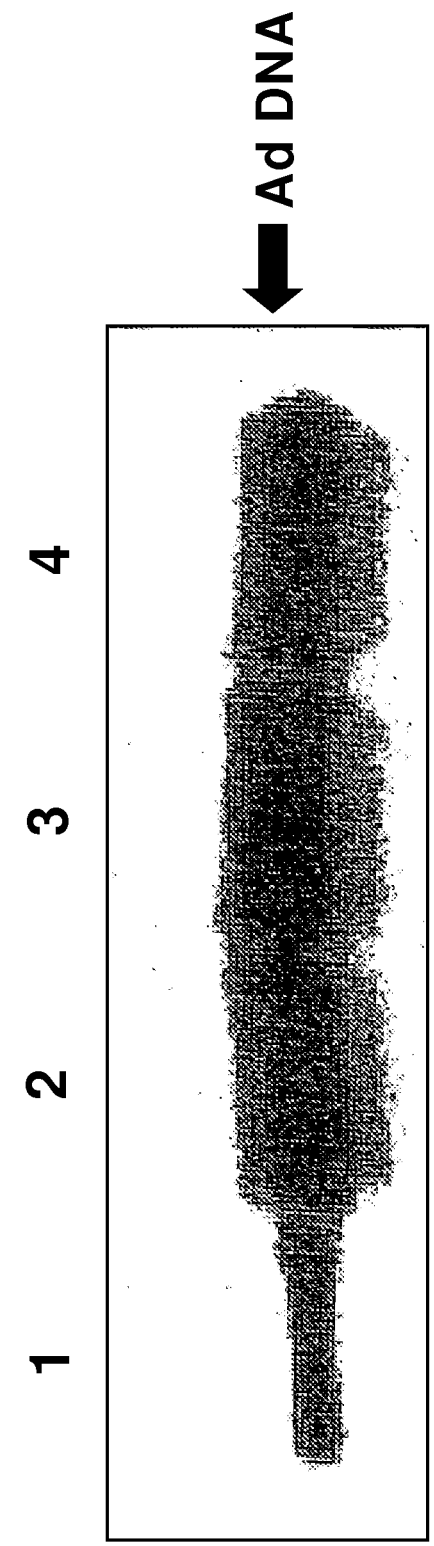
Figure 21:
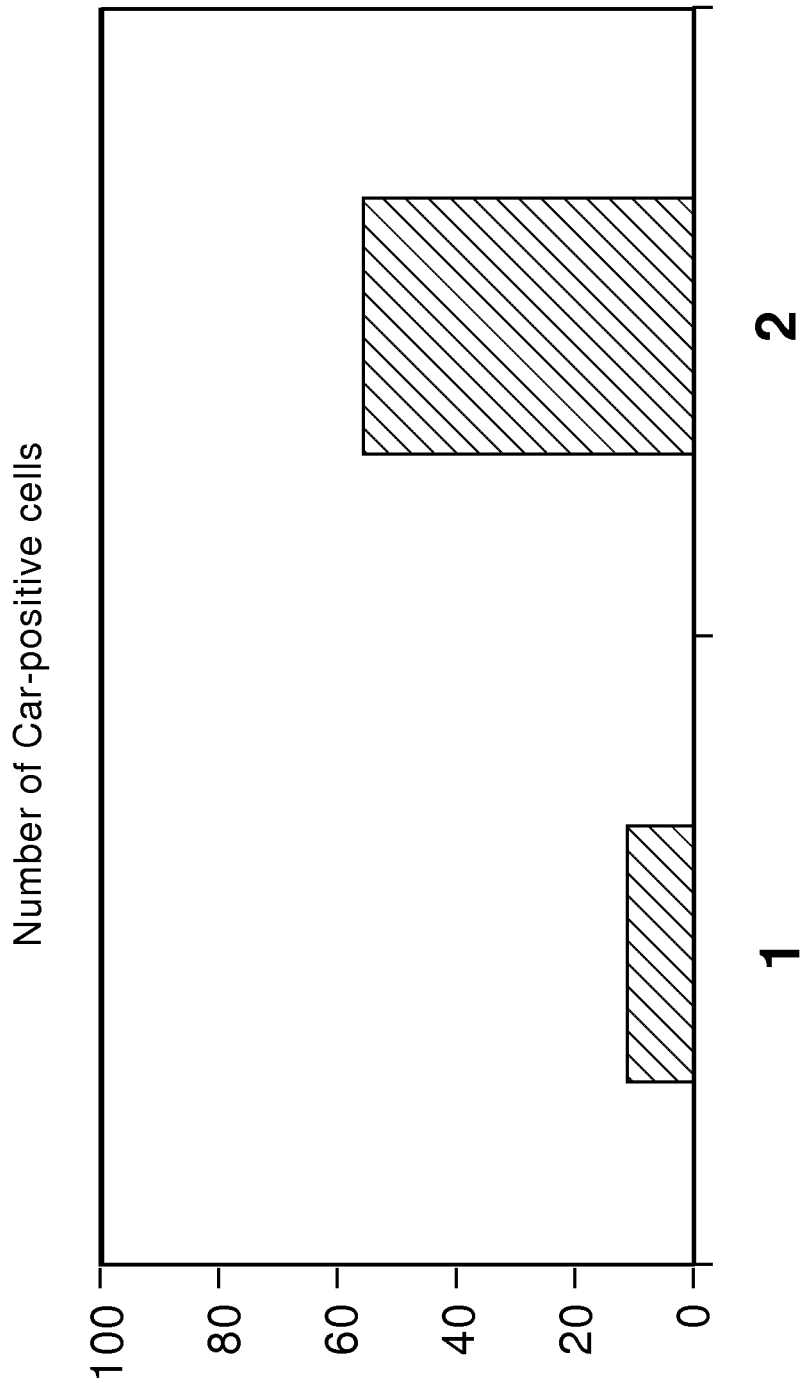
Figure 22:
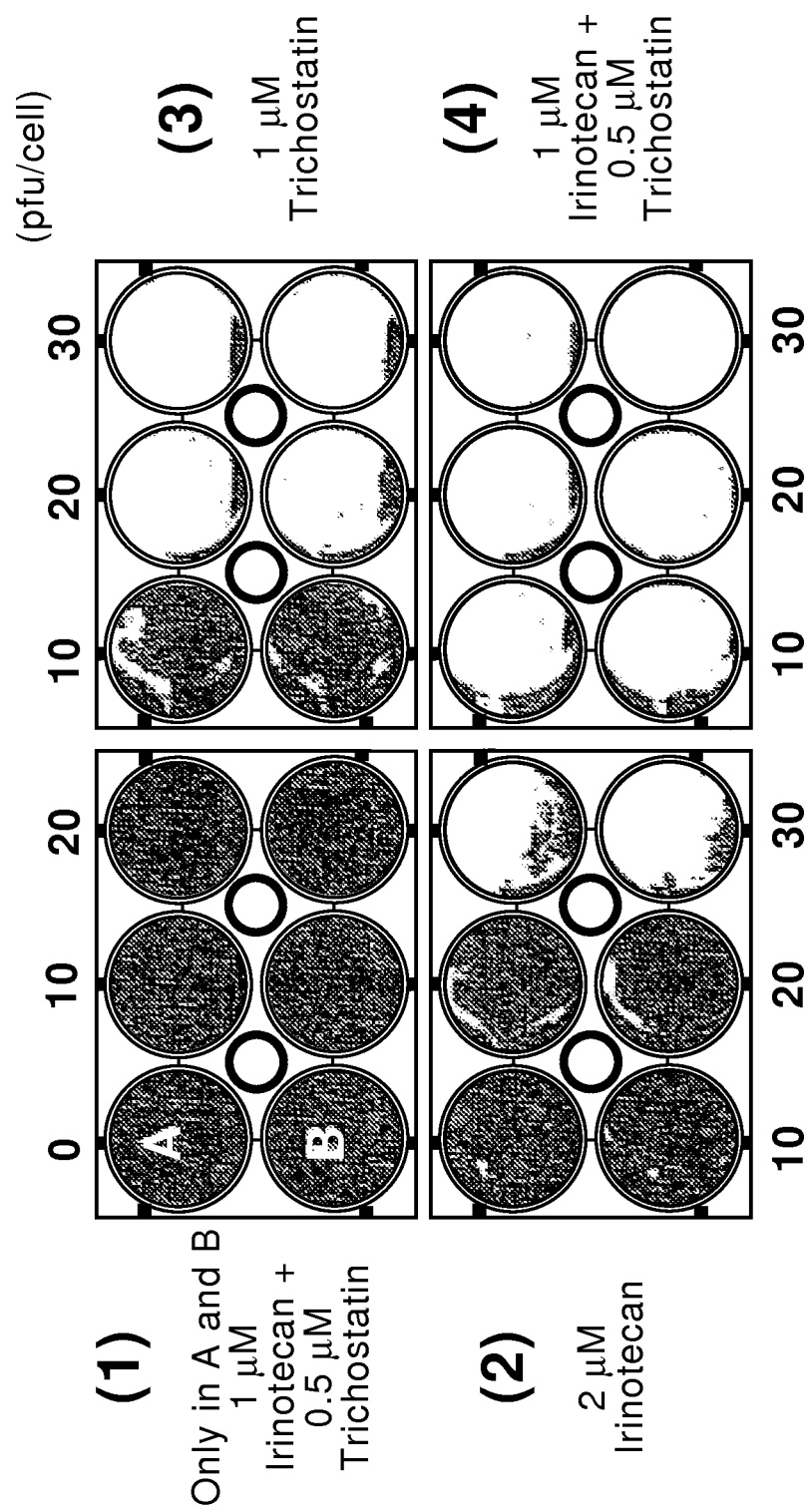
Figure 23:
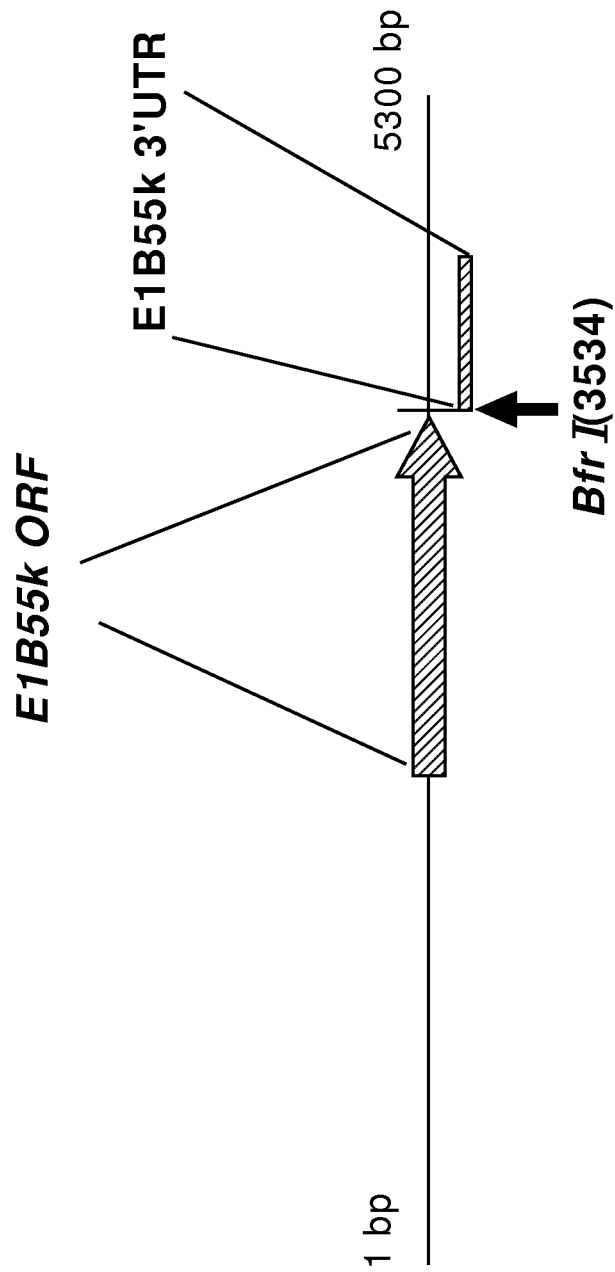

FIG. 18A/B shows wells grown with 181RDB cells (FIG. 18A) and 272RDB cells (FIG. 18B) after crystal violet staining and infection with Ad312 (20 pfu/cell), Xvir03 (5 pfu/cell) and control (non-infected), whereby crystal violet staining was performed five days past infection;

FIG. 19 is the result of a Southern blot analysis of the replication behaviour of adenovirus dl 520 in U373 cells with and without treatment of the cells with irinotecan;

FIG. 20 is the result of a Southern blot analysis of the replication behaviour of adenovirus dl 520 in U373 cells with and without treatment of the cells with trichostatin A;

FIG. 21 is the result of a FACS analysis of trichostatin treated U 373 cells related to the expression of the Coxsackie virus adenovirus receptor (CAR), expressed as percentage of CAR positive cells; and FIG. 22 shows four different panels of cell layers for depicting the effect of replicating adenovirus dl520 and irinotecan and trichostatin in different combinations;

FIG. 23 shows a schematic representation of the ORF of E1B 55K with the 3'UTR fragment and the restriction cleavage site Bfr I at position 3532; and FIG. 24 shows the sequence of the E1B55k-3'UTR region corresponding to sequence position 3507 to 4174 of wildtype Ad 5; (SEQ ID NO: 35)

Figure 25:
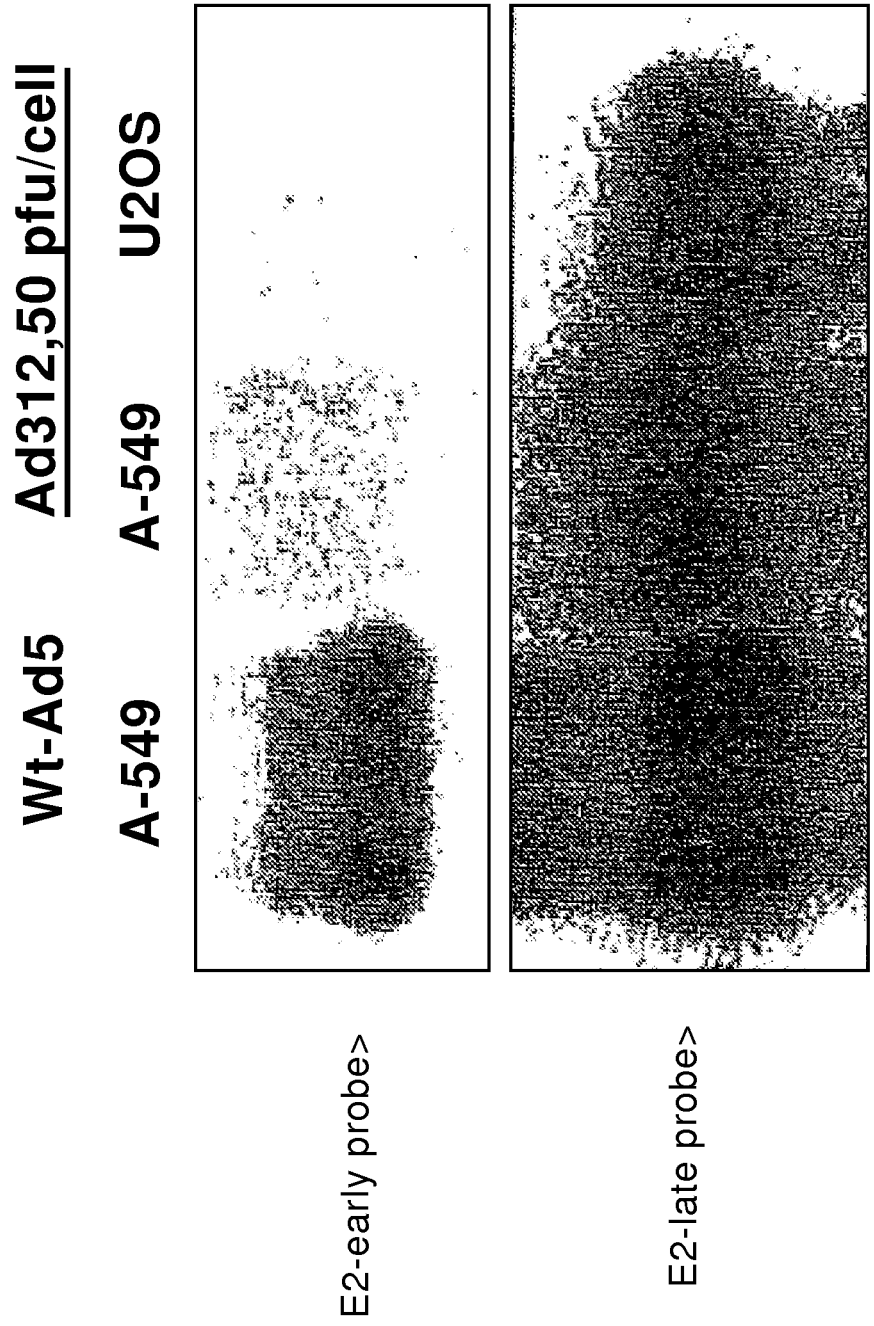
Figure 26:
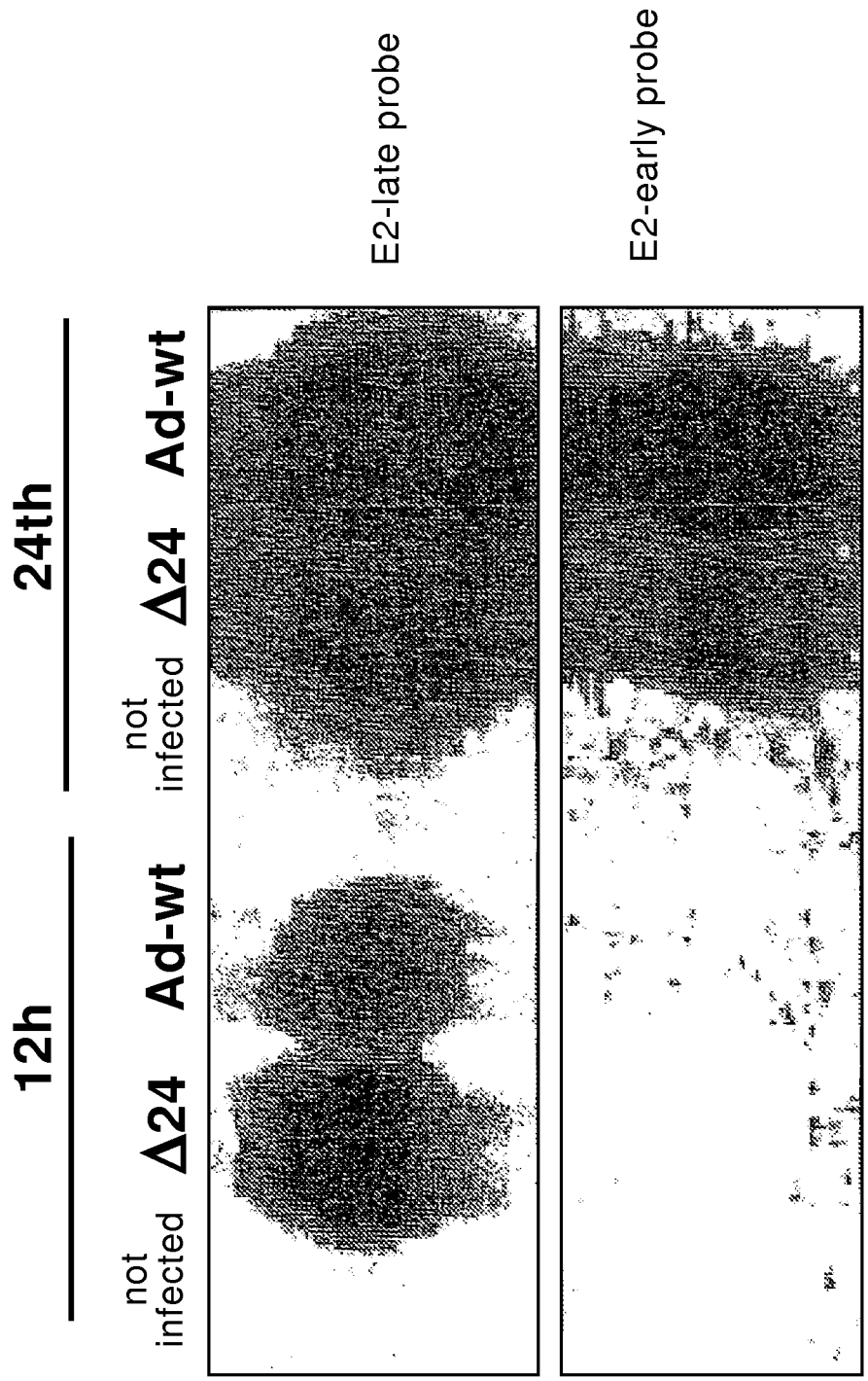
Figure 27:
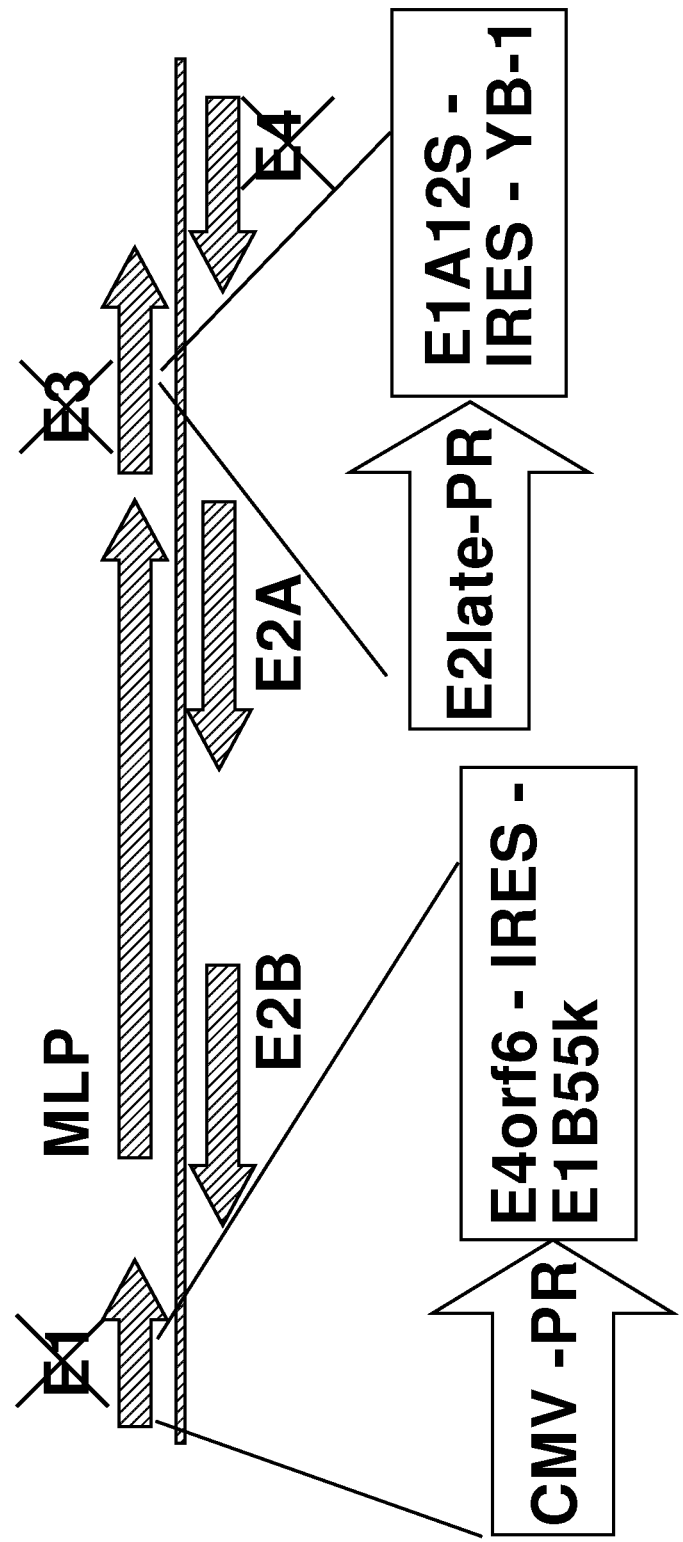
Figure 28:
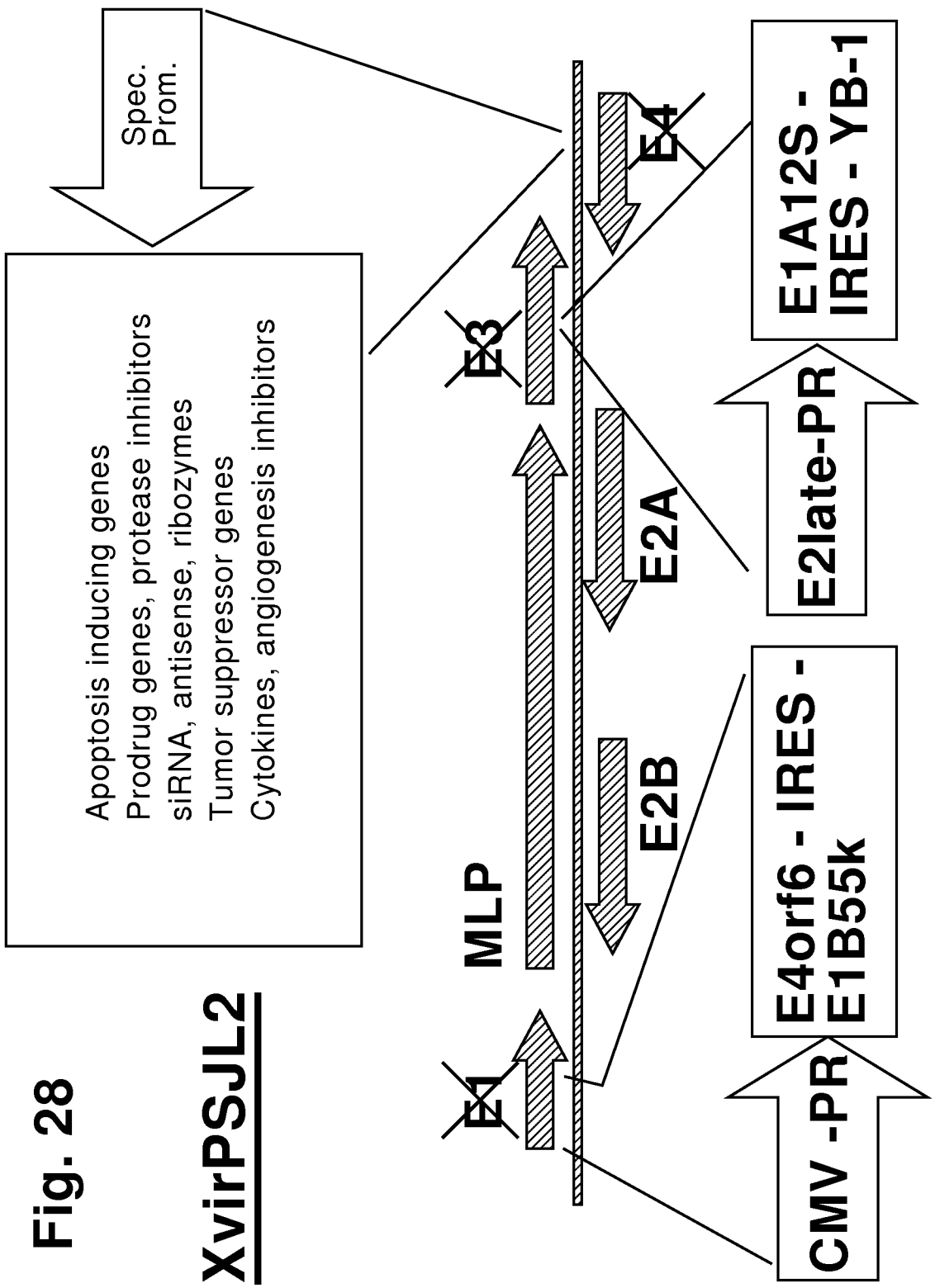
Figure 29:
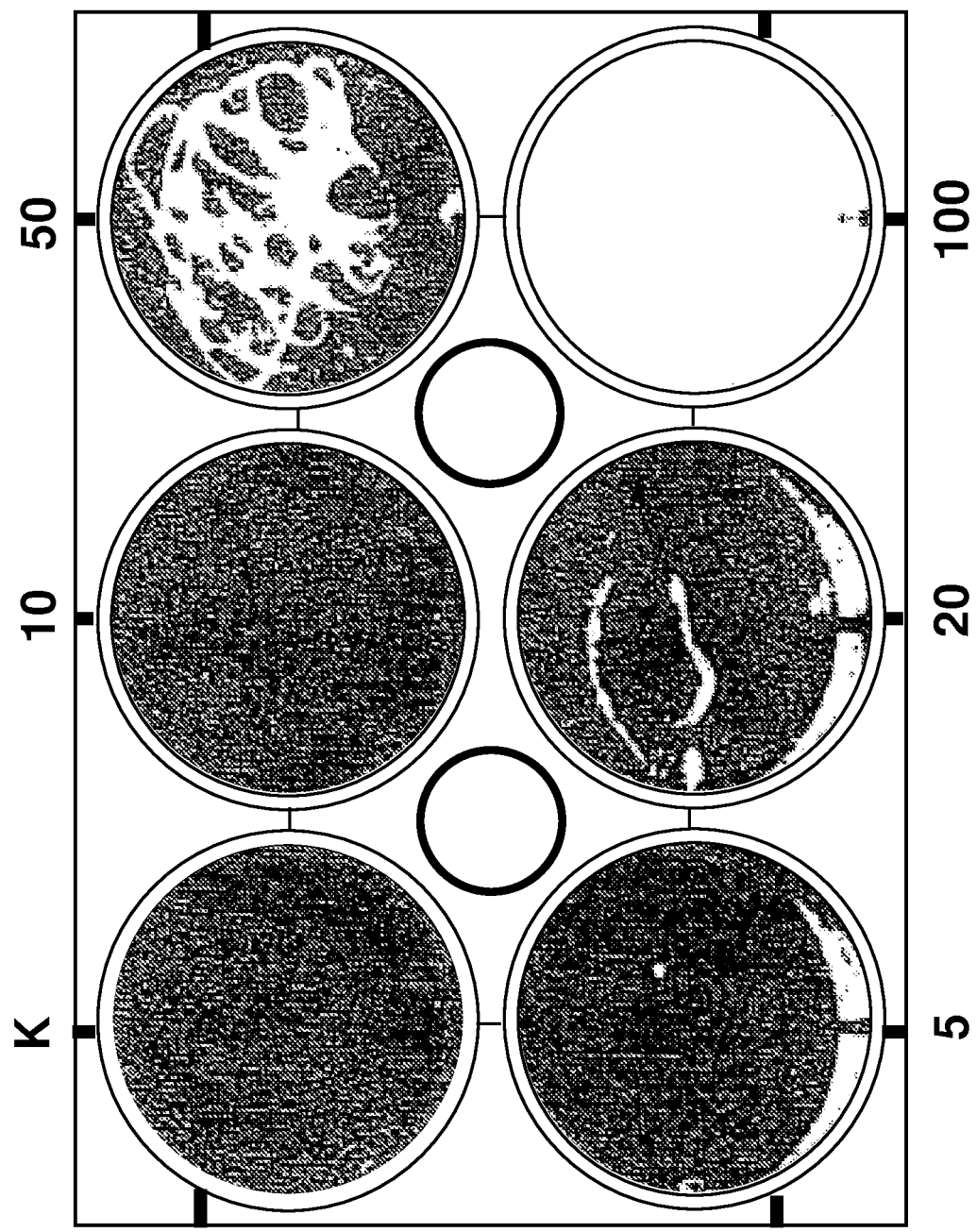
Figure 30:
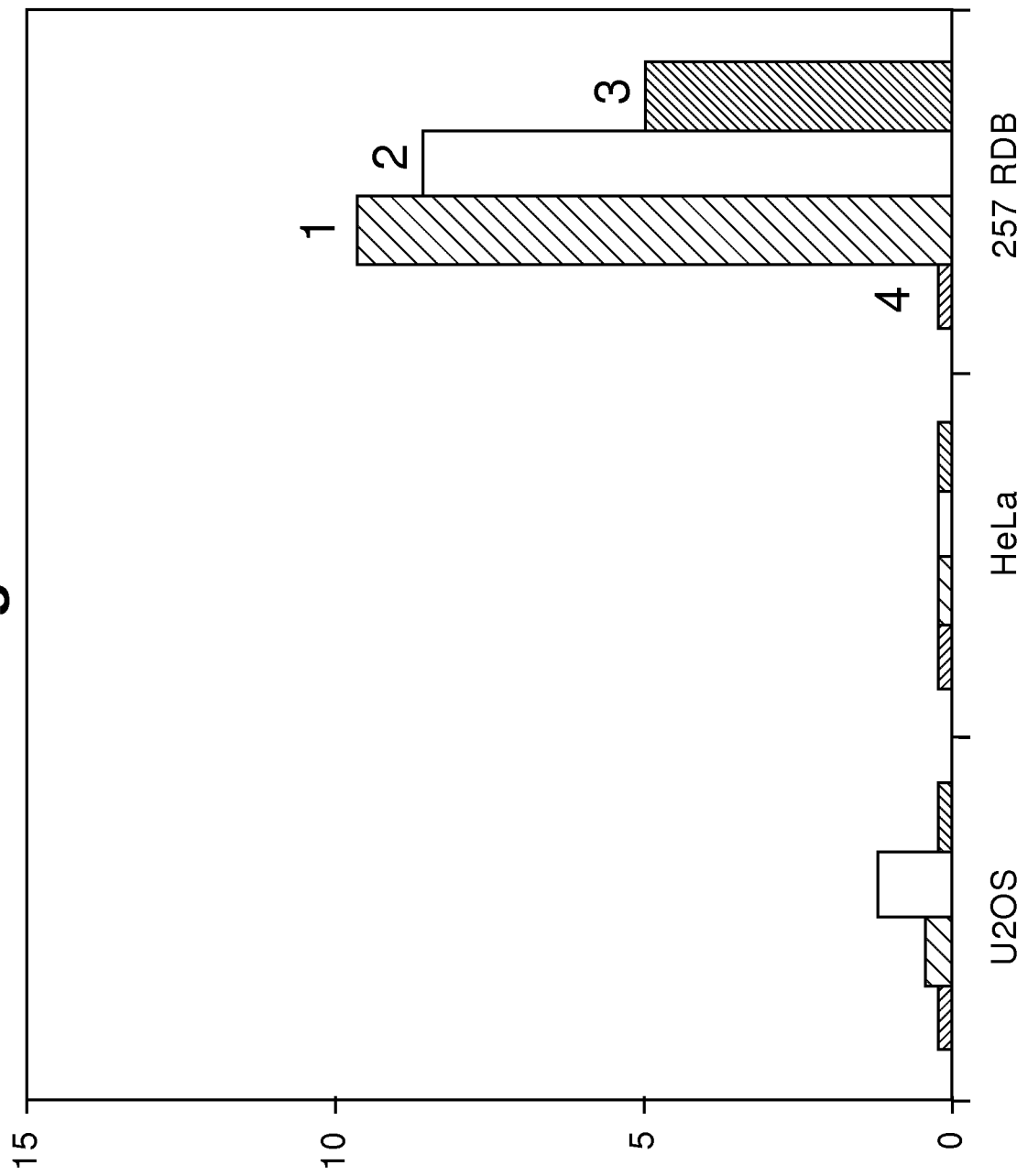
Figure 31:
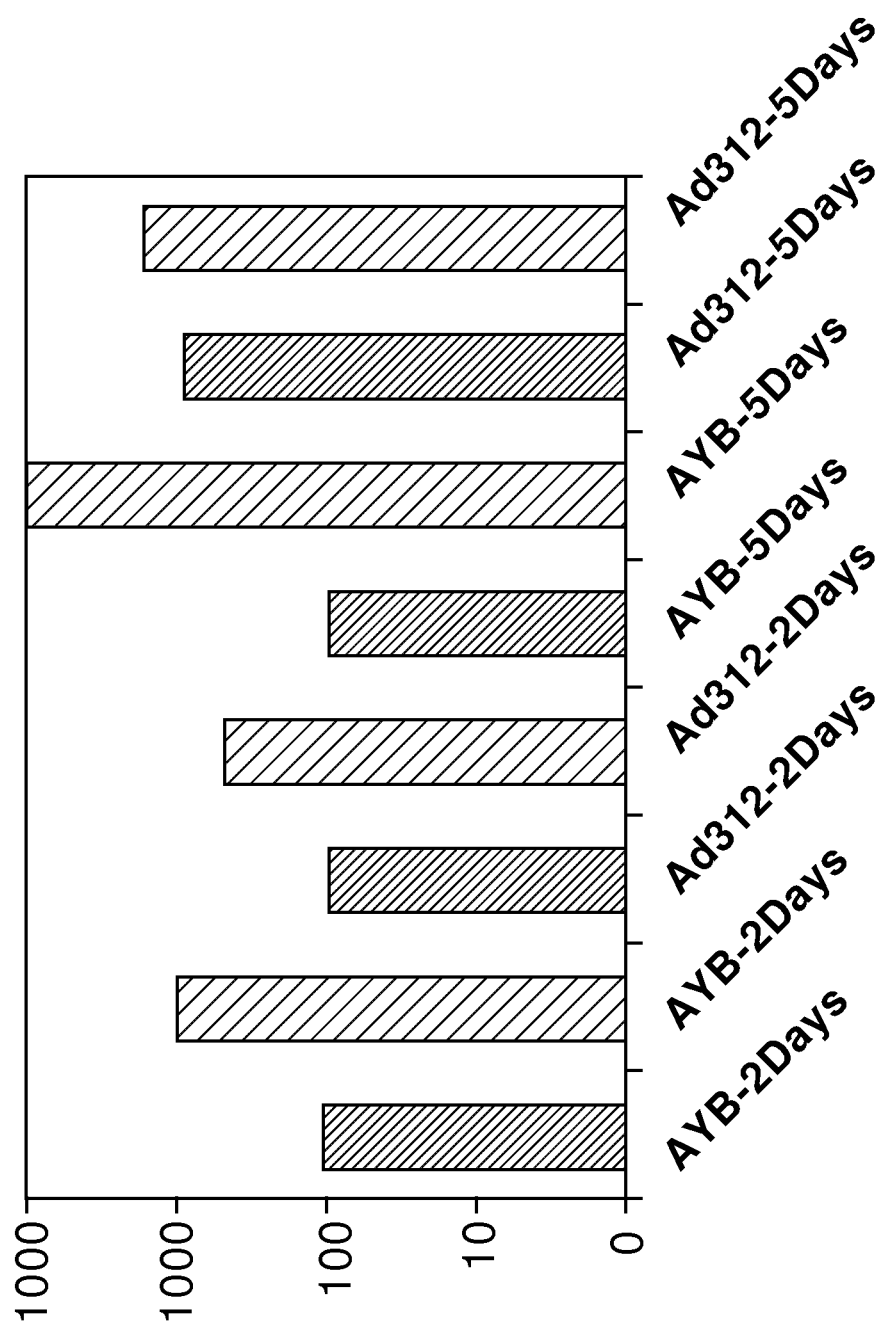
Figure 32:
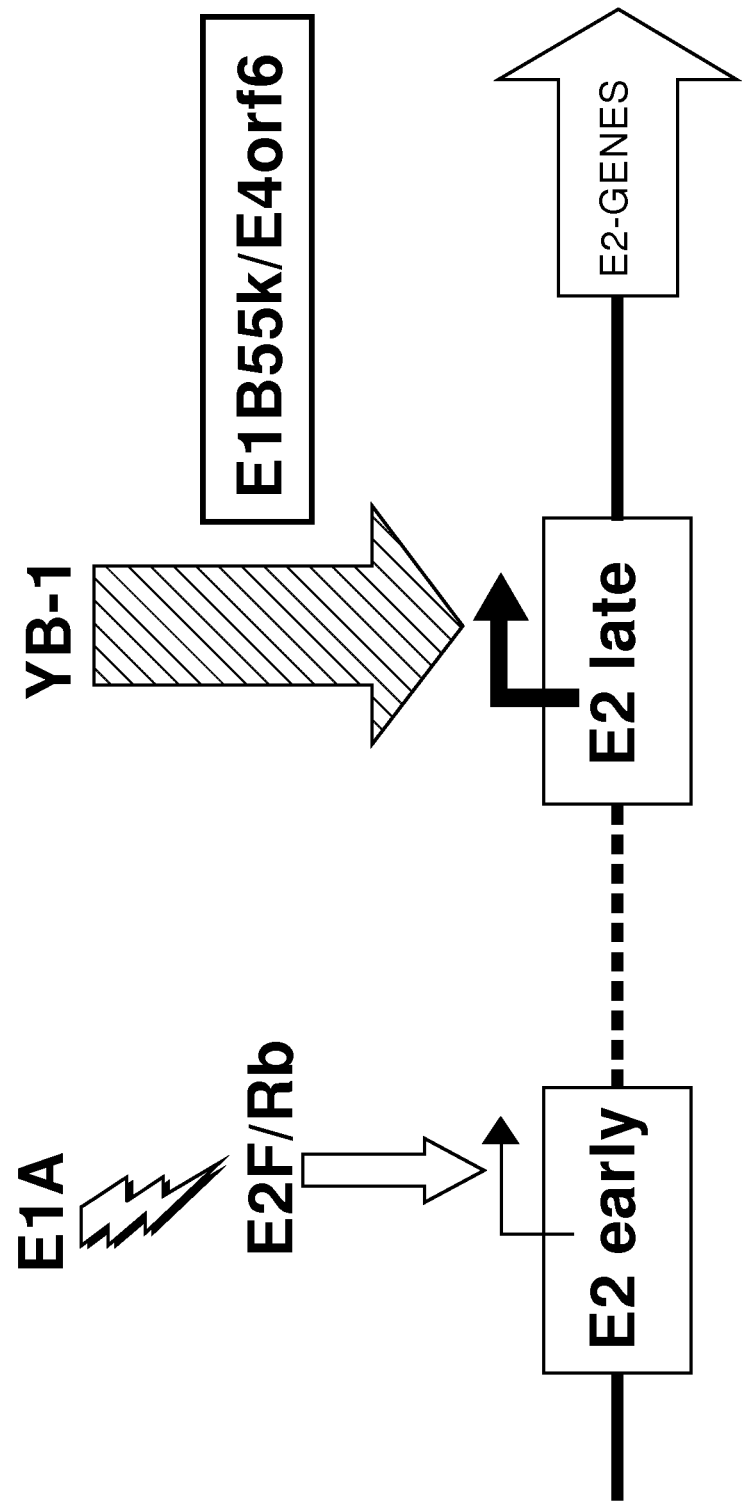
Figure 33:
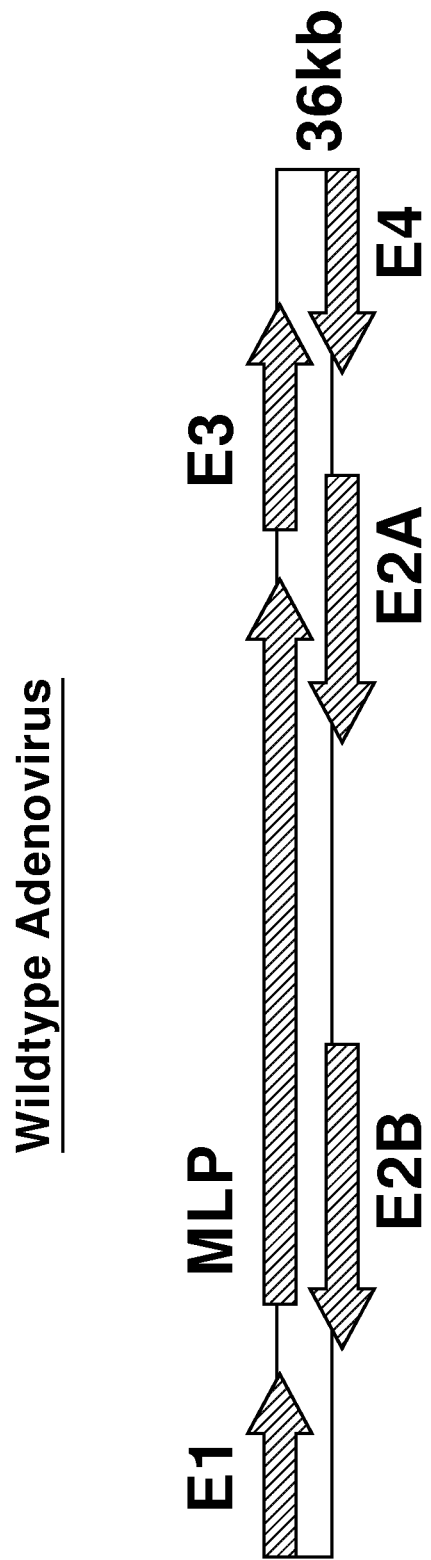
Figure 34:
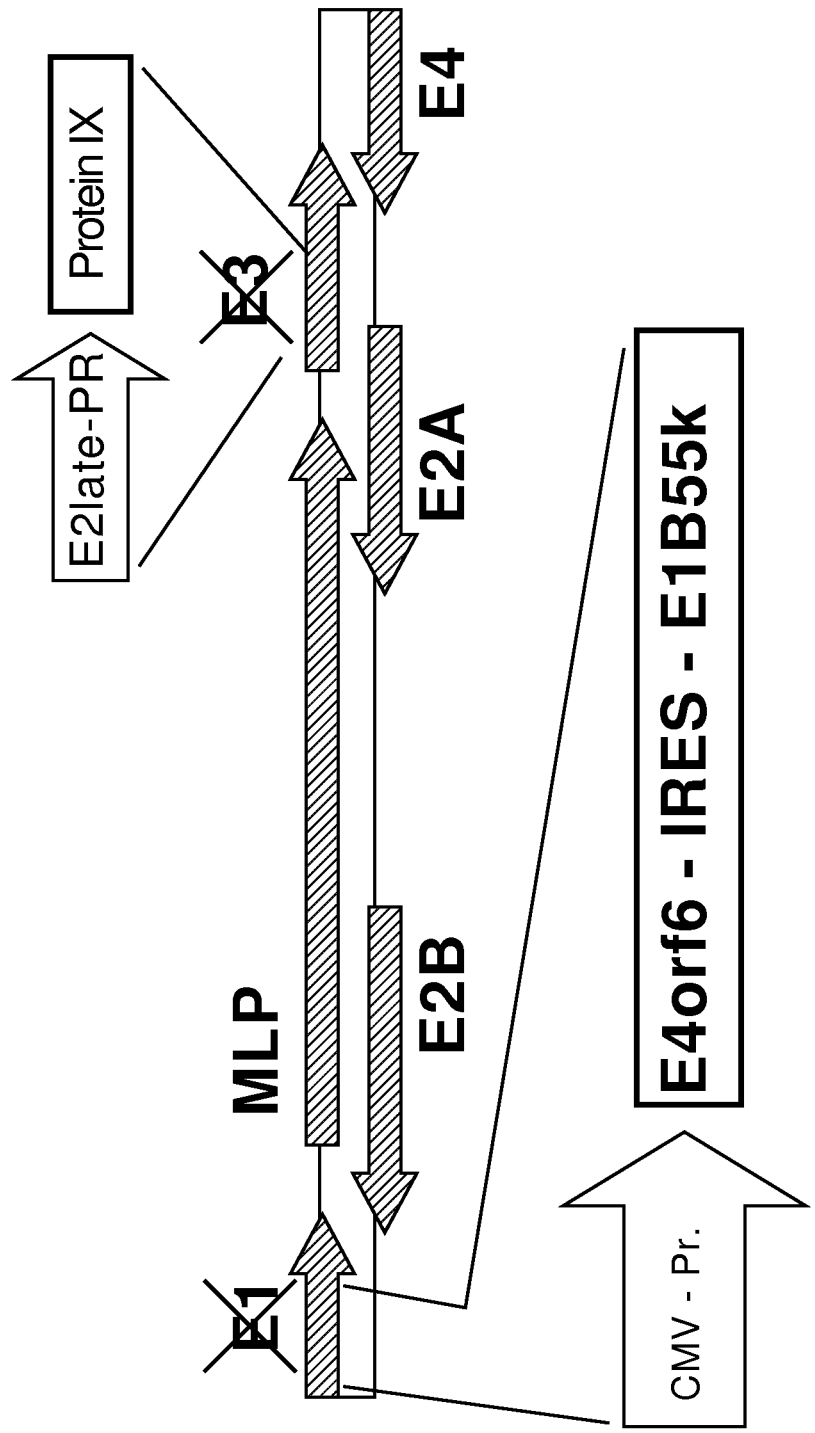
Figure 35:
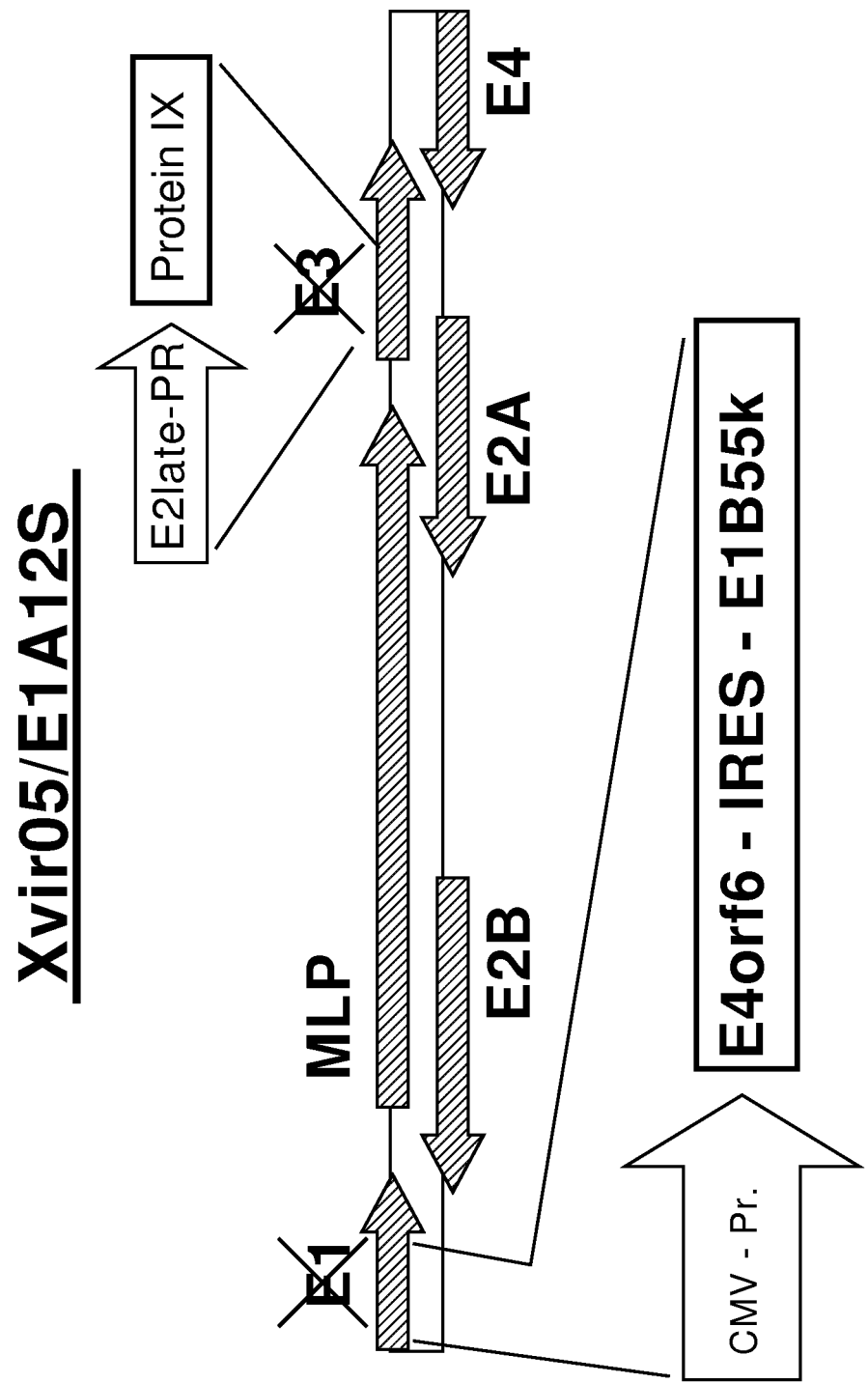
Figure 36:
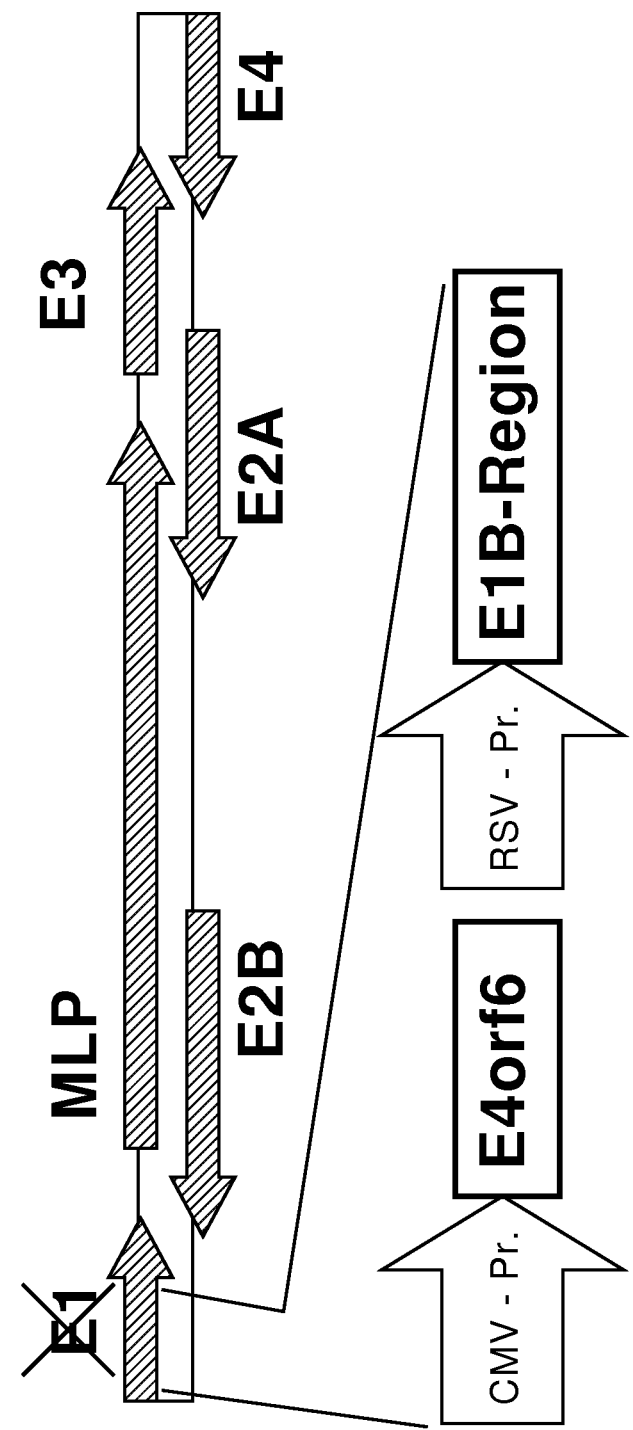
Figure 37:
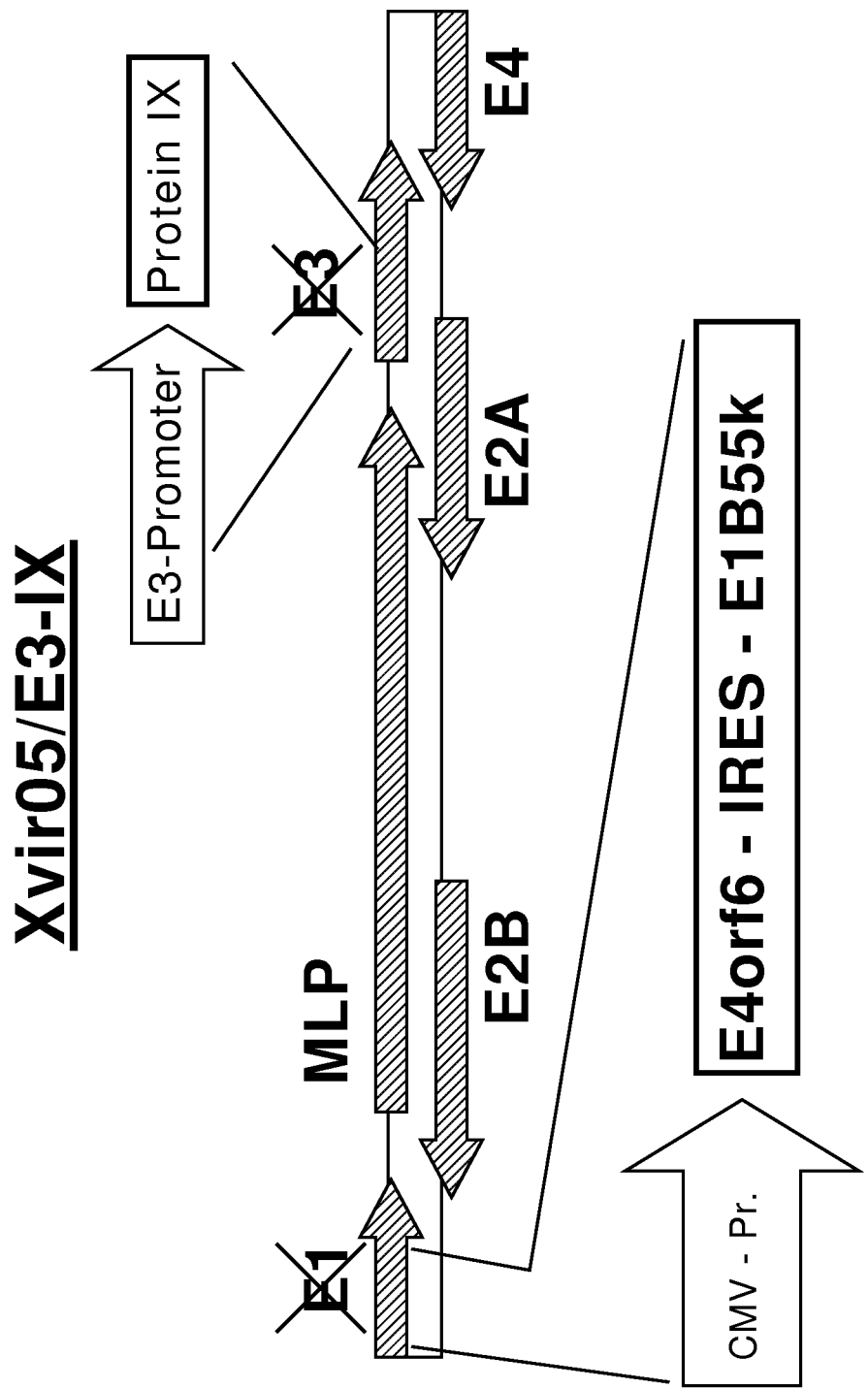
Figure 38:
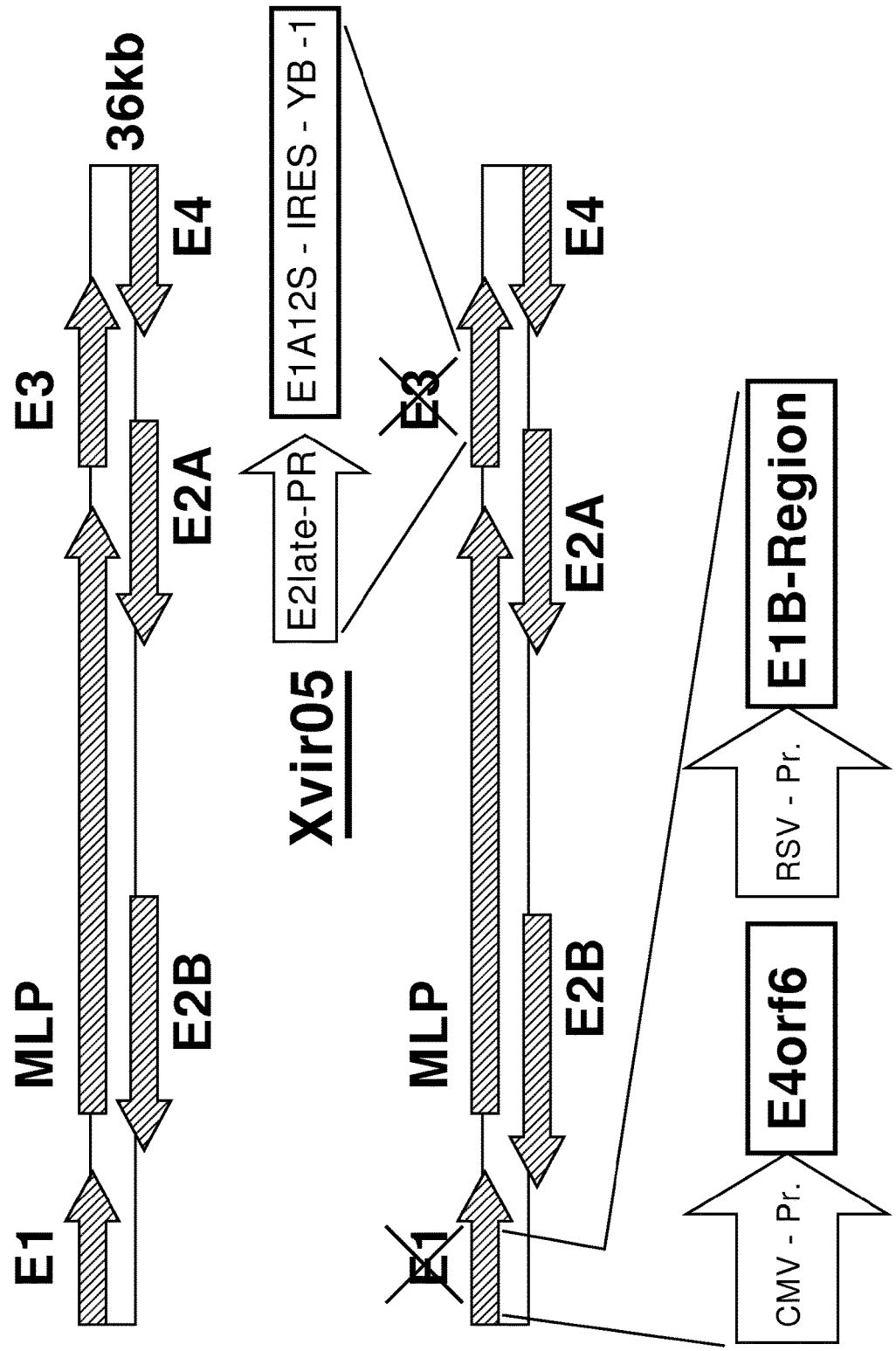
Figure 40:
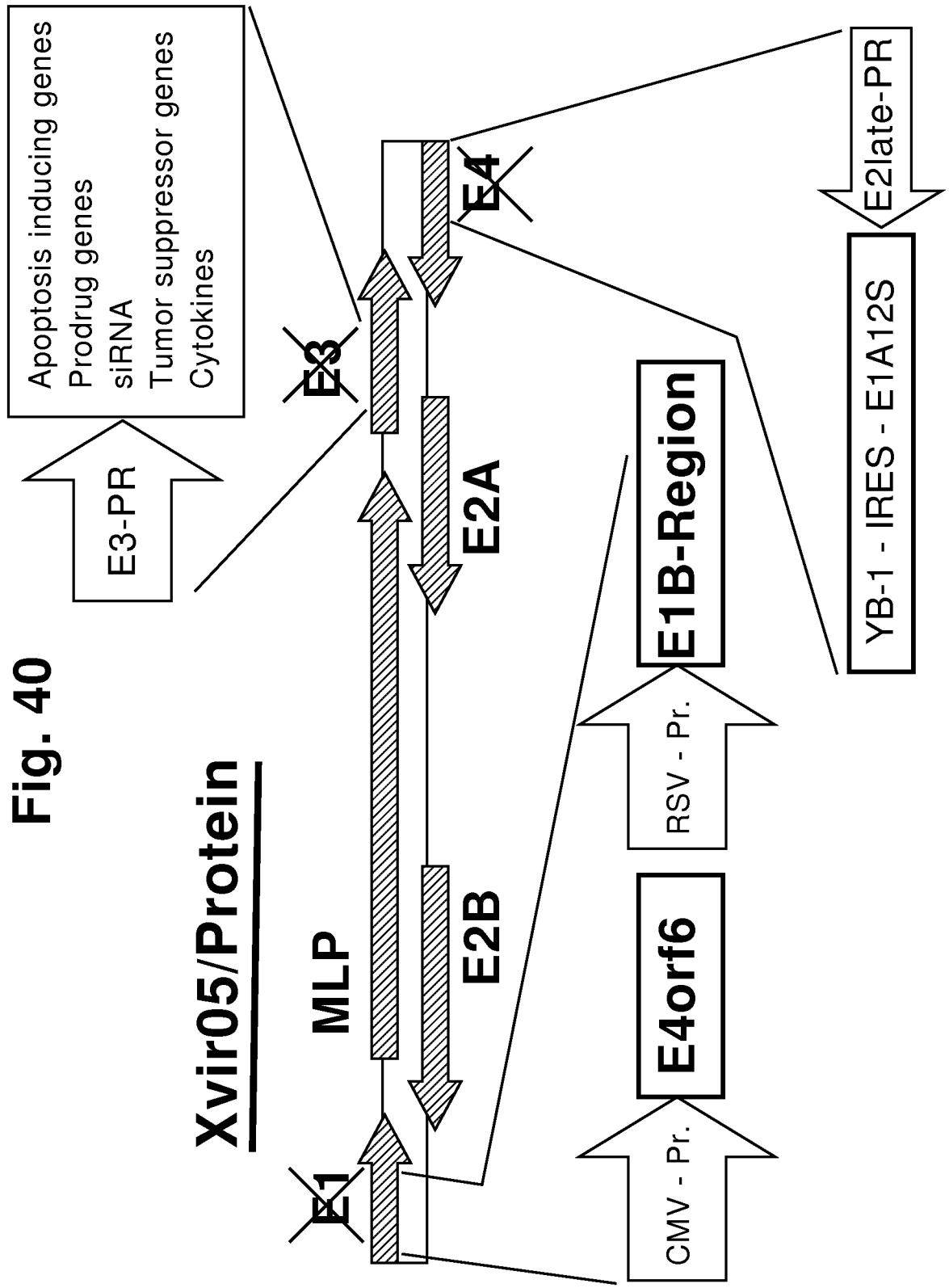
Figure 41:
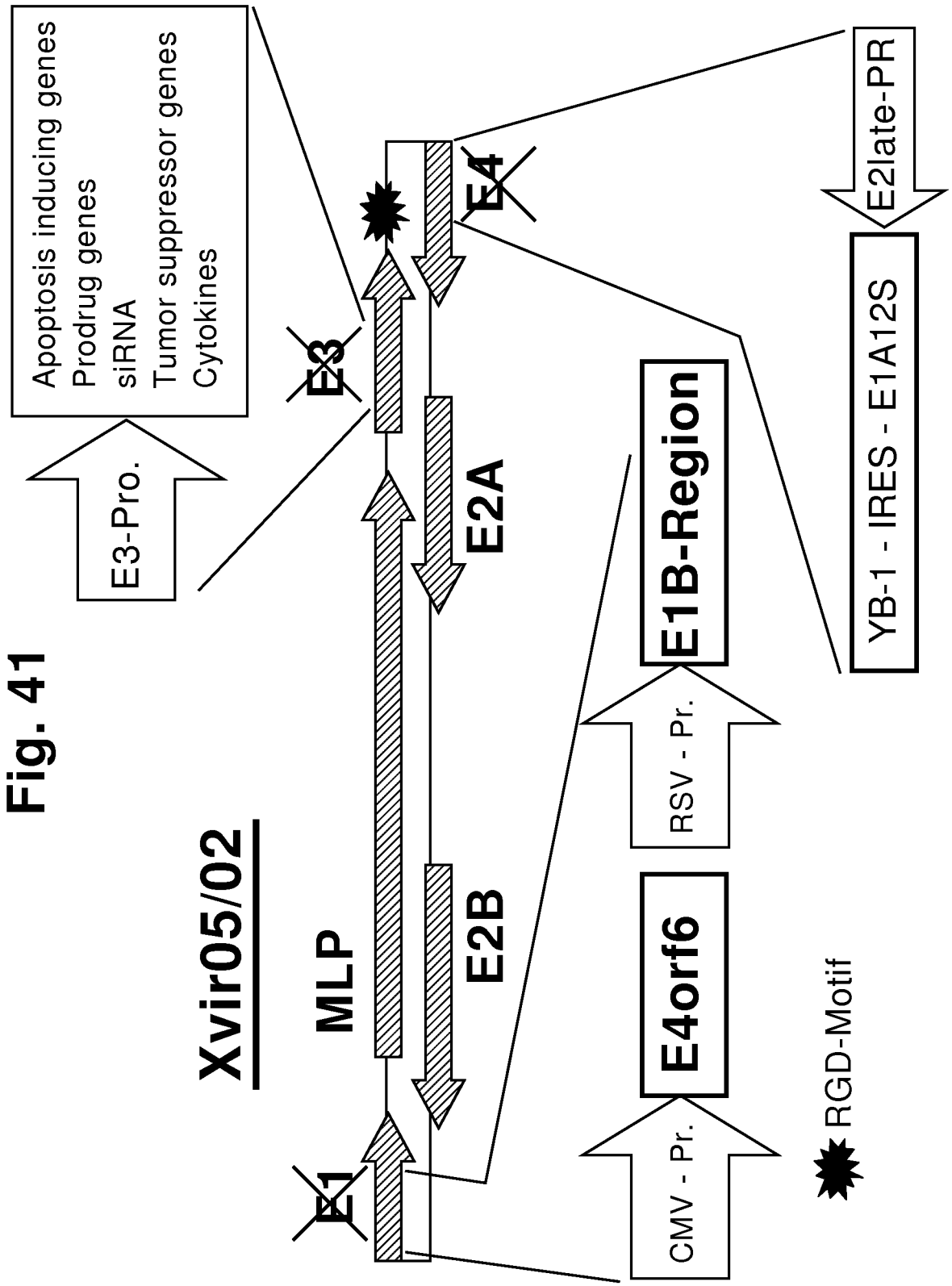
Figure 42:
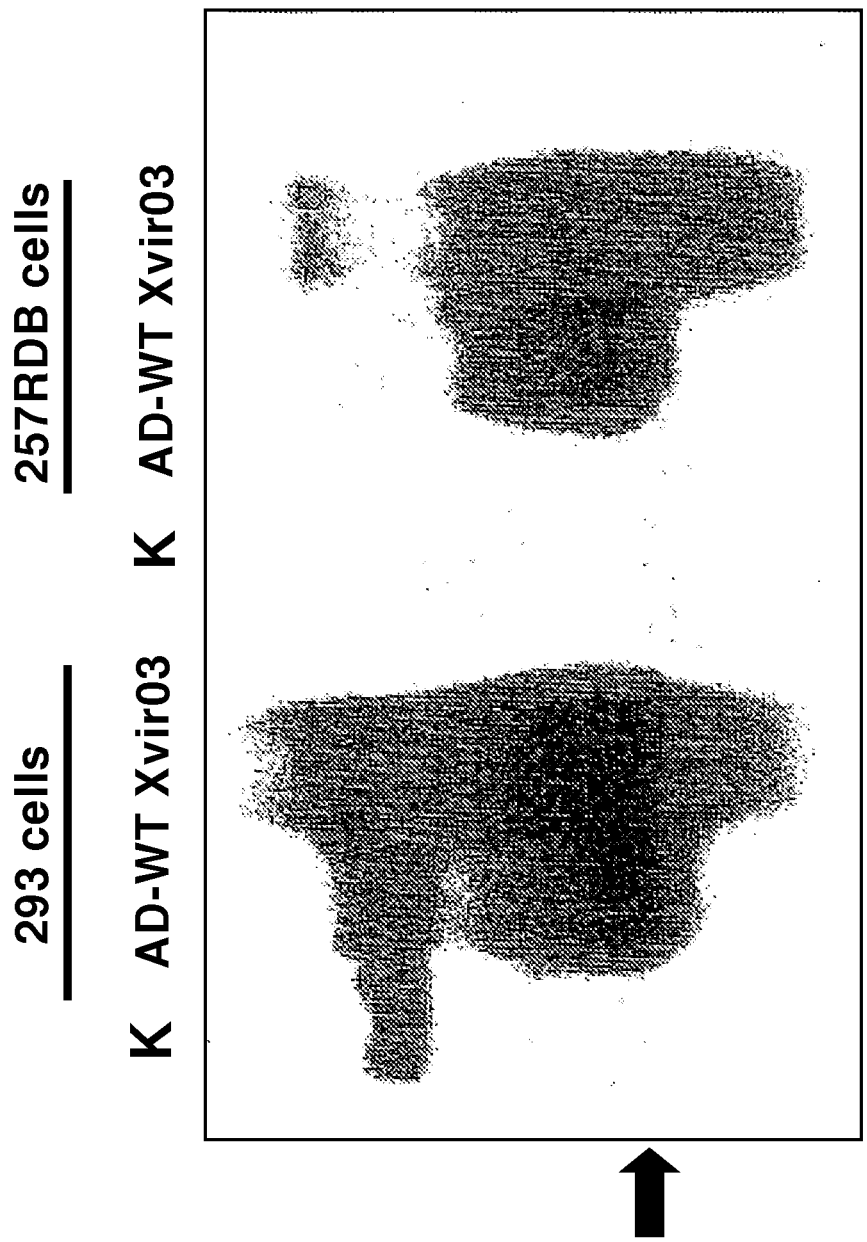

FIG. 25 shows the result of a Northern blot analysis of the expression of the E2 gene in A549 cells and U2OS cells after infection with wildtype adenovirus Ad5 and adenovirus Ad312;

FIG. 26 shows the result of a Northern blot analysis of the expression of the E2 gene in U2OS cells after infection with wildtype adenovirus and adenovirus delta24 after 12 and 24 hours;

FIG. 27 shows the structural design of the adenoviral vector XvirPSJL1;

FIG. 28 shows the structural design of the adenoviral vector XvirPSJL2;

FIG. 29 shows wells with HeLa cells grown therein after crystal violet staining and infection with adenovirus dl520 using different pfu/cells;

FIG. 30 shows a bar graph indicating the activity of luciferase in U2OS cells, HeLa cells and 257RDB cells upon usage of different promoter fragments of the adenoviral E2-late promoter;

FIG. 31 shows a bar graph indicating the number of viral particles after infection of U2OS cells with a YB-1 expressing adenovirus and virus Ad312 after two and five days, whereby a distinction is made between intracellularly remaining viral particles (represented in black) and released extracellular viral particles (horizontally striped);

FIG. 32 shows schematic representation of the regulation of the E2 region of adenovirus by the E2-late and E2 early promoters by E2F and YB-1;

FIG. 33 shows the schematic design of wildtype adenovirus;

FIG. 34 is a schematic representation of the adenovirus Xvir 05/promoter in accordance with the present invention which expresses protein IX under the control of the E2 late promoter;

FIG. 35 is a schematic representation of the adenovirus Xvir 05/E1A12S in accordance with the present invention which expresses the protein IX as part of the E1B55K reading frame under the control of E1A12S;

FIG. 36 is a schematic representation of an adenovirus Xvir 05E1B19K in accordance with the present invention, which expresses protein IX under the control of E1B19K;

FIG. 37 is a schematic representation of the adenovirus Xvir 05/E3-IX promoter in accordance with the present invention which expresses protein IX under the control of the E3 promoter;

FIG. 38 is a schematic representation of the wildtype adenovirus and the adenovirus Xvir 05 in accordance with the present invention which is an embodiment of virus Xvir 05/E1B19K;

FIG. 39 is a schematic representation of wildtype adenovirus and the adenovirus Xvir 05/protein IX in accordance with the present invention which is an embodiment of the virus Xvir 05/E1A12S;

FIG. 40 is a schematic representation of the wildtype adenovirus and the adenovirus Xvir 05/01 in accordance with the present invention which is an embodiment of the virus Xvir 05/protein IX;

FIG. 41 is a schematic representation of the wildtype adenovirus and the adenovirus Xvir 05/02 in accordance with the present invention which is an embodiment of the virus Xvir 05/protein IX; and FIG. 42 shows the result of a Northern blot analysis for the detection of protein IX.

Figure 43:
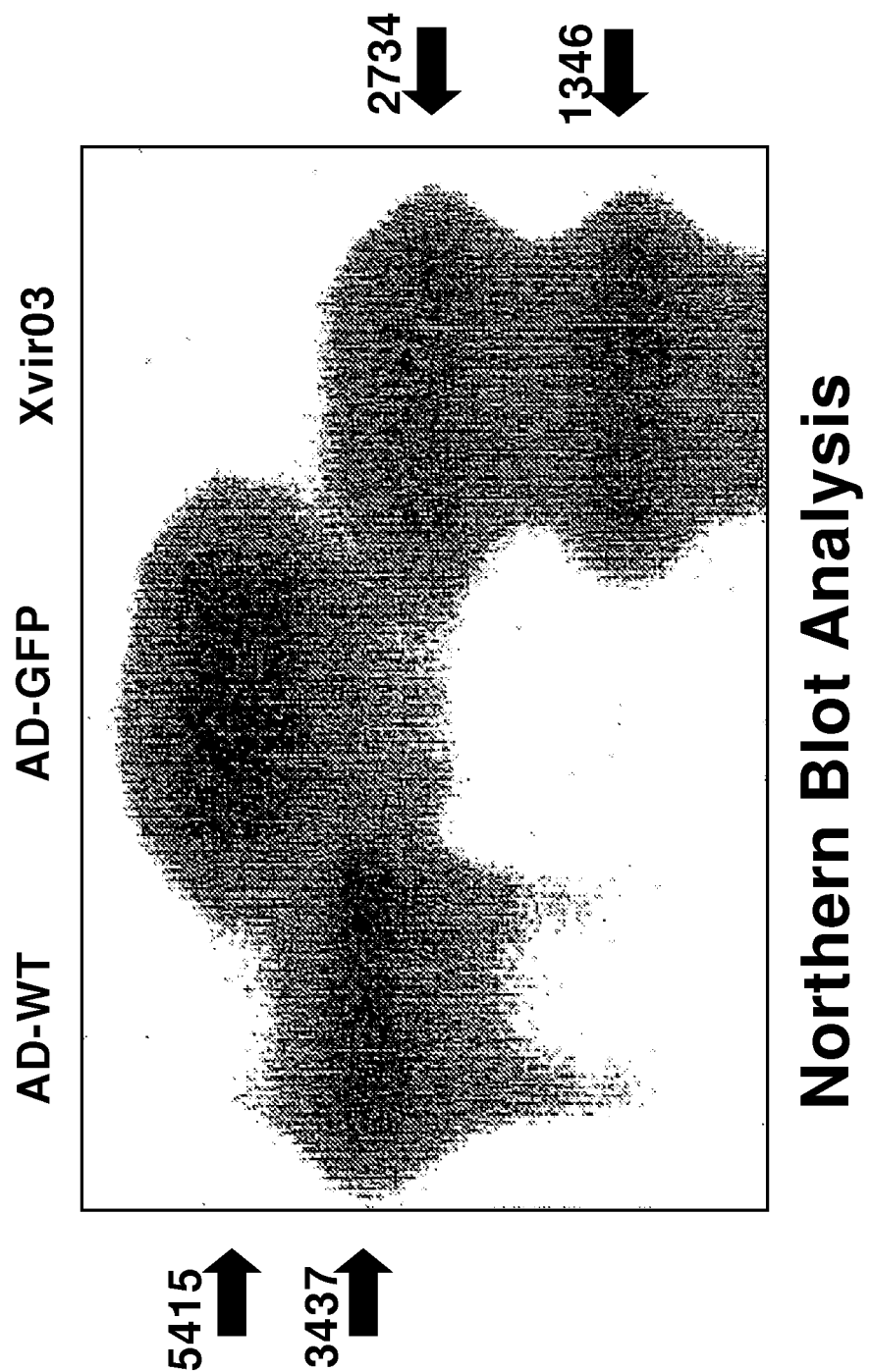

FIG. 43 shows the result of a Southern blot analysis of Xvir03-3'UTR

Figure 44:
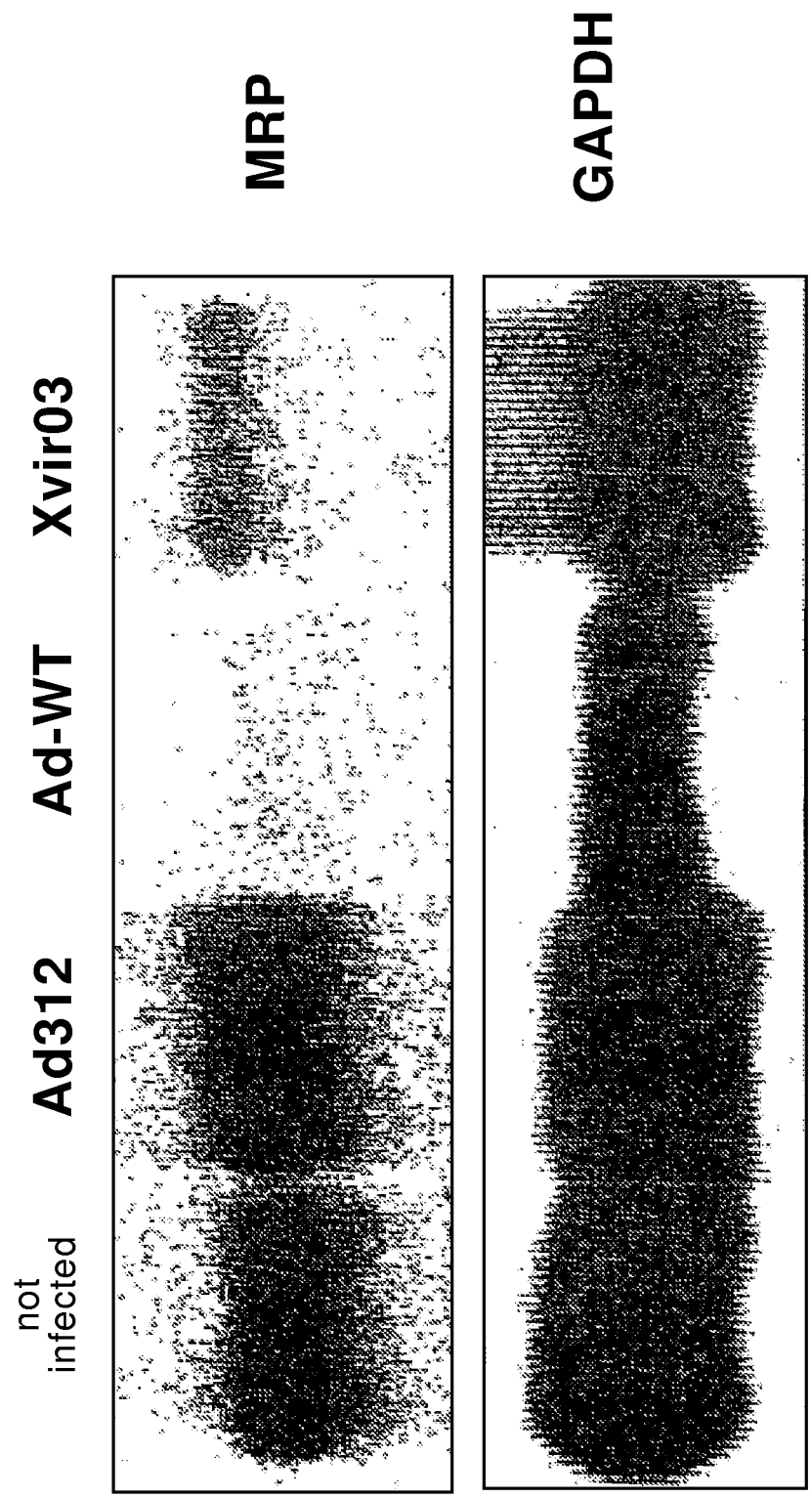
Figure 45:
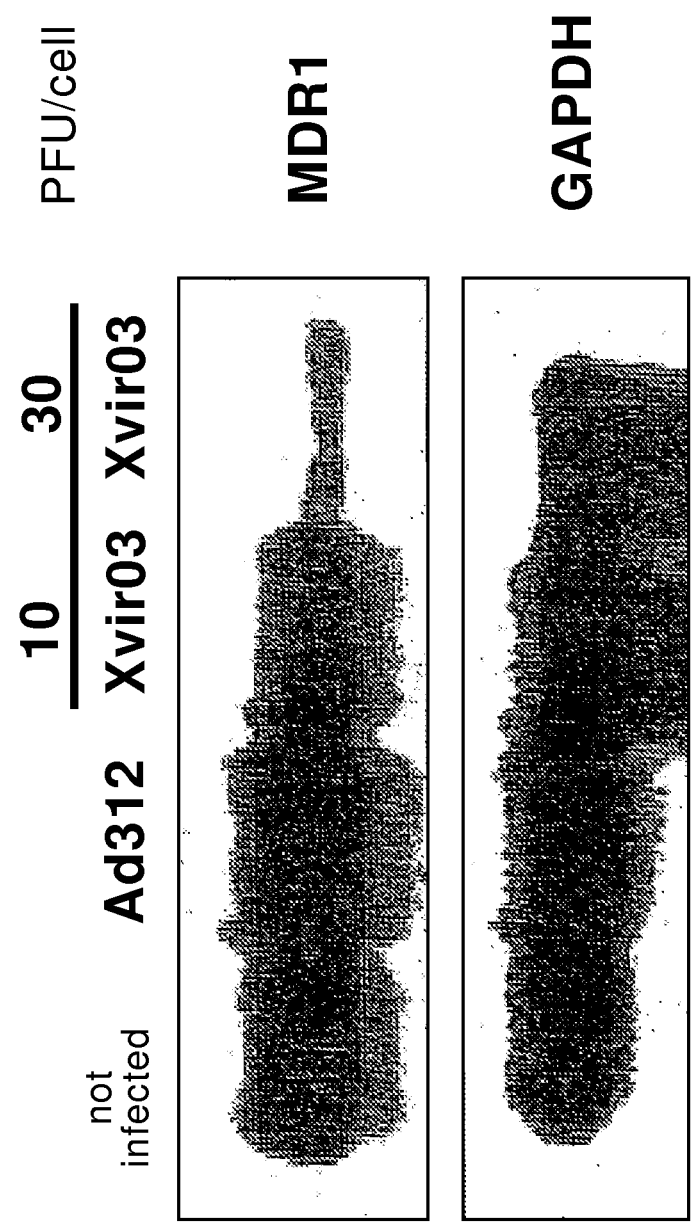
Figure 46:
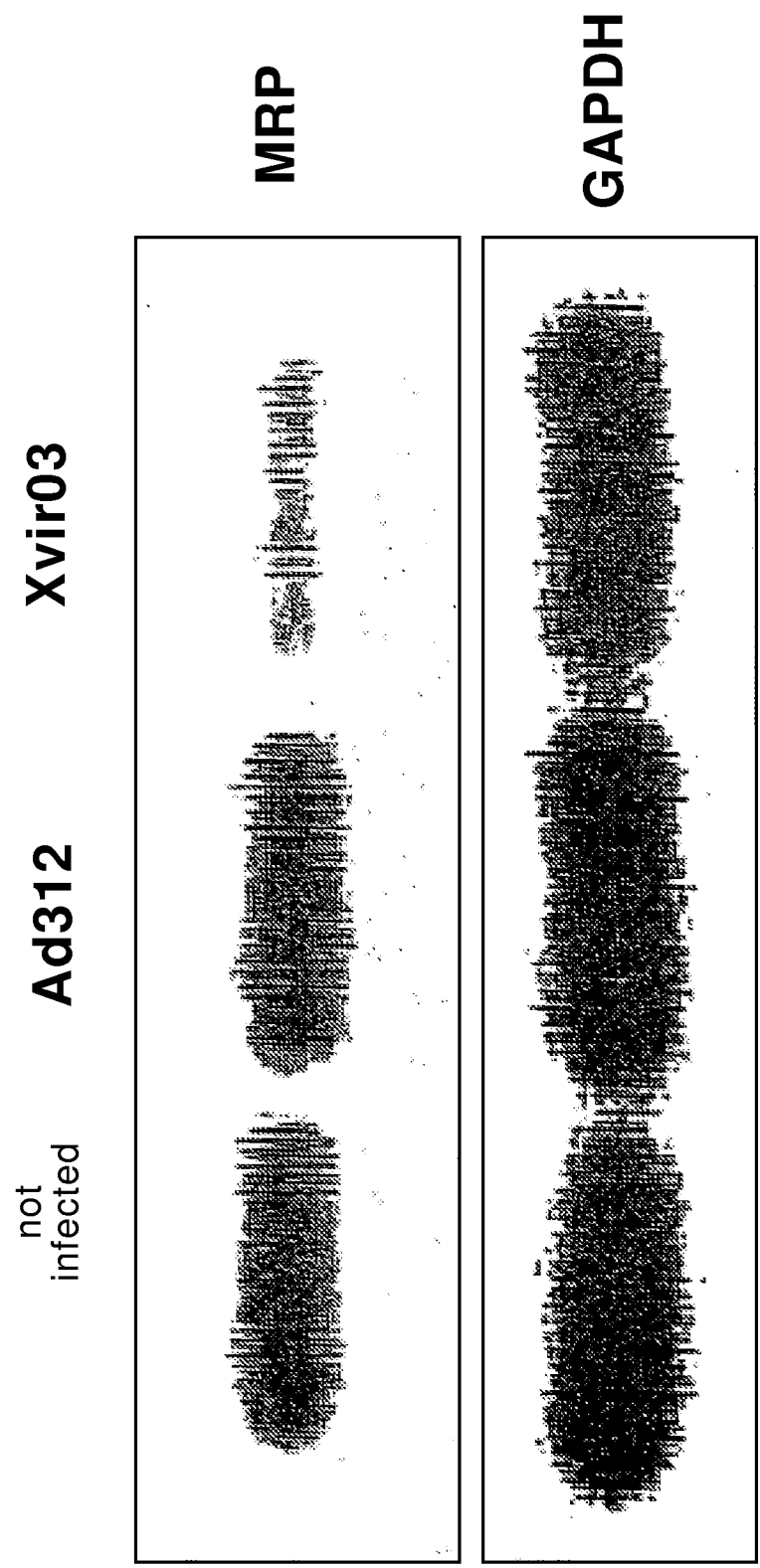
Figure 47:
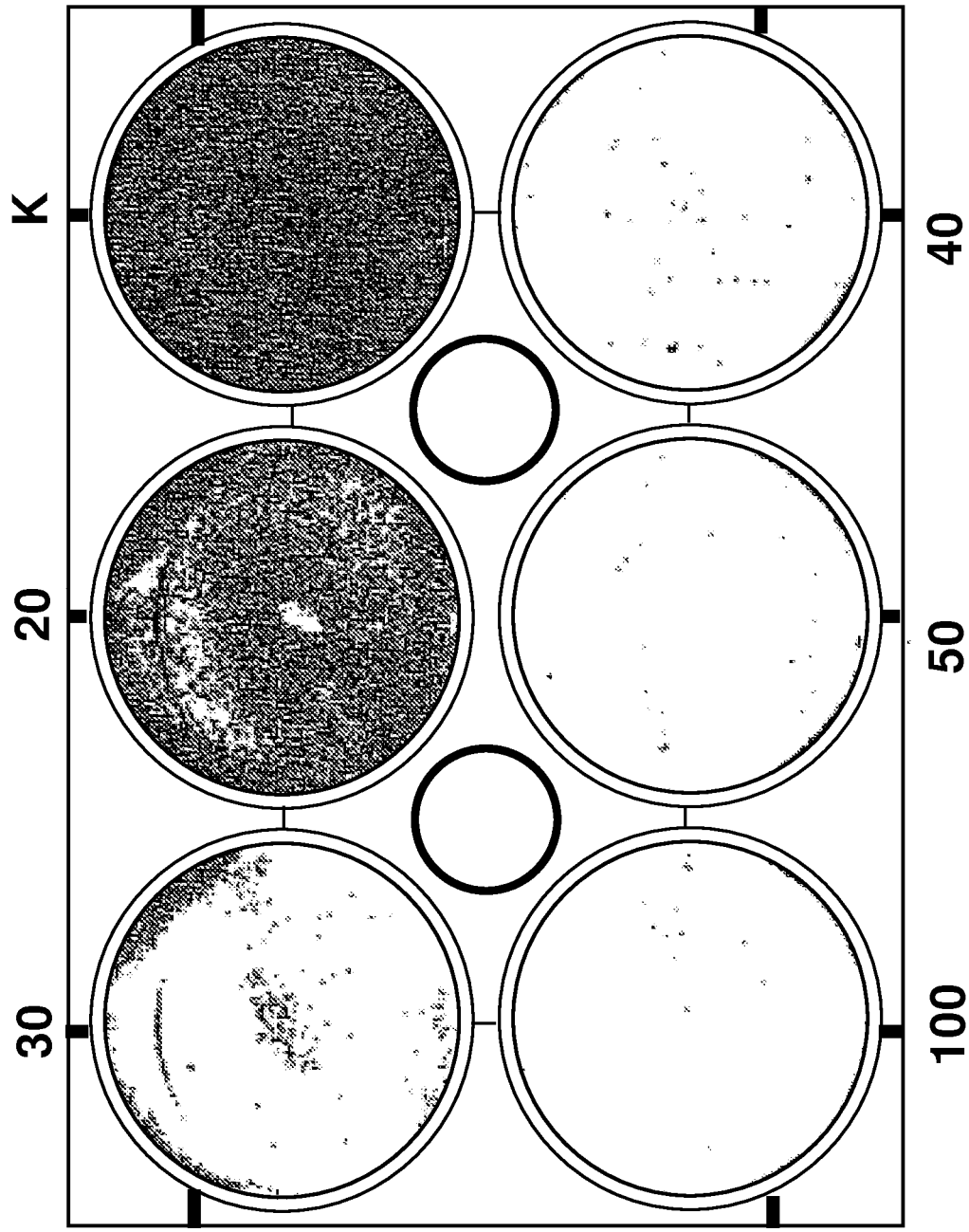
Figure 48:
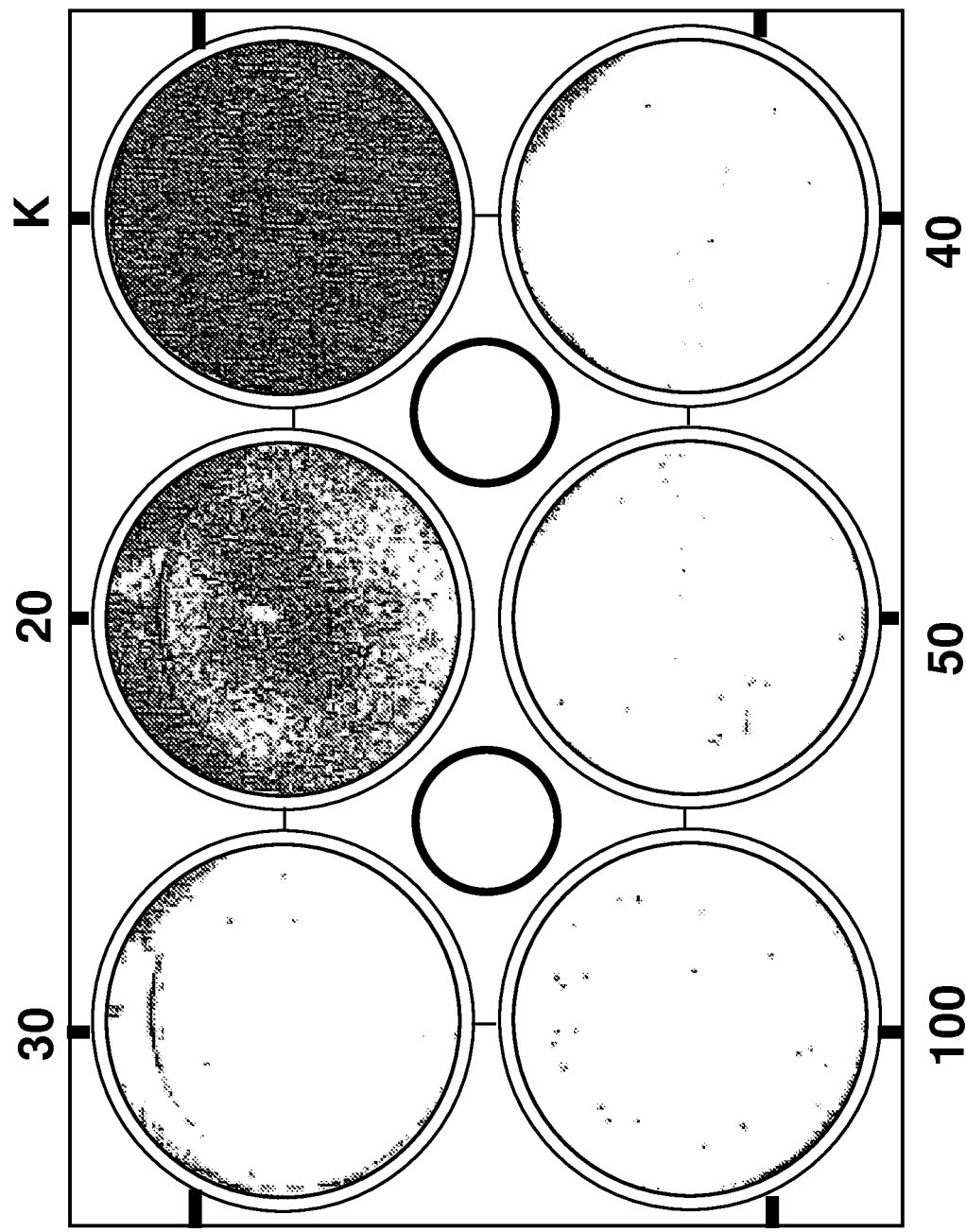
Figure 49:
Figure 50:
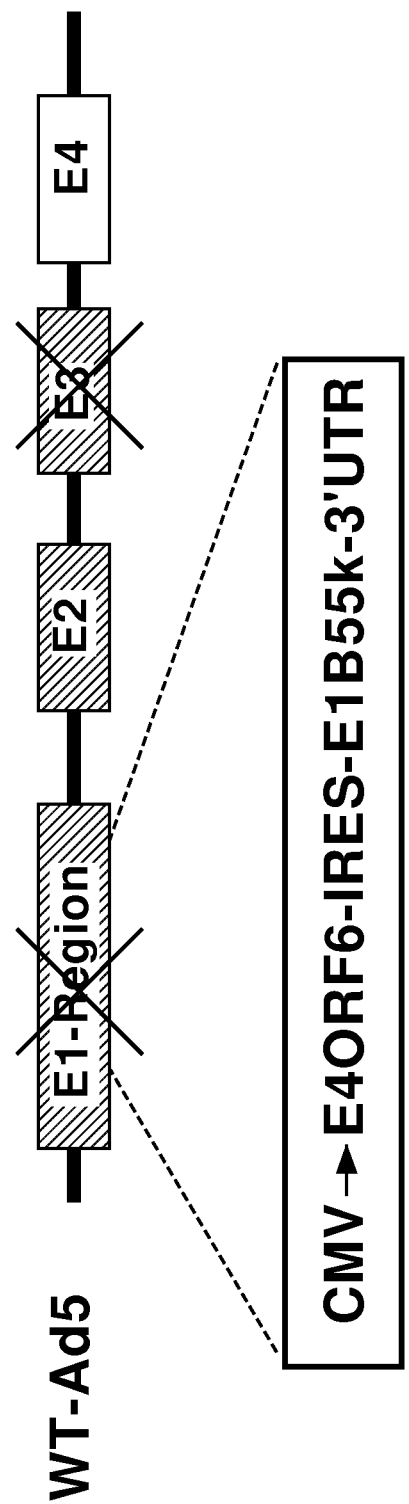

FIG. 44 shows the result of the MRP expression using Northern blot analysis after infection with Xvir03-3'UTR FIG. 45 shows the result of the MDR expression using Northern blot analysis after infection with Xvir03-3'UTR FIG. 46 shows the result of the MRP expression using Northern blot analysis after infection with Xvir03-3'UTR FIG. 47 shows wells grown with DU145 cells after crystal violet staining and infection with adenovirus Xvir03 with different pfu/cells;

FIG. 48 shows wells grown with PC-3 cells after crystal violet staining and infection with adenovirus Xvir03 using different pfu/cells;

FIG. 49 shows four different panels of cell layers for illustrating the effect of replicating adenovirus Xvir03 and daunorubicin; and FIG. 50 shows the structural design of adenoviral vectors Xvir03 and Xvir03-3'UTR, respectively.

EXAMPLE 1: TYPES OF E1A MODIFICATIONS AS MAY BE COMPRISED BY THE ADENOVIRUSES WHICH ARE USED IN ACCORDANCE WITH THE INVENTION

Figure 1:
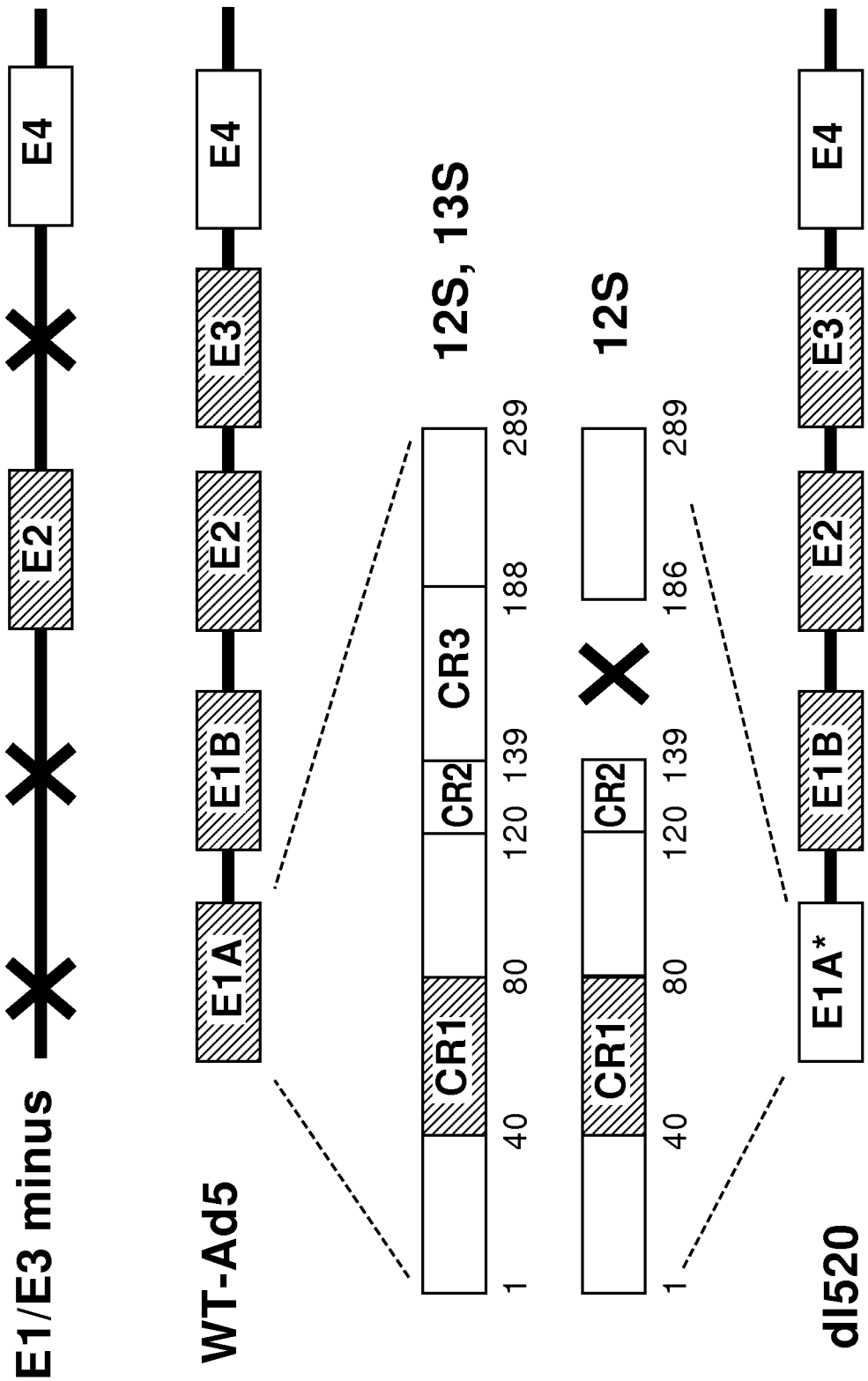
FIG. 1 shows the structural design of the adenoviral vectors referred to as AdE1/E3-minus herein which are E1/E3-deleted adenoviruses, of wildtype adenovirus and adenovirus dl520.

FIG. 1 shows the structural design of adenoviral vectors AdE1/E3-minus, i. e. E1/E3-deleted adenoviruses, wildtype adenovirus and adenovirus dl520.

Adenovirus AdE1/E3-minus does not have a region coding for a functional E1A or a functional E1B or E3 and is used in the present experiments as a control for toxicity.

Wildtype E1A gene codes for a total of 5 proteins which are generated through alternative splicing of the E1A RNA. Among others, two different proteins are generated, namely a 289 amino acid protein and a 243 amino acid protein. dl520 does not code for the 289 amino acid protein as it has a deletion in the CR3 stretch of the E1A gene which results in the lack of the 13S gene product. The adenovirus dl520 which may be used in accordance with the invention is referred to as 12S-E1A virus by those skilled in the art. Adenovirus dl347 (Wong and Ziff, J. Virol., 68, 4910-4920, 1994) known in the prior art is also a 12S-E1A virus which can be used in accordance with the present invention.

Within the 289 amino acid protein which is encoded by the 13S-E1A mRNA, there are 3 regions which are conserved among various adenoviral subtypes. These are referred to as CR1, CR2 and CR3. While CR1 and CR2 are present in both E1A proteins (E1A 12S and E1A 13S), i. e. in both the 289 amino acid and the 243 amino acid protein, the CR3 region is only present in the bigger one of the two aforementioned proteins.

The CR3 region is required for the activation of viral genes, in particular of E1B, E2, E3 and E4. Viruses which only comprise the smaller, i. e. 243 amino acid protein are only very weakly transactivating the viral genes and do not promote adenoviral replication in those cells which do not have YB-1 in the nucleus. As YB-1 is present in the nucleus only in tumor cells and can be detected only there, this vector is suitable to induce tumor-specific replication.

Due to the deletion of CR3 in dl520 this adenovirus cannot translocate cellular YB-1 into the cell's nucleus which is also referred to herein as translocation, and is thus not in a position to replicate in cells which are YB-1 nucleus-negative and is thus a virus which can be used in accordance with the present invention, whereby this virus comprises the transactivation required in accordance with the present invention.

EXAMPLE 2: MODE OF ACTION OF ADENOVIRUSES IN DEPENDING ON THE RB STATUS OF CELLS

Figure 2:
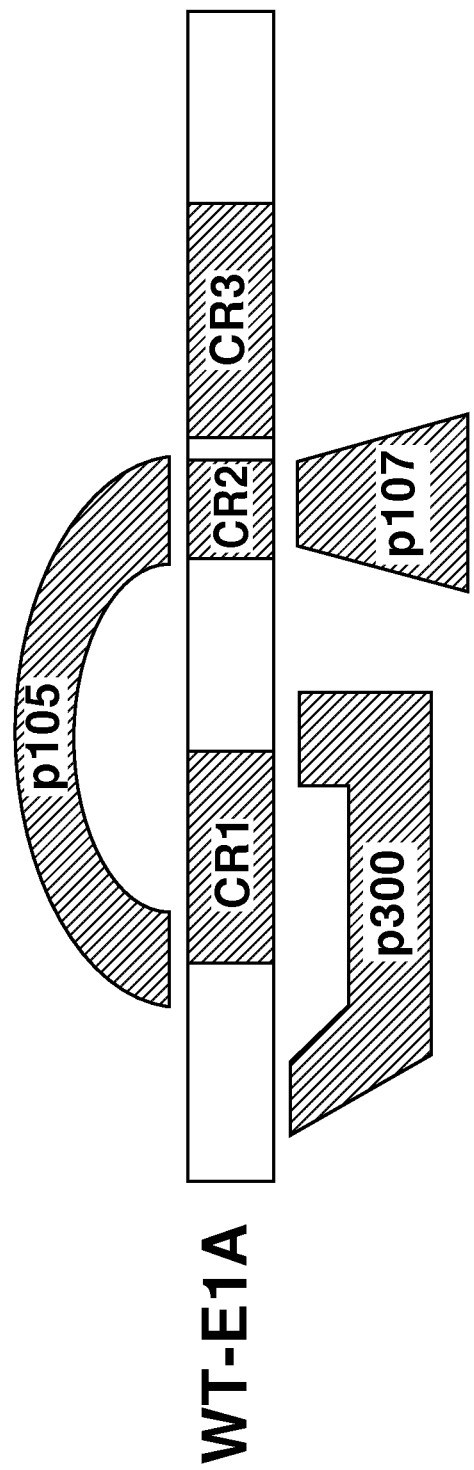
FIG. 2 shows the binding domains of the E1A protein with regard to the binding of p300, p107 and p105.

FIG. 2 shows the binding domains of the E1A protein with regard to the binding of p300, p107 and p105. P300, as well as p107, is a cellular binding protein. The binding of the retinoblastoma protein (pRb), a tumor suppressor protein, is mediated through CR1 and CR2. Studies have shown that pRb and p107/p300 are in combination with the cellular transcription factor E2F effective in regulating transcription. The wildtype E1A protein interferes with the binding of E2F to Rb. The thus released E2F binds to the E2 early promoter and induces adenoviral replication thereby.

It is known from the prior art that certain deletions in the E1A oncoprotein may result in recombinant adenoviral vectors such as those mentioned in the following, which are capable of replicating predominantly in Rb-negative cells and can be used in accordance with the present invention. For example, the adenoviral vector dl922-947 comprises a deletion in the CR2 region (amino acid positions 122-129) and the vector CB016 has deletions in the CR1 region (amino acid positions 27-80) and CR2 region (amino acid positions 122-129). The vector E1Ad/01/07 comprises a deletion in the CR2 region (amino acid positions 111-123). Additionally, because of an additional deletion at the N-terminus (amino acid positions 4-25), additionally, there is no binding to protein p300. The adenoviral vector AdΔ24 comprises a deletion in the CR2 region (amino acid positions 120-127). The adenoviral vector described in patent EP 0 931 830 comprises deletions in the CR1 region and CR2 region.

The binding mechanism of E2F/RB and the release of E2F mediated through E1A is fundamentally different from the mechanism underlying the present invention. Unlike assumed in the prior art it is not the release of E2F from the Rb protein which is essential, not to say critical for viral replication, but it is the nuclear localisation of the human transcription factor YB-1. This transcription factor is, in normal cells, only present in the cytoplasm over most of the cell cycle. After infection with an adenovirus it is induced into the nucleus under certain circumstances or is already present in the nucleus in distinct cellular systems, such as distinct tumor diseases including, for example, but not limited thereto, breast cancer, ovary carcinoma, prostate carcinoma, osteosarcoma, glioblastoma, melanoma, small cell lung carcinoma and colorectal carcinoma.

Figure 3:
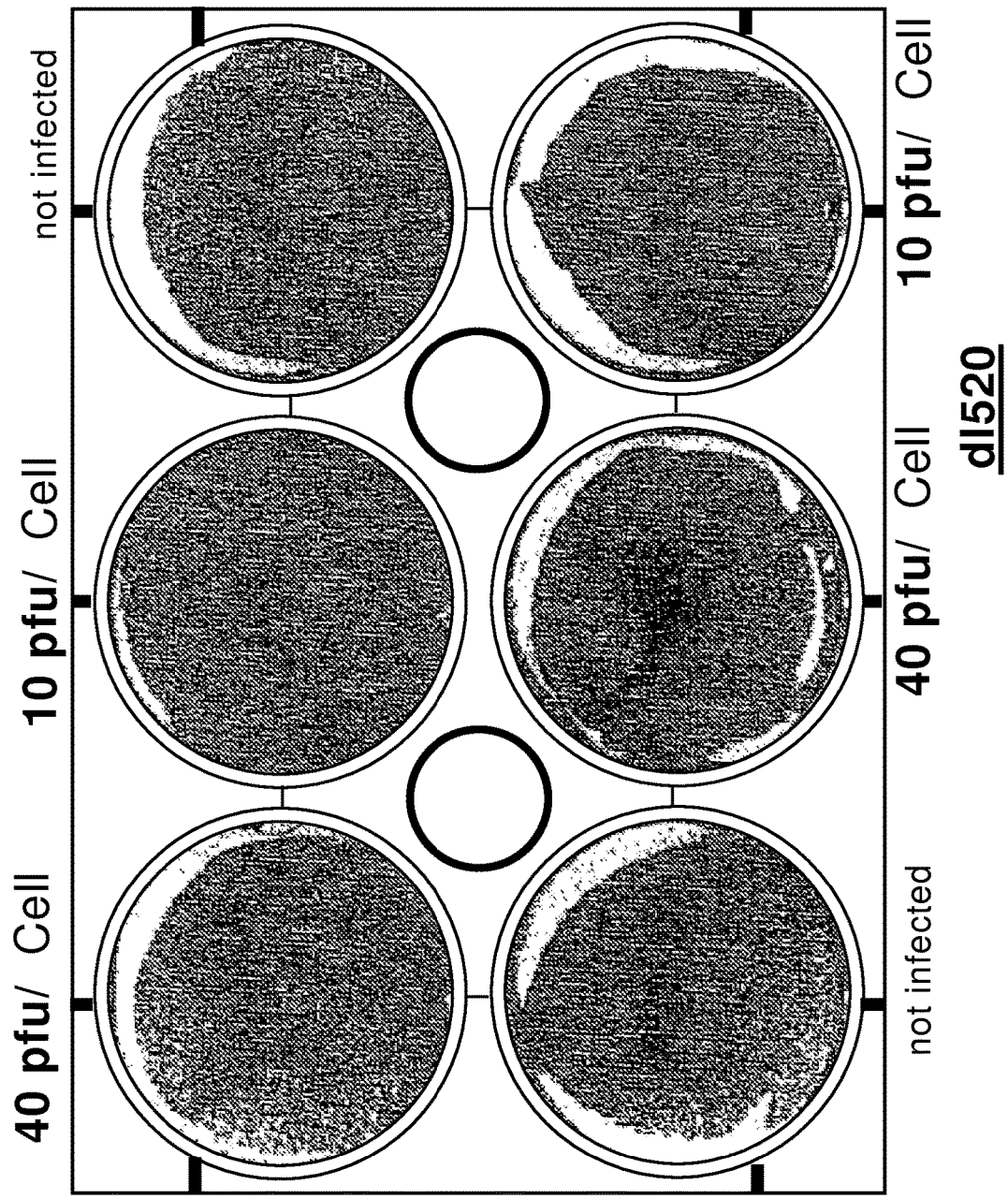
FIG. 3 shows U2OS cells which do not have YB-1 in the nucleus, after infection with the E1/E3-deleted adenoviruses Ad5, referred to as E1/E3-minus Ad5, and dl520.

EXAMPLE 3: INFECTION OF U2OS CELLS 100,000 U2OS cells were plated per well. On the next day the cells were infected with the various adenoviruses as depicted in FIG. 3. The infection was performed in 500 μl serum free DMEM medium at 37° C. for 1 h. Subsequently, the infection medium was removed and replaced by 2 ml complete medium (10% FCS/DMEM). The analysis was performed after 3 days using crystal violet staining.

As may be taken from FIG. 3, the U2OS cells which do not have YB-1 in the nucleus, show no lysis as illustrated by crystal violet staining after infection with two different adenoviruses, namely the E1/E3-deleted adenovirus referred to as E1/E3-minus, and adenovirus dl520, which can be used in accordance with the present invention. In connection therewith, first, the medium is removed. Subsequently, the cells are overlaid with crystal violet (50% ETOH, 3% formaldehyde, 5% acetic acid, 1% crystal violet) and incubated at room temperature for 5-10 min. Subsequently, the plates having 6 wells are thoroughly rinsed with water and dried at room temperature.

This confirms the finding underlying the present invention that the presence of YB-1 is required in order to induce the viruses used in accordance with the present invention, to lyse the infected cells.

Figure 4:
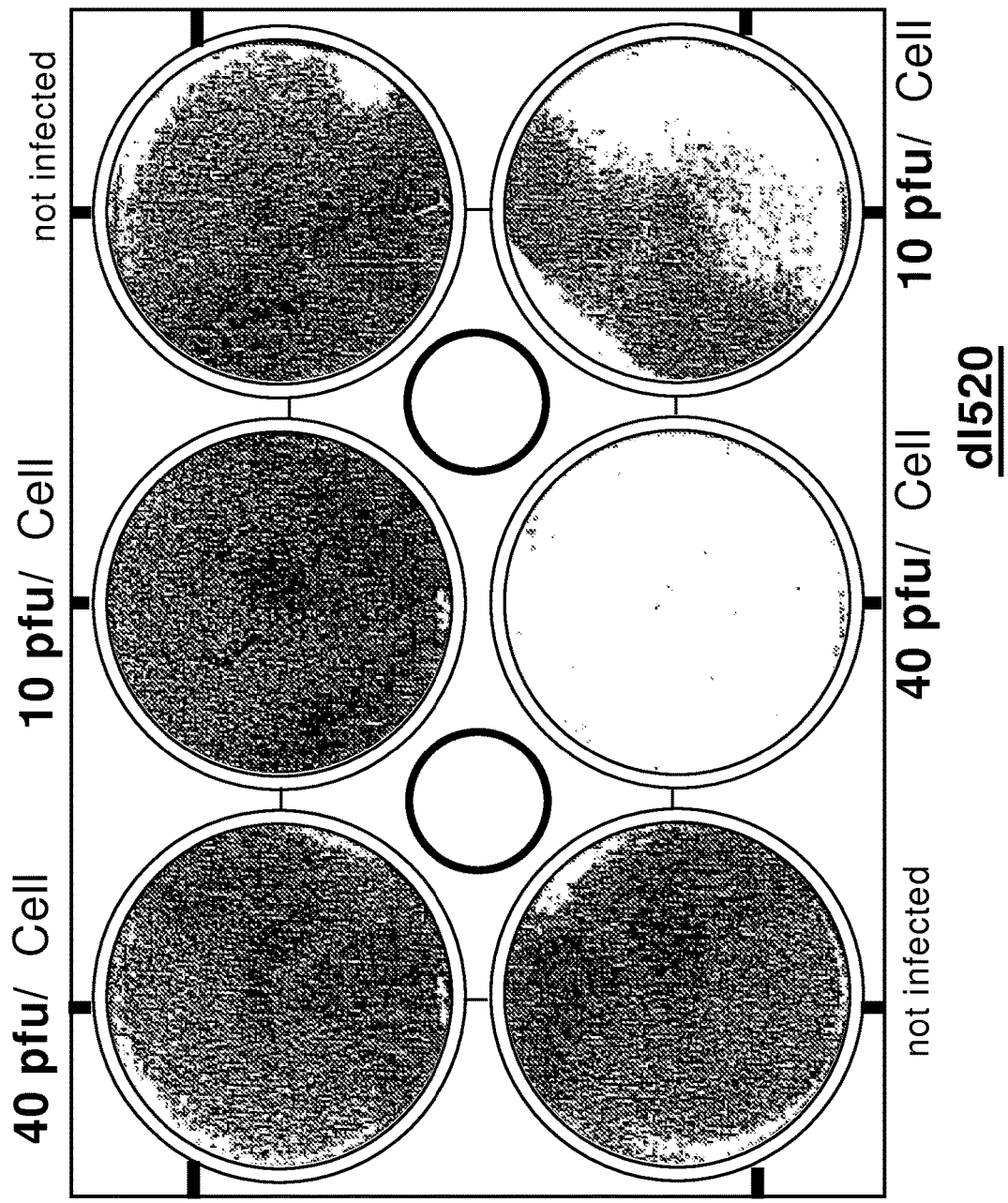
FIG. 4 shows 257RDB cells which have YB-1 in the nucleus, after infection with the E1/E3-deleted adenoviruses Ad5, referred to as E1/E3-minus Ad5, and adenovirus dl520.

EXAMPLE 4: INFECTION OF 257RDB CELLS 100,000 257RDB cells were plated per well. On the next day the cells were infected with the various adenoviruses as depicted in FIG. 4. The infection was performed in 500 μl serum free DMEM medium for 1 h at 37° C. Subsequently, the infection medium was removed and replaced by 2 ml complete medium (10% FCS/DMEM). The analysis was performed after three days using crystal violet staining.

The result of this experiment is depicted in FIG. 4. The adenovirus referred to as E1/E3-minus Ad5 which is E1/E3-deleted, did not show any lysis at low MOIs (pfu/cell) upon infection of 257RDB cells which have YB-1 in the nucleus. In contrast thereto, dl520 which, as shown in example 3, does not replicate in YB-1 nucleus-negative cells and at the same time codes with E1A for a transactivating oncogene protein in accordance with the present invention, results in a factually complete lysis at an MOI (multiplicity of infection) of 40 pfu per cell and a still predominant lysis at an MOI of 10 pfu per cell. It can be concluded therefrom that dl520 and similar viruses such as described herein by dl1119/1131 or AdXvir 03, require an MOI which is reduced by about 1 magnitude (factor of ten) compared to E1-deleted or an E1/E3-deleted adenovirus which justifies their clinical use.

Figure 7:
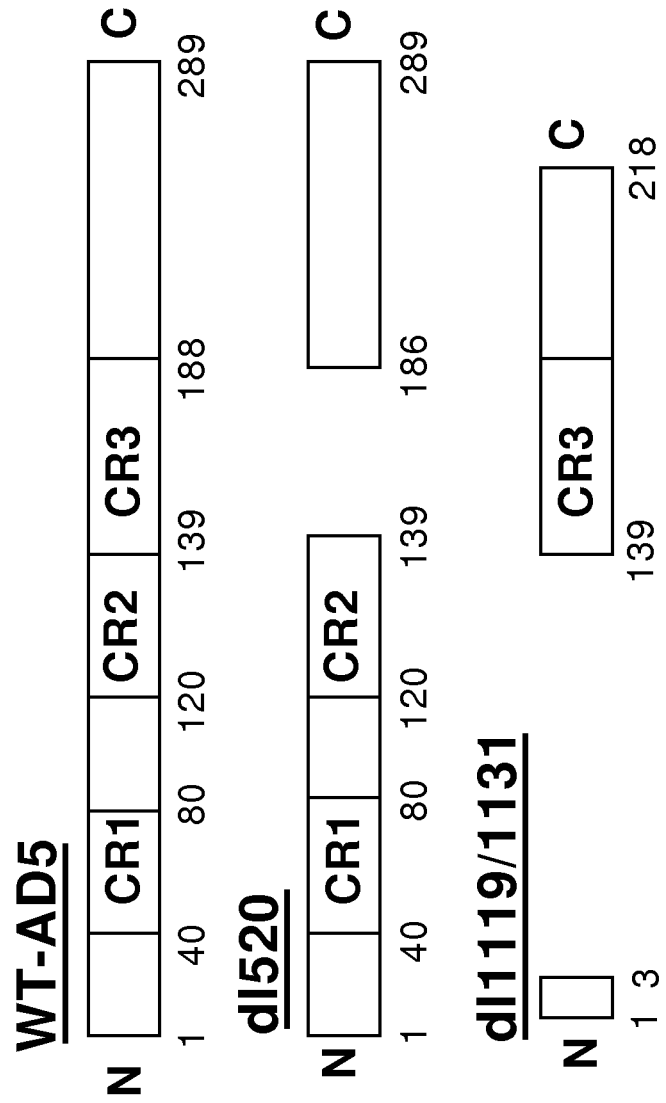
FIG. 7 shows the structural design of the E1A protein of wildtype adenovirus, of adenovirus dl520 and adenovirus dl1119/1131.

As depicted in FIG. 7, the protein E1A of dl520 is characterised in that the CR3 region thereof is deleted which results in the transactivation required for the use in accordance with the present invention and replication in YB-1 nucleus-positive cells.

EXAMPLE 5: INFECTION OF 257RDB AND U2OS CELLS WITH DL1119/1131

Figure 5:
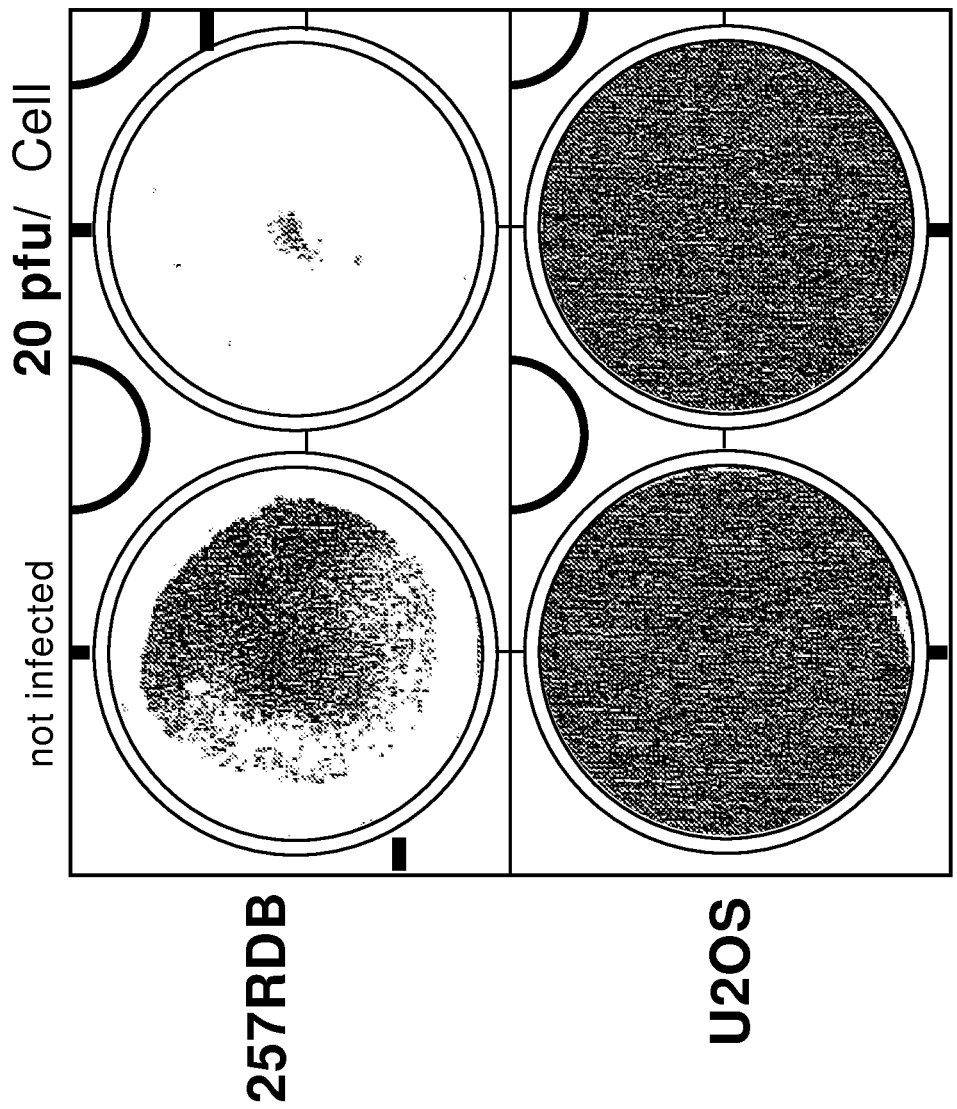
FIG. 5 shows 257RDB cells and U2OS cells after infection with adenovirus dl1119/1131.

As depicted in FIG. 5, there is no lysis at an MOT of 20 pfu per cell upon infection of YB-1 nucleus-negative U2OS cells with adenovirus dl1119/1131 which exhibits a deletion of amino acids 4-138 of the E1A protein and the nucleic acid coding therefor, and further comprises a stop codon after amino acid 218, whereby the expressed truncated E1A protein comprises the CR3 region of the complete E1A protein. As a negative control a non-infected cell layer was used.

In contrast thereto, there was factually a complete lysis of the cell layer at an MOI of 20 pfu per cell under the influence of adenovirus dl1119/1131 in a cellular system such as 257RDB which contains YB-1 in the nucleus, i. e. is YB-1 nucleus-positive. Insofar this example is another proof that a modified E1A oncogene protein which, as depicted in FIG. 7, comprises, for example, only the CR3 region and which is lacking the CR1 region and CR2 region, provides for the required transactivation in YB-1 nucleus-positive cells which is required for the replication of adenoviruses in accordance with the present invention, which results in viral replication. The adenovirus dl1119/1131 is thus a further adenovirus which can be used in accordance with the present invention. It is within the present invention that also viruses can be used which are designed similar to dl1119/1131 with regard to the CR3 region, but, in contrast thereto, have the CR1 region and/or CR2 region.

EXAMPLE 6: DETECTION OF NUCLEAR YB-1 IN MULTIDRUG RESISTANT CELLS

The example is based on the consideration that nuclear YB-1 should bind as a transcription factor to the Y-box (CAAT sequence) within the mdr1 promoter (engl. multiple drug resistance promoter). In order to detect this, a so-called EMSA analysis (electrophoretic mobility shift assay) was performed. In connection therewith, nuclear protein is isolated and subsequently 1-10 µg protein is incubated together with a short DNA fragment (oligo) at 37° C. In order to determine nuclear YB-1, the following oligonucleotide was used: mdr1 promoter in contrast to U203 (Position −86 to −67): TGAGGCTGATTGGCTGGGCA (SEQ ID NO: 1)(the X-box is underlined).

This DNA fragment is radioactively labelled at the 5' end with $^{32}$P prior to that. Subsequently, separation is performed in a native polyacryl amide gel. In case the protein YB-1 is binding to a sequence in the oligonucleotide, this can be detected as any non-bound oligonucleotide is migrating faster in the gel than bound oligonucleotide (Holm, P. S. et al., JBC 277, 10427-10434, 2002; Bargou, R. C. et al., Nature Medicine 3, 447-450, 1997).

Figure 6:
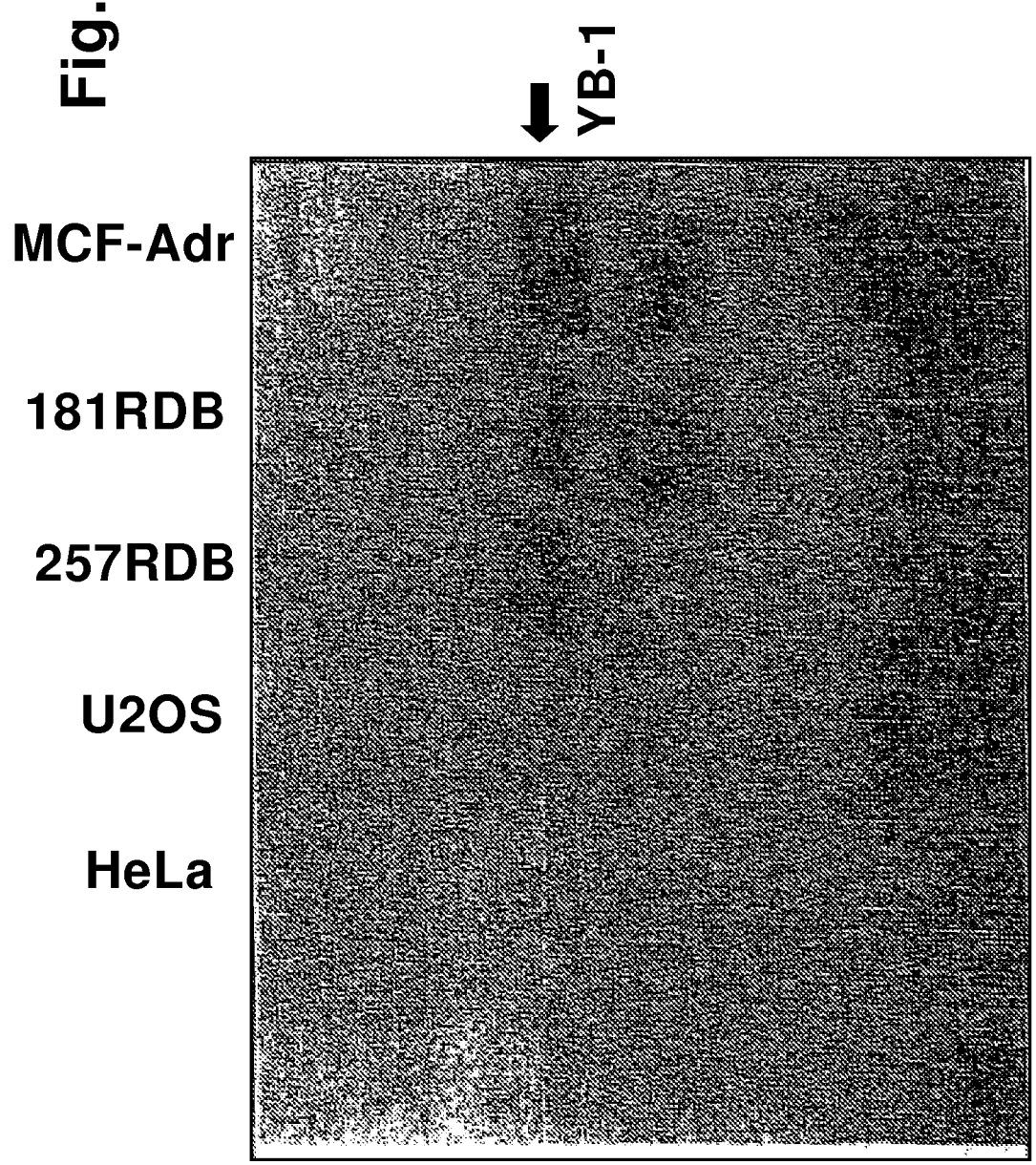
FIG. 6 shows the result of an EMSA analysis which confirms that YB-1 is present in multidrug resistant cells and cell lines 257RDB, 181 RDB, MCF-7Ad, respectively, whereas YB-1 is not present in the nucleus of U2OS and HeLa cells.

As depicted in FIG. 6, it could be shown with the EMSA analysis that YB-1 is present in the nucleus of multidrug resistant cells 257RDB, 181RDB and MCF-7Ad cells in contrast to cell lines U2OS and HeLa cells.

The results shown in example 4 and 5 confirm that the adenoviruses dl520 and dl1119/1131 replicate in YB-1 nucleus-positive cells such as, e. g., 257RDB in contrast to U2OS, and induce lysis thereof. This confirms the finding about the use of the adenoviruses in accordance with the present invention. Additionally, the results confirm that already a, compared to wildtype adenovirus, weak transactivation of viral genes in YB-1 nucleus-positive cells through modified or deleted E1A gene products results in successful replication and lysis of such cells in the presence of YB-1 in the nucleus, including, for example, multidrug resistant cells and that the adenoviruses as described herein, can thus be used in the lysis of such tumors.

EXAMPLE 7: INCREASE OF REPLICATION EFFICIENCY OF E1-MINUS ADENOVIRUSES

This example shows that the early viral genes E1B-55K and E4orf6 can be substituted through transfection with the plasmid pE4orf6 and infection with the E1/E3-deleted adenovirus Ad-55K. Ad-55K is an E1/E3 deleted virus, whereby E1B-55K is cloned into E1 and is under the control of CMV (Dobbelstein, M. et al., EMBO Journal, 16, 4276-4284, 1997). This substitution is necessary with regard to the fact that AdYB-1, i. e. an adenovirus which expresses YB-1, does not express these early genes and that the present inventor has recognised that a substitution of these early genes in a replication system which contains YB-1 in the nucleus, is capable of increasing replication efficiency and particle formation efficiency, respectively, to an extent comparable to the one of wildtype adenoviruses of type Ad5.

The following was done:

Transfection of each $10^5$ U2OS cells with the plasmid pE4orf6 using lipofectamine. The plasmid pE4orf6 carries the DNA sequence coding for the early viral gene E4orf6 under the control of CMV.

24 h after transfection with the plasmid pE4orf6 the cells were infected with the YB-1 expressing E1/E3-deleted adenovirus AdYB-1 (50 pfu/cell) and the E1/E3-deleted E1B-55K adenovirus Ad-55K (50 pfu/cell). Ad-55K is an E1/E3-deleted virus which carries as transgene the viral gene E1B-55K under CMV control.

Figure 8:
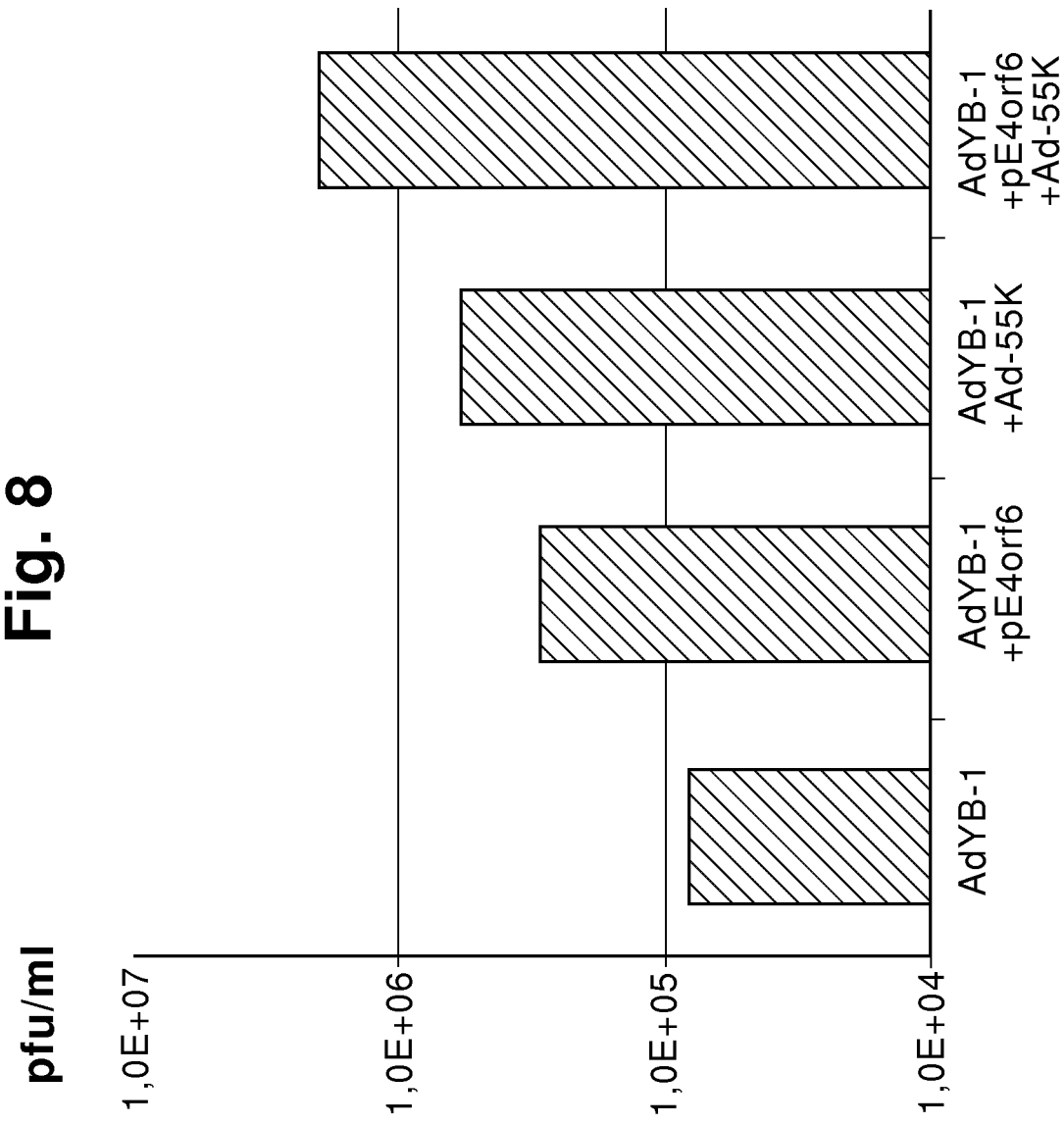
FIG. 8 is a column diagram showing the replication efficiency of adenoviruses in the presence of additionally expressed viral proteins in absolute figures.
Figure 9:
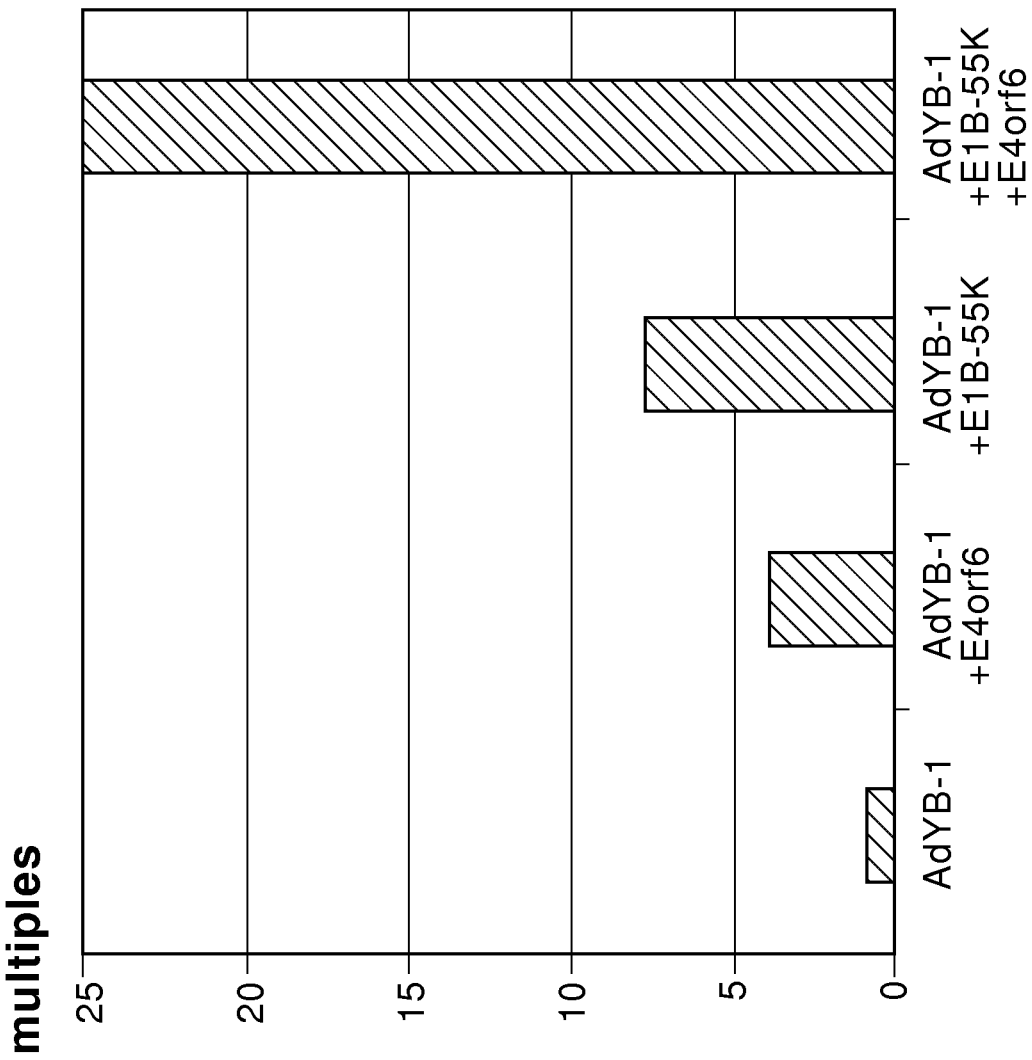
FIG. 9 is a column diagram showing the increase of replication efficiency of adenoviruses in the presence of additionally expressed viral proteins.

Subsequently, the cells were removed from the medium (2 ml) 5 days after infection (=post infection). The release of the viral particles from the isolated cells was done by alternating freezing and thawing for three times (thaw/freeze). Subsequently, a plaque assay was performed on 293 cells for determining the generated infectious particles (plaque forming units per ml (pfu/ml)). The result is depicted in FIGS. 8 and 9. FIG. 8 shows the result of the plaque assay, represented in absolute figures. The most significant difference compared to infection with AdYB-1 alone is shown by transfection with the plasmid pE4orf6 and co-infection with the two viruses AdYB-1 and Ad-55K. FIG. 9 shows the result of FIG. 8, whereby the increase of the replication efficiency is represented as multifold of the replication determined for AdYB-1. The cells infected with plasmid pE4orf6 and subsequently with AdYB-1 and E1B-55K (Ad-55K) produced up to 25 times more pfu/ml.

Based on these results it can be concluded that the substitution of E1B-55K and E4orf6 increases the number of viruses formed (pfu/ml) after infection with the E1/E3-deleted adenovirus AdYB-1 by a factor of up to 25. The additive effects of E1B-55K and E4orf6 on the production of plaque forming units (pfu) is significantly higher compared to the effects of each of the two gene products.

Control experiments with one plasmid which expresses EGFP, clearly showed that in the experimental approach chosen only 10% of the cells were successfully transfected with plasmid pE4orf6. The number of the particles formed in the cells which express both E1B-55K and E4orf6 is comparable to the one of human adenovirus type 5 (wildtype). This confirms the finding underlying the present invention that the expression of E4orf6 and E1B-55K is, in combination with the nuclear localisation of YB-1, able to provide for adenoviral replication and particle formation, in particular of E1A-deleted adenoviruses, which is comparable to the one of wildtype Ad5.

EXAMPLE 8: INCREASED REPLICATION OF ADENOVIRUSES WHICH ARE NOT REPLICATING IN YB-1 NUCLEUS-NEGATIVE CELLS, IN YB-1 NUCLEUS-POSITIVE CELLS UPON ADMINISTRATION OF CYTOSTATICS

It is known in the prior art that the addition of different cytostatics induces nuclear localisation of the human transcription factor YB-1. As has been found by the present inventor, YB-1 localised in the nucleus controls adenoviral replication by means of activation of the adenoviral E2-late promoter. The combination of both effects can be used in order to provide for specific tumor lysis.

In the practising of the oncolytic assays the following procedure was followed: 200,000 cells (HeLa and U2OS, respectively) were plated into each well of a 6 well plate. On the next day 40 ng/ml (final concentration) of daunorubicine were added. After 3 hours of incubation the cells were infected with 10 and 30 pfu dl520/cell, respectively. Subsequently, the cells were incubated in cytostatic free medium. After 3-5 days the cells were stained using crystal violet.

Figure 10:
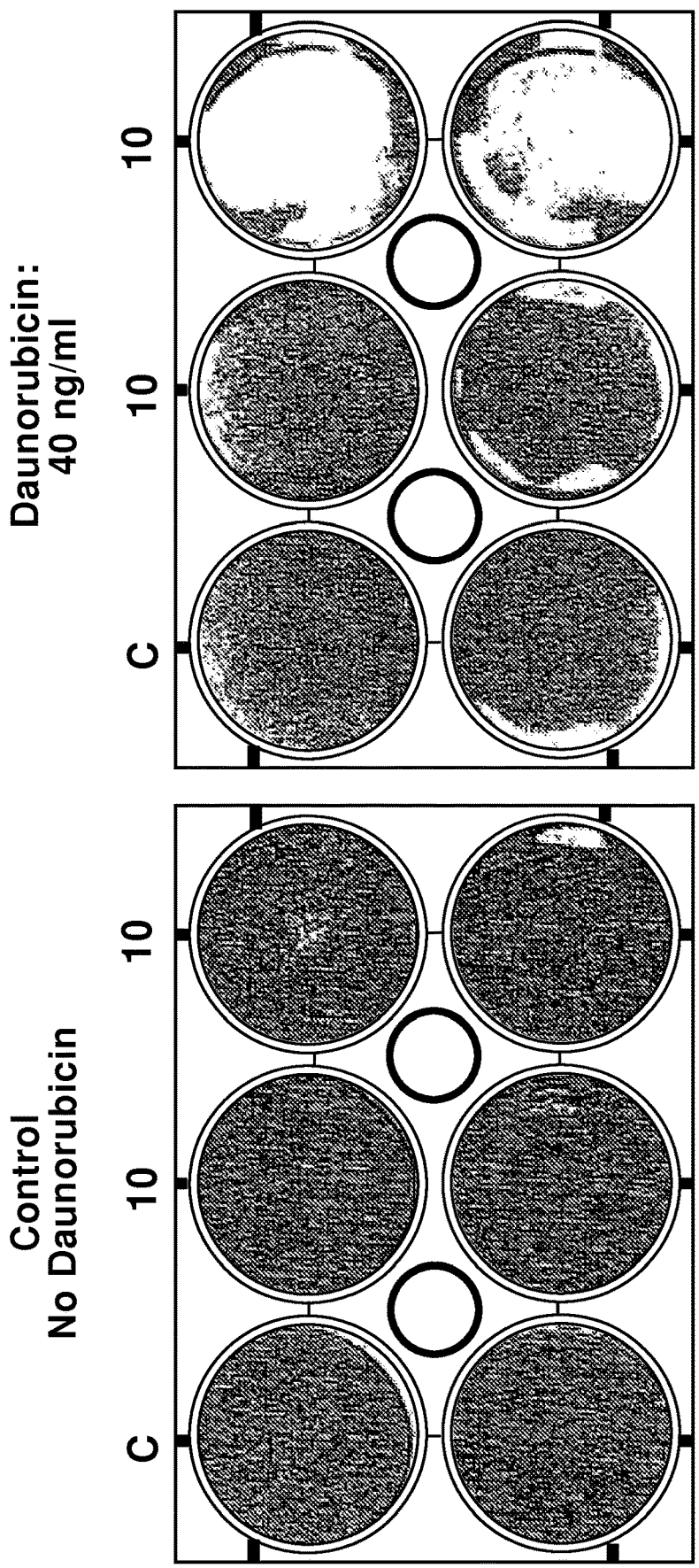
FIG. 10 shows wells grown with U2OS cells after crystal violet staining and infection with dl520 with 10 and 30 pfu/cell, respectively, and control (K) without administration of daunorubicine and with the administration of 40 ng daunorubicine per ml, respectively.
Figure 11:
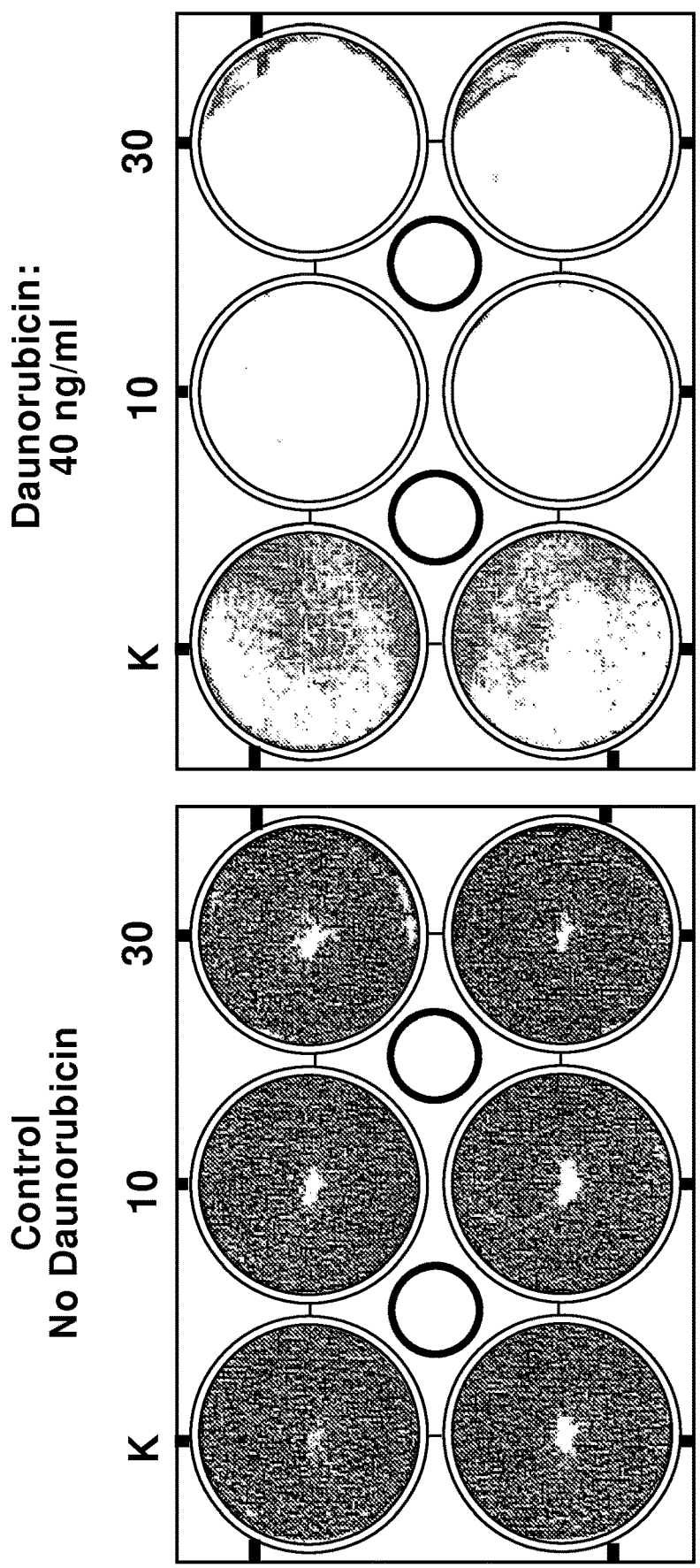
FIG. 11 shows wells grown with HeLa cells, after crystal violet staining and infection with dl520 and 10 and 30 pfu/cell and control (K), respectively, without administration of daunorubicine and administration of 40 ng daunorubicine per ml, respectively.

As may be taken from FIGS. 10 and 11, the addition of daunorubicine induces the replication of dl520 through nuclear localisation of YB-1. Thus, dl520 creates a bigger tumorlytic effect in combination with the cytostatic daunorubicine compared to daunorubicine alone.

EXAMPLE 9: IN VIVO TUMOR LYSIS BY DL520

The HeLa (YB-1 nucleus-negative) and 257RDB (YB-1 nucleus-positive) cells used in this in vivo study, were expanded under sterile cell culture conditions. Prior to the injection of the cells into mice (strain CD1NuNu) in order to generate a subcutaneous tumor, the cells are harvested by trypsinization, taken up in DMEM medium (10% FCS), counted and washed with PBS one time. Subsequently, the cells are centrifuged, the PBS aspired and the cells are portioned in fresh PBS with the desired cell number. The cell number which was subcutaneously injected in this study, was each $5 \times 10^6$ cells of both cell lines. The injection was performed subcutaneously into one flank of the animals, whereby HeLa cells were injected into the right side and 257RDB cells were injected into the left side for better distinction. The growth of the tumors was controlled twice a week and thereby the length and the width of the tumors was measured using vernier calipers. Based thereon, the tumor volume was calculated based on the following mathematical formula:

$$\tfrac{3}{4}\pi * a/2 * (b/2)^2 \quad a=\text{length}, b=\text{width}$$

Once the tumor has reached a volume of 200 to 520 mm$^3$, the virus and PBS as negative control, respectively, were intratumorally applied. The volumes to be injected were identical and were 50 µl each time. This was repeated on 3 consecutive days. The overall dosage of applied viruses was $5 \times 10^8$ pfu. Subsequently, the tumor growth was continued to be documented twice a week and the volume was calculated. At the end of the study the mice were sacrificed and the tumors removed for further analysis.

The results are depicted in FIGS. 12 and 13.

FIG. 12 shows a diagram representing the tumor volume as a function of time and the various treatment schemes. In case the tumor was formed by RDB257, there was a significant growth of the tumor to about 438 mm$^3$ to 1466 mm$^3$ upon injection of PBS. Under the influence of the vector dl520 which was used in accordance with the invention, tumor growth could be reduced significantly. Starting from a mean tumor size of 344 mm$^3$, the tumor size increased only by 21% to a total of 543 mm$^3$.

In the present example the tumor consisting of HeLa cells was used as a control which upon administration of PBS behaved similarly to the RDB257 based tumor upon administration of PBS. Tumors based on HeLa cells and treated with dl520, however, still showed a significant increase in tumor growth starting from 311 mm$^3$ and increasing to 1954 mm$^3$.

FIG. 13 shows a picture of the sacrificed nude mice which had a tumor grown using RDB257. It can be clearly seen that after the application of adenovirus dl520 in accordance with the present invention a significant reduction of the tumor occurred. In the present case there was even a reduction in the tumor volume (day 1 after administration of virus dl520: 515 mm$^3$; day 30 after administration of virus dl520: 350 mm$^3$).

EXAMPLE 10: SOUTHERN BLOT OF TUMOR DNA

DNA was extracted from a tumor sample which has been taken from the middle of the tumor developed in example 9. For isolation the Dneasy Tissue Kit of Qiagen is used. The DNA isolation is done in accordance with manufacturer's instructions. In accordance therewith, the DNA was released from the cells through alkaline lysis. Subsequently, the isolated DNA is purified over a column. Subsequently, the concentration of the isolated DNA is determined by photometry at 260 nm. The analysis was performed using 2 µg of the DNA samples which were digested with 10 units of restriction enzyme Kpn I. Subsequently, an electrophoretic separation of the samples was performed in a 0.8% agarose gel. Subsequently, the DNA was blotted onto a nylon membrane (performed according to the system of Schleicher & Schuell). The DNA blotted onto the membrane is hybridised against a specific 1501 bp DNA probe. The 1501 bp DNA probe specifically binds to the 3369 bp Kpn I fragment within the E2A coding Ad5 sequence. The probe was prepared prior to that by PCR (primer: 5'-GTC GGA GAT CAG ATC CGC GT (SEQ ID NO: 2), 5'-GAT CCT CGT CGT CTT CGC TT (SEQ ID NO: 3)) and radioactively labelled using $^{32}$P. Subsequently, the membrane is washed and exposed to a film.

The result of the Southern Blot of tumor DNA is depicted in FIG. 14. The analysis confirms that only dl520 replicates in vitro in resistant cells RDB257, as depicted in lanes 3, 4 and 5. Lane 1 shows as positive control Ad-5d, lane 6, 7 and 8 show DNA from HeLa cells which were infected with dl520. As HeLa cells are not YB-1 nucleus positive the virus dl520 did not replicate so that, in accordance therewith, the E2A sequence could not be detected.

A further result with dl520 is depicted in FIG. 15. Based on a plaque assay the particle formation (pfu/ml) was investigated after infection with dl520 and wildtype adenovirus. Various YB-1 nucleus-positive (257RDB and 181RDB) tumor cells and YB-1 nucleus-negative tumor cells were infected with dl520 and wildtype adenovirus.

The following procedure was practiced:

100,000-200,000 cells each were plated in so-called plates having 6 wells (engl. 6 well plates) in L 15 medium (resistant cells) and DMEM (non-resistant cells) having 10% FCS. After 24 h infection with dl520 and wildtype adenoviruses (10 pfu/cell) was performed. 3 days after infection (post infection) the viral particles were released from the cell suspension (3 ml) by alternating freezing and thawing for three times. Subsequently, a plaque assay was performed on 293 cells for determining the formed infectious particles (plaque forming units per ml (pfu/ml)). The result is depicted in FIG. 15. The result of the plaque assay shows that dl520 is replicating in YB-1 nucleus-positive cells (257RDB and 181RDB) similar to wildtype adenovirus. Insofar a replication efficiency can be observed similar to the one of wildtype adenoviruses when using, in accordance with the present invention, the adenoviruses described herein.

EXAMPLE 11: STRUCTURAL DESIGN OF THE ADENOVIRAL VECTOR XVIR03

FIG. 16 shows the structural design of the adenoviral vector Xvir03. The adenovirus Xvir03 is a so-called E1/E3-deleted adenovirus. This means that no E1A, E1B (E1B55k and E1B19K proteins) and E3 proteins are manufactured which are functional in adenoviral replication. The deletion of the E1 region extends from 342-3528; the deletion of the E3 region of the base position 27865-30995. As used herein, the term "E1-deleted virus" means a virus in which E1 is no longer functionally active. This can be achieved by inactivation with an otherwise mostly intact nucleic acid and amino acid sequence, however, can also mean a deletion of the E1 region coding proteins having various sizes. Because of the lack of the E1A and E1B protein and the nucleic acids coding therefor, the E4 region, such as E4orf6, is only weakly expressed (about 1-5% compared to wildtype adenoviruses) or expressed not at all. The viral genes E1B55k and E4orf6 are expressed in the E1 region by means of the heterologous CMV promoter (Clontech: Plasmid pShuttle) introduced into Xvir03. Instead of the CMV promoter each and any of the promoters as disclosed herein in connection with the expression of E1A can be used. The open reading frame of both genes is linked with each other by means of a so-called IRES sequence (engl. internal ribosomal entry site) (Pelletier, J. and Sonenberg, N. Nature, 1988, 334, 320-325). This element (Novagen: pCITE) provides for the expression of 2 proteins from one mRNA.

The Vector was Manufactured as Follows: System Adeno-X of the Company Clontech

The plasmid E1B55k-pShuttle was created by cloning the open reading frame of E1B55k from pCGNE1B from M. Dobelstein (University of Marburg) with XbaI and BfrI into the pShuttle vector from Clontech and only BamH I, whereby in this case the ends are made blunt ended and cloned into the blunt ended pShuttle. Subsequently, E1B55k in pShuttle was linearised with ApaI, the ends blunt ended and cut with NheI.

In a second vector, pcDNA3.1(+) (Invitrogen), subsequent to each other the IRES element as a PCR product was cloned with pCITE-4a(+) of the company Novagen as template by means of TA cloning into the EcoRV cleaving site, and the E4orf6 from the plasmid pCMV-E4orf6 (M. Dobelstein, University of Marburg) was cloned by means of BamHI=IRES-E4orf6-pcDNA3.1(+). IRES-E4orf6 in pcDNA3.1(+) was linearised with NotI, the ends blunt ended and subsequently the fragment IRES-E4orf6 was cut out with NheI. The fragment IRES-E4orf6 was linked with the open vector E1B55k-pShuttle (blunt, NheI). The cassette was subsequently cloned from the E1B55k-IRES-E4orf6-pShuttle together with the CMV promoter and the bovine growth hormone (BGH)-PolyA into the ΔE1, ΔE3 Adeno-X-Plasmid (Clontech) with I-Ceu I and PI-SceI, and referred to as AdcmvE1B/IRES/E4orf6. Subsequently, the adenovirus was made in accordance with manufacturer's instructions (Clontech). The adeno plasmid which was linearised with PacI having the expression element CMV-E1B55k-IRES-E4orf6-BGH polyA was transfected into HEK293 cells and 11 days post transfection the ablating cells were removed together with the medium in order to release the adenoviruses through repeated freeze-thaw cycles.

It is within the present invention and feasible for the one skilled in the art with regard to the technical teaching provided herein, that other systems such as the system AdEasy of QBIOGENE and Microbix may be used for the manufacture of the adenoviruses according to the present invention, preferably the recombinant adenovirus, in particular those which contain, individually and/or together, the cassettes E4orf6-IRES-E1B55k and YB-1-IRES-E1A12S. Additionally, individual transgenes may be exchanged between the cassettes. It is within the present invention that also such adenoviruses can be manufactured and used in accordance with the present invention, where the cassette has the following design: E1B55k-IRES-E4orf6 and E1A12S-IRES-YB1.

In connection with the present invention a so called E1/E3 deleted recombinant Adenovirus was used which contains the cassette E4orf6-IRES-E1B55k. It is, however, within an embodiment that the virus comprises only an E1-deletion, which means that the E3-region remains intact. Optionally, the E4-region may be partially and/or completely deleted.

In the manufacture of the vector using different systems it was proceeded as follows. Manufacture of the adenovirus Ad-Xvir 3'UTR having an intact E3-region with the vector system according to Graham (company Microbix).

Cloning of the Vector CMV-E4ORF6-IRES-E1B55k 3'UTR-polyA in pDelta E1sp1A

For the plasmid E1B55k 3'UTR-pShuttle (Clontech) the open reading frame having the 3'-UTR was prepared by amplification from the DNA of adenovirus type 5 (E1B55k forward primer=5'-ATGGAGCGAAGAAACCC-3' (SEQ ID NO: 4) and E1B55k 3'UTR backward primer=5'-CACGTCCTGGAAAAAATACAC-3' (SEQ ID NO: 5)) and introduced in the blunt ended NheI restriction site, which was provided with T-ends (TA-cloning) and cloned into the pShuttle plasmid of the company Clontech. Thus, the transgene was provided with a hCMV-promoter at the 5'end and with the bovine growth hormone polyadenylation signal at the 3'end. However, it is also within the present invention that E1B55k is used from the plasmid pCGNE1B from Dobbelstein (Dobbelstein, M. et al., EMBO Journal, 16, 4276-4284, 1997) by means of Bam HI and blunt ending and TA-cloning, respectively. The E1B55k-3'UTR which has been cloned, is, among others, described in more detail in FIGS. 23 and 24.

Cloning of the Vector E4ORF6-IRES-pcDNA3.1(+)

The amplificates E4orf6 using the adenovirus type 5 DNA as template (E4orf6 forward primer 5'-CTTCAGGATC-CATGACTACGTCCGGCG-3' (SEQ ID NO: 8) and E4orf6 backward primer 5'-GAAGTGAATTCCTA-CATGGGGGTAGAGTCATAATCGT-3' (SEQ ID NO: 9)) and from the plasmid pCMVE4-34 kD which has been cut with Bam HI (Dobbelstein et al., EMBO, 16, 4276-4284, 1997), and the IRES element having the pCITE-4a(+) of the company Novagen as template (IRES forward primer=5'-TCCGGTTATTTTCCACCATATTGC-3' (SEQ ID NO: 10) and IRES backward primer=5'-TTATCATCGTGTTTTT-CAAAGG-3' (SEQ ID NO: 11) were subsequently cloned into the multiple cloning site of the pcDNA3.1(+)-vector. For such purpose, primers were used for the E4orf6 transgene which create a BamHI cleavage site at the 5'-end and a EcoRI cleavage site at the 3'-end of the open reading frame. The amplificate was digested with the respective restriction enzymes and the ends thereof were made compatible for the directed cloning into the vector which has been opened using BamHI and EcoRI. Subsequently, plasmid E4orf6 in pcDNA3.1(+) was linearized with EcoRV, the T-ends added and the amplificate cloned into the IRES element. After checking the correct orientation of the IRES element, the vector was used for further cloning.

The linkage of both transgenes with the IRES element resulted from a cloning of the E4orf6-IRES cassette into the previously generated plasmid CMV-E1B55k 3'UTR-polyA-pShuttle (Clontech) which was linearized with NotI, blunt ended and subsequently cut with XbaI. E4orf6-IRES in pcDNA3.1 (+) was linearized with NotI, the ends made blunt ended and further digested with NheI. By ligating the E4orf6-IRES insert with the CMV-E1B55k 3'UTR-polyA-pShuttle (Clontech) XVIR-3'UTR was generated in pShuttle (Clontech).

Generation of the Used Adenoviral Shuttle Vector

As the shuttle vector pΔE1sp1A, now used for the adenoviral generation system of the company Microbix, did neither contain a CMV promoter nor a bovine growth hormone polyadenylation signal, these elements were cloned into pΔE1sp1A. For such purpose, pΔE1sp1A was linearized with ClaI, made blunt ended and cut with EcoPJ. The element CMV-MCS (multiple cloning site)-poly-A was linearized from pShuttle (Clontech) with MfeI, the ends made blunt ended and further cut with EcoRI. Subsequently, the cassette (Xvir-3'UTR pShuttle from Clontech) was cloned with PmeI into the CMV-MCS-poly-A pΔE1sp1A vector which had also been cut with PmeI and subsequently diphosphorylated. The cloning product Xvir-3'UTR-pΔE1sp1A was used for virus generation.

Virus Generation

Xvir-3'UTR-pΔE1sp1A and pBHGE3 (from Microbix, contains the E3-region which corresponds to wildtype adenovirus type 5) was cotransfected into HEK 293 cells, whereupon virus Ad-Xvir-3'UTR E3 was generated due to recombination of homologous sequences of both vectors.

Generation of Adenovirus Ad-Xvir3'UTR-AdEASY E3 Using the AdEASY-System (Company Qbiogene)

Generation of the Used Adenoviral Shuttle Vector

As, for the present used system, the vector pShuttle-AdEASY did neither contain a CMV-promotor nor the bovine growth hormone polyadenylation signal, these elements were cloned into pShuttle-AdEASY. For such purpose, the plasmid was digested with EcoRI, the ends made blunt ended by fling them up with T4-polymerase and dNTPs, the backbone was dephosphorylated and both of the generated digestion products ligated again. By doing so the restriction recognition site for EcoRI was eliminated. The thus resulting plasmid was referred to as pShuttle(-EcoRI)-AdEASY.

Subsequently, the cassette CMV-MCS-polyA from the pShuttle of Clontech was cut with MfeI and EcoRI, the ends made blunt ended and cloned into the vector pShuttle (-EcoRI)-AdEASY which was, for such purpose, linearized with XbaI, made blunt ended and dephosphorylated. Thus plasmid CMV-MCS-polyA-pShuttle-AdEASY was generated. The cassette E4Orf6-IRES-E1B55k-3'UTR was cloned into this plasmid using MluI and EcoRI. By doing so the plasmid Xvir-3'UTR in pShuttle AdEASY was generated. This was linearized with Bst1107I and MroI and introduced into BJ5183 (EC) bacteria together with rescue-plasmid pAdEASY by means of electroporation. By homologous recombination the adenoviral plasmid Ad-Xvir-3'UTR-pAdEASY was generated which resulted in virus production after transfection in HEK293 cells.

Introducing the Wt E3 Region into pAdEASY

As the E3 region is substantially deleted in plasmid pAdEASY, the E3 region was cloned from plasmid pAdEASY with SpeI and PacI into plasmid CMV-MCS-polyA pShuttle (AdEASY) for reconstruction and thus the plasmid E3E4-pShuttle-AdEASY generated.

By restriction with NdeI and religation one out of two NdeI restriction sites was deleted and so was the multiple cloning site from the plasmid. By this procedure plasmid E3E4-pShuttle(-NdeI)-AdEASY was generated.

Subsequently the 4007 bp wtE3-region fragment from wildtype adenovirus type 5 was excised by SpeI and NdeI and cloned into the E3E4-pShuttle (-NdeI)-AdEASY which was opened by SpeI and NdeI. The thus generated vector was referred to as wtE3E4-pShuttle (NdeI)-AdEASY.

Subsequently the wildtype E3E4-region from the E3E4-pShuttle (-NdeI)-AdEASY was cut with SpeI and PacI and cloned into the pAdEASY and cut with SpeI and PacI, whereby in plasmid pAdEASY the E3-region was re-established (pAdEASY-E3). XVir-3'UTR-pAdEASY-E3 was generated by homologous recombination upon transforming BJ5183 (EC) bacteria with plasmids Xvir-3'UTR in pShuttle AdEASY and pAdEASY-E3.

Manipulation of E4 for all of the Systems Mentioned

In order to provide space for therapeutic transgenes and in order to avoid undesired homologous recombination the E4 region in plasmid E3E4-pShuttle (-NdeI)-AdEASY can be deleted specifically. For such purpose, the E4orf6 region is shortened by about 0.6 kB, preferably 629 or 634 bp, by excision with PstI and religation. This can, as described in FIG. 17, be performed in connection with Xvir03/01. Respective deletions are also feasible by the one skilled in the art in different systems for the generation of recombinant adenovirus.

Cloning of the RGD-Motif in Ad-Xvir 3'UTR-AdEASY E3 in Particular (Also Applicable to Other Systems)

For increasing the infectivity the HI Loop of the fibre knob domain was modified following Dmitriev et al. 1998 (An Adenovirus Vector with Genetically Modified Fibers Demonstrates Expanded Tropism via Utilization of a Coxsackievirus and Adenovirus Receptor-Independent Cell Entry Mechanism): The respective region was amplified using the primers RGD-Hpa fw (5'-GAGgttaacCTAAGCACTGCCAAG-3' (SEQ ID NO: 12), RGD-EcoRV rev (5'-CATAGAGTATGCAGATATCGTTAGTGT-TACAGGTTTAGTTTTG-3' (SEQ ID NO: 13)) and RGD-EcoRV fw (5'-GTAACACTAACGATATCTGCATACTCTATGTCATTTT-CATGG-3 (SEQ ID NO: 14)) and RGD-Bfr rev (5'-

CAGCGACATGAActtaagTGAGCTGC-3'(SEQ ID NO: 15)) and thus an EcoRV restriction site generated. In this restriction site the paired oligonucleotides were cloned which code for an Arg-Gly-Asp (RGD)-peptide: RGD-oligo 1 (5'-CACACTAAACGGTACACAGGAAACAGGA-GACACAACTTGTGACTGCCGCGGAGACT GTTTCTGCCC-3'(SEQ ID NO: 16)) and RGD-oligo 2 (5'-GGGCAGAAACAGTCTCCGCGGCAGT-CACAAGTTGTGTCTCCTGTTTCCTGTGTACCG TTTAGTGTG-3'(SEQ ID NO: 17)). Thus, the RGD motif is present in the HI Loop of the fibre knob domain.

The vector described above is in principle suitable as are the other viruses described herein for use in accordance with the present invention. In particular the afore-described vector is suitable to replicate and trigger lysis insofar, in cells which are YB-1 nucleus-positive cells as well as in cells where YB-1 is deregulated, i. e. is overexpressed compared to normal cells and non-tumor cells, respectively. The use of this vector particularly applies to those diseases and groups of patients or collectives of patients which are disclosed in connection with the other adenoviruses which are described herein to be used in accordance with the present invention and the other adenoviruses of the present invention disclosed herein.

EXAMPLE 12: STRUCTURAL DESIGN OF THE ADENOVIRAL VECTOR XVIR03/01

As may be taken from FIG. 17, Xvir03/01 is a further development of Xvir03. Therapeutic genes such as, for example, the genes described herein and the transgene can be cloned into the E3 region. Additionally, a deletion was introduced into the E4 region so as to avoid homologous recombination with the E4orf6 from the expression cassette of Xvir03. This allows that larger transgenes can be cloned in this construct. The deleted E3 region contains SacI, NdeI and NheI restriction sites for introducing a cassette, into which, for example, the therapeutic transgenes can be cloned. However, the E3 may also stay intact and the therapeutic genes be cloned into the E4 region. By doing so the expression of the adenoviral death protein is provided.
Preparation of a Plasmid for Cloning Therapeutic Genes into the E3 Region as Well as for Making Deletions in the E4 Region:

The pAdenoX-Plasmid of Clontech has a restriction site for SfuI behind the 3' ITR region which is absent in wildtype adenovirus. The E3-E4 region was taken from pAdenoX (Clontech) with the SpeI (position 23644) and SfuI and transferred into pcDNA3.1(+) (Invitrogen)=pcDNA3.1-E3Δ27865-30995-E4. The majority of E4ORF6, namely 33241-33875 was removed by means of PstI=pcDNA3.1-E3Δ27865-30995,E4Δ33241-33875. For the further development of Xvir03 the deleted E3/E4 region from pcDNA3.1-E3Δ27865-30995,E4Δ33241-33875 was cloned by means of SfuI and SpeI into plasmid pAdenoX=pAdenoX E3Δ27865-30995,E4Δ33241-33875.

The expression cassette was subsequently, as described for Xvir03, cloned with I-Ceu I and PI-SceI from the E1B55k-IRES-E4orf6-pShuttle together with the CMV promoter and the bovine growth hormone (BGH)-PolyA into pAdenoX E3×27865-30995,E4Δ33241-33875 and referred to as AdcmvE1B/IRES/E4orf6-ΔE4. Subsequently, the adenovirus was made in accordance with manufacturer's instructions (Clontech).

It is within the present invention and feasible for the one skilled in the art in the light of the present disclosure that other systems may be used for the manufacture of the adenoviruses in accordance with the present invention and in particular the recombinant adenoviruses, such as the systems of the companies QBIOGENE and Nicrobix.

The afore-described vector is in principle useful as are the other viruses described herein to be used in accordance with the present invention. In particular the afore-described vector is suitable to replicate in YB-1 nucleus-positive cells as well as cells in which YB-1 is deregulated, i. e. is overexpressed compared to normal cells and non-tumor cells, and to cause lysis insofar. This vector can also be used for those diseases and groups of patients and collectives of patients which are disclosed herein for the other adenoviruses to be used in accordance with the present invention and the adenoviruses in accordance with the present invention.

EXAMPLE 13: ONCOLYTIC EFFECT OF XVIR 03 IN 257 RDB AND 181 RDB CELLS 100,000 cells (257RDB and 181RDB) were plated per well of a plate having six wells (engl.: 6 well plate). On the next day the cells were, as depicted in FIG. 18, infected with Ad312 (20 pfu/cell) and Xvir03 (5 pfu/cell). The infection was performed in 500 µl serum free DMEM medium at 37° C. for 1 h. Subsequently, the infection medium was removed and replaced by 2 ml complete medium (10% FCS/DMEM). The analysis was done by means of crystal violet staining after 5 days. The result is depicted in FIGS. 18A and 18B.

As may be taken from FIGS. 18A and 18B, the multidrug resistant cells which have YB-1 in the nucleus, show lysis after infection with Ad312 and Xvir03 only in case of Xvir03 as represented by the crystal violet staining of the cells. In connection therewith, first the medium is removed. Subsequently the cells are covered with crystal violet (50% ETOH, 3% formaldehyde, 5% acetic acid, 1% crystal violet) and incubated at room temperature for 5-10 min. Subsequently, the six well plates are thoroughly rinsed with water and dried at room temperature.

It is known to the present inventor that E1A-deleted viruses (e. g. Ad312) which, however, are not transactivating adenoviruses in the sense of the present invention, may very efficiently replicate at higher MOIs (Nevins J. R., Cell 26, 213-220, 1981), which, however, cannot be realised in clinical application. This phenomenon is referred to in the literature as "E1A-like activity". The adenovirus Ad312 as used herein, is an E1A-deleted virus. At the titer used (20 pfu/cell), which is still above the clinically desirable titer, the early adenoviral genes such as E1B55k and E4orf6 are not expressed or expressed only to a very small extent (Nevins J. R., Cell 26, 213-220, 1981). As already described herein, these genes and proteins play an important role in viral replication. In contrast thereto, these genes and proteins, respectively, are expressed by adenovirus Xvir03 (FIG. 16). As may be taken from FIGS. 18A and 18B, the expression of the genes E1B55k and E4orf6 will result in an efficient viral replication and cell lysis at a concomitantly lower infection titer required (expressed as pfu/cell). This confirms the finding underlying the present invention, namely that the expression of E4orf6 and E1B-55K (and the absence of E1A) in combination with nuclear localisation of YB-1 is capable of inducing a very efficient adenoviral replication. The titer required therefor of only 1 to 5 pfu/cell now allows for clinical application.

This confirms the finding underlying the present invention, namely that the presence of YB-1 in the nucleus, particularly the presence independent from the cell cycle, is required in order to make the viruses which are to be used in accordance with the present invention, lyse infected cells.

EXAMPLE 14: REPLICATION OF ADENOVIRUS IN CELLS AFTER ADDITION OF IRINOTECAN

In order to determine the effect of Irinotecan on adenoviral replication $10^6$ U373 tumour cells were plated in 10 cm$^2$ Petri dishes. In a first reaction 5 µM Irinotecan was added after 24 hours. After another 24 hours the cells were infected with 10 pfu/cell dl520. After incubation of 3 days without Irinotecan DNA was isolated in accordance with the procedure described in example 10.

In a parallel reaction the thus prepared U373-cells were not pre-incubated with Irinotecan. After 48 hours of cultivating the cells without Irinotecan, they were infected with 10 pfu/cell dl520 and subsequently incubated without Irinotecan for another 3 days. DNA was isolated as described above.

Subsequently 2µ DNA were digested with restriction enzyme Kpn I and a Southern Blot analysis performed. A part of the adenoviral genome (position: 22734-24235) generated by means of PCR was used as a probe.

The result is depicted in FIG. 19. FIG. 19 shows that after incubation with Irinotecan adenoviral replication is significantly increased in U373 cells after treatment with Irinotecan (lane 2) compared to untreated control where no incubation with Irinotecan was performed (lane 1). This means that adenoviral replication is increased under the influence of Irinotecan.

EXAMPLE 15: REPLICATION OF ADENOVIRUS IN CELLS AFTER ADMINISTRATION OF TRICHOSTATIN A

In order to test the effect of Trichostatin A on adenoviral replication, $10^6$ U373 tumour cells were plated in 10 cm$^2$ Petri dishes. After 24 hours 0.25, 0.5 and 0.75 µM Trichostatin A was added. After another 24 hours the cells were infected with 10 pfu/cell dl520.

After 3 days of incubation in medium without Trichostatin DNA was isolated. Subsequently 2 µg DNA were digested with restriction enzyme Kpn I and a Southern Blot analysis performed. A part of the adenoviral genome (position: 22734-24235) generated by means of PCR was used as a probe.

The result is depicted in FIG. 20. FIG. 20 shows that after incubation with increasing concentrations of Trichostatin A viral replication in U373 cells (lanes 2, 3 and 4) is significantly increased compared to untreated controls where no incubation with Trichostatin A was performed (lane 1). This means that viral replication is increased under the influence of Trichostatin A.

EXAMPLE 16: INFLUENCING THE EXPRESSION OF COXSACKIEVIRUS-ADENOVIRUS-RECEPTOR (CAR) ON U373 CELLS IN RESPONSE TO ADDITION OF TRICHOSTATIN A 200,000 U373 cells were plated in 6 well plates. After 24 hours the cells were cultivated with 1 µM Trichostatin for 24 hours. After another 24 hours the cells were isolated. Subsequently, analysis of CAR expression was performed according to a standard protocol using Facs-analysis and the primary antibody anti-CAR clone RmcB from the company Upstate, and a rabbit-anti-mouse FITC as secondary antibody (company DAKO).

The result is depicted in FIG. 21. Without Trichostatin treatment 11.3% of the cells were CAR-positive, whereby after incubation of the cells with 1 µM Trichostatin 56.2% of the cells were CAR-positive. The figures are percentages of the overall cells used in the test.

From FIG. 21 it can be taken that under the influence of the histone deacylase inhibitor Trichostatin A CAR, which is an important factor for the binding of adenovirus, is expressed at a higher level and more available, respectively, which increases the efficacy of transfection of the thus treated cells.

EXAMPLE 17: ONCOLYSIS OF U373 CELLS BY ADENOVIRUS AFTER COMBINED TREATMENT OF THE CELLS WITH IRINOTECAN AND TRICHOSTATIN A 200,000 U373 cells were plated in a 6 well plate. After 24 hours either 2 µM Irinotecan or only 1 µM Trichostatin A or 1 µM Irinotecan+0.5 µM Trichostatin were added to the medium. After 24 hours of incubation the cells were infected with 10, 20 and 30 pfu/cell dl520. After 3-5 days the analysis was performed using crystal violet staining. The assays were performed in duplicate.

The result is depicted in FIG. 22. The six plates represented in panel 1 show a complete cell layer which was not affected by incubation with a combination of Irinotecan and Trichostatin A as shown by crystal violet staining. The next two wells of panel 1 show the cell layer after infection with 10 and 20 pfu/cell dl520, respectively. Also under such conditions there is no lysis of the cells which is due to the absence of replication of dl520. Thus it is shown that neither dl520 at 10 or 20 pfu/cells nor 1 µM Irinotecan+0.5 µM Trichostatin A alone are suitable to induce cell lysis.

The further 6 well plates 2, 3 and 4 depicted in FIG. 22, herein also referred to as panels 2, 3 and 4, were basically treated in accordance with this scheme. The individual wells were inoculated with U373 cells as previously described and the cells cultivated therein. The wells were inoculated with 10, 20 or 30 pfu/cell dl520 in duplicate, whereby the difference between the three 6 well plates resided in the kind of cytostatics used. In panel 2 2 µM Irinotecan, in panel 3 µM Trichostatin A and in panel 4 1 µM Irinotecan and 0.5 µM Trichostatin A was added to the individual plates.

In the 6 well plate 2 (panel 2) with 2 µM Irinotecan the cells were lysed with 30 pfu/cell dl520. In the 6 well plate 3 (panel 3) with 1 µM Trichostatin A the cells were lysed at 20 and 30 pfu/cell dl520. In the 6 well plate 4 (panel 4) with 1 µM Irenotecan+0.5 µM Trichostatin A the cells, in contrast thereto, were already lysed at 10 pfu/cell dl 520.

The test, the results of which are depicted in FIGS. 19 to 23, shows that the combination consisting of Irinotecan+Trichostatin A+dl520 induces a more effective cell lyses of tumour cells as any compound alone. This results, on the one hand, from Trichostatin A increasing CAR-expression and thus significantly improves infectability of the cells. On the other hand, Irinotecan translates YB-1 into the cell nucleus and thus induces an improved adenoviral replication. Additionally, the cellular YB-1 is assisting adenoviral replication after infection with dl520 and is no longer available for DNA-repair processes. Depending on the point of view, this results in an improved efficacy of dl520 on the one hand and an increased efficacy of the cytostatics on the other hand.

EXAMPLE 18: NORTHERN BLOT ANALYSIS OF THE E2 GENE EXPRESSION OF ADENOVIRUS AD312

In each case 1 million A549 and U2OS cells were plated in 10 cm Petri dishes. At the next day the cells were infected with Ad312 (50 pfu/cell) and Adwt (which served as control, 5 pfu/cell). The high virus titer of Ad312 which was used resulted in an E1-independent replication in tumor cells. The infection was done in 1-2 ml serum-free DMEM medium for 1 h at 37° C. Subsequently, the infection medium was removed and replaced by 10 ml complete medium (10% FCS/DMEM). After 3 days the RNA was isolated. Subsequently, the concentration of the isolated RNA was measured in a photometer at 260 nm. Then the RNA samples were electrophoretically separated in a 0.8% formaldehyde agarose gel. Subsequently, the RNA was blotted on a nylon membrane (conducted according to the system of Schleicher & Schuell). The RNA blotted on the membrane is blotted against an "early probe" E2 and a "late probe" E2. The 1501 bp "late probe" specifically binds behind the E2-late promoter. The probe was prepared prior to that by PCR (primer: 5'-GTC GGA GAT CAG ATC CGC GT (SEQ ID NO: 2), 5'-GAT CCT CGT CGT CTT CGC TT (SEQ ID NO: 3)) and radioactively labelled using $^{32}$P. In contrast, the early probe binds between the E2-early promoter and the E2-late promoter (position: 226791-227002) and was also generated by means of PCR (primer: 5'-AGCTGATCTTCGCTTTTG (SEQ. ID. NO. 6), 5'-GGATAGCAAGACTCTGAC AAAG (SEQ. ID. NO. 7)). Subsequently, the membrane was washed and exposed to a film.

The result is depicted in FIG. 25. Both the early as well as the late probe provided specific signals in the control infection with wildtype adenovirus, whereas tumor cells infected with Ad312 only provided a specific signal when the late probe was used. This confirms the finding underlying the present invention that the expression of E4orf6 and E1B55K and the absence of E1A transports overexpressed and deregulated YB-1, respectively, into the nucleus and thus induces E2 gene expression as a prerequisite for efficient adenoviral replication.

EXAMPLE 19: NORTHERN BLOT ANALYSIS OF THE E2 GENE EXPRESSION OF ADENOVIRUS ADDELTA 24

In each 1 million U2OS cells were plated in 10 cm Petri dishes. At the next day the cells were infected with adenovirus delta 24 (Addelta24) (10 pfu/cell) and wildtype adenovirus (Adwt) (served as a control, 10 pfu/cell). The used recombinant adenovirus Addelta24 (Fueyo, J. et al., Oncogene 19, 2-12, 2000) has a specific deletion in the CR2 region of the E1A protein and is thus only capable of replicating in Rb-negative tumors. Additionally, the virus expresses the genes E1B55k and E4orf6 comparable to the wildtype adenovirus. The infection occurred in 1-2 ml serum-free DMEM medium for 1 h at 37° C. Subsequently, the infection medium was removed and replaced by 10 ml complete medium (10% FCS/DMEM). The RNA was isolated after 12 h and 24 h. Subsequently, the concentration of the isolated RNA was determined in a photometer at 260 nm. Then the RNA samples were electrophoretically separated in a 0.8% formaldehyde agarose gel. Subsequently, the RNA was blotted on a nylon membrane (conducted according to the system of Schleicher & Schuell). The RNA blotted onto the membrane is hybridised against the "early probe" and against the "late probe". The "late probe" comprising 1501 bp, binds specifically behind the E2-late promoter. The probe was prepared prior to that by PCR (primer: 5'-GTC GGA GAT CAG ATC CGC GT (SEQ ID NO: 2), 5'-GAT CCT CGT CGT CTT CGC TT (SEQ ID NO: 3)) and radioactively labelled using $^{32}$P. The early probe, however, binds between the E2-early promoter and the E2-late promoter and was also prepared by PCR (primer: 5'-AGCT-GATCTTCGCTTTTG (SEQ. ID. NO. 6), 5'-GGA-TAGCAAGACTCTGACAAAG (SEQ. ID. NO. 7)). Subsequently, the membrane was washed and exposed to a film.

The result is shown in FIG. 26.

After 12 h only the late probe provided for a specific signal. Only after 24 h also the early probe provided a signal in cells infected with Addelta24. Compared to wildtype adenoviruses, however, the signal is significantly weaker. Also this result confirms the finding underlying the present invention that the expression of E4orf6 and E1B-55K transports overexpressed and deregulated YB-1, respectively, into the nucleus which subsequently binds to the E2-late promoter and induces E2 gene expression.

EXAMPLE 20: STRUCTURAL DESIGN OF THE ADENOVIRAL VECTORS XVIRPSJL1 AND XVIRPSJL2

Description of the vectors: The vectors of the XvirPSJL group which are embodiments of the viruses referred to herein as group I adenoviruses and which are exemplified by the vectors and adenoviruses, respectively, XvirPSJL1 and XvirPSJL2, are not only, like adenovirus dl520, capable of replicating in YB-1 nucleus-positive cells, in particular tumor cells, but also in tumor cells in which YB-1 is overexpressed and deregulated, respectively. While the viral genes E1B55k and E4orf6 are expressed only in dl520 infected YB-1 nucleus-positive cells under the influence of the E1B promoter and the E4 promoter, respectively, the expression of E1B55k and E4orf6 in XvirPSJL occurs by means of the cytomegalovirus (cmv) promoter. Instead of the cmv promoter, however, also other promoters, in particular tumor-specific, tissue-specific and organ-specific promoters and the natural E1A promoter, i.e. in particular the E1A promoter as present in Adenoviruses of the wildtype, in particular Ad5, may be used. Because of the expression of E1B55k and E4orf6 the overexpressed YB-1 and the deregulated YB-1, respectively, is transported into the nucleus and adenoviral replication is initiated. The adenoviral vectors of the XvirPSJL group as disclosed herein, thus combine various elements and thus functions of the adenoviral vectors dl520, Xvir03 and AdYB-1 in a single vector. Similar to the vector dl520 the XvirPSJL viruses contain the E1A12S gene. This gene and the corresponding gene product, respectively, is responsible for the induction of the S phase of the infected cell and promotes viral replication and the effect of chemotherapeutics and irradiation.

Like Xvir03 the XvirPSJL viruses contain the expression cassette CMV-E4orf6/IRES/E1B55k, which is required for an efficient replication and indirectly or directly transports deregulated YB-1 into the nucleus which is preferably contained in tumor cells. Thus replication is possible only in cells, particularly tumor cells, where YB-1 is overexpressed or deregulated. Additionally, P53 is made subject to degradation by the E1B55k/E4orf6 complex. The sequence coding for human transcription factor YB-1 is taken from the virus AdYB-1. The endogenous, i. e. the YB-1 already present in the cell amplifies viral replication. The expression of both E1A12S and YB-1 is controlled by the YB-1-dependent adenoviral E2-late promoter. Also in connection therewith specific promoters may be used in an embodiment, in particular tumor-specific, tissue-specific or organ-specific promoters. A further feature of these viruses is that the E4 region is deleted. The vector contains restriction sites there by which, in case of the adenoviral vectors XvirPSJL1 and XvirPSJL2, various transgenes as disclosed in the specification such as ribozymes, antisense molecules, siRNA, apoptosis-inducing genes, cytokines and prodrug genes may be expressed. Their expression may also be controlled by tumor-specific, tissue-specific or organ-specific promoters as disclosed in the specification. The localisation of the expression cassettes is not fixed, particularly not with regard to or within the E1, E3 and E4 region, but can be arranged in any way. The vectors replicate independent of the p53 or Rb status of the tumor cells.

The structural designs of the recombinant adenoviruses XvirPSJL1 and XvirPSJL2 are presented in FIGS. 27 and 28:

Generation of the Vector XvirPSJL According to the System of the Company Clontech Generation of the Cassette E2-Late-YB1IRES/12S:

The pAdenoX plasmid of Clontech/BD Biosciences which is used as a starting material herein, comprises the genomic nucleic acid of adenovirus Ad5 and has a SfuI restriction site behind the 3' ITR region which is ABSENT in wildtype adenovirus. The E3-E4 region was transferred by SpeI (position 23644) and SfuI from pAdenoX (Clontech) into pcDNA3.1(+) (Invitrogen) and referred to as pcDNA3.1-E3Δ27865-30995-E4. The majority of the E4ORF6, namely the bases 33241-33875 were removed by means of PstI. The such obtained fragment was referred to as pcDNA3.1-E3Δ27865-30995, E4Δ33241-33875.

The E2-late promoter was excised from pGL3-EGFP (Holm et al., JBC 2002, 277, 10427-10434) with SacI and NheI and cloned into pcDNA3.1-E3Δ27865-30995, E4Δ33241-33875. In doing so, the E3 region was further deleted in the region of bases 427593-31509. The thus obtained fragment was referred to as E2-late-pcDNA3.1-E3427593-31509, E4433241-33875

The cDNA for the E1A-243AA product was generated by means of RT-PCR, isolated and the sequence checked and cloned into the pcDNA3.1(+) vector (Invitrogen) using BamHI and EcoRI. E1A-12S-pcDNA3.1+ was linearised with NheI and BamHI, made blunt-ended by T4 polymerase and provided with T overhangs by Taq polymerase and dTTPs. The IRES element was cloned as a PCR product (template=pCITE, Novagen) into the E1A-12S-pcDNA 3.1 (+) vector (TA cloning strategy).

The YB-1-EcoRI fragment was isolated from the vector pHVad2c (Holm et al., JBC 2002, 277, 10427-10434) and made blunt-ended. The vector pShuttle (commercially available from BD Biosciences) was linearised with XbaI, the ends made blunt-ended and dephosphorylated and ligated with the previously produced YB-1 coding nucleic acid. The vector thus obtained was referred to as YB-1-pShuttle. The cloning into the pShuttle vector provided the YB-1 fragment coding nucleic acid with an in-frame STOP codon. The YB-1 coding nucleic acid was cloned from the YB-1-pShuttle by means of NheI and BfrI into the vector IRES-E1A-12S in pcDNA3.1 (+). The thus obtained fragment referred to as YB-1 (EcoRI-EcoRI with STOP codon)-IRES-E1A-12S-pcDNA3.1(+).

Subsequently, the cassette YB-1-IRES-E1A12S was excised with PmeI and cloned into the NheI linearised, blunt-ended and dephosphorylated vector E2late-pcDNA3.1 E3427593-31509, E4Δ33241-33875. Thus the second cassette is in the deleted region of the E3 region.

The transgene cassette comprising the nucleic acid construct E2late-YB-1-IRES-E1A12S was cloned together with the remaining adenoviral sequences E3Δ27593-31509, E4Δ33241-33875 by means of SfuI and SpeI into the vector pAdenoX of Clontech (=AdenoX/E2late-YB-1-IRES-E1A12S/E3Δ27593-31509, E4Δ33241-33875).

The cassette CMV-E1B55k/IRES/E4orf6 was excised by means of I-CeuI and PI-SceI from the pShuttle described above in relation to Xvir03 and inserted into the vector AdenoX/E2late-YB-1-IRES-E1A12S/E3Δ27593-31509, E4Δ33241-33875.

Subsequently, the vector was linearised with Pac I, transfected into 293 cells and the recombinant adenovirus XvirPSJL 1 and XvirPSJL 2, respectively, isolated without the transgenes indicated in the figure in accordance with manufacturer's instructions.

It is within the present invention and feasible for the one skilled in the art in the light of the present disclosure that other systems may be used, such as the system of the companies QBIOGENE and MICROBIX, for the generation of the adenoviruses in accordance with the present invention, preferably recombinant adenovirus and in particular those containing, separately and/or together, the cassettes E4orf6-IRES-E1B55k and E1A12S-IRES-YB-1, respectively. Additionally, the individual transgenes can be exchanged within the individual cassettes and in particular among the respective cassettes. Additionally, the cassette E1A12S-IRES-YB-1 may consist only of E1A12S and/or E1A12S can be linked to other relevant genes through IRES.

Generation of the Adenovirus AdPSJL-E2-Late Promoter 12S-AdEASY with E1A12S in the Deleted E3-Region with the AdEASY-System (Company Microbix).

Cloning of PSJL 12S

First, the E2-late promoter was cloned into the HindIII and BglII cleavage site of the pGL3-enhancer plasmid (pGL3-E2-late) as paired oligonucleotides (upper primer 5'-TCGAGCTCCGCATTTGGCGGGCGGGAT-TGGTCTTCGTAGAACCTAATCTCGTGGGCG TGGTAGTCCTCAGGTACAAAT-3' (SEQ ID NO: 18) and lower primer 5'-AGCTTATTTGTACCTGAGGACTAC-CACGCCCACGAGATTAGGTTCTACGAAGACCAA TCCCGCCCGCCAAATGCGGAGC-3'(SEQ ID NO: 19)).

Subsequently, the luciferase gene was excised using NcoI and XbaI, the ends made blunt ended and T-ends added. The transgene E1A 12S which was amplified by the primers E1A 12S forward primer 5'-ATGGCCGCCAGTCTTTTG-3' (SEQ ID NO: 20) and E1A 12S backward primer 5'-TTATGGCCTGGGGCGTTTAC-3' (SEQ ID NO: 21), was introduced by TA-cloning into the thus opened site.

This cassette was excised using PvuI and ClaI, the ends made blunt ended and cloned into the blunt ended and dephosphorylated NheI-cleavage site in the E3-region of E3E4-pShuttle (-NdeI)-AdEASY. The cassette thus contains the E2-late promoter, the open reading frame Ela-12S and the SV-40 late polyadenylation signal. The resulting construct is E2-late-E1a-12S-E3E4-pShuttle(-NdeI)-AdEASY.

Subsequently the E2-late-E1a 12S-E3E4 was excised from the E2-late-E1a 12S-E3E4-pShuttle (-NdeI)-AdEASY using SpeI and PacI and cloned into the SpeI and PacI cut pAdEASY. The thus resulting construct was referred to as E2-late-E1a 12S-E3E4-pAdEASY.

AdPSJL-12S-AdEASY was generated by homologous recombination upon transforming BJ5183 (EC) bacteria with the plasmids Xvir-3'UTR in pShuttle AdEASY and E2-late-E1a 12S-E3E4-pAdEASY.

Generation of the Adenovirus AdPSJL-E2-Late Promoter-12S-YB-1-AdEASY with E1A12S and YB-1 in the Deleted E3-Region Using the AdEASY System (Company Microbix)

Cloning of the Vector E4ORF6-IRES-pcDNA3.1(+)

The amplificates E1a 12S (see above) and the IRES element (see above) were subsequently cloned into the multiple cloning site of the pcDNA3.1(+)-vector. For such purpose the E1a-12S amplificate was introduced into the blunt ended BamHI-cleavage site by TA-cloning. Subsequently, the plasmid E1a-12S in pcDNA3.1(+) was linearized with EcoRV, T-ends added and the amplificate cloned into the IRES element. The thus obtained plasmid was subsequently linearized with XhoI, the ends made blunt ended and the EcoRI-EcoRI-cleavage product of YB-1 which is devoid of a stop codon.

The thus created construct E1A-12S-IRES-pcDNA3.1(+) was linearized using NotI and the ends made blunt ended. Also, the YB-1-EcoRI-cleavage product was made blunt ended and introduced into the dephosphorylated vector E1A-12S-IRES-pcDNA3.1(+). The cassette E1A-12S-IRES-YB-1 was removed using PmeI and cloned into the above described plasmid pGL3-E2-late after removal of the luciferase gene with NcoI and XbaI and blunt ending and dephosphorylation.

The cassette E2-late-E1A-12S-IRES-YB-1 was excised using PvuI and ClaI, the ends made blunt ended and cloned into the blunt ended and dephosphorylated NheI-cleavage site in the E3-region of E3E4-pShuttle (-NdeI)-AdEASY. The thus obtained construct is E2-late promoter-E1A-12S-IRES-YB-1-E3E4-pShuttle (-NdeI)-AdEASY.

Subsequently, the E2-late promoter-E1A-12S-IRES-YB-1-E3E4 cassette was excised from the E2-late promoter-E1A-12S-IRES-YB-1-E3E4-pShuttle (-NdeI)-AdEASY with SpeI and PacI and cloned into the SpeI and PacI cut pAdEASY. The resulting construct was referred to as E1 a-12S-IRES-YB-1-E3E4-pAdEASY.

AdPSJL-12S-Yb-1-AdEASY was generated by homologous recombination upon transformation of BJ5183 (EC) bacteria with the plasmid Xvir-3'UTR in pShuttle AdEASY and E1 a-12S-IRES-YB-1-E3E4-pAdEASY.

Cloning of the Cassette E2-Late Promoter-E1A-12S and/or E2-Late Promoter-E1A-12S-IRES-YB-1 in the E4-Region After manipulation and deletion, respectively, of the E4 region using PstI 634 bp were removed. The cassettes E2-late promoter-E1A-12S and/or E2-late promoter-E1A-12S-IRES-YB-1 can be introduced into the E4-region. Alternatively, the E2-region may remain intact under such conditions.

Cloning of the RGD-Motive

For an improved infectivity the HI loop of the fibre knob domain was modified according to Dmitriev et al. 1998 (An Adenovirus Vector with Genetically Modified Fibers Demonstrates Expanded Tropism via Utilization of a Coxsackievirus and Adenovirus Receptor-Independent Cell Entry Mechanism): The respective region was amplified using the primes RGD-Hpa fw (5'-GAGgttaacCTAAGCACTGC-CAAG-3 (SEQ ID NO: 12)), RGD-EcoRV rev (5'-CAT-AGAGTATGCAGATATCGTTAGTGTTACAGGTT-TAGTTTTG-3'(SEQ ID NO: 13)), as well as RGD-EcoRV fw (5'-GTAACACTAACGATATCTGCATACTCTATGT-CATTTTCATGG-3' (SEQ ID NO: 14)) and RGD-Bfr rev (5'-CAGCGACATGAActtattaagTGAGCTGC-3' (SEQ ID NO: 15)) and an EcoRV-cleavage site thus generated. Paired oligonucleotides were cloned into this cleavage site which code for an Arg-Gly-Asp (RGD)-peptide with RGD oligo 1 (5'-CACACTAAACGGTACACAGGAAACAGGA-GACACAACTTGTGAC TGCCGCGGAG ACTGTTTCTGCCC-3' (SEQ ID NO: 16)) and RGD oligo 2 (5'-GGGCAGAAACAG TCTCCGCGGCAGT-CACAAGTTGTGTCTCCTGTTTCCTGTGTACCGTT-TAGTGTG-3' (SEQ ID NO: 17)).

Thus the RGD motif is contained in the HI loop of the fibre knob domain.

EXAMPLE 21: INFECTION OF HELA CELLS WITH ADENOVIRUS DL520

100.000 HeLa cells were plated per dish. At the next day the cells were infected with various titers (pfu/ml) of adenovirus dl520. The infection was done in 500 µl serum-free DMEM medium for 1 h at 37° C. Subsequently, the infection medium was removed and replaced by 2 ml complete medium (10% FCS/DMEM). After 3-5 days an analysis was performed using crystal violet staining.

The result of this experiment is depicted in FIG. 23. The adenovirus dl520 does not show any lysis at low MOIs (5-10 pfu/cell) upon infection of HeLa cells which do not have YB-1 in the nucleus. In contrast thereto, dl520 showed a factually complete lysis at an MOI (multiplicity of infection) of 100-200 pfu per cell and a still predominant lysis at an MOI of 50 pfu per cell. Therefrom it can be concluded that dl520 and similar viruses which are capable of switching on the adenoviral genes E1B55k and E4orf6 at higher MOIs, are suitable to transport either directly or indirectly overexpressed or deregulated YB-1 into the nucleus and thus to induce cell lysis.

EXAMPLE 22: LUCIFERASE ASSAY FOR DETERMINING THE E2-LATE PROMOTER ACTIVITY

It is known that YB-1 binds to the adenoviral E2-late promoter in the nucleus (Holm et al., JBC 2002, 277, 10427-20434) and that this promoter is also well suited for the expression of nucleic acids. The use of the adenoviral E2-late promoter is particularly motivated by the fact that it can be regulated by YB-1, whereby YB-1 acts as a positive effector, i. e. the promoter is only active in the presence of YB-1 in the nucleus. Insofar said adenoviral E2-late promoter can be regulated in a highly selective manner and thus used in systems in which YB-1 is present in the nucleus and factually avoids any expression of the nucleic acid which is under the control of the adenoviral E2-late promoter in case that YB-1 is not present in the nucleus as an effector and regulator, respectively. The E2-late promoter comprises 3 Y-boxes (CCAAT SEQ ID NO. 36) which are relevant for the activation of the E2 gene. Different E2-late promoter constructions have been prepared and tested for their specificity and activity. The analysis was carried out as follows.

The cell lines EPG-257 RDB (epithelial stomach carcinoma) which has YB-1 in the nucleus, HeLa (epithelial uterine cervix carcinoma) and U2OS (osteosarcoma) were seeded using three different cell concentrations in 6 well plates. The wells which showed confluence of 70% at the next day, were used for transfection. For each well 500 ng SpinMiniprep (Qiagen) purified plasmid DNA of the different E2-late promoter constructions in luciferase vectors (commercially available from Promega, starting plasmid: pGL3-enhancer) were added to 500 µl OptiMEM in a 1.5 ml locking cap reaction vessel and 5 µl DOTAP to 500 µl in a further locking cap reaction vessel. Both solutions were combined and mixed. The mixture was incubated for complex formation for 30 minutes at room temperature. The cells were rinsed three times with PBS and covered with a layer of the transfection mixture. The plates were incubated at 37° C. for 5 hours, subsequently rinsed again three times with PBS and provided with complete medium.

The cells were processed with the Luciferase Assay System Kit of Promega (Cat. No. E1500) 48 h after infection: Each well was provided with a layer of 500 µl lysis buffer, the cells rinsed off from the well plate with a 1 ml pipette after 10 minutes at room temperature and transferred into a 1.5 ml locking cap reaction vessel. The cell lysate was subsequently centrifuged at 4° C. for 15 minutes at 14.000 rpm. To each 50 µl of the supernatant 100 µl luciferase substrate were added and measured with TopCount (Canberra-Packard GmbH, 63303 Dreieich) Microplate Scintillation & Luminescence counter in black plates with 96 wells at a wave length of 945 nm.

Protein was measured with the BCA Protein Assay Reagent Kit, catalogue number 23227 (PIERCE, Rockford, Ill., USA) at 570 nm in a bioluminometer (Biolumin™ 960) kinetic fluorescence/absorbance plate reader of Molecular Dynamics. The relative light signals of the samples were translated into the protein amount (RLU/µg protein).

The following plasmids were used: pGL3-enhancer (Promega) from which the enhancer was removed by means of BamHI (2250 bp) and BsaBI (2003 bp), served as a blank reading. The various E2 promoter constructions were cloned into the MCS in the enhancer-lacking pGL3 vector by means of restriction sites Apa I and Sac I. The hCMV promoter was cloned by means of Bgl II and Hind III into the pGL3 enhancer and served as a positive control. The positive control allowed to estimate transfection efficiency and also served as a reference value for luciferase activity. For each cell line the CMV control was set 100% and the enzyme activity produced by the E2 promoter constructions put in relation thereto and depicted as a bar graph in FIG. 24.

The various constructs were referred to as follows:

1. comprising the Y-box I, II and III corresponding to bases 25932-26179 bp (referring to the wildtype adenovirus sequence, see also the part of the subsequently provided adenoviral E2 region)

2. comprising the Y-box II and III corresponding to bases 25932-26127 bp (referring to the wildtype adenovirus sequence, see also the part of the subsequently provided adenoviral E2 region)

3. comprising the Y-box III corresponding to bases 25932-26004 bp (referring to the wildtype adenovirus sequence, see also the part of the subsequently provided adenoviral E2 region)

4. comprising no Y-box as acting as the blank reading Part of the Adenoviral E2 Region (Taken from Virology 1992, 186, 280-285)

(The YB-1 binding sites are printed in bold):

```
                                                          (SEQ ID NO: 34)
25561   aggaactttatcctagagcgctcaggaatcttgcccgccacctgctgtgcacttcctagc 25621   gactttgtgcccattaagtaccgcgaatgccctccgccgctttggggccactgctacctt 25681   ctgcagctagccaactaccttgcctaccactctgacataatggaagacgtgagcggtgac 25741   ggtctactggagtgtcactgtcgctgcaacctatgcaccccgcaccgctccctggtttgc 25801   aattcgcagctgcttaacgaaagtcaaattatcggtaccttttgagctgcagggtccctcg 25861   cctgacgaaaagtccgcggctccggggttgaaactcactccggggctgtggacgtcggct 25921   taccttcgcaaatttgtacctgaggactaccacgcccacgagattaggttctacgaaga c 25981   caat cccgcccgccaaatgcggagcttaccgcctgcgtcattacccagggccacattctt 26041   gg ccaat gcaagccatcaacaaagcccgccaagagtttctgctacgaaagggacggggg 26101   gtttacttggaccccagtccggcgaggagctcaac ccaat cccccgccgccgcagccc 26161   tatcagcagcagccgcgggcccttgcttcccaggatggcacccaaaaagaagctgcagct 26221   gccgccgccacccacggacgaggaggaatactgggacagtcaggcagaggaggttttgga 26281   cgaggaggaggaggacatgatggaagactgggagagcctagacgaggaagcttccgaggt 26341   cgaagaggtgtcagacgaaacaccgtcaccctcggtcgcattcccctcgccggcgcccca 26401   gaaatcggcaaccggttccagcatggctacaacctccgctcctcaggcgccgccggcact 26461   gcccgttcgccgacccaaccgtagatgggacaccactggaaccagggccggtaagtccaa 26521   gcagccgccgccgttagcccaagagcaacaacagcgccaaggctaccgctcatggcgcgg 26581   gcacaagaacgccatagttgcttgcttgcaagactgtggggcaacatctccttcgcccg 26641   ccgctttcttctctaccatcacgcgtggccttcccccgtaacatcctgcattactaccg 26701   tcatctctacagcccatactgcaccggcggcagcggcagcggcagcaacagcagcggcca 26761   cacagaagcaaaggcgaccggatagcaagactctgacaaagcccaagaaatccacagcgg
```

The results presented in FIG. 30 confirm in an impressive manner that the individual promoter fragments which contain different E2-late/Y-boxes, are suitable for the expression of therapeutic transgenes in YB-1 nucleus-positive tumor cells and may thus be used as promoters in the meaning of the present invention.

EXAMPLE 23: EFFECT OF YB-1 EXPRESSED BY ADENOVIRUS ON PARTICLE RELEASE

Human osteosarcoma cells (U2OS) were infected with the E1/E3-deleted adenoviral vector AdYB-1 and Ad312 only having E1A-deleted, at an MOI of 50 pfu/cell. AdYB-1 contains in its genome the sequence coding for the cellular transcription factor YB-1 and thus expresses the Y-box binding protein 1 (YB-1). In order to evaluate the release of viral particles as "plaque forming units" (pfu) after infection, either the supernatant of the culture medium or the remaining cell layer was isolated 2 and 5 days, respectively, post infection. The intracellular particles were released by 3 cycles of thawing/freezing. The particle number was analysed using the plaque assay on 293 cells.

The result is in depicted in FIG. 31, whereby the solid bars indicate the intracellular remaining viral particles, whereas the cross-striped bars represent the released, extracellular viral particles.

The result depicted in FIG. 31 confirms that AdYB-1, as a whole, produces more pfu than Ad312 and releases more particles. After 5 days the AdYB-1 infected cells clearly show a cytopathic effect (CPE) in contrast to Ad312-infected cells.

FIG. 32 shows a schematic representation of the regulation of the E2 region of adenovirus by the E2-late and E2-early promoters through E2F and YB-1. In FIG. 1 the involved promoters, E2-early and E2-late promoter, are depicted with regard to the binding and activation, respectively, by E2F and YB-1. The wildtype E1A protein interferes with the binding of E2F to the retinoblastoma protein Rb. The thus released E2F binds to the E2-early promoter and induces thereby adenoviral replication. After 8-12 h a so-called switch to the E2-late promoter occurs. This is only enabled upon the translocation of YB-1 from the cytoplasm into the nucleus. After nuclear localisation YB-1 activates E2 gene expression by binding to the E2-late promoter.

The binding mechanism of E2F/RB and the E1A mediated release of E2F is fundamentally different from the mechanism underlying the present invention. The release of E2F from the Rb protein as assumed in the prior art, is not an important, not to say a non-critical process of adenoviral replication, but the nuclear localisation of the human transcription factor YB-1 is the critical factor therefor. This transcription factor is present in normal cells only in the cytoplasm over the bigger part of the cell cycle. After infection with adenovirus it will be induced into the nucleus under distinct conditions or is already present in the nucleus in connection with specific cellular systems, such as distinct tumor diseases, e. g., including but not limited to breast cancer, ovarian cancer, prostate cancer, osteosarcoma, glioblastoma, melanoma, small-cell lung cancer and colorectal cancer.

EXAMPLE 24: CONSTRUCTION OF DIFFERENT PROTEIN IX EXPRESSING ADENOVIRUSES

Starting from the design of the viral nucleic acid of wildtype adenovirus as depicted in FIG. 33, the various design principles as disclosed herein were realized for the expression of protein IX in adenovirus which replicate in a YB-1 dependent manner, and are depicted in FIGS. 34, 35, 36 and 37. All design have in common that they are E1A13S-minus and E1A12S-minus in the meaning that they are not controlled by the naturally occurring and the E1A promoter as present in the wildtype, respectively.

In connection with adenovirus Xvir 05/promoter as depicted in FIG. 34, the promoter is additionally E1B19K-minus and protein IX-minus in the sense that protein IX is not contained in the regulatory context as present in the wildtype and protein IX is not expressed. Rather, the expression is controlled by the E2-late promoter. The protein IX has been cloned into the E3 region, however, can, in principle, also be cloned into the E4 region. The genes for E2A, E2B, E4 and MLP are still present and may also be expressed. The transporter consisting of E4orf6 and E1B55K is formed by the cassette E4orf6-IRES-E1B55K which is under the control of the CMV promoter. The respective cassette has been cloned into the E1 region, however, could also be cloned into other regions such as, for example, the E3 and E4 region.

In the adenovirus Xvir05/E1A12S as depicted in FIG. 35, the adenovirus is additionally E1B19K-minus and protein IX-minus in the sense that protein IX is not contained in the regulatory context as in wildtype and protein IX is not expressed. Rather the expression is caused by the E1A12S which is controlled by the E2-late promoter which results in activating the open reading frame for protein IX which is present in the region coding for E1B55K. The protein E1A12S is cloned into the E3 region, however, can, in principle, also be cloned into the E4 region. The genes for E2A, E2B, E4 and MLP are still present and can also be expressed. The transporter consisting of E4orf6 and E1B55K is formed by the cassette E4orf6-IRES-E1B55K which is under the control of the CMV promoter. The respective cassette has been cloned into the region of the E1 region, however, could also be cloned into different regions such as, e. g., the E3 or E4 region.

In the adenovirus Xvir 05/E1B19K as depicted in FIG. 36, the adenovirus is additionally E1B19K-minus and protein IX-minus in the sense that protein IX is not present in the regulatory context as present in wildtype. Rather the expression is controlled by the protein E1B19K which is expressed under the influence of the CMV promoter and allows that the reading frame of protein IX is expressed which is contained in the E1B55K reading frame. The genes for E2A, E2B, E3, E4 and MLP are still present and may also be expressed. The transporter consisting of E4orf6 and E1B55K is formed by the cassette E4orf6-RSV promoter E1B region which is controlled by the CMV promoter. The respective cassette has been cloned into the E1 region, however, could also be cloned into different regions such as, e. g., the E3 or E4 region.

In the adenovirus Xvir05/E3-IX as depicted in FIG. 37, the adenovirus is additionally E1B19K-minus and protein IX-minus in the sense that protein E1B19K is not present in the regulatory context as present in the wildtype adenovirus and protein IX is not expressed. Rather, the expression is controlled by the natural E3 promoter. The genes for E2A, E2B, E4 and MLP are still present and may also be expressed. The transporter consisting of E4orf6 and E1B55K is formed by the cassette E4orf6-IRES-E1B55K which is under the control of the CMV promoter. The respective cassette has been cloned into the E1 region, however, could also be cloned into different regions such as, e. g., the E3 or E4 region.

FIGS. 38-41 present further embodiments of the adenoviruses in accordance with the present invention.

The virus depicted in FIG. 38 is a further development of the adenovirus Xvir 05/E1B19K as depicted in FIG. 36. In addition to Xvir05/E1B19K this virus exhibits a cassette which is under the control of the E2-late promoter, comprising E1A12S and YB-1 and a nucleic acid coding therefor, respectively, whereby both reading frames are separated by an IRES. In an embodiment it can be envisaged that the nucleic acid coding for YB-1 is not contained in the cassette. The nucleic acid for YB-1 which is expressed by the virus, results in an even more pronounced replication in cells having deregulated YB-1.

The adenovirus depicted in FIG. 40 is a further development of the adenovirus depicted in FIG. 35, whereby the cassette which is under the control of the E2-late promoter, comprises E1A12S and YB-1 and nucleic acids each coding therefor, respectively, and is cloned into the E4 region and several transgenes are cloned into the E3 region under the control of the E3 promoter such as, e. g., apoptosis-inducing genes, prodrug genes, siRNA, tumor suppressor genes or cytokines. Alternatively, the various transgenes disclosed herein may be cloned into this region.

The adenovirus in accordance with the present invention depicted in FIG. 41 is finally a further development of the adenovirus depicted in FIG. 40, whereby in connection therewith the RGD motif has been introduced by cloning which is advantageous for the targeting of the viruses. It is present in the adenoviral genome in the fibre protein approximately in the range of positions 32576-32685. This variation of the precise positioning is caused by the fact that the sequence of wildtype adenoviruses are different in the various data banks and data bank entries and have different lengths, respectively.

The adenovirus in accordance with the present invention and depicted in FIG. 39 is based on the adenovirus presented in FIG. 36. In contrast thereto, this adenovirus, however, does not comprise a cassette consisting of E4orf6 and E1B55K, but both are controlled by different promoters, namely the CMV promoter and the RSV promoter. The cloning has been done into the E1 region. Additionally, the adenovirus comprises apart from the nucleic acid coding for E1A12S which is under the control of the E2-late promoter, still a further nucleic acid coding for protein IX, which is separated from the one coding for E1A12S by an IRES. Also this cassette could, in principle, also lack a nucleic acid coding for protein IX. A further possible embodiment could be such that the cassette is cloned into the E4 region. Finally, also this virus could still contain in the E3 or E4 region the transgenes as described in connection with the virus depicted in FIG. 8. In a further embodiment of these viruses, the RGD motif is contained.

EXAMPLE 25: DETECTION OF PROTEIN IX EXPRESSION

This experiment was performed in order to confirm the importance of the expression of protein IX for an effective particle formation in YB-1 mediated replication. Therefor the oncolytic YB-1 dependent replicating adenovirus Xvir 03-3'UTR has been used which is described in the prior art and is depicted in FIG. 50.

The experiment was performed as follows: For each 10 cm dish $10^6$ 293 and 257 RDB cells were plated. The next day the cells were, as depicted in FIG. 10, either not infected (K), infected with wildtype adenovirus or with Xvir03. The infection occurred in 1.5 ml serum-free DMEM medium for 1 h at 37° C. Subsequently, the infection medium was removed and replaced by 10 ml complete medium (10% FKS/DMEM). After 24-48 h the RNA was isolated. Subsequently, a Northern blot analysis was performed. For such purpose each 10 µg RNA were separated electrophoretically in an agarose gel with 3% formaldehyde, subsequently blotted onto a nylon membrane and hybridised against a specific 386 bp probe. A P32 labelled probe directed against protein IX was used as a probe and generated using PCR. The following primers were used for the PCR: 5'-TATTGACAACGCG (SEQ ID NO: 28); 5'-TTTTAAACCG-CATTGGG (SEQ ID NO: 29). The position of the probe in wildtype adenovirus genome is between position 3648 and 4033. The virus which is used, is Xvir 03 which does not expression of protein IX.

The results of the experiment are depicted in FIG. 42.

As may be taken from FIG. 42, the virus Xvir03-3'UTR shows a decreased expression in tumor cells 257RDB compared to wildtype adenovirus. In 293 cells which express E1A and E1B proteins, among others also the E1B19K protein, sufficient protein IX is expressed.

EXAMPLE 26: RECOMBINATION ANALYSIS OF VECTOR XVIR03-3'UTR

Per each 10 cm dish $10^6$ 293 cells were plated. The next day the cells were infected with the various adenoviruses as depicted in FIG. 43. The infection was performed in 1.5 ml serum-free DMEM medium for 1 h at 37° C. Subsequently, the infection medium was removed and replaced by 10 ml complete medium (10% FKS/DMEM). After 48 h the DNA was released by alkaline lysis and purified over a column. Subsequently, 2 µg DNA were cut with Hind III. The samples were separated electrophoretically in a 1-2% agarose gel and subsequently blotted onto a nylon membrane. The DNA blotted onto the membrane was hybridised against a specific 386 bp probe. A P32 labelled probe targeting the protein IX was used as a probe and generated by means of PCR. The following primers were used for the PCR: 5'-TATTGACAACGCG (SEQ ID NO: 28); 5'-TTTTAAACCG-CATTGGG (SEQ ID NO: 29). The position of the probe in the wildtype adenovirus genome is between position 3468 and 4033. The result shows that adenovirus Xvir03 does not recombine after infection of 293 cells. The sizes of the cleavage products are represented in the figure.

EXAMPLE 27: MRP EXPRESSION ANALYSIS IN 257RDB CELLS

Per 10 cm dish $10^6$ 257RDB cells were plated. The next day the cells were infected with the various adenoviruses as depicted in FIG. 44. The infection occurred in 1.5 ml serum-free DMEM medium for 1 h at 37° C. Subsequently, the infection medium was removed and replaced by 10 ml complete medium (10% FKS/DMEM). After 3-4 days the RNA was isolated. Subsequently, a Northern blot analysis was performed. For such purpose each 10 µg RNA were electrophoretically separated in an agarose gel with 3% formaldehyde, subsequently blotted onto a nylon membrane and hybridised against the specific P32 labelled MRP probe. The probe is generated by restriction EcoRI from plasmid pCRII-MRP. The result shows that the adenovirus Xvir03 is capable of inhibiting the expression of the ABC transporter MRP.

EXAMPLE 28: MDR EXPRESSION ANALYSIS IN 257RDB CELLS

Per 10 cm dish $10^6$ 257RDB cells were plated. The next day the cells were infected with the various adenoviruses as depicted in FIG. 45. The infection was performed in 1.5 ml serum-free DMEM medium for 1 h at 37° C. Subsequently, the infection medium was removed and replaced by 10 ml complete medium (10% FKS/DMEM). After 3-4 days the RNA was isolated. Subsequently, a Northern blot analysis was performed. For such purpose each 10 µg RNA were electrophoretically separated in an agarose gel containing 3% formaldehyde, subsequently blotted onto a nylon membrane and hybridised against a specific P32 labelled MDR probe (Holm et al., British J. Cancer, 1994, 70, 239-243). The result shows that the adenovirus Xvir03 is capable of inhibiting the expression of the ABC transporter MDR1.

EXAMPLE 29: MRP EXPRESSION ANALYSIS IN DU145 CELLS $10^6$ DU145 cells were plated per 10 cm dish. The next day the cells were infected with the various adenoviruses as depicted in FIG. 46. The infection was performed in 1.5 ml serum-free DMEM medium for 1 h at 37° C. Subsequently, the infection medium was removed and replaced by 10 ml complete medium (10% FKS/DMEM). After 3-4 days the RNA was isolated. Subsequently, a Northern blot analysis was performed. For such purpose each 10 µg RNA were electrophoretically separated in an agarose gel containing 3% formaldehyde, subsequently blotted onto a nylon membrane and hybridised against a specific P32 labelled MRP probe. The result shows that the adenovirus Xvir03 is capable of inhibiting the expression of the ABC transporter MRP.

From the given examples it can be taken that the recombinant adenovirus Xvir03 is capable of inhibiting the expression of the resistance relevant genes MRP and MDR1. This is perfected by the complex consisting of E4orf6 and E1B55k recruiting the human cellular transcription factor YB-1 for adenoviral replication. Thus, this transcription factor which is otherwise involved in the expression of the genes MDR1 and MRP, is no longer available for their expression. Consequently, the expression of MRP and MDR1 proteins is reduced after infection with Xvir03. This results in a sensitisation of tumor cells against various cytostatics, e. g. daunorubicin (FIG. 9).

EXAMPLE 30: REPRESENTATION OF THE LYTIC EFFECT OF XVIR03 IN PROSTATE CARCINOMA CELLS DU145 CELLS AND PC3 CELLS

Per dish 100,000 DU145 and PC3 cells were plated. The next day the cells were infected with different concentrations of Xvir03 (PFU/cell) as depicted in FIGS. 47 and 48. The infection was performed in 500 µl serum-free DMEM medium for 1 h at 37° C. Subsequently, the infection medium was removed and replaced by 2 ml complete medium (10% FKS/DMEM). After 5-7 days the evaluation was performed using crystal violet staining. For such purpose, first the medium is removed. Subsequently, the cells are overlayed with crystal violet (50% ETOH, 3% formaldehyde, 5% acetic acid, 1% crystal violet) and incubated at room temperature for 5-15 min. Subsequently, the plates are thoroughly rinsed with water and dried at room temperature.

The results of the experiment are depicted in FIGS. 47 and 48. The adenovirus Xvir03 is capable of lysing tumor cells at an MOI of about 30-50.

EXAMPLE 31: ENHANCING THE EFFECT OF THE CYTOSTATIC DAUNORUBICIN BY INFECTION WITH XVIR03

It is known in the prior art that the addition of various cytostatics induces nuclear localisation of the human transcription factor YB-1. It is also known that YB-1 is involved in the activation and regulation, respectively, of MDR1 and MRP expression. As has been found by the present inventor the recruiting of YB-1 through the complex E4orf6/E1B55k results in the inhibition of the expression of the ABC transporter MRP and MDR1. This results in an increased efficacy of cytostatics.

For performing the oncolytic assays it was proceeded as follows: 100,000 cells (DU145) were plated in each well of a 6 well plate. The next day the cells were infected with 15 PFU/cell. After 24 h daunorubicin was added as indicated. After 15-25 h of incubation the medium including daunorubicin was replaced by cytostatic-free medium. After another 4-6 days the cells were stained using crystal violet.

As may be taken from FIG. 49 the infection of tumor cells by Xvir03 results in a more pronounced inhibitory effect of daunorubicin in combination with Xvir03 on tumor cell growth compared to daunorubicin alone.

EXAMPLE 32: STRUCTURE OF RECOMBINANT ADENOVIRUSES XVIR05, XVIR05/PROTEIN IX, XVIR05/01 AND XVIR05/02

The expression of the viral proteins E4orf6 and E1B55k, among others, is ensured in vector Xvir05 by the expression cassettes CMV-E4orf6 and RSV-E1B region. This results in a translocation of YB-1 into the nucleus. The E1A12S gene product as well as the YB-1 gene product controlled by the E2-late promoter additionally promote viral replication. Additionally, the virus is capable of inhibiting the expression of the ABC transporter MRP and MDR1. Additionally, the proteins E1B19K and protein IX are expressed as constituents of the cassette RSV-E1B region.

The vector Xvir05 protein IX is a further development of the vector. There, the expression of the adenoviral protein IX is ensured by the expression cassette E2late-E1A12S-IRES-protein IX. The vector does not comprise the complete E1B region but only the open reading frame of E1B55k.

In the vector Xvir05/01 the complete E1B region, i. e. the E1B19k, E1B55k and the protein IX are controlled by a viral, non-adenoviral promoter such as, for example, the RSV promoter. The expression cassette E2late-E1A12S-IRES-YB-1 is present in the E4 region. Thus specific therapeutic transgenes may be cloned into the E3 region. The E3 deletion is such that the adenoviral ADP protein "adenoviral death protein", is still expressed. Additionally, the expression of E1A12S and E1B19k effect the expression of protein IX.

The vector Xvir05/02 additionally comprises an RGD motif in the H loop of the fibre knob in order to increase a better infection rate.

The generation of the viruses was performed as follows:
Modification of the Rescue Plasmid pAdEASY (Company Qbiogene)
Use of the Shuttle Vector pShuttle-AdEASY for the Generation of a ΔE3E4 Shuttle Vector First a CMV promoter and a Bovine Growth Hormone polyadenylation signal was cloned into the present vector pShuttle-AdEASY. For such purpose the plasmid was digested with EcoRI, the ends made blunt-ended by filling with T4 polymerase and dNTPs, the backbone dephosphorylated and the two cleavage products generated re-ligated. By this the restriction recognition site for EcoRI was destroyed. The plasmid resulting therefrom was referred to as pShuttle(-EcoRI)-AdEASY.

Subsequently, the cassette CMV-MCS-polyA was cut out of the pShuttle from Clontech using MfeI and EcoRI, the ends made blunt-ended and cloned into the vector pShuttle (-EcoRI)-AdEASY, which has been linearised using XbaI for such purpose, made blunt-ended and dephosphorylated. Plasmid CMV-MCS-PolyA-pShuttle-AdEASY was created therefrom.

For manipulating the E3 and the E4 region the ΔE3E4 region of plasmid pAdEASY was cloned with SpeI and PacI into plasmid CMV-MCS-PolyA-pShuttle-AdEASY and thus the plasmid ΔE3E4-pShuttle-AdEASY generated. By restriction with NdeI and religation one of the two NdeI restriction sites was deleted and thus also a multiple cloning site from the plasmid. By this procedure plasmid ΔE3E4-pShuttle (-NdeI)-AdEASY was generated.

E4 Manipulation

In order to provide space for potential therapeutic transgenes and in order to avoid an undesired homologous recombination, the E4 region in plasmid ΔE3E4-pShuttle (-NdeI)-AdEASY was specifically deleted. When doing so, the E4orf6 region is shortened by about 634 bp by excising with PstI and religation=ΔE3E4ΔORF6-pShuttle (-NdeI)-AdEASY. Respective deletions may be performed in different systems for the generation of recombinant adenoviruses by the one skilled in the art.

Cloning of the RGD Motif in ΔE3E4ΔORF6-pShuttle (-NdeI)-AdEASY

For the improved infectivity the HI loop of the fibre knob domain was modified in accordance with Dmitriev et al. 1998 (An Adenovirus Vector with Genetically Modified Fibers Demonstrates Expanded Tropism via Utilization of a Coxsackievirus and Adenovirus Receptor-Independent Cell Entry Mechanism): The respective region was amplified using the primers RGD-Hpa fw (5'-GAGgt-taacCTAAGCACTGCCAAG-3' (SEQ ID NO: 12)), RGD-EcoRV rev (5'-CATAGAGTATGCAGATATCGTTAGTGT-TACAGGTTTAGTTTTG-3' (SEQ ID NO: 13)) as well as RGD-EcoRV fw (5'-GTAACACTAACGATATCTGCAT-ACTCTATGTCATTTTCATGG-3' (SEQ ID NO: 14)) and RGD-BfrI rev (5'-CAGCGACATGAActtaagTGAGCTGC-3' (SEQ ID NO: 15)) and thereby an EcoRV-cleavage site generated. Paired oligonucleotides were cloned into this cleavage site coding for an Arg-Gly-Asp (RGD) peptide: RGD-Oligo 1 (5'-CACACTAAACGGTACACAG-GAAACAGGAGACACAACTTGTGACTGCCGCGGA-GACT GTTTCTGCCC-3' (SEQ ID NO: 16)) and RGD-Oligo 2 (5'-GGGCAGAAACAG TCTCCGCGGCAGT-CACAAGTTGTGTCTCCTGTTTCCTGTGTACCGTT-TAGTGTG-3' (SEQ ID NO: 17)). By cloning using the HpaI and BfrI cleavage sites in ΔE3E4ΔORF6-pShuttle (-NdeI)-AdEASY the ΔE3-RGD-E4ΔORF6-pShuttle (-NdeI)-AdEASY was generated. The RGD motif is present in the HI loop of the fibre knob domain.

Cloning of the E3a Region in ΔE3 Region of ΔE3RGD-E4ΔORF6-pShuttle (-NdeI)-AdEASY.

For such purpose the vector pcDNA3.1(+) of the company Invitrogen was cleaved with BglII and BamHI, whereby the CMV promoter was removed and the vector religated (pcDNA3.1(+) without CMV=oCMV). Using these SpeI and XhoI restriction sites of the pcDNA3.1(+) oCMV vector the 2709 bp fragment was cloned which was excised with SpeI (27083 bp) and XhoI (29792 bp) from wildtype virus DNA (pcDNA3.1(+) oCMV/E3aXhoI). Alternatively, one can cleave with HpaI (30570 bp) rather than XhoI at the 3' end. For such purpose the vector pcDNA3.1(+) oCMV is then cleaved with SpeI and EcoRV and the adenoviral SpeI-HpaI fragment is cloned therein (pcDNA3.1(+) oCMV/E3aHpaI). A further option is the 2718 bp EcoRI fragment of adenovirus wildtype DNA (positions 27332 bp and 30050 bp) which is cloned into the pcDNA3.1(+) oCMV which has been opened using EcoRI (pcDNA3.1(+) oCMV/E3aEcoRI).

Using the von pcDNA3.1(+) oCMV/E3a the E3a region could be cloned into the vector ΔE3RGD-E4ΔORF6-pShuttle (-NdeI)-AdEASY: The shuttle vector ΔE3RGD-E4ΔORF6-pShuttle (-NdeI)-AdEASY was cleaved for such purpose with NheI, the ens made blunt-ended and further cleaved with SpeI. The insert from pcDNA3.1(+) oCMV/E3aXhoI was cloned into this site. For such purpose the plasmid was cleaved with XhoI, the ends made blunt-ended and further cleaved with SpeI. The fragment thus cut out was cloned into the previously cut plasmid ΔE3RGD-E4ΔORF6-pShuttle (-NdeI)-AdEASY.

The fragments SpeI-HpaI (position 27083 bp to 30570 bp) and EcoRI (position 27332 bp to 30050 bp) may be excised the same way from the respective pcDNA3.1(+) oCMV/E3a constructs and transferred by cloning.

Alternatively, the E3a region may be amplified by PCR using the primers E3a forward (SpeI) 5'-CT-TAAGGACTAGTTTCGCGC-3' (SEQ ID NO: 30) and E3a reverse (XhoI, NheI) 5'-CAAGCTAGCTCGAGGAAT-CATG-3' (SEQ ID NO: 37) with the adenovirus type 5 wildtype DNA as template. Using the E3a reverse primer an NheI cleavage site is generated. The amplificate is restricted with SpeI and NheI and cloned into the similarly SpeI and NheI cleaved vector ΔE3RGD-E4ΔORF6-pShuttle (-NdeI)-AdEASY.

For the SpeI-HpaI Fragment

Alternatively, the E3a region can be amplified using the primers E3a forward (SpeI) 5'-CT-TAAGGACTAGTTTCGCGC-3' (SEQ ID NO: 30) and E3a reverse (HpaI, NheI) 5'-CACGCTAGCAAGTTAAC-CATGTCTTGG-3' (SEQ ID NO: 31) using adenovirus type 5 wildtype DNA as template. Using the E3a reverse primer an NheI cleavage site is generated. The amplificate is restricted with SpeI and NheI and is cloned into the vector ΔE3RGD-E4ΔORF6-pShuttle (-NdeI)-AdEASY which is also cleaved by SpeI and NheI.

For the EcoRI Fragment

Alternatively, the E3a region can be amplified by PCR using the primers E3a forward (EcoRI) 5'-GAAACCGAAT-TCTCTTGGAAC-3' (SEQ ID NO: 32) and E3a reverse (NheI, EcoRI) 5'-GAATTCTAGCTAGCTCAGCTATAG-3' (SEQ ID NO: 33) with adenovirus type 5 wildtype DNA as template. Using the E3a reverse primer an NheI cleavage site is generated. The amplificate is restricted with EcoRI and NheI and cloned into the vector ΔE3RGD-E4ΔORF6-pShuttle (-NdeI)-AdEASY which is also cleaved by EcoRI and NheI.

By transferring the E3a region through cloning from pcDNA3.1(+) oCMV/E3a in ΔE3RGD-E4ΔORF6-pShuttle (-NdeI)-AdEASY E3aΔE3RGD-E4ΔORF6-pShuttle (-NdeI)-AdEASY was generated.

The thus cloned region comprises the E3 region until the open reading frame for the E3 ADP (position 29772 bp) and thus the E3 promoter, the complete E3A region with polyadenylation signal, the transcription start and the open reading frame for 12.5 K, E3 6.7 K, E3 gp19 K and E3 ADP.

The E3 region is, compared to the adenovirus type 5 DNA sequence, in case of SpeI-XhoI cloning deleted from position 29796 to 31509 bp (=1713 bp).

Further deletions are possible between the E3 promoter and the open reading frame for the ADP in plasmid pcDNA3.1(+) oCMV/E3a: By further restrictions between positions 27596 bp and 29355 bp, for example with EcoRII, BsiWI, DraI, MunI, the open reading frames for 6.7 K and gp19 K positioned in between, may be removed and thus provided 1.8 kb more space for incorporating further transgenes. The above mentioned E3a amplificates can also be truncated by a corresponding restriction and as previously described transferred by cloning.

Cloning of the Second Expression Cassette E1a 12S Under the Control of the E2Late Promoter First the E2Late promoter was cloned as paired oligonucleotide (Upper Primer 5'-TCGAGCTCCGCAT-TTGGCGGGCGGGAT-TGGTCTTCGTAGAACCTAATCTCGTGGGCG TGGTAGTCCTCAGGTACAAAT-3' (SEQ ID NO: 18) and Lower Primer 5'-AGCTTATTTGTACCTGAGGACTAC-CACGCCCACGAGATTAGGTTCTACGAAGACCAA TCCCGCCCGCCAAATGCGGAGC-3' (SEQ ID NO: 19) into the HindIII and BglII cleavage site of the pGL3 enhancer plasmid of the company Promega (pGL3-E2Late). Subsequently, the luciferase gene was excised with NcoI and XbaI, the ends made blunt-ended and T ends added. At the thus opened site the transgene E1A12S which was amplified by RT-PCR using the primers E1a 12S forward 5'-ATGGCCGCCAGTCTTTTG-3' (SEQ ID NO: 20) and E1a 12S reverse 5'-TTATGGCCTGGGGCGTTTAC-3' (SEQ ID NO: 21), was introduced by TA cloning.

The cassette thus contains the E2Late promoter, the open reading frame Ela-12S and the SV-40 Late polyadenylation signal of the vector pGL3.

This cassette was excised with PvuI and ClaI, the ends made blunt-ended and can now be cloned optionally into the EcoRII, BsiWI, DraI, MunI deleted E3a region (after removal of the open reading frames for E3 6.7 K and gp19 K, see above) or in the deletion of E4ORF6 cloned, for example into the blunt-ended and dephosphorylated BfrI cleavage site.

The resulting construct is E3a/E2Late-Ela-12S/ΔE3RGD-E4ΔORF6-pShuttle (-NdeI)-AdEASY or E3aΔE3RGD-E4ΔORF6/E2Late-Ela-12S-pShuttle (-NdeI)-AdEASY.

Cloning of the Second Expression Cassette E1a 12S with YB-1 Under the Control of the E2Late Promoter The amplificates E1a 12S (see above) and the IRES element (pCITE-4a(+) of the company Novagen as template, IRES forward=5'-TCCGGTTATTTTCCACCATATTGC-3' ((SEQ ID NO: 10) and IRES reverse=5'-TTAT-CATCGTGTTTTTCAAAGG-3' (SEQ ID NO: 11)) were subsequently cloned into the multiple cloning site of the pcDNA3.1(+) vector (Invitrogen). For such purpose the Ela-12S amplificate was introduced into the blunt-ended BamHI restriction site through TA cloning. Subsequently the plasmid Ela-12S in pcDNA3.1(+) was linearised with EcoRV, the T ends added and the amplificate for the IRES element cloned. The thus generated construct E1 a-12S-IRES-pcDNA3.1(+) was linearised using NotI and the ends blunt-ended, also the YB-1 EcoRI cleavage product of plasmid pHVad2c CMV/S40+Yb-1 s (Stephan Bergmann) blunt-ended and introduced into the dephosphorylated vector E1A-12S-IRES-pcDNA3.1(+). Alternatively, the PCR amplificate for the open reading frame of protein IX can be introduced into the blunt-ended NotI cleavage site of the vector E1 a-12S-IRES-pcDNA3.1(+) after adding T ends, specifically with the primers IX forward 5'-ATGAGCAC-CAACTCGTTTG-3' (SEQ ID NO: 22) and IX reverse 5'-GTTTTAAACCGCATTGGGAGG-3' (SEQ ID NO: 23).

The cassette E1A-12S-IRES-YB-1 or E1A-12S-IRES protein IX were excised with PmeI and cloned into the above described plasmid pGL3-E2Late after removal of the luciferase gene with NcoI and XbaI and blunt-ending and dephosphorylation.

This cassette E2late-E1A-12S-IRES-YB-1 was excised with PvuI and ClaI, the ends blunt-ended and can now optionally be cloned into the EcoRII, BsiWI, DraI, MunI deleted E3a region (after removal of the open reading frames for E3 6.7 K and gp19 K, see above) or in deletion of the E4ORF6, for example in the blunt-ended and dephosphorylated BfrI cleavage site.

The resulting construct is E3a/E2Late-Ela-12S-IRES-YB-1/ΔE3RGD-E4ΔORF6-pShuttle (-NdeI)-AdEASY or E3aΔE3RGD-E4ΔORF 6/E2Late-Ela-12S-IRES-YB-1-pShuttle (-NdeI)-AdEASY.

Generation of the Rescue Plasmid E3a/E2Late-Ela-12S/ΔE3RGD-E4ΔORF6-pAdEASY or E3 aΔE3RGD-E4ΔORF6/E2Late-E1 a-12S-pAdEASY and E3a/E2Late-Ela-12S-IRES-YB-1/ΔE3RGD-E4ΔORF 6-pAdEASY, Respectively, or E3aΔE3RGD-E4ΔORF6/E2Late-Ela-12S-IRES-YB-1-pAdEASY The E3aΔE3RGD-E4ΔORF6 region with the second expression cassette E2Late-E1 a-12S or E2Late-Ela-12S-IRES-YB-1 in E3a or E4ΔORF6 were excised using SpeI and PacI from the corresponding pShuttle plasmid E3aΔE3RGD-E4ΔORF6-pShuttle (-NdeI)-AdEASY and cloned into the accordingly opened vector pAdEASY, whereby the new rescue vector E3a/E2Late-Ela-12S/ΔE3RGD-E4ΔORF6-pAdEASY or E3 aΔE3RGD-E4ΔORF 6/E2Late-Ela-12S-pAdEASY and E3a/E2Late-E1 a-12S-IRES-YB-1/ΔE3RGD-E4ΔORF6-pAdEASY, respectively, or E3 aΔE3RGD-E4ΔORF6/E2Late-Ela-12S-IRES-YB-1-pAdEASY were generated. E3aΔE3RGD-E4ΔORF6-pAdEASY contains the E3a region, an RGD motif and a deleted E4ORF6, as a second expression cassette either the E2Late-Ela-12S or the E2Late-Ela-12S-IRES-YB-1 are present in E3a or E4ΔORF6. This construct is the rescue plasmid for introducing further transgenes into the E1 region through a shuttle plasmid.

Generating the Transgene Cassette for the E1 Region

Cloning of the E1B Region

The adenogenome was restricted with XbaI (position 1340 bp) and MunI (position 3925 bp) for the E1B region and the 2585 bp fragment cloned into the pShuttle of AdEASY into the XbaI and MunI cleavage sites which thus contains the complete E1B region (pShuttle/E1B).

Alternatively, the E1B region can be amplified by PCR using the primers E1B forward 5'-GTGTCTAGAGAATGCAATAGTAG-3' (SEQ ID NO: 24) and E1B reverse 5'-GTCAAAGAATCCAATTGTGC-3' (SEQ ID NO: 25) using the adenovirus type 5 wildtype DNA as template, can be restricted with XbaI and MunI and cloned into the XbaI and MunI restriction sites of the pShuttle of AdEASY.

Thus the pShuttle/E1B comprises the E1B promoter, the open reading frames for E1B19K, E1B55K and the protein IX and the natural poly-A portion. The E1B promoter was removed using XbaI and HpaI, the ends of the vectors blunt-ended and replaced by the CMV promoter from the pcDNA3.1(+) of the company Invitrogen, which was cut with MluI and XhoI and the ends of which have also been blunt-ended. Alternatively, an RSV promoter used instead of the CMV promoter or a tumor specific and viral promoter, respectively, can control the expression of the E1B region, for example the promoters recited in the patent.

Preparing the RSV Plasmid for the Preparation of the Cassette RSV-E4ORF6-polyA.

The plasmid pRc/RSV of the company Invitrogen was cleaved with XhoI, SpeI and XbaI. The thus generated 2810 bp and 278 bp fragments were again ligated so that the F1 origin and the neomycine resistance gene (oNeo) were removed.

The thus generated vector pRc/RSV (oNeo) contains one BamHI cleavage site only into which the open reading frame of E4ORF6 from the plasmid CGN from Dobbelstein was cloned. Alternatively, the amplificate of a PCR using the primers E4ORF6-forward 5'-ATGAC-TACGTCCGGCGTTCC-3' (SEQ ID NO: 26) and E4ORF6-reverse 5'-CTACATGGGGGTAGAGTC-3' (SEQ ID NO: 27) can be introduced into the EcoRV cleavage site of the vector pRc/RSV (oNeo) after adding the T ends (TA cloning). Alternatively, a CMV promoter (taken from pcDNA3.1 (+) with MluI and HindIII) instead of the RSV promoter (by removal with MluI and HindIII) or a tumor-specific and viral promoters, respectively, direct the expression of the E4orf6, for example the promoters recited in the patent.

The cassette RSV-E4ORF6-polyA (the Bovine Growth Hormone polyadenylation signal is derived from plasmid pRC/RSV) was cleaved with MunI, the ends made blunt-ended and further retrieved from the plasmid with XhoI. The expression cassette was subsequently cloned into the vector pShuttle/E1B which had been cleaved with NotI, made blunt-ended and subsequently cleaved with XhoI. By doing so, the vector RSV-E4ORF6-polyA/E1B-pShuttle-AdEASY was generated.

Introducing the Transgene Cassette into the Rescue Vector

The vector RSV-E4ORF6-polyA/E1B-pShuttle-AdEASY for the E1 region was linearised using Bst1107I and MroI and introduced into BJ5183 (EC) bacteria together with the rescue plasmid (see above) by means of electroporation. The adenoviral plasmid RSV-E4ORF6-polyA/E1B-E3a/E2Late-E1a-12S/ΔE3RGD-E4ΔORF6-pAdEASY generated by homologous recombinant (or correspondingly with the other above recited rescue vector variants) which resulted in virus production after transfection in HEK293 cells.

It is within the present invention and feasible for the one skilled in the art in the light of the present invention that the generation of the adenoviruses in accordance with the present invention, preferably recombinant adenoviruses, and in particular those which contain the above-mentioned expression cassettes either individually and/or together, also other systems may be used, e. g. pAdenoX system of the company Clontech/BD Biosciences or the system of the company Microbix.

The features of the invention as disclosed in the preceding specification, the claims and the figures may be individually as well as in any combination be relevant for the practising of the invention and its various embodiments.

The invention claimed is:

1. A method for restoring drug sensitivity in a subject having a tumor comprising drug resistant cells, wherein the drug resistance is mediated by an ABC transporter, which expression is induced by YB-1, the method comprising:

intratumorally administering an effective amount of an adenovirus to the tumor in said subject, whereby the adenovirus replicates in the subject in a YB-1 dependent manner to restore drug sensitivity and wherein the adenovirus comprises a modification rendering the adenovirus E1B19k-minus, and an additional deletion in the E1A gene corresponding to the deletion of dl520; and further administering to said subject a pharmaceutically active agent and/or radiation, wherein the pharmaceutically active agent is a drug to which the drug resistant cells are resistant prior to restoration of drug sensitivity, and wherein the adenovirus is administered 1 to 3 days prior to the administration of the pharmaceutically active agent and/or the radiation.

2. The method according to claim 1, whereby the ABC transporter is selected from the group comprising MRP and MDR, in particular MDR-1.

3. The method according to claim 1, wherein the adenovirus is administered about 1 to 2 days prior to the administration of the pharmaceutically active agent and/or the radiation.

4. The method according to claim 3, wherein the pharmaceutically active agent is a cytostatic.

5. The method according to claim 1, whereby the adenovirus further comprises a nucleic acid coding for a transgene.

6. The method according to claim 5, whereby the transgene is selected from the group comprising a gene coding for a prodrug, a cytokine, an apoptosis-inducing protein, a tumor suppressor gene, a metalloproteinase inhibitor and an angiogenesis inhibitor.

7. The method according to claim 5, whereby the transgene is a sequence that targets a target molecule and is selected from the group comprising an siRNA, an aptamer, an antisense molecule, and a ribozyme.

8. The method according to claim 1, whereby the pharmaceutically active agent is selected from the group comprising a cytokine, a metalloproteinase inhibitor, an angiogenesis inhibitor, a cytostatic, a cell cycle inhibitor, a proteosome inhibitor, a recombinant antibody, an inhibitor of the signal transduction pathway and an inhibitor of a protein kinase.

9. The method according to claim 1, wherein the adenovirus comprises an additional modification rendering the adenovirus protein IX-minus.

* * * * *

SEQUENCE LISTING

```
<160> NUMBER OF SEQ ID NOS: 37

<210> SEQ ID NO 1
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 1
tgaggctgat tggctgggca                                              20

<210> SEQ ID NO 2
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 2
gtcggagatc agatccgcgt                                              20

<210> SEQ ID NO 3
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 3
gatcctcgtc gtcttcgctt                                              20

<210> SEQ ID NO 4
<211> LENGTH: 17
<212> TYPE: DNA
<213> ORGANISM: Artificial sequence
```

```
<220> FEATURE:
<223> OTHER INFORMATION: Description of Artificial Sequence: Synthetic
      oligonucleotide

<400> SEQUENCE: 4
atggagcgaa gaaaccc                                                     17

<210> SEQ ID NO 5
<211> LENGTH: 21
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 5
cacgtcctgg aaaaaataca c                                                21

<210> SEQ ID NO 6
<211> LENGTH: 18
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 6
agctgatctt cgcttttg                                                    18

<210> SEQ ID NO 7
<211> LENGTH: 22
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 7
ggatagcaag actctgacaa ag                                               22

<210> SEQ ID NO 8
<211> LENGTH: 27
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 8
cttcaggatc catgactacg tccggcg                                          27

<210> SEQ ID NO 9
<211> LENGTH: 37
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 9
gaagtgaatt cctacatggg ggtagagtca taatcgt                               37

<210> SEQ ID NO 10
<211> LENGTH: 24
<212> TYPE: DNA
<213> ORGANISM: Artificial sequence
```

```
<220> FEATURE:
<223> OTHER INFORMATION: Description of Artificial Sequence: Synthetic
      oligonucleotide

<400> SEQUENCE: 10
tccggttatt ttccaccata ttgc                                              24

<210> SEQ ID NO 11
<211> LENGTH: 22
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 11
ttatcatcgt gttttcaaa gg                                                 22

<210> SEQ ID NO 12
<211> LENGTH: 24
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 12
gaggttaacc taagcactgc caag                                              24

<210> SEQ ID NO 13
<211> LENGTH: 43
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 13
catagagtat gcagatatcg ttagtgttac aggtttagtt ttg                         43

<210> SEQ ID NO 14
<211> LENGTH: 42
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 14
gtaacactaa cgatatctgc atactctatg tcattttcat gg                          42

<210> SEQ ID NO 15
<211> LENGTH: 26
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 15
cagcgacatg aacttaagtg agctgc                                            26

<210> SEQ ID NO 16
<211> LENGTH: 66
<212> TYPE: DNA
<213> ORGANISM: Artificial sequence
```

```
<220> FEATURE:
<223> OTHER INFORMATION: Description of Artificial Sequence: Synthetic
      oligonucleotide

<400> SEQUENCE: 16
cacactaaac ggtacacagg aaacaggaga cacaacttgt gactgccgcg gagactgttt    60
ctgccc                                                              66

<210> SEQ ID NO 17
<211> LENGTH: 66
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 17
gggcagaaac agtctccgcg gcagtcacaa gttgtgtctc ctgtttcctg tgtaccgttt    60
agtgtg                                                              66

<210> SEQ ID NO 18
<211> LENGTH: 78
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 18
tcgagctccg catttggcgg gcgggattgg tcttcgtaga acctaatctc gtgggcgtgg    60
tagtcctcag gtacaaat                                                 78

<210> SEQ ID NO 19
<211> LENGTH: 79
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 19
agcttatttg tacctgagga ctaccacgcc cacgagatta ggttctacga agaccaatcc    60
cgcccgccaa atgcggagc                                                79

<210> SEQ ID NO 20
<211> LENGTH: 18
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 20
atggccgcca gtcttttg                                                 18

<210> SEQ ID NO 21
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide
```

-continued

<400> SEQUENCE: 21
ttatggcctg gggcgtttac                                            20

<210> SEQ ID NO 22
<211> LENGTH: 19
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 22
atgagcacca actcgtttg                                             19

<210> SEQ ID NO 23
<211> LENGTH: 21
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 23
gttttaaacc gcattgggag g                                          21

<210> SEQ ID NO 24
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 24
gtgtctagag aatgcaatag tag                                        23

<210> SEQ ID NO 25
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 25
gtcaaagaat ccaattgtgc                                            20

<210> SEQ ID NO 26
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 26
atgactacgt ccggcgttcc                                            20

<210> SEQ ID NO 27
<211> LENGTH: 18
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 27
ctacatgggg gtagagtc                                                        18

<210> SEQ ID NO 28
<211> LENGTH: 14
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 28
tatttgacaa cgcg                                                            14

<210> SEQ ID NO 29
<211> LENGTH: 17
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 29
ttttaaaccg cattggg                                                         17

<210> SEQ ID NO 30
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 30
cttaaggact agtttcgcgc                                                      20

<210> SEQ ID NO 31
<211> LENGTH: 27
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 31
cacgctagca agttaaccat gtcttgg                                              27

<210> SEQ ID NO 32
<211> LENGTH: 21
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 32
gaaaccgaat tctcttggaa c                                                    21

<210> SEQ ID NO 33
<211> LENGTH: 24
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 33

```
gaattctagc tagctcagct atag                                        24
```

<210> SEQ ID NO 34
<211> LENGTH: 1260
<212> TYPE: DNA
<213> ORGANISM: Adenovirus

<400> SEQUENCE: 34

```
aggaacttta tcctagagcg ctcaggaatc ttgcccgcca cctgctgtgc acttcctagc   60
gactttgtgc ccattaagta ccgcgaatgc cctccgccgc tttggggcca ctgctacctt  120
ctgcagctag ccaactacct tgcctaccac tctgacataa tggaagacgt gagcggtgac  180
ggtctactgg agtgtcactg tcgctgcaac ctatgcaccc cgcaccgctc cctggtttgc  240
aattcgcagc tgcttaacga aagtcaaatt atcggtacct ttgagctgca gggtccctcg  300
cctgacgaaa agtccgcggc tccggggttg aaactcactc cggggctgtg gacgtcggct  360
taccttcgca aatttgtacc tgaggactac cacgcccacg agattaggtt ctacgaagac  420
caatcccgcc cgccaaatgc ggagcttacc gcctgcgtca ttacccaggg ccacattctt  480
ggccaattgc aagccatcaa caaagcccgc aagagtttc tgctacgaaa gggacggggg  540
gtttacttgg accccagtc cggcgaggag ctcaacccaa tcccccgcc gccgcagccc  600 tatcagcagc agccgcgggc ccttgcttcc caggatggca cccaaaaaga agctgcagct  660
gccgccgcca cccacggacg aggaggaata ctgggacagt caggcagagg aggttttgga  720
cgaggaggag gaggacatga tggaagactg ggagagccta gacgaggaag cttccgaggt  780
cgaagaggtg tcagacgaaa caccgtcacc ctcggtcgca ttcccctcgc cggcgcccca  840
gaaatcggca accggttcca gcatggctac aacctccgct cctcaggcgc cgccggcact  900 gccgttcgc cgacccaacc gtagatggga caccactgga accagggccg gtaagtccaa  960
gcagccgccg ccgttagccc aagagcaaca acagcgccaa ggctaccgct catggcgcgg 1020
gcacaagaac gccatagttg cttgcttgca agactgtggg ggcaacatct ccttcgcccg 1080
ccgctttctt ctctaccatc acggcgtggc cttcccccgt aacatcctgc attactaccg 1140
tcatctctac agcccatact gcaccggcgg cagcggcagc ggcagcaaca gcagcggcca 1200
cacagaagca aaggcgaccg gatagcaaga ctctgacaaa gcccaagaaa tccacagcgg 1260
```

<210> SEQ ID NO 35
<211> LENGTH: 600
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 35

```
tgaggtactg aaatgtgtgg gcgtggctta agggtgggaa agaatatata aggtgggggt   60
cttatgtagt tttgtatctg ttttgcagca gccgccgccg ccatgagcac caactcgttt  120 gatgaagca ttgtgagctc atatttgaca acgcgcatgc ccccatgggc cggggtgcgt  180
cagaatgtga ggggctccag cattgatggt cgccccgtcc tgcccgcaaa ctctactacc  240
ttgacctacg agaccgtgtc tggaacgccg ttggagactg cagcctccgc cgccgcttca  300
gccgctgcag ccaccgcccg cgggattgtg actgactttg ctttcctgag cccgcttgca  360
agcagtgcag cttcccgttc atccgcccgc gatgacaagt tgacggctct tttggcacaa  420
```

```
ttggattctt tgacccggga acttaatgtc gtttctcagc agctgttgga tctgcgccag    480
caggtttctg ccctgaaggc tcctcccctc ccaatgcggt ttaaaacata aataaaaaac    540
cagactctgt ttggatttgg atcaagcaag tgtcttgctg tctttattta ggggttttgc    600

<210> SEQ ID NO 36
<211> LENGTH: 5
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 36 ccaat                                                                  5

<210> SEQ ID NO 37
<211> LENGTH: 22
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 37
caagctagct cgaggaatca tg                                              22
```